United States Patent
Marks et al.

(10) Patent No.: US 12,221,612 B2
(45) Date of Patent: Feb. 11, 2025

(54) PLANTS HAVING INCREASED OIL QUALITY

(71) Applicants: REGENTS OF THE UNIVERSITY OF MINNESOTA, Minneapolis, MN (US); THE BOARD OF TRUSTEES OF ILLINOIS STATE UNIVERSITY, Normal, IL (US)

(72) Inventors: Michael David Marks, Roseville, MN (US); Ratan Chopra, St. Paul, MN (US); Nicole Folstad, Minneapolis, MN (US); Donald L. Wyse, Wyoming, MN (US); John C. Sedbrook, Bloomington, IL (US)

(73) Assignees: Regents of the University of Minnesota, Minneapolis, MN (US); The Board of Trustees of Illinois State University, Normal, IL (US)

( * ) Notice: Subject to any disclaimer, the term of this patent is extended or adjusted under 35 U.S.C. 154(b) by 0 days.

(21) Appl. No.: 16/969,434

(22) PCT Filed: Feb. 12, 2019

(86) PCT No.: PCT/US2019/017660
§ 371 (c)(1),
(2) Date: Aug. 12, 2020

(87) PCT Pub. No.: WO2019/157504
PCT Pub. Date: Aug. 15, 2019

(65) Prior Publication Data
US 2020/0370062 A1    Nov. 26, 2020

Related U.S. Application Data

(60) Provisional application No. 62/629,387, filed on Feb. 12, 2018.

(51) Int. Cl.
A01H 5/00    (2018.01)
A01H 1/00    (2006.01)
A01H 6/20    (2018.01)
C12N 15/00   (2006.01)
C12N 15/82   (2006.01)

(52) U.S. Cl.
CPC ........... *C12N 15/8247* (2013.01); *A01H 1/00* (2013.01); *A01H 6/20* (2018.05); *C12N 15/8213* (2013.01); *C12Y 101/01098* (2013.01); *C12Y 203/01199* (2015.07)

(58) Field of Classification Search
None
See application file for complete search history.

(56) References Cited

U.S. PATENT DOCUMENTS

| | | | |
|---|---|---|---|
| 2008/0160530 | A1 | 7/2008 | Li |
| 2015/0143573 | A1 | 5/2015 | Denolf et al. |
| 2017/0051299 | A1 | 2/2017 | Fabijanski et al. |
| 2019/0053457 | A1 | 2/2019 | Marks et al. |
| 2019/0053458 | A1 | 2/2019 | Marks et al. |
| 2020/0131523 | A1 | 4/2020 | Marks et al. |
| 2020/0308596 | A1 | 10/2020 | Marks et al. |

FOREIGN PATENT DOCUMENTS

| | | |
|---|---|---|
| WO | WO 2000/036114 | 6/2000 |
| WO | WO 2006/052912 | 5/2006 |
| WO | WO 2013/112578 | 8/2013 |
| WO | WO 2017/004375 | 1/2017 |
| WO | WO 2017/117633 | 7/2017 |
| WO | WO 2018/140782 | 8/2018 |

OTHER PUBLICATIONS

Batsale et al., "Biosynthesis and Functions of Very-Long-Chain Fatty Acids in the Responses of Plants to Abiotic and Biotic Stresses," Cells, May 21, 2021, 10:1284, 26 pages.
Dorn et al., "A draft genome of field pennycress (*Thlaspi arvense*) provides tools for the domestication of a new winter biofuel crop," DNA Research, Apr. 2015, 22(2):121-131.
ENA Accession No. PRJEB46635, "Chromosome-level Thlaspi arvense genome provides new tools for translational research and for a newly domesticated cash cover crop of the cooler climates," dated. Aug. 2, 2021, 2 pages.
GenBank Accession No. AZNP01000000.1, "Thlaspi arvense cultivar MN106, whole genome shotgun sequencing project," dated Mar. 19, 2015, 1 page.
Geng et al., "Genomic analysis of field pennycress (*Thlaspi arvense*) provides insights into mechanisms of adaptation to high elevation." BMC Biology, Jul. 22, 2021, 19:143, 14 pages.
Nunn et al., "Chromosome-level Thlaspi arvense genome provides new tools for translational research and for a newly domesticated cash cover crop of the cooler climates," bioRxiv, Aug. 1, 2021, 48 pages.
Tresch et al., "Inhibition of saturated very-long-chain fatty acid biosynthesis by mefluidide and perfluidone, selective inhibitors of 3-ketoacyl-CoA synthases," Phytochemistry, Apr. 2012, 76:162-171.
Yang et al., "Comprehensive analysis of KCS gene family in Citrinae reveals the involvement of CsKCS2 and CsKCS11 in fruit cuticular wax synthesis at ripening," Plant Science, Sep. 2021, 310:110972, 11 pages.
GenBank Accession No. KT223025.1, "Thlaspi arvense cultivar French 3-ketoacyl-CoA synthase (FAEI) mRNA, complete cds," Nov. 29, 2015, 2 pages.

(Continued)

*Primary Examiner* — Phuong T Bui
(74) *Attorney, Agent, or Firm* — Fish & Richardson P.C.

(57) ABSTRACT

This document relates to methods and materials for generating oilseed (e.g., pennycress) plants that have oil with reduced levels of polyunsaturated fatty acids (PUFAs) and/or increased levels of oleic acid. For example, oilseed plants having reduced expression levels of one or more polypeptides involved in fatty acid biosynthesis (e.g., fatty acid desaturase 2 (FAD2) and reduced oleate desaturation 1 (ROD1)), as well as methods and materials for making and using such oilseed plants are provided.

14 Claims, 32 Drawing Sheets

Specification includes a Sequence Listing.

(56) References Cited

OTHER PUBLICATIONS

Xie et al., "RNA-Guided Genome Editing in Plants Using a CRISPR-Cas System," Molecular Plant, Nov. 2013, 6(6):1975-1983.
Blande et al. (GenBank Sequence Accession No. GEVK01020461.1, Published Nov. 4, 2016).
Blacklock et al., "Substrate specificity of *Arabidopsis* 3-ketoacyl-CoA synthases," Biochem. Biohpys, Res. Communications, Jun. 5, 2006, 346(2):583-590.
Joubes et al., "The VLCFA elongase gene family in *Arabidopsis thaliana*: phylogenetic analysis, 3D modelling and expression profiling," Plant Mol. Biology, May 9, 2008, 67(5):547-566.
Millar et al., "Very-long-chain fatty acid biosynthesis is controlled through the expression and specificity of the condensing enzyme," Plant Journal, Jul. 1997, 12(1):121-131.
Morineau et al., "Dual Fatty Acid Elongase Complex Interactions in *Arabidopsis*," PLoS One, Sep. 1, 2016, 11(9):e0160631, 20 pages.
Wang et al., "A functional genomics resource for *Brassica napus*: development of an EMS mutagenized population and discovery of FAEI point mutations by Tilling," New Phytologist, Dec. 2008, 180(4):751-765.
U.S. Appl. No. 16/104,318, filed Aug. 17, 2018, Michael David Marks.
U.S. Appl. No. 16/104,478, filed Aug. 17, 2018, Michael David Marks.
U.S. Appl. No. 16/480,881, filed Jul. 25, 2019, Michael David Marks.
U.S. Appl. No. 16/831,145, filed Mar. 26, 2020, Michael David Marks.
Claver et al., "Functional analysis of B-ketoacyl-CoA synthase from biofuel feedstock Thlaspi arvense reveals differences in the triacylglycerol biosynthetic pathway among Brassicaceae," Plant Mol. Biology, 104(3):283-296, Aug. 1, 2020.
GenBank Accession No. AAC49186.1, "beta-ketoacyl-CoA synthase [Simmondsia chinensis]." dated Oct. 31, 1995, 2 pages.
GenBank Accession No. NP_195178.1, "3-ketoacyl-CoA synthase 18 [*Arabidopsis thaliana*]," dated Jan. 22, 2014, 2 pages.
Gigolashvili et al., "The R2R3-MYB transcription factor HAGI/MYB28 is a regulator of methionine-derived glucosinolate biosynthesis in *Arabidopsis thaliana*," Plant Journal, 51(2):247-261, Jul. 2007.
Haslam et al., "Extending the story of very-long-chain fatty acid elongation," Plant Science, 210:93-107, Sep. 2013.
Kafri et al., "The regulatory utilization of genetic redundancy through responsive backup circuits," Proc. Nat. Acad. Sci. USA, 103(31):11653-11658, Aug. 2006.
Lassner et al., "A jojoba beta-Ketoacyl-CoA synthase cDNA complements the canola fatty acid elongation mutation in transgenic plants," Plant Cell, 8(2):281-292, Feb. 1996.
Shen et al., "Resistance gene candidates identified by PCR with degenerate oligonucleotide primers map to clusters of resistance genes in lettuce," Mol. Plant Microbe Interactions, 11(8):815-823, Aug. 1998.
Bai et al., "The Biochemistry of Headgroup Exchange During Triacylglycerol Synthesis in Canola," The Plant Journal, 103(1):83-94, Jan. 2020.
Baud et al., "Physiological and developmental regulation of seed oil production," Prog Lipid Res., 49(3):235-49, Jul. 2010.
Belide et al., "Modification of seed oil composition in *Arabidopsis* by artificial microRNA-mediated gene silencing," Frontiers in plant science, 3:168, Jul. 2012.
Bell, "Factors affecting the nutritional value of canola meal: a review," Canadian Journal of Animal Science, 73(4):679-697, Dec. 1993.
Bligh et al., "A rapid method of total lipid extraction and purification," Canadian Journal of Biochemistry and Physiology, 37(8):911-917, Aug. 1959.
Boateng et al., "Producing stable pyrolysis liquids from the oil-seed presscakes of mustard family plants: Pennycress (*Thlaspi arvense* L.) and Camelina (*Camelina sativa*)," Energy & Fuels, 24(12):6624-6632, Nov. 2010.
Britt, "From stinkweed to oilseed," Nat. Food, 1:24-25, Jan. 2020.
Chopra et al., "Identification and stacking of crucial traits required for the domestication of pennycress," Nat. Food, 1:84-91, Jan. 2020.
Chopra et al., "The adaptable use of Brassica NIRS calibration equations to identify pennycress variants to facilitate the rapid domestication of a new winter oilseed crop," Industrial Crops and Products, 128:55-61, Feb. 2019.
Chopra et al., "Transcriptome profiling and validation of gene based single nucleotide polymorphisms (SNPs) in sorghum genotypes with contrasting responses to cold stress," BMC Genomics, 16(1):1040, Dec. 2015.
Chopra et al., "Translational genomics using *Arabidopsis* as a model enables the characterization of pennycress genes through forward and reverse genetics," The Plant Journal, 96(6):1093-1105, Dec. 2018.
Claver et al., "Identification of target genes and processes involved in erucic acid accumulation during seed development in the biodiesel feedstock Pennycress (*Thlaspi arvense* L.)," Journal of plant physiology, 208:7-16, Jan. 2017.
Crevillén et al., "Epigenetic reprogramming that prevents transgenerational inheritance of the vernalized state," Nature, 515(7528):587-90, Nov. 2014.
Dorn et al., "De novo assembly of the pennycress (*Thlaspi arvense*) transcriptome provides tools for the development of a winter cover crop and biodiesel feedstock," The Plant Journal, 75(6):1028-38, Sep. 2013.
Downey and Craig, "Genetic control of fatty acid biosynthesis in rapeseed (*Brassica napus* L.)," Journal of the American Oil Chemists' Society, Jul;41(7):475-8, Jul. 1964.
Fauser et al., "Both CRISPR/C as-based nucleases and nickases can be used efficiently for genome engineering in *A rabidopsis thaliana*," Plant J., 79(2):348-359, Jul. 2014.
Ferrándiz et al., "Negative regulation of the Shatterproof genes by Fruitfull during *Arabidopsis* fruit development," Science, 289(5478):436-438, Jul. 2000.
Fourmann et al., "The two genes homologous to *Arabidopsis* FAEI co-segregate with the two loci governing erucic acid content in *Brassica napus*," Theor: Appl. Genet., 96(6-7):852-8, May 1998.
Girin et al., "*Brassicaceae* Indehiscent genes specify valve margin cell fate and repress replum formation," Plant J., 63(2):329-338, Jul. 2010.
Golebiowski et al., "Near infrared reflectance spectroscopy of oil in intact canola seed (*Brassica napus* L.). II. Association between principal components and oil content," Journal of near Infrared Spectroscopy, 13(5):255-264, Oct. 2005.
Han et al., "Functional characterization of beta-ketoacyl-CoA synthase genes from *Brassica napus* L," Plant molecular biology, 46(2):229-39, May 2001.
James et al., "Directed Tagging of the *Arabidopsis* Fatty Acid Elongationi (FAE1) Gene with the Maize Transposon Activator," The Plant Cell, 7:309-319, Mar. 1995.
Javidfar and Cheng, "Single locus, multiallelic inheritance of erucic acid content and linkage mapping of FAE1 gene in yellow mustard," Crop Science, 53(3):825-32, May 2013.
Kano-Murakami et al., "A rice homeotic gene, OSH1, causes unusual phenotypes in transgenic tobacco," FEBS letters, 334(3):365-8, Nov. 1993.
Katavic et al., "Alteration of Seed Fatty Acid Composition by an Ethyl Methanesulfonate-induced Mutation in *Arabidopsis thaliana* Affecting Diacylglycerol Acyltransferase Activity," Plant Physiology, May 1995, 108(1):399-409.
Kim et al., "Toward production of jet fuel functionality in oilseeds: identification of FatB acyl-acyl carrier protein thioesterases and evaluation of combinatorial expression strategies in Camelina seeds," Journal of Experimental Botany, 66(14):4251-4265, May 2015.
Liljegren et al., "ShatterProof MADS-box genes control seed dispersal in *Arabidopsis*." Nature, 404(6779):766-770, Apr. 2000.
Lu et al., "*Arabidopsis* Mutants Deficient in Diacylglycerol Acyltransferase Display Increased Sensitivity to Abscisic Acid,

(56) References Cited

OTHER PUBLICATIONS

Sugars, and Osmotic Stress During Germination and Seedling Development," Plant Physiology, Jul. 2002, 129(3):1352-1358.

Lu et al., "Expression pattern of diacylglycerol acyltransferase-1, an enzyme involved in triacylglycerol biosynthesis, in *Arabidopsis thaliana*," Plant Mol. Biology, May 2003, 52(1):31-41.

McGinn et al., "Molecular tools enabling pennycress (*Thlaspi arvense*) as a modelplant and oilseed cash cover crop," Plant Biotechnology Journal, 17(4):776-788, Apr. 2019.

Montero de Espinosa et al., "Plant oils: The perfect renewable resource for polymer science?!" European Polymer Journal, 47(5):837-852, May 2011.

Moser et al., "Composition and physical properties of cress (*Lepidium sativum* L.) and field pennycress (*Thlaspi arvense* L.) oils," Industrial Crops and Products, 30(2):199-205, Sep. 2009.

Moser et al., "Production and evaluation of biodiesel from field pennycress (*Thlaspi arvense* L.) oil," Energy & Fuels, 23(8):4149-4155, Jul. 2009.

PCT International Preliminary Report on Patentability in International Appln. No. PCT/US2019/017660, dated Aug. 18, 2020, 8 pages.

PCT International Search Report and Written Opinion in International Appln. No. PCT/US2019/017660, dated May 24, 2019, 11 pages.

Phippen et al., "Soybean seed yield and quality as a response to field pennycress residue," Crop Science, 52(6):2767-2773, Nov. 2012.

Riu et al., "[Detection of erucic acid and glucosinolate in intact rapeseed by near-infrared diffuse reflectance spectroscopy]," Spectroscopy and Spectral Analysis, Dec. 2006, 26(12):2190-2192, (with English abstract).

Roeder et al., "The role of the Replumless homeodomain protein in patterning the *Arabidopsis* fruit," Curr. Biol., 13(18):1630-1635, Sep. 2003.

Rosas et al., "One-step, codominant detection of imidazolinone resistance mutations in weedy rice (*Oryza sativa* L.)," Electron. J. Biotechnol., 17:95-101, Mar. 2014.

Roscoe et al., "Mutations in the fatty acid elongation 1 gene are associated with a loss of β-ketoacyl-CoA synthase activity in low erucic acid rapeseed," FEBS letters, 492(1-2):107-11, Mar. 2001.

Routaboul et al., "The TAG1 locus of *Arabidopsis* encodes for a diacylglycerol acyltransferase," Plant Physiol Biochemistry, Nov. 1999, 37(11):831-840.

Sanyal et al., "Stearic sunflower oil as a sustainable and healthy alternative to palm oil. A review," Agron, Sustain. Development, May 17, 2017, 37:18, 11 pages.

Sedbrook et al., "New approaches to facilitate rapid domestication of a wild plant to an oilseed crop: example pennycress (*Thlaspi arvense* L.)," Plant Sci., 227:122-32, Oct. 2014.

Sidhu et al., "Diode Array Near Infrared Spectrometer Calibrations for Composition Analysis of Single Plant Canola (*Brassica napus*) Seed," Applied Engineering in Agriculture, 30(1):69-76, Jan. 2014.

Steinert et al., "Highly efficient heritable plant genome engineering using Cas9 orthologues from *Streptococcus thermophilus* and *Staphylococcus aureus*," Plant J., 84:1295-305, Dec. 2015.

Van Gelderen et al., "An Indehiscent-Controlled Auxin Response Specifies the Separation Layer in Early *Arabidopsis* Fruit," Molecular Plant, Jun. 2016, 9:857-869.

Vogel et al., "Expression of the *Arabidopsis* Wrinkled 1 transcription factor leads to higher accumulation of palmitate in soybean seed," Plant Biotechnol. Journal, Jan. 17, 2019, 17(7):1369-1379.

Warwick et al., "The biology of Canadian weeds. 9. Thlaspi arvense L.(updated)," Canadian Journal of Plant Science, 82(4):803-823, Oct. 2002.

Wu et al., "Zero erucic acid trait of rapeseed (*Brassica napus* L.) results from a deletion of four base pairs in the fatty acid elongase I gene," Theoretical and applied genetics, 116(4):491-9, Feb. 2008.

Xin et al., "Mid-infrared spectral characteristics of lipid molecular structures in *Brassica carinata* seeds: relationship to oil content, fatty acid and glucosinolate profiles, polyphenols, and condensed tannins," J. Agric. Food Chem., 62(32):7977-7988, Aug. 2014.

Yu et al., "Modulation of brassinosteroid-regulated gene expression by Jumonji domain-containing proteins ELF6 and REF6 in *Arabidopsis*," Proceedings of the National Academy of Sciences, 105(21):7618-23, May 2008.

Zarhloul et al., "Breeding high-stearic oilseed rape (*Brassica napus*) with high- and low-erucic background using optimised promoter-gene constructs," Mol. Breeding, Sep. 2006, 18(3):241-251.

Zou et al., "The *Arabidopsis thaliana* TAG1 mutant has a mutation in a diacylglycerol acyltransferase gene.," The Plant Journal, Sep. 1999, 19(6):645-653.

Zeng et al. (Plant cell, 26:2648-2659, Jun. 2014).

```
Oryza         ----------------------------MGAGGRMTEKEREEQQKLLGRAGNGAAVQRSPTDKPPFTLGQ
Glycine       ------------------------------MGAGGRTAVPPAN-------RKSEADPLKRVPFEKPQFSLSQ
Arabidopsis   -----------------------------MGAGGRMPVPTSS-------KKSETDTTKRVPCEKPPFSVGD
Tafad2-1      MSKFDKIYDDDNSGGSQNMGAGGRMTVPTSS-------KKSETNALKRVPCEKPPFTLGE
Tafad2-2      MSKFDKIYDDDNSGGSQNMGAGGRMTVPTSS-------KKSETDALKRVPCEKPPFTLGE
Tafad2-3      MSKFDKIYDDDNSGGSQNMGAGGRMTVPTSS-------KKSETDALKRVPCEKPPFTLGE
TaFAD2        MSKFDKIYDDDNSGGSQNMGAGGRMTVPTSS-------KKSETDALKRVPCEKPPFTLGE
                                           ******   .******  ****:********.*

Oryza         IKKAIPPHCFQRSVIKSFSYVVHDLVIVAALLYFALVMIPVLPSGMEFAAWPLYWIAQGC
Glycine       IKKAIPPHCFQRSVLRSFSYVVYDLTIAFCLYYVATHYFHLLPGPLSFVAWPIYWAVQGC
Arabidopsis   LKKAIPPHCFKRSIPRSFSYLISDIIIASCFYYVATNYFSLLPQPLSYLAWPLYWACQGC
Tafad2-1      LKKAIPQHCFNRSIPRSFSYLIWDIIIASCFYYVATTYFSLLPQPLSYLAWPLYWCQGC
Tafad2-2      LKKAIPQHCFNRSIPRSFSYLIWDIIIASCFYYVATTYFSLLPQPLSYLAWPLYWCQGC
Tafad2-3      LKKAIPQHCFNRSIPRSFSYLIWDIIIASCFYYVATTYFSLLPQPLSYLAWPLYWCQGC
TaFAD2        LKKAIPQHCFNRSIPRSFSYLIWDIIIASCFYYVATTYFSLLPQPLSYLAWPLYWCQGC
              :****** **:**: ****:* *: * :.****.** :***:*** ***:** ***

Oryza         VLTGVWVIAHECGHHAFSDYSVLDDTVGLVLHSSLLVPYFSWKYSHRRHHSNTGSLERDE
Glycine       ILTGIWVIAHECGHHAFSDYQLLIDDIVGLIIHSALLVPYFSWKYSHRRHHSNTGSLERDE
Arabidopsis   VLTGVWVIAHECGHHAFSDYQWLDDTVGLIFHSFLIVPYFSWKYSHRRHHSNTGSLERDE
Tafad2-1      VLTGVWVIAHECGHHAFSDYQWLDDTVDLIFHSFLIVPYFSWKYSHRRHHSNTGSLEKDE
Tafad2-2      VLTGVWVIAHECGHHAFSDYQWLDDTVGLIFHSFLIVPYFSWKYSHRRHHSNTGSLEKDE
Tafad2-3      VLTGVWVIAHECGHHAFSDYQWLDDTVGLIFHSFLIVPYFSWKYSHRRHHSNTGSLEKDE
TaFAD2        VLTGVWVIAHECGHHAFSDYQWLDDTVGLIFHSFLIVPYFSWKYSHRRHHSNTGSLEKDE
              :***:*********** ***: : **:*.** ** *:*********************

Oryza         VFVPKQKSAMAWYTPYVYHNPIGRLVHIFVQLTLGWPLYLAFNVSGRPYPRFACHFDPYG
Glycine       VFVPKQKSSIMNYSKYL-NNPPGRVLTLAVTLTLGWPLYLAFNVSGRPYDRFACHYDPYG
Arabidopsis   VFVPKQKSAIKWYGKYL-NNPLGRIMMLTVQFVLGWPLYLAFNVSGRPYDGFACHFFPNA
Tafad2-1      VFVPKQKSAIKWYGKYL-NNPLGRTVMLTVQFTLGWPLYLAFNVSGRPYDGFACHFHPNA
Tafad2-2      VFVPKQKSAIKWYGKYL-NNPLGRTVMLTVQFTLGWPLYLAFNVSGRPYDGFACHFHPNA
Tafad2-3      VFVPKQKSAIKWYGKYL-NNPLGRTVMLTVQFTLGWPLYLAFNVSGRPYDGFACHFHPNA
TaFAD2        VFVPKQKSAIKWYGKYL-NNPLGRTVMLTVQFTLGWPLYLAFNVSGRPYDGFACHFHPNA
              ********:: *  ::  **  ** : : .: ***********:******  ***  . 
```

FIG. 3

```
Oryza         PIYNDRERVQIFISDVGVVSAGLALFKLSSAFGFWMVVRVYGVPLLIVNAWLVLITYLQH
Glycine       PIYSDRERLQIYISDAGVLAVCYGLFCLAMAKGLAWVCVYGVPLLVVNGFLVLITFLQH
Arabidopsis   PIYNDRERLQIYLSDAGILLAVCFGLYRYAAAQGMASMICLYGVPLLIVNAFLVLITYLQH
Tafad2-1      PIYNDRERLQIYISDAGILAVCYGLYRYAAAQGVASMICVYGVPLLIVNGFLVLITYLQH
Tafad2-2      PIYNDRERLQIYISDAGILAVCYGLYRYAAAQGVASMICVYGVPLLIVNGFLVLITYLQH
Tafad2-3      PIYNDRERLQIYISDAGILAVCYGLYRYAAAQGVASMICVYGVPLLIVNGFLVLITYLQH
TaFAD2        PIYNDRERLQIYISDAGILAVCYGLYRYAAAQGVASMICVYGVPLLIVNGFLVLITYLQH
              *** *** **::**:*.::*. .*  .:*  .:*:*  :******::**.:***::***

Oryza         THPALPHYDSSEWDWLRGALATVDRDYGILNKVFHNITDTHVAHHLFSTMPHYHAMEATK
Glycine       THPALPHYTSSEWDWLRGALATVDRDYGILNKVFHNITDTHVAHHLFSTMPHYHAMEATK
Arabidopsis   THPSLPHYDSSEWDWLRGALATVDRDYGILNKVFHNITDTHVAHHLFSTMPHYNAMEATK
Tafad2-1      THPSLPHYDSSEWDWFRGALATVDRDYGILNKVFHNITDTHVAHHLFSTMPHYHAMEATK
Tafad2-2      THPSLPHYDSSEWDWFRGALATVDRDYGILNKVFHNITDTHVAHHLFSTMPHYHAMEATK
Tafad2-3      THPSLPHYDSSEWDWFRGALATVDRDYGILNKVFHNITDTHVAHHLFSTMPHYHAMEATK
TaFAD2        THPSLPHYDSSEWDWFRGALATVDRDYGILNKVFHNITDTHVAHHLFSTMPHYHAMEATK
              ***:***.******:************************************:******

Oryza         AIRPILGEYYQFDPDTPVAKATWREAKECIYVEPED---NKGVFWYNNKF----
Glycine       AIKPILGEYYRFDGTPFVKAMWREAKECIYVEPDQSTQSKGVFWYNNKL----
Arabidopsis   AIKPILGDYYQFDGTPVFKAMWREAKECIYVEPDREGDKKGVYWYNNKL----
Tafad2-1      AIKPILGDYYQFDGTPVFKAMWREAKECVYVEPDRKGEKKEGTKEEENEAK
Tafad2-2      AIKPILGDYYQFDGTPVFKAMWREAKECVYVEPDRKGEKKEGTKEEENEAK
Tafad2-3      AIKPILGDYYQFDGTPVFKAMYREAKECVYVEPDRKGEKKEGTKEEENEAK
TaFAD2        AIKPILGDYYQFDGTPVFKAMWREAKECVYVEPDRKGEKKEGTKEEENEAK
              **:****:**:** ** .**  ******:****.      *  :
```

FIG. 3(Cont.)

```
Oryza         ----MPPPPPSLTANTASSMGNAEAVVVLPANGGARRRADKVVHPAPMPDRAAGGAMERE
Glycine       ------------------------------------MNGGAEASLNHRRKHQTAPADGAKG-VKVA
Arabidopsis   MSAAAAETDVSLRRRSNSLNGNHTNG---VAIDGTLDN-NNRRVGDTNTHMDI-SA-KKTD
Tarod1-2      ----MSTKTVVPLRRRSKPLNGNHTNG---VAIDGSLDDDHNRRIGSVNSQMDN-IA-KKTD
TaROD1        ----MSTKTVVPLRRRSKPLNGNHTNG---VAIDGSLDDDHNRRIGSVNSQMDN-IA-KKTD
Tarod1-1      ----MSTKTVVPLRRRSKPLNGNHTNG---VAIDGSLDDDHNRRIGSVNSQMDN-IA-KKTD
                                                    :  *                  :  :

Oryza         GGGVGGGGEVGGWRR------PEWCSAAGVAGVLRRHPAAAAFGCGLLLEMAVEYTIPMVPP
Glycine       NG-AMGKPSSSKHSCGASFMKWTV-ADAVHVVTHHWMPCLFALGLLFFMAVEYTLLMVPP
Arabidopsis   NGYANGVGG-GGWRSKASFTTWTA-RDIVYVVRYHWIPCMFAAGLLFFMGVEYTLQMIPA
Tarod1-2      DGYANGGGGGGGGGKSKASFMTWTA-RDVVYVARYHWIPCLFAVGVLFFTGVEYTLQMIPA
TaROD1        DGYANGGGGGGGGKSKASFMTWTA-RDVVYVARYHWIPCLFAVGVLFFTGVEYTLQMIPA
Tarod1-1      DGYANGGGGGGGGKSKASFMTWTA-RDVVYVARYHWIPCLFAVGVLFFTGVEYTLQMIPA
               *          *            *     *   *  *** ***:  *****: *:.

Oryza         AAPPVDLGFAATAALHAGIAAARPWLNSLLAALNTVFVAMQAAYILWAILGEGRPRAAVAA
Glycine       SSPPFFDLGFIATRSLHALLESSPNLNTLFAGLNTVFFVGMQTSYILWTWLIEGRPRATISA
Arabidopsis   RSEPFDLGFVTRSLNRVLASSPDLNTVLAALNTVFVGMQTTYIVWTWLVEGRARATIAA
Tarod1-2      RSEPFDIGFVATRSLNRVLANSPDLNTVLAALN---------------------------
TaROD1        RSEPFDIGFVATRSLNRVLANSPDLNTVLAALNTVFVGMQTTYIVWTWLMEGRPRATISA
Tarod1-1      RSEPFDIGFVATRSLNRVLANSPDLNTVLAALN---------------------------
              .: *** :  *::  : :::** **.: * **
```

FIG. 5

```
Oryza          MMMFTCRGALGCATQLPLPAEFLGSGMDFPVGNVSFFLFFSGHVAGAVIAAEDMRRAGRR
Glycine        LFMFTCRGILGYSTQLPLPQGFLGSGVDFPVGNVSFFLFFSGHVAGSVIASLDMRRMQRW
Arabidopsis    LPMFTCRGILGYSTQLPLPQDFLGSGVDFPVGNVSFFLFFSGHVAGSMIASLDMRRMQRL
Tarodi-2       ----------------------TDFLGSGVDFPVGNVSFFLFYSGHVAGSMIASLDMRRMQRM
TaROD1         CFMFTCRGILGYSTQLPLP TDFLGSGVDFPVGNVSFFLFYSGHVAGSMIASLDMRRMQRM
Tarodi-1       ----------------------TDFLGSGVDFPVGNVSFFLFYSGHVAGSMIASLDIRRMQRM
                                     *****:************.:***; *.** *

Oryza          GMARLYDALNLLQGVRLLACRGHYTIDLAVGVGAGLLFDMLAGRYLDGKNTVDGGAAVAP
Glycine        RLAWTFDVLNVLQAVRLLGTRGHYTIDLAVGVGAGILFDSLAGKYEDSKRNGALKHNLIA
Arabidopsis    RLAMFEDILNVLQSIRLLGTRGHYTIDLAVGVGAGILFDSLAGKYERMMSKR----H-LGT
Tarodi-2       RLAMLFDILNVLQSIKLLGTRGHYTIDLAVGVGAGILFDSFAGKYEEMISKR----HNLVN
TaROD1         RLAMLFDILNVLQSIRLLGTRGHYTIDLAVGVGAGILFDSFAGKYEEMISKR----HNLVN
Tarodi-1       RLAMLFDILNVLQSIRLLGTRGHYTIDLAVGVGAGILFDSFAGKYEEMISKR----HNLVN
                 :*     **.:;**; ****************.***  :**;** *   .

Oryza          GSRCCSCHKALLSQ
Glycine        --------------
Arabidopsis    GFSLISK-DSLVN-
Tarodi-2       GFGLISK-DSLVN-
TaROD1         GFGLISK-DSLVN-
Tarodi-1       GFGLISK-DSLVN-
```

FIG. 5(Cont.)

| | | |
|---|---|---|
| At_FAE1 | ------------------------------MTS----VNVKLLYRVLTNFFNLCL | 22 |
| Ta-FAE1 | ------------------------------MTS----VNVKLLYHYVITNFFNLCF | 22 |
| Ta-fae1-1 | ------------------------------MTS----VNVKLLYHYVITNFFNLCF | 22 |
| Ta-fae1-2 | ------------------------------MTS----VNVKLLYHYVITNFFNLCF | 22 |
| Ta-fae1-3 | ------------------------------MTS----VNVKLLYHYVITNFFNLCF | 22 |
| Os_FAE1 | ------------------------AATPSHRRLPDFLQSVNLKYVKLGYHYLITHLLTLLL | 46 |
| Gm_FAE1 | -------------MTVTMSGEEEAAVGVQIQQKSRMVLPDFLQSVNLKYVKLGYHYLISNLVTLFL | 53 |
| Sl_FAE1 | MNGATGTQVNTANGGGEPVGVQIQSR---RLPDFLQSVNLKYVKLGYHYLISHLLTLCL | 58 |
| At_FAE1 | FPLTAFLAGKASRLTINDLHNF--LSYLQHNLITVTLLFAFTVFGLVLYIVTRPNPVYLVD | 81 |
| Ta-FAE1 | FPLAAIVAGKASRLTTNDLHHFYSYLQHNLITISLLFAFTVFGLALYIVTRPKPVYLVD | 82 |
| Ta-fae1-1 | FPLAAIVAGKASRLTTNDLHHFYSYLQHNLITISLLFAFTVFGLALYIVTRPKPVYLVD | 82 |
| Ta-fae1-2 | FPLAAIVAGKASRLTTNDLHHFYSYLQHNLITISLLFAFTVFGLALYIVTRPKPVYLVD | 82 |
| Ta-fae1-3 | FPLAAIVAGKASRLTTNDLHHFYSYLQHNLITISLLFAFTVEGLALYIPGPNRFTSLTI | 82 |
| Os_FAE1 | LPLMAVIVLEAGRTDPDDLRQLWL--HLQYNLVSVLVLSAVLVFGATVVVLTRPRPVYLVD | 105 |
| Gm_FAE1 | VPLLIVTLIQVSQ---TTDLRHLWL--HLQYNLLITILTLTCSAVLVFGLTLYAVTCPRPVYLLD | 110 |
| Sl_FAE1 | IPVMAVILLEASQMNPDDIRQLWL--HLQYNLVSVIICSAVLVFGSTVYIMTRPRPVYLID | 117 |
| At_FAE1 | YSCYLPPPHLKVSVSKVMDIFYQIRKADTSSRNVACDDPSSLDFLRKIQERSGLGDETYS | 141 |
| Ta-FAE1 | HSCYLPPSHLRSSISKVMDIFYQVRLADP-LRNAASDDSSWLDFLRKIQERSGLGDETHG | 141 |
| Ta-fae1-1 | HSCYLPPSHLRSSISKVMDIFYQVRLADP-LRNAASDDSSWLDFLRKIQERSGLGDETHG | 141 |
| Ta-fae1-2 | HSCYLPPSHLRSSISKVMDIFYQVRLADP-LRNAASDDSSWLDFLRKIQERSGLGDETHG | 141 |

FIG. 11

```
Ta-fae1-3                                        ------PATFHHRILEA---------------------VSLRSWTISSIK*---                    104
Os_FAE1   FACYKPPDKLKVREDEELHH------------------SKLCG-FSDDCLEFQRKILERSGLSEETYV                                               154
Gm_FAE1   SACFRPADHLKAPFRSFMDH------------------SRLTGDFEESSLEFQRKILERSGLGEETYV                                               160
Sl_FAE1   YSCYKAPEHLKAPYEREMQH------------------SRLTGDFDESSLEFQRKILERSGLGDETYV                                               167
At_FAE1   PEGLIHVPPRKTFAASREETEKVIIGALENLFENTKVNPREIGILVVNSSMFNPTPSLSA                                                        201
Ta-fae1   PEGLLQVPPRKTFAAAREETEQVIIGALEKLFENTKVNPKEIGILVVNSSMFNPTPSLSA                                                        201
Ta-fae1-1 PEGLLQVPPRKTFAAAREETEQVIIGALEKLFENTKVNPKEIGILVVNSSMFNPTPSLSA                                                        201
Ta-fae1-2 PEGLLQVPPRKTFAAAREETEQVIIGALEKLFENTKVNPKEIGILVVNSSMFNPTPSLSA                                                        201
Ta-fae1-3                                        ----------------------------------------------------                     104
Os_FAE1   PEAMHLIPPEPTMANARAEAESVMFGALDKLFTGVKPKDVGLVVNCSLFNPTPSLSA                                                           214
Gm_FAE1   PDAMHSIPPQPSMAAARAEAEQVMFGALDNLFQSTNIKPKDIGILIVNCSLFNPTPSLSS                                                        220
Sl_FAE1   PEAMHQLPPQPSMQAAREEAEQVMFGALDKLFEANTSVKPKKIGVLVVNCSLFNPTPSLSA                                                       227
At_FAE1   MVVNTFKLRSNIKSFNLGGMGCSAGVIAIDLAKDLLHVKNTYALVVSTENITTQGIYAGE                                                        261
Ta-fae1   MVVNTFKLRSNIRSFNLGGMGCSAGVIAIDLAKDLLHVHKNTYALVVSTENITYNIYAGD                                                        261
Ta-fae1-1 MVVNTFKLRSNIRSFNLGGMGCSAGVIAIDLAKDLLHVHKNTYALVVSTENITYNIYAGD                                                        261
Ta-fae1-2 MVVNTFKLRSNIRSFNLGGMGCSAGVIAIDLAKDLLHVHKNTYALVVSTENITYNIYAGD                                                        261
Ta-fae1-3                                        ----------------------------------------------------                     104
Os_FAE1   MIVNKYKLRGNIKSFNLGGMGCSAGVIAVDLARDMLQVHRNTYAVVVSTENITQNWYFGN                                                        274
Gm_FAE1   MIVNKYKLRGNIRSFNLGGMGCSAGVIAVDLAKDLLQVHRNTYAVVVSTENITQNWYFGN                                                        280
Sl_FAE1   MIVNKYKLRGNIRSFNLGGMGCSAGVIAVDLAKDMLQVHRNTYAVVVSTENITQNWYFGN                                                        287
```

FIG. 11 (Cont.)

```
At_FAE1    NRSMMVSNCLFRVGGAAILLSNKSGDRRRSKYKLVHTVRTHTGADDKSFRCVQQEDDESG  321
Ta-FAE1    NRSMMVSNCLFRVGGAAILLSNKPRDRRRSKYQLLHTVRTHTGADDKSFRCVQQEDDESG  321
Ta-fae1-1  NRSMMVSNCLFRVGGAAILLSNKPRDRRRSKYQLLHTVRTHTGADDKSFRCVQQEDDESG  321
Ta-fae1-2  NRSMMVSNCLFRVGGAAILLSNKPRDRRRSKYQLLHTVRTHTGADDKSFRCVQQEDDESG  321
Ta-fae1-3  --------------------------------------------------------- 104
Os_FAE1    RKSMLIPNCLFRVGGAVLLSNRGADRRRAKYALKHVRTHKGADNKAFNCVYQEQDDEG    334
Gm_FAE1    KKSMLIPNCLFRVGCSVLLLSNKPADRRRAKYRLVHVVRTHRGADDKAFRCVYQEQDDAG  340
Sl_FAE1    KKSMLIPNCLFRVGGSAVLLSNKSVDRRRAKYKLVHVVRTHRGADDKAFRCVYQEQDDAG  347

At_FAE1    KIGVCLSKDITNVAGTTLTKNIATLGPLILPLSEKFLFFATFVAKLLLKDKIKHYYVPDF  381
Ta-FAE1    KTGVCLSKDITGVAGRTVQKNITTLGPLVLPFSEKFLFVTFIAKLLFKDKIKHYYVPDF   381
Ta-fae1-1  KTGVCLSKDITGVAGRTV*---------------------------------------- 339
Ta-fae1-2  KTGVCLSKDITGVAGRTVQKNITTLGPLVLPFSEKFLFVTFIAKKLFKDKIKHYYVPDF   381
Ta-fae1-3  --------------------------------------------------------- 104
Os_FAE1    KTGVSLSKDLMAIAGGALKTNITTLGPLVLPFSEQLLFFATLVAKKLFNAKIKP-YIPDF  393
Gm_FAE1    KTGVSLSKDLMAIAGGALKTNITTLGPLVLPISEQLLFFVTLLMKKLFKADVKP-YIPDF  399
Sl_FAE1    KTGVSLSKDLMAIAGGALKTNITTLGPLVLPISEQLLFFGSLIIKKLFNKHIKP-YIPDF  406

At_FAE1    KLAVDHFCIHAGGRAVIDELEKNLGLSPIDVEASRSTLHRFGNTSSSSIWYELAYIEAKG  441
Ta-FAE1    KLAIDHFCIHAGGRAVIDVLQKNLGLLPIDVEASRSTLHRFGNTSSSSIWYELAYIEAKG  441
Ta-fae1-1  --------------------------------------------------------- 339
Ta-fae1-2  KLAIDHFCIHAGGRAVIDVLQKNLGLLPIDVEASRSTLHRFGNTSSSSIWYELAYIEAKG  441
```

FIG. 11(Cont.)

```
Ta-fae1-3   ---------------------------------------------------------  104
Os_FAE1     KLAFEHFCIHAGGRAVIDELEKNLQLQPVHVEASRMTLHRFGNTSSSSIWYELAYMEAKG  453
Gm_FAE1     KLAFDHFCIHAGGRAVIDELEKNLQLLPEHVEASRMTLHRFGNTSSSSIWYELAYIEAKG  459
Sl_FAE1     KLAFDHFCIHAGGRAVIDELEKNLQLTQVHVEASRMTLHRFGNTSSSSIWYELAYIEAKG  466
At_FAE1     RMKKGNKAWQIALGSGFKCNSAVWVALRNVKASANSPWQHCIDRYPVKIDSDLSKSKTHV  501
Ta-fae1-1   RMKRGNKVWQIALGSGFKCNSAVWVALRNVKASTNSPWEHCIDRYPDAIDSDGKSETRV   501
Ta-fae1-2   ---------------------------------------------------------  339
Ta-fae1-3   RMKRGNKV*---------------------------------------------------  449
Ta-fae1-3   ---------------------------------------------------------  104
Os_FAE1     RVRRGHRIWQIAFGSGFKCNSAVWHALRNVNPSPESPWEDCIDRYPVELVDGEATHNNTQ  513
Gm_FAE1     RIKKGNRIWQIAFGSGFKCNSAVWQALRNVRPSPNGPWEDCIDKYPVEIVS---------  510
Sl_FAE1     RMKKGNKVWQIAFGSGFKCNSAVWQALRNVKPSPDGPWEDCIDRYPVKVVS*--------  517

At_FAE1     QNGRS-  506
Ta-fae1-1   QNGRS*  506
Ta-fae1-2   ------  339
Ta-fae1-2   ------  449
Ta-fae1-3   ------  104
Os_FAE1     Q*----  514
Gm_FAE1     ------  510
Sl_FAE1     ------  517
```

FIG. 11(Cont.)

| | | |
|---|---|---|
| At_FAD2 | ------------------------------------------------- | |
| Ta_FAD2 | MSKFDKIYDDDNSGGSQNMGAGGRMTVPTSS------------------- | |
| Ta-fad2-1 | MSKFDKIYDDDNSGGSQNMGAGGRMTVPTSS------------------- | |
| Ta-fad2-2 | MSKFDKIYDDDNSGGSQNMGAGGRMTVPTSS------------------- | |
| Ta-fad2-3 | MSKFDKIYDDDNSGGSQNMGAGGRMTVPTSS------------------- | |
| Ta_fad2-4, | MSKFDKIYDDDNSGGSQNMGAGGRMTVPTSS------------------- | |
| Ta_fad2-5, | MSKFDKIYDDDNSGGSQNMGAGGRMTVPTSS------------------- | |
| Ta_fad2-6, | MSKFDKIYDDDNSGGSQNMGAGGRMTVPTSS------------------- | |
| Os_FAD2 | ------------------MGAGGRMTEKEREEQQKLLGRAGNGAAVQRSPTDKPPFTLGQ | |
| Gm_FAD2 | ------------------MGAGGRTDVPPAN------------------- | |
| Sl_FAD2 | ------------------MGAGGRMSAPNGG------------------- | |

|  |  |  |
|---|---|---|
| At_FAD2 | ----------------KKSETDTTKRVPCEKPPFSVGD | 35 |
| Ta_FAD2 | ----------------KKSETDALKRVPCEKPPFTLGE | 53 |
| Ta-fad2-1 | ----------------KKSETWALKRVPCEKPPFTLGE | 53 |
| Ta-fad2-2 | ----------------KKSETDALKRVPCEKPPFTLGE | 53 |
| Ta-fad2-3 | ----------------KKSETDALKRVPCEKPPFTLGE | 53 |
| Ta_fad2-4, | ----------------KKSETDALKRVPCEKPPFTLGE | 53 |
| Ta_fad2-5, | ----------------KKSETDALKRVPCEKPPFTLGE | 53 |
| Ta_fad2-6, | ----------------KKSETDALKRVPCEKPPFTLGE | 53 |
| Os_FAD2 | ------KKPPFTLGQ | 42 |
| Gm_FAD2 | ----------------RKSEVDPLKRVPFFEKPQFSLSQ | 35 |
| Sl_FAD2 | ----------------TEVKKNPLQKVPTSKPPFTVGD | 35 |

| | | |
|---|---|---|
| At_FAD2 | LKKAIPPHCFEKRSIPRSFSYLISDIIIASCFYYVATNYFSLLPQPLSYLAWPLYWACQGC | 95 |
| Ta_FAD2 | LKKAIPQHCFNRSIPRSFSYLIWDIIIASCFYYVATTYFSLLPQPLSYLAWPLYWVCQGC | 113 |
| Ta-fad2-1 | LKKAIPQHCFNRSIPRSFSYLIWDIIIASCFYYVATTYFSLLPQPLSYLAWPLYWVCQGC | 113 |
| Ta-fad2-2 | LKKAIPQHCFNRSIPRSFSYLIWDIIIASCFYYVATTYFSLLPQPLSYLAWPLYWVCQGC | 113 |
| Ta-fad2-3 | LKKAIPQHCFNRSIPRSFSYLIWDIIIASCFYYVATTYFSLLPQPLSYLAWPLYWVCQGG | 112 |
| Ta_fad2-4, | LKKAIPQHCFNRSIPRSFSYLIWDIIIASCFYYVATTYFSLLPQPLSYLAWPL-LGLSRL | 103 |
| Ta_fad2-5, | LKKAIPQHCFNRSIPRSFSYLIWDIIIASCFYYVATTYFSLLPQPLSYLA---------- | |
| Ta_fad2-6, | LKKAIPQHCFNRSIPRSFSYLIWDIIIASCFYYVATTYFSLLPQPLSYLAWPLLLGLSRL | 113 |
| Os_FAD2 | IKKAIPPHCFQRSVIKSFSYVVRFSFVVVDLIVIVAALLYFALVMIPVLPSGMEFAAWPLYWIAQGC | 102 |
| Gm_FAD2 | IKKAIPPHCFQRSVLRSFSYVVVYDLTIAFCLYYVATHYFHLLPGPLSFRGMAIYWAVQGC | 95 |
| Sl_FAD2 | IKKAIPPHCFQRSLIRSFSYVVVYDLLVSIMYYVANTYFHLLPSPYCYIAWPIYWICQGC | 95 |

FIG. 13

| | | |
|---|---|---|
| At_FAD2 | VLTGIWVIAHECGHHAFSDYQWLDDTVGLIFHSFLLVPYFSWKYSHRRHHSNTGSLERDE | 155 |
| Ta_FAD2 | VLTGVWVIAHECGHHAFSDYQWLDDTVGLIFHSFLLVPYFSWKYSHRRHHSNTGSLEKDE | 173 |
| Ta-fad2-1 | VLTGVWVIAHECGHHAFSDYQWLDDTVGLIFHSFLLVPYFSWKYSHRRHHSNTGSLEKDE | 173 |
| Ta-fad2-2 | VLTGVWVIAHECGHHAFSDYQWLDDTVGLIFHSFLLVPYFSWKYSHRRHHSNTGSLEKDE | 173 |
| Ta-fad2-3 | VLTGVWVIAHECGHHAFSDYQWLDDTVGLIFHSFLLVPYFSWKYSHRRHHSNTGSLEKDE | 173 |
| Ta_fad2-4, | CLNR------SLGHSSRMRPPRLQ-------RLPMA*------------------------ | 135 |
| Ta_fad2-5, | CLNR------SLGHSSRMRPPRLQ-------RLPMA*------------------------ | 126 |
| Ta_fad2-6, | CLNR------SLGHSSRMRPERLQ-------RLPMA*------------------------ | 136 |
| Os_FAD2 | VLTGVWVIAHECGHHAFSDYSVLDDIVGLVLHSSLLVPYFSWKYSHRRHHSNTGSLERDE | 162 |
| Gm_FAD2 | ILTGVWVIAHECGHHAFSDYQLLDDIVGLIIHSALLVPYFSWKYSHRRHHSNTGSLERDE | 155 |
| Sl_FAD2 | VCTGIWVNAHECGHHAFSDYQLVDDTVGLIIHSALLVPYFSWKYSHRRHHSNTGSLERDE | 155 |
| At_FAD2 | VFVPKQKSAIKWYGKYL-NNPLGRIMMLTVQFVLGWPLYLAFNVSGRPYDGFACHFFPNA | 214 |
| Ta_FAD2 | VFVPKQKSAIKWYGKYL-NNPLGRTVMLTVQFTLGWPLYLAFNVSGRPYDGFACHFHPNA | 232 |
| Ta-fad2-1 | VFVPKQKSAIKWYGKYL-NNPLGRTVMLTVQFTLGWPLYLAFNVSGRPYDGFACHFHPNA | 232 |
| Ta-fad2-2 | VFVPKQKSAIKWYGKYL-NNPLGRTVMLTVQFTLGWPLYLAFNVSGRPYDGFACHFHPNA | 232 |
| Ta-fad2-3 | VFVPKQKSAIKWYGKYL-NNPLGRTVMLTVQFTLGWPLYLAFNVSGRPYDGFACHFHPNA | 232 |
| Ta_fad2-4, | ------------------------------------------------------------ | 135 |
| Ta_fad2-5, | ------------------------------------------------------------ | 126 |
| Ta_fad2-6, | ------------------------------------------------------------ | 136 |
| Os_FAD2 | VFVPKQKSAMAWYTPYVYHNPIGRLVHIFVQLTILGWPLYLAFNVSGRPYRFACHFDPYG | 222 |
| Gm_FAD2 | VFVPKQKSCIKWYSKYL-NNPPGRVLTLAVTITLGWPLYLALNVSGRPYDRFACHYDPYG | 214 |
| Sl_FAD2 | VFVPKSKSQLGWYSKYL-NNPLGRVITLTVTLTLGWPLYLAFNVSGRPYDRFACHYDPYG | 214 |

FIG. 13 (Cont.)

| | | |
|---|---|---|
| At_FAD2 | PIYNDRERLQIYLSDAGILAVCFGLYRYAAAQGMASMICLYGVPLLIVNAFLVLITYLQH | 274 |
| Ta_FAD2 | PIYNDRERLQIYISDAGILAVCYGLYRYAAAQGVASMICVYGVPLLIVNGFLVLITYLQH | 292 |
| Ta-fad2-1 | PIYNDRERLQIYISDAGILAVCYGLYRYAAAQGVASMICVYGVPLLIVNGFLVLITYLQH | 292 |
| Ta-fad2-2 | PIYNDRERLQIYISDAGILAVCYGLYRYAAAQGVASMICVYGVPLLIVNGFLVLITYLQH | 292 |
| Ta_fad2-3 | PIYNDRERLQIYISDAGILAVCYGLYRYAAAQGVASMICVYGVPLLIVNGFLVLITYLQH | 292 |
| Ta_fad2-4, | ------------------------------------------------------------ | 135 |
| Ta_fad2-5, | ------------------------------------------------------------ | 126 |
| Ta_fad2-6, | ------------------------------------------------------------ | 136 |
| Os_FAD2 | PIYNDRERVQIFISDVGVVSAGLALFKLSSAFGFWMVVRVYGVPLLIVNAWLVLITYLQH | 282 |
| Gm_FAD2 | PIYSDRERLQIYISDAGVLAVVYGLERLAMAKGLAWVCCVYGVPLLVVNGFLVLITFLQH | 274 |
| Sl_FAD2 | PIYNNRERLQIFLSDAGVLGACYLLIYRVALVKGLAWLVCTYGVPLLVVNGFLVLITYLQH | 274 |

| | | |
|---|---|---|
| At_FAD2 | THPSLPHYDSSEWDWLRGALATVDRDYGILNKVFHNITDTHVAHHLFSTMPHYNAMEATK | 334 |
| Ta_FAD2 | THPSLPHYDSSEWDWFRGALATVDRDYGILNKVFHNITDTHVAHHLFSTMPHYHAMEATK | 352 |
| Ta-fad2-1 | THPSLPHYDSSEWDWFRGALATVDRDYGILNKVFHNITDTHVAHHLFSTMPHYHAMEATK | 352 |
| Ta-fad2-2 | THPSLPHYDSSEWDWFRGALATVDRDYGILNKVFHNITDTHVAHHLFSTMPHYHAMEATK | 352 |
| Ta_fad2-3 | THPSLPYDSSEWDWFRGALATVDRDYGILNKVFHNITDTHVAHHLFSTMPHYHAMEATK | 352 |
| Ta_fad2-4, | ------------------------------------------------------------ | 135 |
| Ta_fad2-5, | ------------------------------------------------------------ | 126 |

FIG. 13(Cont.)

| | | |
|---|---|---|
| Ta_fad2-6, | ------------------------------------------- | 136 |
| Os_FAD2 | THPALPHYDSSEWDWLRGALATVDRDYGILNKVFHNITDTHVAHHLFSTMPHYHAMEATK | 342 |
| Gm_FAD2 | THPALPHYTSSEWDWLRGALATVDRDYGILNKVFHNITDTHVAHHLFSTMPHYHAMEATK | 334 |
| Sl_FAD2 | THPSLPHYDSTEWDWLRGALATCDRDYGVLNKVFHNITDTHVRHHLFSAMPHYNAMEATK | 334 |
| | | |
| At_FAD2 | AIKPILGDYYQFDGTPWYVAMYREAKECIYVEPDREGDKKGVYWYNNKL----- | 383 |
| Ta_FAD2 | AIKPILGDYYQFDGTPVFKAMWREAKECVYVEPDRKGEKKEGTKEEENEAK | 404 |
| Ta-fad2-1 | AIKPILGDYYQFDGTPVFKAMWREAKECVYVEPDRKGEKKEGTKEEENEAK | 404 |
| Ta-fad2-2 | AIKPILGDYYQFDGTPVFKAMWREAKECVYVEPDRKGEKKEGTKEEENEAK | 404 |
| Ta-fad2-3 | AIKPILGDYYQFDGTPVFKAMWREAKECVYVEPDRKGEKKEGTKEEENEAK | 404 |
| Ta_fad2-4, | --------------------------------------------- | 135 |
| Ta_fad2-5, | --------------------------------------------- | 126 |
| Ta_fad2-6, | --------------------------------------------- | 136 |
| Os_FAD2 | AIRPILGEYYQFDPTPVAKATWREAKECIYVEPE----DNKGVFWYNNKF----- | 388 |
| Gm_FAD2 | AIKPILGEYYRFDETPFVKAMWREARECIYVEPDQSTESKGVFWYNNKL----- | 383 |
| Sl_FAD2 | AVKPLLGDYYQFDGTPIFKAMWREAKECLYVEKDESSQGKGVFWYKNKL*--- | 383 |

FIG. 13(Cont.)

```
At_ROD1   MSAAAAETDVSLRRRSNSLNGNHTNGV---AIDGTLDN-----NNRRVGDTNTHMDISAKKTD  55
Ta_ROD1   ----MSTKTVVPLRRRSKPLNGNHTNGV---AIDGSLDDD---HNRRIGSVNSQMDNIAKKTD  53
Ta-rod1-1 ----MSTKTVVPLRRRSKPLNGNHTNGV---AIDGSLDDD---HNRRIGSVNSQMDNIAKKTD  53
Ta_rod1-2 ----MSTKTVVPLRRRSKPLNGNHTNGV---AIDGSLDDD---HNRRIGSVNSQMDNIAKKTD  53
Ta_rod1-3, ----MSTKTVVPLRRRSKPLNGNHTNGV---AIDGSLDDD---HNRRIGSVNSQMDNIAKKTD  53
Ta_rod1-4, ----MSTKTVVPLRRRSKPLNGNHTNGV---AIDGSLDDD---HNRRIGSVNSQMDNIAKKTD  53
Ta_rod1-5, ----MSTKTVVPLRRRSKPLNGNHTNGV---AIDGSLDDD---HNRRIGSVNSQMDNIAKKTD  53
Os_ROD1   ----MPPPPPPSLTANTASSMGNAEAVVVLPANG-----GARRRADKVHPAPMPDRAA       50
Gm_ROD1   -------------------------------------------MNGGAEASVNHRRRHQAASAN----G--VKIA  26
Sl_ROD1   ----------------------------------MNGDTFHSR---NSSSSTL-----SKRNTTERKVDVTEMKKKSA  36

At_ROD1   NGYANGV------GGG-GWRSKASFTTW-TARDIVYVVRYHWIPCMFAAGLLFFMGVEY    106
Ta_ROD1   DGYANGG------GGGGGGKSKASFMTW-TARDVVYVARYHWIPCLFAVGVLFFTGVEY    105
Ta-rod1-1 DGYANGG------GGGGGGKSKASFMTW-TARDVVYVARYHWIPCLFAVGVLFFTGVEY    105
Ta_rod1-2 DGYANGG------GGGGGGKSKASFMTW-TARDVVYVARYHWIPCLFAVGVLFFTGVEY    105
Ta_rod1-3, DG*                                                           55
Ta_rod1-4, DGYAKRR------RRRRRREKQGVVYDV-DGA*                              78
Ta_rod1-5, DGYANRR------RRRRRREKQGVVYDV-DGA*                              78
Os_ROD1   GGAMEREGGGVGGGGEVGGWRRP-----EWCSAAGVAGVLRRHPAAAAFGCGLLLFMAVEY  106
Gm_ROD1   NGAM---A-----------KPSSTLCYDASFMKW-TVADAVHVATHHWMPCLFALGLLFFMAVEY  76
Sl_ROD1   SATGTEV------GGYGWWLGNAVFMKW-RMEDVFGVVKYHPIPCIFAASLLFFMGVEY    88
```

FIG. 15

| | | |
|---|---|---|
| At_ROD1 | TLQMIPARSEPFDLGFVVTRSLNRVLASSPDLNTVLAALNTVFVGMQTTYIVWTWLVEGR | 166 |
| Ta_ROD1 | TLQMIPARSEPFDIGFVATRSLNRVLANSPDLNTVLAALNTVFVGMQTTYIVWTWLMEGR | 165 |
| Ta-rod1-1 | TLQMIPARSEPFDIGFVATRSLNRVLANSPDLNTVLAALNTVFVGMQTTYIVWTWLMEGR | 165 |
| Ta-rod1-2 | TLQMIPARSEPFDIGFVATRSLNRVLANSPDLNTVLAALNTVFVGMQTTYIVWTWLMEGR | 165 |
| Ta_rod1-3 | ------------------------------------------------------------ | 55 |
| Ta_rod1-4 | ------------------------------------------------------------ | 78 |
| Ta_rod1-5 | ------------------------------------------------------------ | 78 |
| Os_ROD1 | TIPMVPPEAAPPVDLGFAATAALHAGIAARPWLNSLLAALNTVFVAMQAAYILWAILGEGR | 166 |
| Gm_ROD1 | TLLMVPPSSPPFFDLGFIATRSLHALLESSPNLNTLFAGLNTVFVGMQTSYILWTWLIEGR | 136 |
| Sl_ROD1 | TLHMIPASAPPFDLGFIVTVPLNRLLAAKPALNTLFAGLNTVFVAMQTAYILGTFLIEGR | 148 |
| | | |
| At_ROD1 | ARATIAALFMFTCRGILGYSTQLPLPQDFLGSGVDFPVGNVSFFLFFSGHVAGSMIASLD | 226 |
| Ta_ROD1 | PRATISACFMFTCRGILGYSTQLPLPQDFLGSGVDFPVGNVSFFLFYSGHVAGSMIASLD | 225 |
| Ta-rod1-1 | PRATISACFMFTCRGILGYSTQLPLPQDFLGSGVDFPVGNVSFFLFYSGHVAGSMIASLD | 225 |
| Ta-rod1-2 | PRATISACFMFTCRGILGYSTQLPLPQDFLGSGVDFPVGNVSFFLFYSGHVAGSMIASLD | 225 |
| Ta_rod1-3 | ------------------------------------------------------------ | 55 |
| Ta_rod1-4 | ------------------------------------------------------------ | 78 |
| Ta_rod1-5 | ------------------------------------------------------------ | 78 |
| Os_ROD1 | PRAAVAAMMFTCRGALGCATQLPLPAEFLGSGMDFPVGNVSFFLFFSGHVAGAVIAAED | 226 |
| Gm_ROD1 | PRATISALFMFTCRGILGYSTQLPLPQGFLGSGVDFPVGNVSFFLFFSGHVAGSVIASLD | 196 |
| Sl_ROD1 | PRATISALFMFTFRGILGYATQLPLPEDFLGSGVDFPVGNVSFFLFYSGHVAASVIASLD | 208 |

FIG. 15(Cont.)

| | | |
|---|---|---|
| At_ROD1 | MRRMQRLRLAMVFDILNVLQSIRLLLGTRGHYTIDLAVGVGAGILFDSLAGKYEEMMSKRH | 286 |
| Ta_ROD1 | MRRMQRMRLAMLFDILNVLQSIRLLLGTRGHYTIDLAVGVGAGILFDSFAGKYEEMISKRH | 285 |
| Ta_rod1-1 | IRRMQRMRLAMLFDILNVLQSIRLLLGTRGHYTIDLAVGVGAGILFDSFAGKYEEMISKRH | 285 |
| Ta_rod1-2 | MRRMQRMRLAMLFDILNVLQSIKLLLGTRGHYTIDLAVGVGAGILFDSFAGKYEEMISKRH | 285 |
| Ta_rod1-3, | ------------------------------------------------------------ | 55 |
| Ta_rod1-4, | ------------------------------------------------------------ | 78 |
| Ta_rod1-5, | ------------------------------------------------------------ | 78 |
| Os_ROD1 | MRRAGRRGMARLYDALNLLQGVRLLACRGHYTIDLAVGVGAGLLFDMLAGRYLDGKNTVD | 286 |
| Gm_ROD1 | MRRMQRMRWELAWTFDVLNVLQAVRLLGTRGHYTIDLAVGVGAGILFDSLAGKYEDSKRNAA | 256 |
| Si_ROD1 | MKRMQRWEMARVFDALNVLQVVRLLSTRGHYTIDLAVGIGAGILFDSMAGNYVETRTKLS | 268 |

| | | |
|---|---|---|
| At_ROD1 | -LG----TGFSLISKDSLVN--------- | 301 |
| Ta_ROD1 | NLV----NGFGLISKDSLVN*--------- | 301 |
| Ta_rod1-1 | NLV----NGFGLISKDSLVN*--------- | 301 |
| Ta_rod1-2 | NLV----NGFGLISKDSLVN*--------- | 301 |
| Ta_rod1-3, | ----------------------------- | 55 |
| Ta_rod1-4, | ----------------------------- | 78 |
| Ta_rod1-5, | ----------------------------- | 78 |
| Os_ROD1 | GGAAVAPGSRCCSCHKALLSQ--------- | 307 |
| Gm_ROD1 | LSTTHRAQFDCVNNVDIAKKINK------- | 279 |
| Si_ROD1 | ATNGIGVEYS---PKHENGVKYQSVSSD | 293 |

FIG. 15(Cont.)

| Sample Name | 16:0 | 16:1 | 18:0 | 18:1 | 18:2 | 18:3 | 20:0 | 20:1 | 20:2 | 20:3 | 22:1 | 22:2 | 24:1 |
|---|---|---|---|---|---|---|---|---|---|---|---|---|---|
| rod1-3 (-18bp) (2B2M) | 3.8 | | 0.5 | 23.2 | 10.1 | 11.2 | 0.2 | 14.2 | 0.4 | | 34.1 | | 2.6 |
| rod1-4 (+A) (5B1K) | 4.0 | | 0.6 | 24.1 | 9.4 | 12.7 | 0.2 | 13.7 | 0.4 | | 32.4 | | 2.4 |
| WT (Spring32-10) | 3.5 | | 0.6 | 11.1 | 19.3 | 14.6 | | 11.3 | 2.0 | 0.8 | 32.7 | 1.1 | 2.8 |

SEQUENCE LISTING

<160> NUMBER OF SEQ ID NOS: 69

<210> SEQ ID NO 1
<211> LENGTH: 2360
<212> TYPE: DNA
<213> ORGANISM: Thlaspi arvense

<400> SEQUENCE: 1

```
atgtctaaat ttgataaaat atatgatgac gacaattccg gtggatcaca gtttgcttca      60
tttggctttt tttgtgtgtt tgtcaagttg ctattcaata agaatttgtg attttgattg     120
gtctcctcaa aattctgtga aattttagta acaaggaaga aattaacaaa tcacaacaag     180
aaagagatgt gagctgtcgt atcaaatctt attcgttttc tcaacgcaat cgttttagtt     240
ttttttaact taacgccact tctctgctcc atacactcct ttttgtccac gtacttttca     300
tttgtggtaa tccatttctt cactttggat ctttcatctg aacaacaatt tcttgactca     360
atcaattacc acccgttctt gtgcttttgt atagattcat aatcttgtgt gtttcagctt     420
ctcattgctt tggttcttgt tttttttttct gcagaaacat gggtgcaggt ggaagaatga     480
cggttcctac ttcttccaag aagtctgaaa ccgatgcctt aaagcgtgtg ccgtgcgaga     540
aaccgccgtt cacgctcgga gaactgaaga aagcaatccc acagcattgt ttcaatcgct     600
```

```
caatccctcg ctctttctcc taccttatct gggacatcat catagcctct tgcttctact    660
acgttgccac cacttacttc tctctcctcc ctcagcctct ctcttacttg gcttggcctc    720
tctattgggt ctgtcaaggc tgtgtcttaa ccggagtctg ggtcatagct cacgaatgcg    780
gccaccacgc cttcagcgac taccaatggc ttgacgacac agtcggtctg atcttccatt    840
ctttcctcct cgtcccttac ttctcctgga aatacagcca ccgccgtcac cattccaaca    900
ccggatcact tgaaaaggac gaagtgtttg tccctaaaca gaaatccgcc atcaaatggt    960
acggcaagta cctcaacaac cctctgggac gcaccgtgat gttaaccgtc cagttcaccc   1020
ttggctggcc cttgtactta gccttcaacg tctcggggag accctacgac gggttcgctt   1080
gccacttcca cccaaaacgct cccatctaca acgaccgtga acgcctccag atatacatct   1140
```

```
cggatgctgg tatcctcgcc gtctgttacg gtctctaccg ttacgctgct gcacaaggag   1200
tggcctcgat gatctgcgtc tacggagttc cgcttctgat agtcaacggg ttcctcgtct   1260
tgatcacata cttgcagcac acccatccct cgttgcctca ctacgattca tccgagtggg   1320
attggttcag gggagctttg gctaccgtag acagagacta tggaatcctg aacaaggtct   1380
tccacaacat cacggacacg cacgtggctc accacctgtt ctcgacgatg ccgcattacc   1440
atgcgatgga ggccacgaag gcgataaagc cgatactcgg ggactattac cagtttgatg   1500
gaacaccggt cttcaaggcg atgtggaggg aggcgaagga gtgtgtctat gtagaaccgg   1560
acaggaaagg tgagaagaaa ggtgtgttct ggtacaacaa caagtgtga ggatgatcag   1620
gtgaaagaag aaggaagaaa atcgtcggc ctttctcttg tctggttatc tttgttttaa   1680
gaagatatat gtttgtttca ataatcttat tgtccatttt gttgtgttct gacattgtgg   1740
cttaaattat tatgtgatgt tagtgtccaa ttgttctgcg tctgtattgt tcttctcatc   1800
gctgttttgt tgggatcgta gaaatgtgac tttcggacaa ttaaactctt gtactcaagc   1860
tatcactctg ttggcagcat caaaagtgtt ttcatagttt cggtcttttg gtctctgttt   1920
gtttgatact gttggtgaga atggctcttc aagtgttgga atctacctaa ggtgaacaca   1980
ttgtaggatt tttcttttat ttaattgcca ttgtatacca cactgcagtg aaccgcaact   2040
atgttgacca tgtcgatgaa tgtaagtgaa ccatgaaact aatctttctg tacaatttac   2100
ttacttctga gtcattgtga tgtttggttg gcaggtcacc tttatttctc acactccctc   2160
cactcatgtg atgtggttgg gattttcttt tcataagtag cttttttgtaa agaactcagt   2220
ctttctcttt caaatcatgg aaacctttt caacaaaagcc aaatccatgt tacataagca   2280
aaatatctgc tttcttcatc tttccttcct ttcatatttg agagggaaca aaagaagagg   2340
aagaaaatga agcaaagtaa                                                2360
```

<210> SEQ ID NO 2
<211> LENGTH: 404
<212> TYPE: PRT
<213> ORGANISM: Thlaspi arvense

<400> SEQUENCE: 2

Met Ser Lys Phe Asp Lys Ile Tyr Asp Asp Asp Asn Ser Gly Gly Ser
1               5                   10                  15

Gln Asn Met Gly Ala Gly Gly Arg Met Thr Val Pro Thr Ser Ser Lys
            20                  25                  30

Lys Ser Glu Thr Asp Ala Leu Lys Arg Val Pro Cys Glu Lys Pro Pro
        35                  40                  45

Phe Thr Leu Gly Glu Leu Lys Lys Ala Ile Pro Gln His Cys Phe Asn
    50                  55                  60

```
Arg Ser Ile Pro Arg Ser Phe Ser Tyr Leu Ile Trp Asp Ile Ile
 65                  70                  75                  80

Ala Ser Cys Phe Tyr Tyr Val Ala Thr Thr Tyr Phe Ser Leu Leu Pro
                 85                  90                  95

Gln Pro Leu Ser Tyr Leu Ala Trp Pro Leu Tyr Trp Val Cys Gln Gly
            100                 105                 110

Cys Val Leu Thr Gly Val Trp Val Ile Ala His Glu Cys Gly His His
            115                 120                 125

Ala Phe Ser Asp Tyr Gln Trp Leu Asp Asp Thr Val Gly Leu Ile Phe
130                 135                 140

His Ser Phe Leu Leu Val Pro Tyr Phe Ser Trp Lys Tyr Ser His Arg
145                 150                 155                 160

Arg His His Ser Asn Thr Gly Ser Leu Glu Lys Asp Glu Val Phe Val
                165                 170                 175

Pro Lys Gln Lys Ser Ala Ile Lys Trp Tyr Gly Lys Tyr Leu Asn Asn
            180                 185                 190

Pro Leu Gly Arg Thr Val Met Leu Thr Val Gln Phe Thr Leu Gly Trp
        195                 200                 205

Pro Leu Tyr Leu Ala Phe Asn Val Ser Gly Arg Pro Tyr Asp Gly Phe
210                 215                 220

Ala Cys His Phe His Pro Asn Ala Pro Ile Tyr Asn Asp Arg Glu Arg
225                 230                 235                 240

Leu Gln Ile Tyr Ile Ser Asp Ala Gly Ile Leu Ala Val Cys Tyr Gly
                245                 250                 255

Leu Tyr Arg Tyr Ala Ala Ala Gln Gly Val Ala Ser Met Ile Cys Val
            260                 265                 270

Tyr Gly Val Pro Leu Leu Ile Val Asn Gly Phe Leu Val Leu Ile Thr
        275                 280                 285

Tyr Leu Gln His Thr His Pro Ser Leu Pro His Tyr Asp Ser Ser Glu
290                 295                 300

Trp Asp Trp Phe Arg Gly Ala Leu Ala Thr Val Asp Arg Asp Tyr Gly
305                 310                 315                 320

Ile Leu Asn Lys Val Phe His Asn Ile Thr Asp Thr His Val Ala His
                325                 330                 335

His Leu Phe Ser Thr Met Pro His Tyr His Ala Met Glu Ala Thr Lys
            340                 345                 350

Ala Ile Lys Pro Ile Leu Gly Asp Tyr Tyr Gln Phe Asp Gly Thr Pro
        355                 360                 365

Val Phe Lys Ala Met Trp Arg Glu Ala Lys Glu Cys Val Tyr Val Glu
370                 375                 380

Pro Asp Arg Lys Gly Glu Lys Lys Glu Gly Thr Lys Glu Glu Glu Glu
385                 390                 395                 400

Asn Glu Ala Lys

<210> SEQ ID NO 3
<211> LENGTH: 2360
<212> TYPE: DNA
<213> ORGANISM: artificial
<220> FEATURE:
<223> OTHER INFORMATION: modified FAD2 coding sequence

<400> SEQUENCE: 3
atgtctaaat tgataaaaat atatgatgac gacaattccg gtggatcaca gtttgcttca      60
tttggctttt tttgtgtgtt tgtcaagttg ctattcaata agaatttgtg attttgattg     120
```

```
gtctcctcaa aattctgtga aattttagta acaaggaaga aattaacaaa tcacaacaag      180
aaagagatgt gagctgtcgt atcaaatctt attcgttttc tcaacgcaat cgttttagtt      240
ttttttaact taacgccact tctctgctcc atacactcct ttttgtccac gtacttttca      300
tttgtggtaa tccatttctt cactttggat ctttcatctg aacaacaatt tcttgactca      360
atcaattacc acccgttctt gtgcttttgt atagattcat aatcttgtgt gtttcagctt      420
ctcattgctt tggttcttgt ttttttttct gcagaaacat gggtgcaggt ggaagaatga      480
cggttcctac ttcttccaag aagtctgaaa ccaatgcctt aaagcgtgtg ccgtgcgaga      540
aaccgccgtt cacgctcgga gaactgaaga aagcaatccc acagcattgt ttcaatcgct      600
caatccctcg ctctttctcc taccttatct gggacatcat catagcctct tgcttctact      660
acgttgccac cacttacttc tctctcctcc ctcagcctct ctcttacttg gcttggcctc      720
tctattgggt ctgtcaaggc tgtgtcttaa ccggagtctg ggtcatagct cacgaatgcg      780
gccaccacgc cttcagcgac taccaatggc ttgacgacac agtcggtctg atcttccatt      840 cttcctcct cgtcccttac ttctcctgga aatacagcca ccgccgtcac cattccaaca      900
ccggatcact tgaaaaggac gaagtgtttg tccctaaaca gaaatccgcc atcaaatggt      960
acggcaagta cctcaacaac cctctgggac gcaccgtgat gttaaccgtc cagttcaccc     1020
ttggctggcc cttgtactta gccttcaacg tctcggggag accctacgac gggttcgctt     1080
gccacttcca cccaaacgct cccatctaca acgaccgtga acgcctccag atatacatct     1140
cggatgctgg tatcctcgcc gtctgttacg gtctctaccg ttacgctgct gcacaaggag     1200
tggcctcgat gatctgcgtc tacggagttc cgcttctgat agtcaacggg ttcctcgtct     1260
tgatcacata cttgcagcac acccatccct cgttgcctca ctacgattca tccgagtggg     1320
attggttcag gggagctttg gctaccgtag acagagacta tggaatcctg aacaaggtct     1380
tccacaacat cacggacacg cacgtggctc accacctgtt ctcgacgatg ccgcattacc     1440
atgcgatgga ggccacgaag gcgataaagc cgatactcgg ggactattac cagtttgatg     1500
gaacaccggt cttcaaggcg atgtggaggg aggcgaagga gtgtgtctat gtagaaccgg     1560
acaggaaagg tgagaagaaa ggtgtgttct ggtacaacaa caagttgtga ggatgatcag     1620
gtgaaagaag aaggaagaaa aatcgtcggc cttctcttg tctggttatc tttgttttaa      1680
gaagatatat gtttgtttca ataatcttat tgtccatttt gttgtgttct gacattgtgg     1740
cttaaattat tatgtgatgt tagtgtccaa ttgttctgcg tctgtattgt tcttctcatc     1800
gctgttttgt tgggatcgta gaaatgtgac tttcggacaa ttaaactctt gtactcaagc     1860
tatcactctg ttggcagcat caaaagtgtt ttcatagttt cggtcttttg gtctctgttt     1920
gtttgatact gttggtgaga atggctcttc aagtgttgga atctacctaa ggtgaacaca     1980
ttgtaggatt tttctttttat ttaattgcca ttgtatacca cactgcagtg aaccgcaact     2040
atgttgacca tgtcgatgaa tgtaagtgaa ccatgaaact aatctttctg tacaatttac     2100
ttacttctga gtcattgtga tgtttggttg gcaggtcacc tttatttctc acactccctc     2160
cactcatgtg atgtgttgg gatttttcttt tcataagtag cttttgtaa agaactcagt     2220 cttttctcttt caaatcatgg aaaccttttc aacaaaagcc aaatccatgt tacataagca     2280
aaatatctgc tttcttcatc tttcctttct ttcatatttg agagggaaca aaagaagagg     2340
aagaaaatga agcaaagtaa                                                  2360
```

<210> SEQ ID NO 4

<211> LENGTH: 404
<212> TYPE: PRT
<213> ORGANISM: artificial
<220> FEATURE:
<223> OTHER INFORMATION: modified FAD2 polypeptide

<400> SEQUENCE: 4

| | | | | | | | | | | | | | | |
|---|---|---|---|---|---|---|---|---|---|---|---|---|---|---|
| Met | Ser | Lys | Phe | Asp | Lys | Ile | Tyr | Asp | Asp | Asp | Asn | Ser | Gly | Gly | Ser |
| 1 | | | | 5 | | | | | 10 | | | | | 15 |
| Gln | Asn | Met | Gly | Ala | Gly | Gly | Arg | Met | Thr | Val | Pro | Thr | Ser | Ser | Lys |
| | | | 20 | | | | | 25 | | | | | 30 | | |
| Lys | Ser | Glu | Thr | Asn | Ala | Leu | Lys | Arg | Val | Pro | Cys | Glu | Lys | Pro | Pro |
| | | 35 | | | | | 40 | | | | | 45 | | | |
| Phe | Thr | Leu | Gly | Glu | Leu | Lys | Lys | Ala | Ile | Pro | Gln | His | Cys | Phe | Asn |
| 50 | | | | | 55 | | | | | 60 | | | | | |
| Arg | Ser | Ile | Pro | Arg | Ser | Phe | Ser | Tyr | Leu | Ile | Trp | Asp | Ile | Ile | Ile |
| 65 | | | | | 70 | | | | | 75 | | | | | 80 |
| Ala | Ser | Cys | Phe | Tyr | Tyr | Val | Ala | Thr | Thr | Tyr | Phe | Ser | Leu | Leu | Pro |
| | | | | 85 | | | | | 90 | | | | | 95 | |
| Gln | Pro | Leu | Ser | Tyr | Leu | Ala | Trp | Pro | Leu | Tyr | Trp | Val | Cys | Gln | Gly |
| | | | 100 | | | | | 105 | | | | | 110 | | |
| Cys | Val | Leu | Thr | Gly | Val | Trp | Val | Ile | Ala | His | Glu | Cys | Gly | His | His |
| | | | 115 | | | | | 120 | | | | | 125 | | |
| Ala | Phe | Ser | Asp | Tyr | Gln | Trp | Leu | Asp | Asp | Thr | Val | Gly | Leu | Ile | Phe |
| | 130 | | | | | 135 | | | | | 140 | | | | |
| His | Ser | Phe | Leu | Leu | Val | Pro | Tyr | Phe | Ser | Trp | Lys | Tyr | Ser | His | Arg |
| 145 | | | | | 150 | | | | | 155 | | | | | 160 |
| Arg | His | His | Ser | Asn | Thr | Gly | Ser | Leu | Glu | Lys | Asp | Glu | Val | Phe | Val |
| | | | | 165 | | | | | 170 | | | | | 175 | |
| Pro | Lys | Gln | Lys | Ser | Ala | Ile | Lys | Trp | Tyr | Gly | Lys | Tyr | Leu | Asn | Asn |
| | | | 180 | | | | | 185 | | | | | 190 | | |
| Pro | Leu | Gly | Arg | Thr | Val | Met | Leu | Thr | Val | Gln | Phe | Thr | Leu | Gly | Trp |
| | | 195 | | | | | 200 | | | | | 205 | | | |
| Pro | Leu | Tyr | Leu | Ala | Phe | Asn | Val | Ser | Gly | Arg | Pro | Tyr | Asp | Gly | Phe |
| | 210 | | | | | 215 | | | | | 220 | | | | |
| Ala | Cys | His | Phe | His | Pro | Asn | Ala | Pro | Ile | Tyr | Asn | Asp | Arg | Glu | Arg |
| 225 | | | | | 230 | | | | | 235 | | | | | 240 |
| Leu | Gln | Ile | Tyr | Ile | Ser | Asp | Ala | Gly | Ile | Leu | Ala | Val | Cys | Tyr | Gly |
| | | | | 245 | | | | | 250 | | | | | 255 | |
| Leu | Tyr | Arg | Tyr | Ala | Ala | Ala | Gln | Gly | Val | Ala | Ser | Met | Ile | Cys | Val |
| | | | 260 | | | | | 265 | | | | | 270 | | |
| Tyr | Gly | Val | Pro | Leu | Leu | Ile | Val | Asn | Gly | Phe | Leu | Val | Leu | Ile | Thr |
| | | 275 | | | | | 280 | | | | | 285 | | | |
| Tyr | Leu | Gln | His | Thr | His | Pro | Ser | Leu | Pro | His | Tyr | Asp | Ser | Ser | Glu |
| | 290 | | | | | 295 | | | | | 300 | | | | |
| Trp | Asp | Trp | Phe | Arg | Gly | Ala | Leu | Ala | Thr | Val | Asp | Arg | Asp | Tyr | Gly |
| 305 | | | | | 310 | | | | | 315 | | | | | 320 |
| Ile | Leu | Asn | Lys | Val | Phe | His | Asn | Ile | Thr | Asp | Thr | His | Val | Ala | His |
| | | | | 325 | | | | | 330 | | | | | 335 | |
| His | Leu | Phe | Ser | Thr | Met | Pro | His | Tyr | His | Ala | Met | Glu | Ala | Thr | Lys |
| | | | 340 | | | | | 345 | | | | | 350 | | |
| Ala | Ile | Lys | Pro | Ile | Leu | Gly | Asp | Tyr | Tyr | Gln | Phe | Asp | Gly | Thr | Pro |
| | | 355 | | | | | 360 | | | | | 365 | | | |
| Val | Phe | Lys | Ala | Met | Trp | Arg | Glu | Ala | Lys | Glu | Cys | Val | Tyr | Val | Glu |
| | 370 | | | | | 375 | | | | | 380 | | | | |

Pro Asp Arg Lys Gly Glu Lys Glu Gly Thr Lys Glu Glu Glu Glu
385                 390                 395                 400

Asn Glu Ala Lys

<210> SEQ ID NO 5
<211> LENGTH: 2360
<212> TYPE: DNA
<213> ORGANISM: artificial
<220> FEATURE:
<223> OTHER INFORMATION: modified FAD2 coding sequence

<400> SEQUENCE: 5

| | | | | | |
|---|---|---|---|---|---|
| atgtctaaat | ttgataaaat | atatgatgac | gacaattccg | gtggatcaca | gtttgcttca | 60 |
| tttggctttt | tttgtgtgtt | tgtcaagttg | ctattcaata | agaatttgtg | attttgattg | 120 |
| gtctcctcaa | aattctgtga | aatttttagta | acaaggaaga | aattaacaaa | tcacaacaag | 180 |
| aaagagatgt | gagctgtcgt | atcaaatctt | attcgttttc | tcaacgcaat | cgttttagtt | 240 |
| ttttttaact | taacgccact | tctctgctcc | atacactcct | ttttgtccac | gtactttttca | 300 |
| tttgtggtaa | tccatttctt | cactttggat | cttttcatctg | aacaacaatt | tcttgactca | 360 |
| atcaattacc | acccgttctt | gtgctttttgt | atagattcat | aatcttgtgt | gtttcagctt | 420 |
| ctcattgctt | tggttcttgt | ttttttttct | gcagaaacat | gggtgcaggt | ggaagaatga | 480 |
| cggttcctac | ttcttccaag | aagtctgaaa | ccgatgcctt | aaagcgtgtg | ccgtgcgaga | 540 |
| aaccgccgtt | cacgctcgga | gaactgaaga | agcaatccc | acagcattgt | tcaatcgct | 600 |
| caatccctcg | ctctttctcc | taccttatct | gggacatcat | catagcctct | tgcttctact | 660 |
| acgttgccac | cacttacttc | tctctcctcc | ctcagcctct | ctcttacttg | gcttggcctc | 720 |
| tctattgggt | ctgtcaaggc | tgtgtcttaa | ccggagtctg | ggtcatagct | cacgaatgcg | 780 |
| gccaccacgc | cttcagcgac | taccaatggc | ttgacgacac | agtcgatctg | atcttccatt | 840 |
| ctttcctcct | cgtcccttac | ttctcctgga | aatacagcca | ccgccgtcac | cattccaaca | 900 |
| ccggatcact | tgaaaaggac | gaagtgtttg | tccctaaaca | gaaatccgcc | atcaaatggt | 960 |
| acggcaagta | cctcaacaac | cctctgggac | gcaccgtgat | gttaaccgtc | cagttcaccc | 1020 |
| ttggctggcc | cttgtactta | gccttcaacg | tctcggggag | accctacgac | gggttcgctt | 1080 |
| gccacttcca | cccaaacgct | cccatctaca | acgaccgtga | acgcctccag | atatacatct | 1140 |
| cggatgctgg | tatcctcgcc | gtctgttacg | gtctctaccg | ttacgctgct | gcacaaggag | 1200 |
| tggcctcgat | gatctgcgtc | tacggagttc | cgcttctgat | agtcaacggg | ttcctcgtct | 1260 |
| tgatcacata | cttgcagcac | acccatccct | cgttgcctca | ctacgattca | tccgagtggg | 1320 |
| attggttcag | gggagctttg | gctaccgtag | acagagacta | tggaatcctg | aacaaggtct | 1380 |
| tccacaacat | cacggacacg | cacgtggctc | accacctgtt | ctcgacgatg | ccgcattacc | 1440 |
| atgcgatgga | ggccacgaag | gcgataaagc | cgatactcgg | ggactattac | cagtttgatg | 1500 |
| gaacaccggt | cttcaaggcg | atgtggaggg | aggcgaagga | gtgtgtctat | gtagaaccgg | 1560 |
| acaggaaagg | tgagaagaaa | ggtgtgttct | ggtacaacaa | caagttgtga | ggatgatcag | 1620 |
| gtgaaagaag | aaggaagaaa | aatcgtcggc | ctttctcttg | tctggttatc | tttgttttaa | 1680 |
| gaagatatat | gtttgtttca | ataatcttat | tgtccatttt | gttgtgttct | gacattgtgg | 1740 |
| cttaaattat | tatgtgatgt | tagtgtccaa | ttgttctgcg | tctgtattgt | tcttctcatc | 1800 |
| gctgtttgt | tgggatcgta | gaaatgtgac | tttcggacaa | ttaaactctt | gtactcaagc | 1860 |
| tatcactctg | ttggcagcat | caaaagtgtt | ttcatagttt | cggtcttttg | gtctctgttt | 1920 |

```
gtttgatact gttggtgaga atggctcttc aagtgttgga atctacctaa ggtgaacaca      1980
ttgtaggatt tttcttttat ttaattgcca ttgtatacca cactgcagtg aaccgcaact      2040
atgttgacca tgtcgatgaa tgtaagtgaa ccatgaaact aatctttctg tacaatttac      2100
ttacttctga gtcattgtga tgtttggttg gcaggtcacc tttatttctc acactccctc      2160
cactcatgtg atgtggttgg gattttcttt tcataagtag cttttttgtaa agaactcagt     2220 cttctctttt caaatcatgg aaaccttttc aacaaaagcc aaatccatgt tacataagca      2280
aaatatctgc tttcttcatc tttcctttct ttcatatttg agagggaaca aaagaagagg      2340
aagaaaatga agcaaagtaa                                                  2360
```

<210> SEQ ID NO 6
<211> LENGTH: 404
<212> TYPE: PRT
<213> ORGANISM: artificial
<220> FEATURE:
<223> OTHER INFORMATION: modified FAD2 polypeptide

<400> SEQUENCE: 6

```
Met Ser Lys Phe Asp Lys Ile Tyr Asp Asp Asp Asn Ser Gly Gly Ser
1               5                   10                  15

Gln Asn Met Gly Ala Gly Gly Arg Met Thr Val Pro Thr Ser Ser Lys
            20                  25                  30

Lys Ser Glu Thr Asp Ala Leu Lys Arg Val Pro Cys Glu Lys Pro Pro
        35                  40                  45

Phe Thr Leu Gly Glu Leu Lys Lys Ala Ile Pro Gln His Cys Phe Asn
    50                  55                  60

Arg Ser Ile Pro Arg Ser Phe Ser Tyr Leu Ile Trp Asp Ile Ile Ile
65                  70                  75                  80

Ala Ser Cys Phe Tyr Tyr Val Ala Thr Thr Tyr Phe Ser Leu Leu Pro
                85                  90                  95

Gln Pro Leu Ser Tyr Leu Ala Trp Pro Leu Tyr Trp Val Cys Gln Gly
            100                 105                 110

Cys Val Leu Thr Gly Val Trp Val Ile Ala His Glu Cys Gly His His
        115                 120                 125

Ala Phe Ser Asp Tyr Gln Trp Leu Asp Asp Thr Val Asp Leu Ile Phe
    130                 135                 140

His Ser Phe Leu Leu Val Pro Tyr Phe Ser Trp Lys Tyr Ser His Arg
145                 150                 155                 160

Arg His His Ser Asn Thr Gly Ser Leu Glu Lys Asp Glu Val Phe Val
                165                 170                 175

Pro Lys Gln Lys Ser Ala Ile Lys Trp Tyr Gly Lys Tyr Leu Asn Asn
            180                 185                 190

Pro Leu Gly Arg Thr Val Met Leu Thr Val Gln Phe Thr Leu Gly Trp
        195                 200                 205

Pro Leu Tyr Leu Ala Phe Asn Val Ser Gly Arg Pro Tyr Asp Gly Phe
    210                 215                 220

Ala Cys His Phe His Pro Asn Ala Pro Ile Tyr Asn Asp Arg Glu Arg
225                 230                 235                 240

Leu Gln Ile Tyr Ile Ser Asp Ala Gly Ile Leu Ala Val Cys Tyr Gly
                245                 250                 255

Leu Tyr Arg Tyr Ala Ala Ala Gln Gly Val Ala Ser Met Ile Cys Val
            260                 265                 270

Tyr Gly Val Pro Leu Leu Ile Val Asn Gly Phe Leu Val Leu Ile Thr
```

```
                275                 280                 285
Tyr Leu Gln His Thr His Pro Ser Leu Pro His Tyr Asp Ser Ser Glu
        290                 295                 300
Trp Asp Trp Phe Arg Gly Ala Leu Ala Thr Val Asp Arg Asp Tyr Gly
305                 310                 315                 320
Ile Leu Asn Lys Val Phe His Asn Ile Thr Asp Thr His Val Ala His
                325                 330                 335
His Leu Phe Ser Thr Met Pro Tyr His Ala Met Glu Ala Thr Lys
        340                 345                 350
Ala Ile Lys Pro Ile Leu Gly Asp Tyr Tyr Gln Phe Asp Gly Thr Pro
            355                 360                 365
Val Phe Lys Ala Met Trp Arg Glu Ala Lys Glu Cys Val Tyr Val Glu
        370                 375                 380
Pro Asp Arg Lys Gly Glu Lys Lys Glu Gly Thr Lys Glu Glu Glu
385                 390                 395                 400
Asn Glu Ala Lys

<210> SEQ ID NO 7
<211> LENGTH: 2360
<212> TYPE: DNA
<213> ORGANISM: artificial
<220> FEATURE:
<223> OTHER INFORMATION: modified FAD2 coding sequence

<400> SEQUENCE: 7
atgtctaaat tgataaaat atatgatgac  gacaattccg  gtggatcaca  gtttgcttca        60
tttggctttt  tttgtgtgtt  tgtcaagttg  ctattcaata  agaatttgtg  attttgattg     120
gtctcctcaa  aattctgtga  aattttagta  acaaggaaga  aattaacaaa  tcacaacaag    180
aaagagatgt  gagctgtcgt  atcaaatctt  attcgttttc  tcaacgcaat  cgttttagtt    240 tttttaact   taacgccact  tctctgctcc  atacactcct  ttttgtccac  gtacttttca    300
tttgtggtaa  tccatttctt  cactttggat  cttctcatctg  aacaacaatt  tcttgactca   360
atcaattacc  acccgttctt  gtgcttttgt  atagattcat  aatcttgtgt  gtttcagctt    420
ctcattgctt  tggttcttgt  ttttttttct  gcagaaacat  gggtgcaggt  ggaagaatga    480
cggttcctac  ttcttccaag  aagtctgaaa  ccgatgcctt  aaagcgtgtg  ccgtgcgaga    540
aaccgccgtt  cacgctcgga  gaactgaaga  agcaatccc   acagcattgt  ttcaatcgct    600
caatccctcg  ctctttctcc  taccttatct  gggacatcat  catagcctct  tgcttctact    660
acgttgccac  cacttacttc  tctctcctcc  ctcagcctct  ctcttacttg  gcttggcctc    720
tctattgggt  ctgtcaaggc  tgtgtcttaa  ccggagtctg  ggtcatagct  cacgaatgcg    780
gccaccacgc  cttcagcgac  taccaatggc  ttgacgacac  agtcggtctg  atcttccatt    840
ctttcctcct  cgtcccttac  ttctcctgga  aatacagcca  ccgccgtcac  cattccaaca    900
ccggatcact  tgaaaaggac  gaagtgtttg  tccctaaaca  gaaatccgcc  atcaaatggt    960
acggcaagta  cctcaacaac  cctctgggac  gcaccgtgat  gttaaccgtc  cagttcaccc   1020
ttggctggcc  cttgtactta  gccttcaacg  tctcggggag  accctacgac  gggttcgctt   1080
gccacttcca  cccaaacgct  cccatctaca  acgaccgtga  acgcctccag  atatacatct   1140
cggatgctgg  tatcctcgcc  gtctgttacg  gtctctaccg  ttacgctgct  gcacaaggag   1200
tggcctcgat  gatctgcgtc  tacggagttc  cgcttctgat  agtcaacggg  ttcctcgtct   1260
tgatcacata  cttgcagcac  acccatccct  cgttgccttt  ctacgattca  tccgagtggg   1320
```

```
attggttcag gggagctttg gctaccgtag acagagacta tggaatcctg aacaaggtct    1380
tccacaacat cacggacacg cacgtggctc accacctgtt ctcgacgatg ccgcattacc    1440
atgcgatgga ggccacgaag gcgataaagc cgatactcgg ggactattac cagtttgatg    1500
gaacaccggt cttcaaggcg atgtggaggg aggcgaagga gtgtgtctat gtagaaccgg    1560
acaggaaagg tgagaagaaa ggtgtgttct ggtacaacaa caagttgtga ggatgatcag    1620
gtgaaagaag aaggaagaaa aatcgtcggc ctttctcttg tctggttatc tttgttttaa    1680
gaagatatat gtttgtttca ataatcttat tgtccatttt gttgtgttct gacattgtgg    1740
cttaaattat tatgtgatgt tagtgtccaa ttgttctgcg tctgtattgt tcttctcatc    1800
gctgttttgt tgggatcgta gaaatgtgac tttcggacaa ttaaactctt gtactcaagc    1860
tatcactctg ttggcagcat caaaagtgtt tcatagtttt cggtcttttg gtctctgttt    1920
gtttgatact gttggtgaga atggctcttc aagtgttgga atctacctaa ggtgaacaca    1980
ttgtaggatt tttcttttat ttaattgcca ttgtatacca cactgcagtg aaccgcaact    2040
atgttgacca tgtcgatgaa tgtaagtgaa ccatgaaact aatctttctg tacaatttac    2100
ttacttctga gtcattgtga tgtttggttg gcaggtcacc tttatttctc acactccctc    2160
cactcatgtg atgtggttgg gattttcttt tcataagtag cttttgtaa agaactcagt    2220
ctttctcttt caaatcatgg aaaccttttc aacaaaagcc aaatccatgt tacataagca    2280
aaatatctgc tttcttcatc tttcctttct ttcatatttg agagggaaca aaagaagagg    2340
aagaaaatga agcaaagtaa                                                2360
```

<210> SEQ ID NO 8
<211> LENGTH: 404
<212> TYPE: PRT
<213> ORGANISM: artificial
<220> FEATURE:
<223> OTHER INFORMATION: modified FAD2 polypeptide
<400> SEQUENCE: 8

```
Met Ser Lys Phe Asp Lys Ile Tyr Asp Asp Asn Ser Gly Gly Ser
1               5                   10                  15

Gln Asn Met Gly Ala Gly Gly Arg Met Thr Val Pro Thr Ser Ser Lys
            20                  25                  30

Lys Ser Glu Thr Asp Ala Leu Lys Arg Val Pro Cys Glu Lys Pro Pro
        35                  40                  45

Phe Thr Leu Gly Glu Leu Lys Lys Ala Ile Pro Gln His Cys Phe Asn
    50                  55                  60

Arg Ser Ile Pro Arg Ser Phe Ser Tyr Leu Ile Trp Asp Ile Ile
65                  70                  75                  80

Ala Ser Cys Phe Tyr Tyr Val Ala Thr Thr Tyr Phe Ser Leu Leu Pro
                85                  90                  95

Gln Pro Leu Ser Tyr Leu Ala Trp Pro Leu Tyr Trp Val Cys Gln Gly
            100                 105                 110

Cys Val Leu Thr Gly Val Trp Val Ile Ala His Glu Cys Gly His His
        115                 120                 125

Ala Phe Ser Asp Tyr Gln Trp Leu Asp Asp Thr Val Gly Leu Ile Phe
    130                 135                 140

His Ser Phe Leu Leu Val Pro Tyr Phe Ser Trp Lys Tyr Ser His Arg
145                 150                 155                 160

Arg His His Ser Asn Thr Gly Ser Leu Glu Lys Asp Glu Val Phe Val
                165                 170                 175
```

```
Pro Lys Gln Lys Ser Ala Ile Lys Trp Tyr Gly Lys Tyr Leu Asn Asn
            180                 185                 190

Pro Leu Gly Arg Thr Val Met Leu Thr Val Gln Phe Thr Leu Gly Trp
        195                 200                 205

Pro Leu Tyr Leu Ala Phe Asn Val Ser Gly Arg Pro Tyr Asp Gly Phe
    210                 215                 220

Ala Cys His Phe His Pro Asn Ala Pro Ile Tyr Asn Asp Arg Glu Arg
225                 230                 235                 240

Leu Gln Ile Tyr Ile Ser Asp Ala Gly Ile Leu Ala Val Cys Tyr Gly
                245                 250                 255

Leu Tyr Arg Tyr Ala Ala Ala Gln Gly Val Ala Ser Met Ile Cys Val
            260                 265                 270

Tyr Gly Val Pro Leu Leu Ile Val Asn Gly Phe Leu Val Leu Ile Thr
        275                 280                 285

Tyr Leu Gln His Thr His Pro Ser Leu Pro Tyr Tyr Asp Ser Ser Glu
    290                 295                 300

Trp Asp Trp Phe Arg Gly Ala Leu Ala Thr Val Asp Arg Asp Tyr Gly
305                 310                 315                 320

Ile Leu Asn Lys Val Phe His Asn Ile Thr Asp Thr His Val Ala His
                325                 330                 335

His Leu Phe Ser Thr Met Pro His Tyr His Ala Met Glu Ala Thr Lys
            340                 345                 350

Ala Ile Lys Pro Ile Leu Gly Asp Tyr Tyr Gln Phe Asp Gly Thr Pro
        355                 360                 365

Val Phe Lys Ala Met Trp Arg Glu Ala Lys Glu Cys Val Tyr Val Glu
    370                 375                 380

Pro Asp Arg Lys Gly Glu Lys Lys Glu Gly Thr Lys Glu Glu Glu Glu
385                 390                 395                 400

Asn Glu Ala Lys

<210> SEQ ID NO 9
<211> LENGTH: 2146
<212> TYPE: DNA
<213> ORGANISM: Thlaspi arvense

<400> SEQUENCE: 9
atgtcaacta aaaccgtcgt ccctctccgt cgcagatcta agccccttaa cggaaatcac      60
actaacggcg tcgccattga cggaagcctc gacgacgacc acaaccgtcg catcggatca     120
gtaaatagcc aaatggataa cattgctaag aaaacggacg acggctacgc aaacggcgga     180
ggaggaggag gaggagggaa aagcaaggcg tcgtttatga cgtggacggc gcgtgacgtt     240
gtgtacgtgg cgaggtacca ttggataccg tgtttgttcg cggtcggggt tctgttcttc     300
acgggcgtgg agtacacgct ccagatgatt cccgcgaggt ctgagccgtt cgatattggg     360
tttgtggcca cgcgctctct gaatcgcgtc ttggcaaatt caccggatct taacaccgtc     420
ttagccgctc taaacacggt aatttcgtac taattaattt agggtaaaaa atatagtatt     480
taataatgac tatcctcaat tcctttcatg cttcacctaa tattttgttt tttttcgttg     540
tcattaaaat cgtaataata tattgagtta gtcaaatgaa aaaaacaagt ggcggtagtg     600
attggaaaca atctcagat cttttatctg tttaataagg tatttaatta ccagctgga      660 attatgctgt caagtgtcaa cacagtagta gtaacatgca atggaatttc tcaatagaaa     720
aaggtcttaa ttagtataga taattagtgg acaaaaatgt agttaatgta atctctttgc     780
taagtagtta tcataatcat cttttttaaca actgccattt tgtctgtgtg tttgtttttac    840
```

```
aacgaagtag tagtagaata gatcgctttt tagcttttga aagtttcgaa cccaaggaaa      900
agggacacat gggttatgag ttggagacac gatcacatgc aaacagagag attggttaaa      960
ttatcgactt tttgtagtac tttttaaaaa aaaactattt atataaaaaa catggtggat     1020
ggtggggaca ggtgttcgta gggatgcaaa cgacgtatat tgtatggaca tggttaatgg     1080
aaggacgacc acgagccacc atctcggctt gcttcatgtt tacttgtcga ggcattcttg     1140
gttactctac tcagctccct cttcctcagg ttccaatcaa cacttttctt ctatctcttt     1200
tcttaattaa ataattacc aattaactaa atgctaatca gtcgatatat catagttcca     1260
acgttttgga cgtgtgattt ccattggcca ctaccatata aaacaacaga gtctctttat     1320
tcattattca atatatattt gagtattgat attattcata gggaggtttc atttgtacta     1380
tcaataaaat ttctacaact cttggatttt ttctgctaca ttttgtagtt attttttttaa    1440
ttacttttaa aaacttgtga ataggagaga ctaatagtag tacgtaatat gattgtatca     1500
aatgctttaa catgtggggt ttgggttaac tatcatcatt tcatagatca ctattttgtt     1560
ttcgtttgtt acctaacttt ttgttatctt tgaaaaataa tgttccacga gttgattgac     1620
tggacataaa aatcagattc tctcactcat ttacgttcta cggttctagc cactcgtttt     1680
tttcttttc tttctgtggt gtaacacgta gataatggat tttctatgtg tgtcgtcttg     1740
ctcaagaata ataaatgtgg ttaaaggtta aatatagctc tggaaattaa ttatctcctc     1800
ttttttatt aaccaggatt ttctaggatc aggtgtcgat tttccggtgg gaaacgtctc     1860
gttcttcctc ttctactcgg gtcacgtcgc cggttcgatg atcgcatctt tggacatgag     1920
gagaatgcag aggatgagac tagcgatgct ttttgacatc ctcaatgtat tacaatcgat     1980
caggctgctc gggacgagag gacactacac gattgatctc gctgtcggag ttggcgctgg     2040
gattctcttt gattcattcg ccggcaagta cgaagagatg ataagcaaga gacacaattt     2100
agtcaatggt tttggtttga tttcgaaaga ctcgctagtc aattaa                   2146
```

<210> SEQ ID NO 10
<211> LENGTH: 301
<212> TYPE: PRT
<213> ORGANISM: Thlaspi arvense

<400> SEQUENCE: 10

```
Met Ser Thr Lys Thr Val Val Pro Leu Arg Arg Ser Lys Pro Leu
1               5                   10                  15

Asn Gly Asn His Thr Asn Gly Val Ala Ile Asp Gly Ser Leu Asp Asp
            20                  25                  30

Asp His Asn Arg Arg Ile Gly Ser Val Asn Ser Gln Met Asp Asn Ile
        35                  40                  45

Ala Lys Lys Thr Asp Asp Gly Tyr Ala Asn Gly Gly Gly Gly Gly
    50                  55                  60

Gly Gly Lys Ser Lys Ala Ser Phe Met Thr Trp Thr Ala Arg Asp Val
65                  70                  75                  80

Val Tyr Val Ala Arg Tyr His Trp Ile Pro Cys Leu Phe Ala Val Gly
                85                  90                  95

Val Leu Phe Phe Thr Gly Val Glu Tyr Thr Leu Gln Met Ile Pro Ala
            100                 105                 110

Arg Ser Glu Pro Phe Asp Ile Gly Phe Val Ala Thr Arg Ser Leu Asn
        115                 120                 125

Arg Val Leu Ala Asn Ser Pro Asp Leu Asn Thr Val Leu Ala Ala Leu
    130                 135                 140
```

Asn Thr Val Phe Val Gly Met Gln Thr Thr Tyr Ile Val Trp Thr Trp
145                 150                 155                 160

Leu Met Glu Gly Arg Pro Arg Ala Thr Ile Ser Ala Cys Phe Met Phe
            165                 170                 175

Thr Cys Arg Gly Ile Leu Gly Tyr Ser Thr Gln Leu Pro Leu Pro Gln
        180                 185                 190

Asp Phe Leu Gly Ser Gly Val Asp Phe Pro Val Gly Asn Val Ser Phe
    195                 200                 205

Phe Leu Phe Tyr Ser Gly His Val Ala Gly Ser Met Ile Ala Ser Leu
210                 215                 220

Asp Met Arg Arg Met Gln Arg Met Arg Leu Ala Met Leu Phe Asp Ile
225                 230                 235                 240

Leu Asn Val Leu Gln Ser Ile Arg Leu Leu Gly Thr Arg Gly His Tyr
                245                 250                 255

Thr Ile Asp Leu Ala Val Gly Val Gly Ala Gly Ile Leu Phe Asp Ser
            260                 265                 270

Phe Ala Gly Lys Tyr Glu Glu Met Ile Ser Lys Arg His Asn Leu Val
        275                 280                 285

Asn Gly Phe Gly Leu Ile Ser Lys Asp Ser Leu Val Asn
    290                 295                 300

<210> SEQ ID NO 11
<211> LENGTH: 2146
<212> TYPE: DNA
<213> ORGANISM: artificial
<220> FEATURE:
<223> OTHER INFORMATION: modified ROD1 coding sequence

<400> SEQUENCE: 11
atgtcaacta aaaccgtcgt ccctctccgt cgcagatcta agccccttaa cggaaatcac      60
actaacggcg tcgccattga cggaagcctc gacgacgacc acaaccgtcg catcggatca     120
gtaaatagcc aaatggataa cattgctaag aaaacggacg acggctacgc aaacggcgga     180
ggaggaggag gaggagggaa aagcaaggcg tcgtttatga cgtggacggc gcgtgacgtt     240
gtgtacgtgg cgaggtacca ttggataccg tgtttgttcg cggtcggggt tctgttcttc     300
acgggcgtgg agtacacgct ccagatgatt cccgcgaggt ctgagccgtt cgatattggg     360
tttgtggcca cgcgctctct gaatcgcgtc ttggcaaatt caccggatct taacaccgtc     420
ttagccgctc taaacacggg aatttcgtac taattaattt agggtaaaaa atatagtatt     480
taataatgac tatcctcaat tcctttcatg cttcacctaa tattttgttt tttttcgttg     540
tcattaaaat cgtaataata tattgagtta gtcaaatgaa aaaaacaagt ggcggtagtg     600
attggaaaca aatctcagat cttttatctg tttaataagg tatttaatta tccagctgga     660
attatgctgt caagtgtcaa cacagtagta gtaacatgca atggaatttc tcaatagaaa     720
aaggtcttaa ttagtataga taattagtgg acaaaaatgt agttaatgta atctctttgc     780
taagtagtta tcataatcat cttttttaaca actgccattt tgtctgtgtg tttgttttac     840
aacgaagtag tagtagaata gatcgctttt tagcttttga aagtttcgaa cccaaggaaa     900
agggacacat gggttatgag ttggagacac gatcacatgc aaacagagag attggttaaa     960
ttatcgactt tttgtagtac tttttaaaaa aaaactattt atataaaaaa catggtggat    1020
ggtggggaca ggtgttcgta gggatgcaaa cgacgtatat tgtatggaca tggttaatgg    1080
aaggacgacc acgagccacc atctcggctt gcttcatgtt tacttgtcga ggcattcttg    1140

```
gttactctac tcagctccct cttcctcagg ttccaatcaa cacttttctt ctatctcttt    1200
tcttaattaa aataattacc aattaactaa atgctaatca gtcgatatat catagttcca    1260
acgttttgga cgtgtgattt ccattggcca ctaccatata aaacaacaga gtctctttat    1320
tcattattca atatatattt gagtattgat attattcata gggaggtttc atttgtacta    1380
tcaataaaat ttctacaact cttggatttt ttctgctaca ttttgtagtt attttttaa     1440 ttacttttaa aaacttgtga ataggagaga ctaatagtag tacgtaatat gattgtatca    1500
aatgctttaa catgtggggt ttgggttaac tatcatcatt tcatagatca ctattttgtt    1560
ttcgtttgtt acctaacttt ttgttatctt tgaaaaataa tgttccacga gttgattgac    1620
tggacataaa aatcagattc tctcactcat ttacgttcta cggttctagc cactcgtttt    1680 tttcttttc tttctgtggt gtaacacgta gataatggat tttctatgtg tgtcgtcttg    1740
ctcaagaata ataaatgtgg ttaaaggtta aatatagctc tggaaattaa ttatctcctc    1800 ttttttatt aaccaggatt ttctaggatc aggtgtcgat tttccggtgg gaaacgtctc     1860
gttcttcctc ttctactcgg gtcacgtcgc cggttcgatg atcgcatctt tggacataag    1920
gagaatgcag aggatgagac tagcgatgct ttttgacatc ctcaatgtat tacaatcgat    1980
caggctgctc gggacgagag gacactacac gattgatctc gctgtcggag ttggcgctgg    2040
gattctcttt gattcattcg ccggcaagta cgaagagatg ataagcaaga gacacaattt    2100
agtcaatggt tttggtttga tttcgaaaga ctcgctagtc aattaa                  2146
```

<210> SEQ ID NO 12
<211> LENGTH: 255
<212> TYPE: PRT
<213> ORGANISM: artificial
<220> FEATURE:
<223> OTHER INFORMATION: modified ROD1 polypeptide

<400> SEQUENCE: 12

Met Ser Thr Lys Thr Val Val Pro Leu Arg Arg Arg Ser Lys Pro Leu
1               5                   10                  15

Asn Gly Asn His Thr Asn Gly Val Ala Ile Asp Gly Ser Leu Asp Asp
            20                  25                  30

Asp His Asn Arg Arg Ile Gly Ser Val Asn Ser Gln Met Asp Asn Ile
        35                  40                  45

Ala Lys Lys Thr Asp Asp Gly Tyr Ala Asn Gly Gly Gly Gly Gly Gly
    50                  55                  60

Gly Gly Lys Ser Lys Ala Ser Phe Met Thr Trp Thr Ala Arg Asp Val
65                  70                  75                  80

Val Tyr Val Ala Arg Tyr His Trp Ile Pro Cys Leu Phe Ala Val Gly
                85                  90                  95

Val Leu Phe Phe Thr Gly Val Glu Tyr Thr Leu Gln Met Ile Pro Ala
            100                 105                 110

Arg Ser Glu Pro Phe Asp Ile Gly Phe Val Ala Thr Arg Ser Leu Asn
        115                 120                 125

Arg Val Leu Ala Asn Ser Pro Asp Leu Asn Thr Val Leu Ala Ala Leu
    130                 135                 140

Asn Thr Asp Phe Leu Gly Ser Gly Val Asp Phe Pro Val Gly Asn Val
145                 150                 155                 160

Ser Phe Phe Leu Phe Tyr Ser Gly His Val Ala Gly Ser Met Ile Ala
                165                 170                 175

Ser Leu Asp Ile Arg Arg Met Gln Arg Met Arg Leu Ala Met Leu Phe
            180                 185                 190

```
Asp Ile Leu Asn Val Leu Gln Ser Ile Arg Leu Gly Thr Arg Gly
        195                 200                 205

His Tyr Thr Ile Asp Leu Ala Val Gly Val Gly Ala Gly Ile Leu Phe
    210                 215                 220

Asp Ser Phe Ala Gly Lys Tyr Glu Glu Met Ile Ser Lys Arg His Asn
225                 230                 235                 240

Leu Val Asn Gly Phe Gly Leu Ile Ser Lys Asp Ser Leu Val Asn
                245                 250                 255

<210> SEQ ID NO 13
<211> LENGTH: 2146
<212> TYPE: DNA
<213> ORGANISM: artificial
<220> FEATURE:
<223> OTHER INFORMATION: modified ROD1 coding sequence

<400> SEQUENCE: 13
```

| | | | | | |
|---|---|---|---|---|---|
| atgtcaacta | aaaccgtcgt | ccctctccgt | cgcagatcta | agccccttaa | cggaaatcac | 60 |
| actaacggcg | tcgccattga | cggaagcctc | gacgacgacc | acaaccgtcg | catcggatca | 120 |
| gtaaatagcc | aaatggataa | cattgctaag | aaaacggacg | acggctacgc | aaacggcgga | 180 |
| ggaggaggag | gaggagggaa | aagcaaggcg | tcgtttatga | cgtggacggc | gcgtgacgtt | 240 |
| gtgtacgtgg | cgaggtacca | ttggataccg | tgtttgttcg | cggtcggggt | tctgttcttc | 300 |
| acgggcgtgg | agtacacgct | ccagatgatt | cccgcgaggt | ctgagccgtt | cgatattggg | 360 |
| tttgtggcca | cgcgctctct | gaatcgcgtc | ttggcaaatt | caccggatct | taacaccgtc | 420 |
| ttagccgctc | taaacacggt | aatttcgtac | taattaattt | agggtaaaaa | atatagtatt | 480 |
| taataatgac | tatcctcaat | tcctttcatg | cttcacctaa | tattttgttt | tttttcgttg | 540 |
| tcattaaaat | cgtaataata | tattgagtta | gtcaaatgaa | aaaacaagt | ggcggtagtg | 600 |
| attggaaaca | aatctcagat | cttttatctg | tttaataagg | tatttaatta | tccagctgga | 660 |
| attatgctgt | caagtgtcaa | cacagtagta | gtaacatgca | atggaatttc | tcaatagaaa | 720 |
| aaggtcttaa | ttagtataga | taattagtgg | acaaaaatgt | agttaatgta | atctcttttgc | 780 |
| taagtagtta | tcataatcat | cttttttaaca | actgccattt | tgtctgtgtg | tttgttttac | 840 |
| aacgaagtag | tagtagaata | gatcgctttt | tagcttttga | agtttcgaa | cccaaggaaa | 900 |
| agggacacat | gggttatgag | ttggagacac | gatcacatgc | aaacagagag | attggttaaa | 960 |
| ttatcgactt | tttgtagtac | ttttttaaaaa | aaaactattt | atataaaaaa | catggtggat | 1020 |
| ggtggggaca | ggtgttcgta | gggatgcaaa | cgacgtatat | tgtatggaca | tggttaatgg | 1080 |
| aaggacgacc | acgagccacc | atctcggctt | gcttcatgtt | tacttgtcga | ggcattcttg | 1140 |
| gttactctac | tcagctccct | cttcctcagg | ttccaatcaa | cactttctct | ctatctcttt | 1200 |
| tcttaattaa | aataattacc | aattaactaa | atgctaatca | gtcgatatat | catagttcca | 1260 |
| acgttttgga | cgtgtgattt | ccattggcca | ctaccatata | aaacaacaga | gtctctttat | 1320 |
| tcattattca | atatatattt | gagtattgat | attattcata | gggaggtttc | atttgtacta | 1380 |
| tcaataaaat | ttctacaact | cttggatttt | ttctgctaca | ttttgtagtt | atttttttaa | 1440 |
| ttacttttaa | aaacttgtga | ataggagaga | ctaaagtag | tacgtaatat | gattgtatca | 1500 |
| aatgctttaa | catgtgggt | ttgggttaac | tatcatcatt | tcatagatca | ctattttgtt | 1560 |
| ttcgtttgtt | acctaactt | ttgttatctt | tgaaaaataa | tgttccacga | gttgattgac | 1620 |
| tggacataaa | aatcagattc | tctcactcat | ttacgttcta | cggttctagc | cactcgtttt | 1680 |

```
tttcttttc  tttctgtggt  gtaacacgta  gataatggat  tttctatgtg  tgtcgtcttg   1740
ctcaagaata  ataaatgtgg  ttaaaggtta  aatatagctc  tggaaattaa  ttatctcctc   1800
tttttttatt  aaccaggatt  ttctaggatc  aggtgtcgat  tttccggtgg  gaaacgtctc   1860
gttcttcctc  ttctactcgg  gtcacgtcgc  cggttcgatg  atcgcatctt  tggacatgag   1920
gagaatgcag  aggatgagac  tagcgatgct  ttttgacatc  ctcaatgtat  tacaatcgat   1980
caagctgctc  gggacgagag  gacactacac  gattgatctc  gctgtcggag  ttggcgctgg   2040
gattctcttt  gattcattcg  ccggcaagta  cgaagagatg  ataagcaaga  gacacaattt   2100
agtcaatggt  tttggtttga  tttcgaaaga  ctcgctagtc  aattaa                   2146
```

<210> SEQ ID NO 14
<211> LENGTH: 255
<212> TYPE: PRT
<213> ORGANISM: artificial
<220> FEATURE:
<223> OTHER INFORMATION: modified ROD1 polypeptide

<400> SEQUENCE: 14

```
Met Ser Thr Lys Thr Val Val Pro Leu Arg Arg Ser Lys Pro Leu
1               5                   10                  15

Asn Gly Asn His Thr Asn Gly Val Ala Ile Asp Gly Ser Leu Asp Asp
            20                  25                  30

Asp His Asn Arg Arg Ile Gly Ser Val Asn Ser Gln Met Asp Asn Ile
        35                  40                  45

Ala Lys Lys Thr Asp Asp Gly Tyr Ala Asn Gly Gly Gly Gly Gly
    50                  55                  60

Gly Gly Lys Ser Lys Ala Ser Phe Met Thr Trp Thr Ala Arg Asp Val
65                  70                  75                  80

Val Tyr Val Ala Arg Tyr His Trp Ile Pro Cys Leu Phe Ala Val Gly
                85                  90                  95

Val Leu Phe Phe Thr Gly Val Glu Tyr Thr Leu Gln Met Ile Pro Ala
            100                 105                 110

Arg Ser Glu Pro Phe Asp Ile Gly Phe Val Ala Thr Arg Ser Leu Asn
        115                 120                 125

Arg Val Leu Ala Asn Ser Pro Asp Leu Asn Thr Val Leu Ala Ala Leu
    130                 135                 140

Asn Thr Asp Phe Leu Gly Ser Gly Val Asp Phe Pro Val Gly Asn Val
145                 150                 155                 160

Ser Phe Phe Leu Phe Tyr Ser Gly His Val Ala Gly Ser Met Ile Ala
                165                 170                 175

Ser Leu Asp Met Arg Arg Met Gln Arg Met Arg Leu Ala Met Leu Phe
            180                 185                 190

Asp Ile Leu Asn Val Leu Gln Ser Ile Lys Leu Leu Gly Thr Arg Gly
        195                 200                 205

His Tyr Thr Ile Asp Leu Ala Val Gly Val Gly Ala Gly Ile Leu Phe
    210                 215                 220

Asp Ser Phe Ala Gly Lys Tyr Glu Glu Met Ile Ser Lys Arg His Asn
225                 230                 235                 240

Leu Val Asn Gly Phe Gly Leu Ile Ser Lys Asp Ser Leu Val Asn
                245                 250                 255
```

<210> SEQ ID NO 15
<211> LENGTH: 1521
<212> TYPE: DNA
<213> ORGANISM: Thlaspi arvense

<400> SEQUENCE: 15

```
atgacgtccg ttaacgttaa gctcctttac cattacgtca tcaccaactt tttcaacctt      60
tgcttcttcc cgttagcggc gatcgttgcc ggaaaagcct ctcggcttac cacaaacgat     120
cttcaccact tctactattc ctatctccaa cacaacctaa taaccatatc tctactcttt     180
gccttcaccg ttttcggttt ggctctctac atcgtaaccc ggcccaaacc ggtttacctc     240
gttgaccatt cctgctacct tccaccatcg catcttagaa gcagtatctc taaggtcatg     300
gatatcttct atcaagtaag attagccgat cctttacgga acgcggcaag cgatgattcg     360
tcctggcttg atttcttgag gaagattcag gagcggtctg gtctaggcga tgaaacccac     420
ggccccgagg gactgcttca ggtccctcca cggaagactt tgccgcggc gcgtgaagaa      480
acagagcaag tgatcatcgg tgcgctcgaa aaactattcg agaacaccaa agttaaccct     540
aaagagattg gtatacttgt ggtgaactca agcatgttta atccgactcc ttcgctctcg     600
gcgatggttg ttaatacttt caagctccga agcaacatca gaagctttaa tcttggagga     660
atgggttgta gtgccggcgt tatagccatt gatctggcta aggacttgtt gcatgtccat     720
aaaaacactt atgctcttgt ggtgagcaca gagaacatca cttacaacat ttatgctggt     780
gataacagat ccatgatggt ttcgaattgc ttgttccgtg ttggtggggc cgcgattttg     840
ctctccaaca agccgaggga ccggagacgg tccaagtacc agctacttca cacgttcgg      900
acgcataccg gagctgacga caagtctttc cgatgtgtgc aacaagaaga cgacgagagc     960
ggtaaaaccg gggtgtgttt gtccaaggac ataaccggtg ttgccgggag aactgttcag    1020
aaaaacataa caacattggg tccgttggtt cttccttta gcgagaaatt tcttttttc     1080
gttaccttca tcgccaagaa actctttaaa gacaagatca aacattacta cgtcccggat    1140
ttcaagcttg ctatcgacca tttttgtatt catgccggag gcagagccgt gatcgatgtg    1200
ctacagaaga acttaggtct attgccgatc gatgtggagg catctaggtc aacgttacat    1260
agatttggga acacttcgtc tagctcaatt tggtatgaat tggcgtacat agaggcaaaa    1320
ggaaggatga agagagggaa caaagtttgg cagattgctt tagggtcagg gtttaagtgt    1380
aatagtgcgg tttgggtggc tctacgcaat gtcaaggctt cgacaaatag tccttgggaa    1440
cattgcattg atagatatcc agatgcaatt gattctgatt cgggtaagtc agagactcgt    1500
gtccaaaacg gtcggtccta a                                              1521
```

<210> SEQ ID NO 16
<211> LENGTH: 506
<212> TYPE: PRT
<213> ORGANISM: Thlaspi arvense

<400> SEQUENCE: 16

```
Met Thr Ser Val Asn Val Lys Leu Leu Tyr His Tyr Val Ile Thr Asn
1               5                   10                  15

Phe Phe Asn Leu Cys Phe Phe Pro Leu Ala Ala Ile Val Ala Gly Lys
            20                  25                  30

Ala Ser Arg Leu Thr Thr Asn Asp Leu His His Phe Tyr Tyr Ser Tyr
        35                  40                  45

Leu Gln His Asn Leu Ile Thr Ile Ser Leu Leu Phe Ala Phe Thr Val
    50                  55                  60

Phe Gly Leu Ala Leu Tyr Ile Val Thr Arg Pro Lys Pro Val Tyr Leu
65                  70                  75                  80

Val Asp His Ser Cys Tyr Leu Pro Pro Ser His Leu Arg Ser Ser Ile
```

```
                     85                  90                  95
Ser Lys Val Met Asp Ile Phe Tyr Gln Val Arg Leu Ala Asp Pro Leu
                100                 105                 110

Arg Asn Ala Ala Ser Asp Asp Ser Ser Trp Leu Asp Phe Leu Arg Lys
                115                 120                 125

Ile Gln Glu Arg Ser Gly Leu Gly Asp Glu Thr His Gly Pro Glu Gly
                130                 135                 140

Leu Leu Gln Val Pro Pro Arg Lys Thr Phe Ala Ala Arg Glu Glu
145                 150                 155                 160

Thr Glu Gln Val Ile Ile Gly Ala Leu Glu Lys Leu Phe Glu Asn Thr
                165                 170                 175

Lys Val Asn Pro Lys Glu Ile Gly Ile Leu Val Val Asn Ser Ser Met
                180                 185                 190

Phe Asn Pro Thr Pro Ser Leu Ser Ala Met Val Val Asn Thr Phe Lys
                195                 200                 205

Leu Arg Ser Asn Ile Arg Ser Phe Asn Leu Gly Gly Met Gly Cys Ser
                210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
                260                 265                 270

Arg Val Gly Gly Ala Ala Ile Leu Leu Ser Asn Lys Pro Arg Asp Arg
                275                 280                 285

Arg Arg Ser Lys Tyr Gln Leu Leu His Thr Val Arg Thr His Thr Gly
                290                 295                 300

Ala Asp Asp Lys Ser Phe Arg Cys Val Gln Gln Glu Asp Asp Glu Ser
305                 310                 315                 320

Gly Lys Thr Gly Val Cys Leu Ser Lys Asp Ile Thr Gly Val Ala Gly
                325                 330                 335

Arg Thr Val Gln Lys Asn Ile Thr Thr Leu Gly Pro Leu Val Leu Pro
                340                 345                 350

Phe Ser Glu Lys Phe Leu Phe Phe Val Thr Phe Ile Ala Lys Lys Leu
                355                 360                 365

Phe Lys Asp Lys Ile Lys His Tyr Tyr Val Pro Asp Phe Lys Leu Ala
                370                 375                 380

Ile Asp His Phe Cys Ile His Ala Gly Gly Arg Ala Val Ile Asp Val
385                 390                 395                 400

Leu Gln Lys Asn Leu Gly Leu Leu Pro Ile Asp Val Glu Ala Ser Arg
                405                 410                 415

Ser Thr Leu His Arg Phe Gly Asn Thr Ser Ser Ser Ile Trp Tyr
                420                 425                 430

Glu Leu Ala Tyr Ile Glu Ala Lys Gly Arg Met Lys Arg Gly Asn Lys
                435                 440                 445

Val Trp Gln Ile Ala Leu Gly Ser Gly Phe Lys Cys Asn Ser Ala Val
                450                 455                 460

Trp Val Ala Leu Arg Asn Val Lys Ala Ser Thr Asn Ser Pro Trp Glu
465                 470                 475                 480

His Cys Ile Asp Arg Tyr Pro Asp Ala Ile Asp Ser Asp Ser Gly Lys
                485                 490                 495

Ser Glu Thr Arg Val Gln Asn Gly Arg Ser
                500                 505
```

<210> SEQ ID NO 17
<211> LENGTH: 1521
<212> TYPE: DNA
<213> ORGANISM: artificial
<220> FEATURE:
<223> OTHER INFORMATION: modified FAE1 coding sequence

<400> SEQUENCE: 17

```
atgacgtccg ttaacgttaa gctcctttac cattacgtca tcaccaactt tttcaacctt      60
tgcttcttcc cgttagcggc gatcgttgcc ggaaaagcct ctcggcttac cacaaacgat     120
cttcaccact tctactattc ctatctccaa cacaacctaa taccatatc tctactcttt      180
gccttcaccg ttttcggttt ggctctctac atcgtaaccc ggcccaaacc ggtttacctc     240
gttgaccatt cctgctacct tccaccatcg catcttagaa gcagtatctc taaggtcatg     300
gatatcttct atcaagtaag attagccgat cctttacgga acgcggcaag cgatgattcg     360
tcctggcttg atttcttgag gaagattcag gagcggtctg gtctaggcga tgaaacccac     420
ggccccgagg gactgcttca ggtccctcca cggaagactt ttgccgcggc gcgtgaagaa     480
acagagcaag tgatcatcgg tgcgctcgaa aaactattcg agaacaccaa agttaaccct     540
aaagagattg gtatacttgt ggtgaactca agcatgttta atccgactcc ttcgctctcg     600
gcgatggttg ttaatacttt caagctccga agcaacatca gaagctttaa tcttggagga     660
atgggttgta gtgccggcgt tatagccatt gatctggcta aggacttgtt gcatgtccat     720
aaaaacactt atgctcttgt ggtgagcaca gagaacatca cttacaacat ttatgctggt     780
gataacagat ccatgatggt ttcgaattgc ttgttccgtg ttggtggggc cgcgattttg     840
ctctccaaca agccgaggga ccggagacgg tccaagtacc agctacttca cacggttcgg     900
acgcataccg gagctgacga caagtctttc cgatgtgtgc aacaagaaga cgacgagagc     960
ggtaaaaccg gggtgtgttt gtccaaggac ataaccggtg ttgccgggag aactgtttag    1020
aaaaacataa caacattggg tccgttggtt cttcctttta gcgagaaatt tcttttttc     1080
gttaccttca tcgccaagaa actctttaaa gacaagatca acattacta cgtcccggat    1140
ttcaagcttg ctatcgacca tttttgtatt catgccggag gcagagccgt gatcgatgtg    1200
ctacagaaga acttaggtct attgccgatc gatgtggagg catctaggtc aacgttacat    1260
agatttggga cacttcgtc tagctcaatt tggtatgaat tggcgtacat agaggcaaaa     1320
ggaaggatga agagagggaa caaagtttgg cagattgctt tagggtcagg gtttaagtgt    1380
aatagtgcgc tttgggtggc tctacgcaat gtcaaggctt cgacaaatag tccttgggaa    1440
cattgcattg atagatatcc agatgcaatt gattctgatt cgggtaagtc agagactcgt    1500
gtccaaaacg gtcggtccta a                                              1521
```

<210> SEQ ID NO 18
<211> LENGTH: 339
<212> TYPE: PRT
<213> ORGANISM: artificial
<220> FEATURE:
<223> OTHER INFORMATION: modified FAE1 polypeptide

<400> SEQUENCE: 18

```
Met Thr Ser Val Asn Val Lys Leu Leu Tyr His Tyr Val Ile Thr Asn
1               5                   10                  15

Phe Phe Asn Leu Cys Phe Phe Pro Leu Ala Ala Ile Val Ala Gly Lys
            20                  25                  30
```

```
Ala Ser Arg Leu Thr Thr Asn Asp Leu His His Phe Tyr Tyr Ser Tyr
         35                  40                  45

Leu Gln His Asn Leu Ile Thr Ile Ser Leu Leu Phe Ala Phe Thr Val
 50                  55                  60

Phe Gly Leu Ala Leu Tyr Ile Val Thr Arg Pro Lys Pro Val Tyr Leu
 65                  70                  75                  80

Val Asp His Ser Cys Tyr Leu Pro Pro Ser His Leu Arg Ser Ser Ile
                 85                  90                  95

Ser Lys Val Met Asp Ile Phe Tyr Gln Val Arg Leu Ala Asp Pro Leu
            100                 105                 110

Arg Asn Ala Ala Ser Asp Asp Ser Ser Trp Leu Asp Phe Leu Arg Lys
        115                 120                 125

Ile Gln Glu Arg Ser Gly Leu Gly Asp Glu Thr His Gly Pro Glu Gly
    130                 135                 140

Leu Leu Gln Val Pro Pro Arg Lys Thr Phe Ala Ala Arg Glu Glu
145                 150                 155                 160

Thr Glu Gln Val Ile Ile Gly Ala Leu Glu Lys Leu Phe Glu Asn Thr
                165                 170                 175

Lys Val Asn Pro Lys Glu Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Ile Arg Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Arg Asp Arg
        275                 280                 285

Arg Arg Ser Lys Tyr Gln Leu Leu His Thr Val Arg Thr His Thr Gly
    290                 295                 300

Ala Asp Asp Lys Ser Phe Arg Cys Val Gln Gln Glu Asp Asp Glu Ser
305                 310                 315                 320

Gly Lys Thr Gly Val Cys Leu Ser Lys Asp Ile Thr Gly Val Ala Gly
                325                 330                 335

Arg Thr Val

<210> SEQ ID NO 19
<211> LENGTH: 388
<212> TYPE: PRT
<213> ORGANISM: Oryza sativa

<400> SEQUENCE: 19

Met Gly Ala Gly Gly Arg Met Thr Glu Lys Glu Arg Glu Glu Gln Gln
1               5                   10                  15

Lys Leu Leu Gly Arg Ala Gly Asn Gly Ala Ala Val Gln Arg Ser Pro
            20                  25                  30

Thr Asp Lys Pro Pro Phe Thr Leu Gly Gln Ile Lys Lys Ala Ile Pro
        35                  40                  45

Pro His Cys Phe Gln Arg Ser Val Ile Lys Ser Phe Ser Tyr Val Val
    50                  55                  60
```

-continued

His Asp Leu Val Ile Val Ala Ala Leu Leu Tyr Phe Ala Leu Val Met
 65                  70                  75                  80

Ile Pro Val Leu Pro Ser Gly Met Glu Phe Ala Ala Trp Pro Leu Tyr
                 85                  90                  95

Trp Ile Ala Gln Gly Cys Val Leu Thr Gly Val Trp Val Ile Ala His
            100                 105                 110

Glu Cys Gly His His Ala Phe Ser Asp Tyr Ser Val Leu Asp Asp Ile
        115                 120                 125

Val Gly Leu Val Leu His Ser Ser Leu Leu Val Pro Tyr Phe Ser Trp
    130                 135                 140

Lys Tyr Ser His Arg Arg His His Ser Asn Thr Gly Ser Leu Glu Arg
145                 150                 155                 160

Asp Glu Val Phe Val Pro Lys Gln Lys Ser Ala Met Ala Trp Tyr Thr
                165                 170                 175

Pro Tyr Val Tyr His Asn Pro Ile Gly Arg Leu Val His Ile Phe Val
            180                 185                 190

Gln Leu Thr Leu Gly Trp Pro Leu Tyr Leu Ala Phe Asn Val Ser Gly
        195                 200                 205

Arg Pro Tyr Pro Arg Phe Ala Cys His Phe Asp Pro Tyr Gly Pro Ile
    210                 215                 220

Tyr Asn Asp Arg Glu Arg Val Gln Ile Phe Ile Ser Asp Val Gly Val
225                 230                 235                 240

Val Ser Ala Gly Leu Ala Leu Phe Lys Leu Ser Ser Ala Phe Gly Phe
                245                 250                 255

Trp Trp Val Val Arg Val Tyr Gly Val Pro Leu Leu Ile Val Asn Ala
            260                 265                 270

Trp Leu Val Leu Ile Thr Tyr Leu Gln His Thr His Pro Ala Leu Pro
        275                 280                 285

His Tyr Asp Ser Ser Glu Trp Asp Trp Leu Arg Gly Ala Leu Ala Thr
    290                 295                 300

Val Asp Arg Asp Tyr Gly Ile Leu Asn Lys Val Phe His Asn Ile Thr
305                 310                 315                 320

Asp Thr His Val Ala His His Leu Phe Ser Thr Met Pro His Tyr His
                325                 330                 335

Ala Met Glu Ala Thr Lys Ala Ile Arg Pro Ile Leu Gly Glu Tyr Tyr
            340                 345                 350

Gln Phe Asp Pro Thr Pro Val Ala Lys Ala Thr Trp Arg Glu Ala Lys
        355                 360                 365

Glu Cys Ile Tyr Val Glu Pro Glu Asp Asn Lys Gly Val Phe Trp Tyr
    370                 375                 380

Asn Asn Lys Phe
385

<210> SEQ ID NO 20
<211> LENGTH: 383
<212> TYPE: PRT
<213> ORGANISM: Glycine max

<400> SEQUENCE: 20

Met Gly Ala Gly Gly Arg Thr Ala Val Pro Ala Asn Arg Lys Ser
1               5                   10                  15

Glu Ala Asp Pro Leu Lys Arg Val Pro Phe Glu Lys Pro Gln Phe Ser
                20                  25                  30

Leu Ser Gln Ile Lys Lys Ala Ile Pro Pro His Cys Phe Gln Arg Ser
        35                  40                  45

Val Leu Arg Ser Phe Ser Tyr Val Tyr Asp Leu Thr Ile Ala Phe
 50                  55                  60

Cys Leu Tyr Tyr Val Ala Thr His Tyr Phe His Leu Leu Pro Gly Pro
 65                  70                  75                  80

Leu Ser Phe Val Ala Trp Pro Ile Tyr Trp Ala Val Gln Gly Cys Ile
                 85                  90                  95

Leu Thr Gly Val Trp Val Ile Ala His Glu Cys Gly His His Ala Phe
            100                 105                 110

Ser Asp Tyr Gln Leu Leu Asp Asp Ile Val Gly Leu Ile Leu His Ser
        115                 120                 125

Ala Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Gln Lys Ser Ser Ile Met Trp Tyr Ser Lys Tyr Leu Asn Asn Pro Pro
                165                 170                 175

Gly Arg Val Leu Thr Leu Ala Val Thr Leu Thr Leu Gly Trp Pro Leu
            180                 185                 190

Tyr Leu Ala Phe Asn Val Ser Gly Arg Pro Tyr Asp Arg Phe Ala Cys
        195                 200                 205

His Tyr Asp Pro Tyr Gly Pro Ile Tyr Ser Asp Arg Glu Arg Leu Gln
210                 215                 220

Ile Tyr Ile Ser Asp Ala Gly Val Leu Ala Val Cys Tyr Gly Leu Phe
225                 230                 235                 240

Cys Leu Ala Met Ala Lys Gly Leu Ala Trp Val Cys Val Tyr Gly
                245                 250                 255

Val Pro Leu Leu Val Val Asn Gly Phe Leu Val Leu Ile Thr Phe Leu
            260                 265                 270

Gln His Thr His Pro Ala Leu Pro His Tyr Thr Ser Ser Glu Trp Asp
        275                 280                 285

Trp Leu Arg Gly Ala Leu Ala Thr Val Asp Arg Asp Tyr Gly Ile Leu
290                 295                 300

Asn Lys Val Phe His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Glu Tyr Tyr Arg Phe Asp Gly Thr Pro Phe Val
            340                 345                 350

Lys Ala Met Trp Arg Glu Ala Arg Glu Cys Ile Tyr Val Glu Pro Asp
        355                 360                 365

Gln Ser Thr Gln Ser Lys Gly Val Phe Trp Tyr Asn Asn Lys Leu
370                 375                 380

<210> SEQ ID NO 21
<211> LENGTH: 383
<212> TYPE: PRT
<213> ORGANISM: Arabidopsis thaliana

<400> SEQUENCE: 21

Met Gly Ala Gly Gly Arg Met Pro Val Pro Thr Ser Ser Lys Lys Ser
1               5                   10                  15

Glu Thr Asp Thr Thr Lys Arg Val Pro Cys Glu Lys Pro Pro Phe Ser
            20                  25                  30

Val Gly Asp Leu Lys Lys Ala Ile Pro Pro His Cys Phe Lys Arg Ser

```
            35                  40                  45
Ile Pro Arg Ser Phe Ser Tyr Leu Ile Ser Asp Ile Ile Ala Ser
 50                  55                  60

Cys Phe Tyr Tyr Val Ala Thr Asn Tyr Phe Ser Leu Leu Pro Gln Pro
 65                  70                  75                  80

Leu Ser Tyr Leu Ala Trp Pro Leu Tyr Trp Ala Cys Gln Gly Cys Val
                 85                  90                  95

Leu Thr Gly Ile Trp Val Ile Ala His Glu Cys Gly His His Ala Phe
            100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Leu
                165                 170                 175

Gly Arg Ile Met Met Leu Thr Val Gln Phe Val Leu Gly Trp Pro Leu
            180                 185                 190

Tyr Leu Ala Phe Asn Val Ser Gly Arg Pro Tyr Asp Gly Phe Ala Cys
            195                 200                 205

His Phe Phe Pro Asn Ala Pro Ile Tyr Asn Asp Arg Glu Arg Leu Gln
210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
                245                 250                 255

Val Pro Leu Leu Ile Val Asn Ala Phe Leu Val Leu Ile Thr Tyr Leu
            260                 265                 270

Gln His Thr His Pro Ser Leu Pro His Tyr Asp Ser Ser Glu Trp Asp
            275                 280                 285

Trp Leu Arg Gly Ala Leu Ala Thr Val Asp Arg Asp Tyr Gly Ile Leu
290                 295                 300

Asn Lys Val Phe His Asn Ile Thr Asp Thr His Val Ala His His Leu
305                 310                 315                 320

Phe Ser Thr Met Pro His Tyr Asn Ala Met Glu Ala Thr Lys Ala Ile
                325                 330                 335

Lys Pro Ile Leu Gly Asp Tyr Tyr Gln Phe Asp Gly Thr Pro Trp Tyr
            340                 345                 350

Val Ala Met Tyr Arg Glu Ala Lys Glu Cys Ile Tyr Val Glu Pro Asp
            355                 360                 365

Arg Glu Gly Asp Lys Lys Gly Val Tyr Trp Tyr Asn Asn Lys Leu
370                 375                 380

<210> SEQ ID NO 22
<211> LENGTH: 307
<212> TYPE: PRT
<213> ORGANISM: Oryza sativa

<400> SEQUENCE: 22

Met Pro Pro Pro Pro Pro Ser Leu Thr Ala Asn Thr Ala Ser Ser
 1               5                  10                  15

Met Gly Asn Ala Glu Ala Val Val Val Leu Pro Ala Asn Gly Gly Ala
                20                  25                  30
```

```
Arg Arg Arg Ala Asp Lys Val Val His Pro Ala Pro Met Pro Asp Arg
            35                  40                  45

Ala Ala Gly Gly Ala Met Glu Arg Gly Gly Val Gly Gly Gly
 50                  55                  60

Gly Glu Val Gly Gly Trp Arg Arg Pro Glu Trp Cys Ser Ala Ala Gly
 65                  70                  75                  80

Val Ala Gly Val Leu Arg Arg His Pro Ala Ala Ala Phe Gly Cys
                 85                  90                  95

Gly Leu Leu Leu Phe Met Ala Val Glu Tyr Thr Ile Pro Met Val Pro
            100                 105                 110

Pro Ala Ala Pro Pro Val Asp Leu Gly Phe Ala Ala Thr Ala Ala Leu
            115                 120                 125

His Ala Gly Ile Ala Ala Arg Pro Trp Leu Asn Ser Leu Leu Ala Ala
            130                 135                 140

Leu Asn Thr Val Phe Val Ala Met Gln Ala Ala Tyr Ile Leu Trp Ala
145                 150                 155                 160

Ile Leu Gly Glu Gly Arg Pro Arg Ala Ala Val Ala Ala Met Met Met
                165                 170                 175

Phe Thr Cys Arg Gly Ala Leu Gly Cys Ala Thr Gln Leu Pro Leu Pro
            180                 185                 190

Ala Glu Phe Leu Gly Ser Gly Met Asp Phe Pro Val Gly Asn Val Ser
            195                 200                 205

Phe Phe Leu Phe Phe Ser Gly His Val Ala Gly Ala Val Ile Ala Ala
            210                 215                 220

Glu Asp Met Arg Arg Ala Gly Arg Arg Gly Met Ala Arg Leu Tyr Asp
225                 230                 235                 240

Ala Leu Asn Leu Leu Gln Gly Val Arg Leu Leu Ala Cys Arg Gly His
                245                 250                 255

Tyr Thr Ile Asp Leu Ala Val Gly Val Gly Ala Gly Leu Leu Phe Asp
            260                 265                 270

Met Leu Ala Gly Arg Tyr Leu Asp Gly Lys Asn Thr Val Asp Gly Gly
            275                 280                 285

Ala Ala Val Ala Pro Gly Ser Arg Cys Cys Ser Cys His Lys Ala Leu
            290                 295                 300

Leu Ser Gln
305

<210> SEQ ID NO 23
<211> LENGTH: 267
<212> TYPE: PRT
<213> ORGANISM: Glycine max

<400> SEQUENCE: 23

Met Asn Gly Gly Ala Glu Ala Ser Leu Asn His Arg Arg Lys His Gln
1               5                   10                  15

Thr Ala Pro Ala Asp Gly Ala Lys Gly Val Lys Val Ala Asn Gly Ala
            20                  25                  30

Met Gly Lys Pro Ser Ser Ser Lys His Ser Cys Gly Ala Ser Phe Met
            35                  40                  45

Lys Trp Thr Val Ala Asp Ala Val His Val Val Thr His His Trp Met
 50                  55                  60

Pro Cys Leu Phe Ala Leu Gly Leu Leu Phe Phe Met Ala Val Glu Tyr
 65                  70                  75                  80

Thr Leu Leu Met Val Pro Pro Ser Ser Pro Pro Phe Asp Leu Gly Phe
                85                  90                  95
```

```
Ile Ala Thr Arg Ser Leu His Ala Leu Leu Glu Ser Ser Pro Asn Leu
                100                 105                 110

Asn Thr Leu Phe Ala Gly Leu Asn Thr Val Phe Val Gly Met Gln Thr
            115                 120                 125

Ser Tyr Ile Leu Trp Thr Trp Leu Ile Glu Gly Arg Pro Arg Ala Thr
        130                 135                 140

Ile Ser Ala Leu Phe Met Phe Thr Cys Arg Gly Ile Leu Gly Tyr Ser
145                 150                 155                 160

Thr Gln Leu Pro Leu Pro Gln Gly Phe Leu Gly Ser Gly Val Asp Phe
                165                 170                 175

Pro Val Gly Asn Val Ser Phe Phe Leu Phe Phe Ser Gly His Val Ala
            180                 185                 190

Gly Ser Val Ile Ala Ser Leu Asp Met Arg Arg Met Gln Arg Trp Glu
        195                 200                 205

Leu Ala Trp Thr Phe Asp Val Leu Asn Val Leu Gln Ala Val Arg Leu
210                 215                 220

Leu Gly Thr Arg Gly His Tyr Thr Ile Asp Leu Ala Val Gly Val Gly
225                 230                 235                 240

Ala Gly Ile Leu Phe Asp Ser Leu Ala Gly Lys Tyr Glu Asp Ser Lys
                245                 250                 255

Arg Asn Gly Ala Leu Lys His Asn Leu Ile Ala
            260                 265

<210> SEQ ID NO 24
<211> LENGTH: 301
<212> TYPE: PRT
<213> ORGANISM: Arabidopsis thaliana

<400> SEQUENCE: 24

Met Ser Ala Ala Ala Glu Thr Asp Val Ser Leu Arg Arg Arg Ser
1               5                   10                  15

Asn Ser Leu Asn Gly Asn His Thr Asn Gly Val Ala Ile Asp Gly Thr
            20                  25                  30

Leu Asp Asn Asn Arg Arg Val Gly Asp Thr Asn Thr His Met Asp
        35                  40                  45

Ile Ser Ala Lys Lys Thr Asp Asn Gly Tyr Ala Asn Gly Val Gly Gly
50                  55                  60

Gly Gly Trp Arg Ser Lys Ala Ser Phe Thr Thr Trp Thr Ala Arg Asp
65                  70                  75                  80

Ile Val Tyr Val Val Arg Tyr His Trp Ile Pro Cys Met Phe Ala Ala
                85                  90                  95

Gly Leu Leu Phe Phe Met Gly Val Glu Tyr Thr Leu Gln Met Ile Pro
            100                 105                 110

Ala Arg Ser Glu Pro Phe Asp Leu Gly Phe Val Val Thr Arg Ser Leu
        115                 120                 125

Asn Arg Val Leu Ala Ser Ser Pro Asp Leu Asn Thr Val Leu Ala Ala
130                 135                 140

Leu Asn Thr Val Phe Val Gly Met Gln Thr Thr Tyr Ile Val Trp Thr
145                 150                 155                 160

Trp Leu Val Glu Gly Arg Ala Arg Ala Thr Ile Ala Ala Leu Phe Met
                165                 170                 175

Phe Thr Cys Arg Gly Ile Leu Gly Tyr Ser Thr Gln Leu Pro Leu Pro
            180                 185                 190

Gln Asp Phe Leu Gly Ser Gly Val Asp Phe Pro Val Gly Asn Val Ser
```

```
                195                 200                 205
Phe Phe Leu Phe Phe Ser Gly His Val Ala Gly Ser Met Ile Ala Ser
    210                 215                 220

Leu Asp Met Arg Arg Met Gln Arg Leu Arg Leu Ala Met Val Phe Asp
225                 230                 235                 240

Ile Leu Asn Val Leu Gln Ser Ile Arg Leu Leu Gly Thr Arg Gly His
                245                 250                 255

Tyr Thr Ile Asp Leu Ala Val Gly Val Gly Ala Gly Ile Leu Phe Asp
            260                 265                 270

Ser Leu Ala Gly Lys Tyr Glu Glu Met Met Ser Lys Arg His Leu Gly
        275                 280                 285

Thr Gly Phe Ser Leu Ile Ser Lys Asp Ser Leu Val Asn
    290                 295                 300
```

<210> SEQ ID NO 25
<211> LENGTH: 1215
<212> TYPE: DNA
<213> ORGANISM: Thlaspi arvense

<400> SEQUENCE: 25

```
atgtctaaat tgataaaat atatgatgac gacaattccg gtggatcaca aaacatgggt    60
gcaggtggaa gaatgacggt tcctacttct tccaagaagt ctgaaaccga tgccttaaag   120
cgtgtgccgt gcgagaaacc gccgttcacg ctcggagaac tgaagaaagc aatcccacag   180
cattgtttca atcgctcaat ccctcgctct ttctcctacc ttatctggga catcatcata   240
gcctcttgct tctactacgt tgccaccact tacttctctc cctcccctca gcctctctct   300
tacttggctt ggcctctcta ttgggtctgt caaggctgtg tcttaaccgg agtctgggtc   360
atagctcacg aatgcggcca ccacgccttc agcgactacc aatggcttga cgacacagtc   420
ggtctgatct tccattcttt cctcctcgtc ccttacttct cctgaaaata cagccaccgc   480
cgtcaccatt ccaacaccgg atcacttgaa aaggacgaag tgtttgtccc taaacagaaa   540
tccgccatca aatggtacgg caagtacctc aacaaccctc tgggacgcac cgtgatgtta   600
accgtccagt tcacccttgg ctggcccttg tacttagcct tcaacgtctc ggggagaccc   660
tacgacgggt tcgcttgcca cttccaccca aacgctccca tctacaacga ccgtgaacgc   720
ctccagatat acatctcgga tgctggtatc ctcgccgtct gttacggtct ctaccgttac   780
gctgctgcac aaggagtggc ctcgatgatc tgcgtctacg gagttccgct tctgatagtc   840
aacgggttcc tcgtcttgat cacatacttg cagcacaccc atccctcgtt gcctcactac   900
gattcatccg agtgggattg gttcaggga gctttggcta ccgtagacag agactatgga   960
atcctgaaca aggtcttcca caacatcacg gacacgcacg tggctcacca cctgttctcg  1020
acgatgccgc attaccatgc gatggaggcc acgaaggcga taaagccgat actcggggac  1080
tattaccagt ttgatggaac accggtcttc aaggcgatgt ggagggaggc gaaggagtgt  1140
gtctatgtag aaccggacag gaaaggtgag aagaaagagg gaacaaaaga gaggaagaa   1200
aatgaagcaa agtaa                                                   1215
```

<210> SEQ ID NO 26
<211> LENGTH: 1215
<212> TYPE: DNA
<213> ORGANISM: artificial
<220> FEATURE:
<223> OTHER INFORMATION: modified FAD coding sequence

<400> SEQUENCE: 26

```
atgtctaaat tgataaaat atatgatgac gacaattccg gtggatcaca aaacatgggt    60
gcaggtggaa gaatgacggt tcctacttct tccaagaagt ctgaaaccaa tgccttaaag   120
cgtgtgccgt gcgagaaacc gccgttcacg ctcggagaac tgaagaaagc aatcccacag   180
cattgtttca atcgctcaat ccctcgctct ttctcctacc ttatctggga catcatcata   240
gcctcttgct tctactacgt tgccaccact tacttctctc cctccctca gcctctctct    300 tacttggctt ggcctctcta ttgggtctgt caaggctgtg tcttaaccgg agtctgggtc   360
atagctcacg aatgcggcca ccacgccttc agcgactacc aatggcttga cgacacagtc   420
ggtctgatct tccattcttt cctcctcgtc ccttacttct cctggaaata cagccaccgc   480
cgtcaccatt ccaacaccgg atcacttgaa aaggacgaag tgtttgtccc taaacagaaa   540
tccgccatca aatggtacgg caagtacctc aacaaccctc tgggacgcac cgtgatgtta   600
accgtccagt tcacccttgg ctggcccttg tacttagcct tcaacgtctc ggggagaccc   660
tacgacgggt tcgcttgcca cttccaccca aacgctccca tctacaacga ccgtgaacgc   720
ctccagatat acatctcgga tgctggtatc ctcgccgtct gttacggtct ctaccgttac   780
gctgctgcac aaggagtggc ctcgatgatc tgcgtctacg gagttccgct tctgatagtc   840
aacgggttcc tcgtcttgat cacatacttg cagcacaccc atccctcgtt gcctcactac   900
gattcatccg agtgggattg gttcagggga gctttggcta ccgtagacag agactatgga   960
atcctgaaca aggtcttcca caacatcacg gacacgcacg tggctcacca cctgttctcg  1020
acgatgccgc attaccatgc gatggaggcc acgaaggcga taaagccgat actcggggac  1080
tattaccagt ttgatggaac accggtcttc aaggcgatgt ggagggaggc gaaggagtgt  1140
gtctatgtag aaccggacag gaaaggtgag aagaaagagg gaacaaaaga agaggaagaa  1200
aatgaagcaa agtaa                                                   1215

<210> SEQ ID NO 27
<211> LENGTH: 1215
<212> TYPE: DNA
<213> ORGANISM: artificial
<220> FEATURE:
<223> OTHER INFORMATION: modified FAD coding sequence

<400> SEQUENCE: 27
atgtctaaat tgataaaat atatgatgac gacaattccg gtggatcaca aaacatgggt    60
gcaggtggaa gaatgacggt tcctacttct tccaagaagt ctgaaaccga tgccttaaag   120
cgtgtgccgt gcgagaaacc gccgttcacg ctcggagaac tgaagaaagc aatcccacag   180
cattgtttca atcgctcaat ccctcgctct ttctcctacc ttatctggga catcatcata   240
gcctcttgct tctactacgt tgccaccact tacttctctc cctccctca gcctctctct    300 tacttggctt ggcctctcta ttgggtctgt caaggctgtg tcttaaccgg agtctgggtc   360
atagctcacg aatgcggcca ccacgccttc agcgactacc aatggcttga cgacacagtc   420
gatctgatct tccattcttt cctcctcgtc ccttacttct cctggaaata cagccaccgc   480
cgtcaccatt ccaacaccgg atcacttgaa aaggacgaag tgtttgtccc taaacagaaa   540
tccgccatca aatggtacgg caagtacctc aacaaccctc tgggacgcac cgtgatgtta   600
accgtccagt tcacccttgg ctggcccttg tacttagcct tcaacgtctc ggggagaccc   660
tacgacgggt tcgcttgcca cttccaccca aacgctccca tctacaacga ccgtgaacgc   720
ctccagatat acatctcgga tgctggtatc ctcgccgtct gttacggtct ctaccgttac   780
```

| | |
|---|---|
| gctgctgcac aaggagtggc ctcgatgatc tgcgtctacg gagttccgct tctgatagtc | 840 |
| aacgggttcc tcgtcttgat cacatacttg cagcacaccc atccctcgtt gcctcactac | 900 |
| gattcatccg agtgggattg gttcagggga gctttggcta ccgtagacag agactatgga | 960 |
| atcctgaaca aggtcttcca caacatcacg gacacgcacg tggctcacca cctgttctcg | 1020 |
| acgatgccgc attaccatgc gatggaggcc acgaaggcga taaagccgat actcggggac | 1080 |
| tattaccagt ttgatggaac accggtcttc aaggcgatgt ggagggaggc gaaggagtgt | 1140 |
| gtctatgtag aaccggacag gaaaggtgag aagaaagagg gaacaaaaga agaggaagaa | 1200 |
| aatgaagcaa agtaa | 1215 |

<210> SEQ ID NO 28
<211> LENGTH: 1215
<212> TYPE: DNA
<213> ORGANISM: artificial
<220> FEATURE:
<223> OTHER INFORMATION: modified FAD coding sequence

<400> SEQUENCE: 28

| | |
|---|---|
| atgtctaaat ttgataaaat atatgatgac gacaattccg gtggatcaca aaacatgggt | 60 |
| gcaggtggaa gaatgacggt tcctacttct tccaagaagt ctgaaaccga tgccttaaag | 120 |
| cgtgtgccgt gcgagaaacc gccgttcacg ctcggagaac tgaagaaagc aatcccacag | 180 |
| cattgtttca atcgctcaat ccctcgctct ttctcctacc ttatctggga catcatcata | 240 |
| gcctcttgct tctactacgt tgccaccact tacttctctc tcctccctca gcctctctct | 300 |
| tacttggctt ggcctctcta ttgggtctgt caaggctgtg tcttaaccgg agtctgggtc | 360 |
| atagctcacg aatgcggcca ccacgccttc agcgactacc aatggcttga cgacacagtc | 420 |
| ggtctgatct tccattcttt cctcctcgtc ccttacttct cctggaaata cagccaccgc | 480 |
| cgtcaccatt ccaacaccgg atcacttgaa aaggacgaag tgtttgtccc taaacagaaa | 540 |
| tccgccatca atggtacggc caagtacctc aacaaccctc tgggacgcac cgtgatgtta | 600 |
| accgtccagt tcacccttgg ctggcccttg tacttagcct tcaacgtctc ggggagaccc | 660 |
| tacgacgggg tcgcttgcca cttccaccca aacgctccca tctacaacga ccgtgaacgc | 720 |
| ctccagatat acatctcgga tgctggtatc ctcgccgtct gttacggtct ctaccgttac | 780 |
| gctgctgcac aaggagtggc ctcgatgatc tgcgtctacg gagttccgct tctgatagtc | 840 |
| aacgggttcc tcgtcttgat cacatacttg cagcacaccc atccctcgtt gccttactac | 900 |
| gattcatccg agtgggattg gttcagggga gctttggcta ccgtagacag agactatgga | 960 |
| atcctgaaca aggtcttcca caacatcacg gacacgcacg tggctcacca cctgttctcg | 1020 |
| acgatgccgc attaccatgc gatggaggcc acgaaggcga taaagccgat actcggggac | 1080 |
| tattaccagt ttgatggaac accggtcttc aaggcgatgt ggagggaggc gaaggagtgt | 1140 |
| gtctatgtag aaccggacag gaaaggtgag aagaaagagg gaacaaaaga agaggaagaa | 1200 |
| aatgaagcaa agtaa | 1215 |

<210> SEQ ID NO 29
<211> LENGTH: 2358
<212> TYPE: DNA
<213> ORGANISM: artificial
<220> FEATURE:
<223> OTHER INFORMATION: modified FAD coding sequence

<400> SEQUENCE: 29

| | |
|---|---|
| atgtctaaat ttgataaaat atatgatgac gacaattccg gtggatcaca gtttgcttca | 60 |

```
tttggctttt tttgtgtgtt tgtcaagttg ctattcaata agaatttgtg attttgattg     120
gtctcctcaa aattctgtga aattttagta acaaggaaga aattaacaaa tcacaacaag     180
aaagagatgt gagctgtcgt atcaaatctt attcgttttc tcaacgcaat cgttttagtt     240 tttttaact taacgccact tctctgctcc atacactcct ttttgtccac gtacttttca      300
tttgtggtaa tccatttctt cactttggat ctttcatctg aacaacaatt tcttgactca     360
atcaattacc acccgttctt gtgcttttgt atagattcat aatcttgtgt gtttcagctt     420
ctcattgctt tggttcttgt ttttttttct gcagaaacat gggtgcaggt ggaagaatga     480
cggttcctac ttcttccaag aagtctgaaa ccgatgcctt aaagcgtgtg ccgtgcgaga     540
aaccgccgtt cacgctcgga gaactgaaga agcaatccc acagcattgt ttcaatcgct      600
caatccctcg ctctttctcc taccttatct gggacatcat catagcctct tgcttctact     660
acgttgccac cacttacttc tctctcctcc ctcagcctct ctcttacttg gcttggcctc     720
tattgggtct gtcaaggctg tgtcttaacc ggagtctggg tcatagctca cgaatgcggc     780
caccacgcct tcagcgacta ccaatggctt gacgacacag tcggtctgat cttccattct     840
ttcctcctcg tcccttactt ctcctggaaa tacagccacc gccgtcacca ttccaacacc     900
ggatcacttg aaaaggacga agtgtttgtc cctaaacaga aatccgccat caaatggtac     960
ggcaagtacc tcaacaaccc tctgggacgc accgtgatgt taaccgtcca gttcacccttt   1020 ggctggccct tgtacttagc cttcaacgtc tcggggagac cctacgacgg ttcgcttgc     1080 cacttccacc caaacgctcc catctacaac gaccgtgaac gcctcagat atacatctcg     1140 gatgctggta tcctcgccgt ctgttacggt ctctaccgtt acgctgctgc acaaggagtg    1200
gcctcgatga tctgcgtcta cggagttccg cttctgatag tcaacgggtt cctcgtcttg    1260
atcacatact tgcagcacac ccatccctcg ttgcctcact acgattcatc cgagtgggat    1320
tggttcaggg gagctttggc taccgtagac agagactatg gaatcctgaa caaggtcttc    1380
cacaacatca cggacacgca cgtggctcac cacctgttct cgacgatgcc gcattaccat    1440
gcgatggagg ccacgaaggc gataaagccg atactcgggg actattacca gtttgatgga    1500
acaccggtct tcaaggcgat gtggagggag gcgaaggagt gtgtctatgt agaaccggac    1560
aggaaaggtg agaagaaagg tgtgttctgg tacaacaaca agttgtgagg atgatcaggt    1620
gaaagaagaa ggaagaaaaa tcgtcggcct ttctcttgtc tggttatctt tgttttaaga    1680
agatatatgt ttgtttcaat aatcttattg tccattttgt tgtgttctga cattgtggct    1740
taaattatta tgtgatgtta gtgtccaatt gttctgcgtc tgtattgttc ttctcatcgc    1800
tgttttgttg ggatcgtaga aatgtgactt tcggacaatt aaactcttgt actcaagcta    1860
tcactctgtt ggcagcatca aaagtgtttt catagtttcg gtcttttggt ctctgtttgt    1920
ttgatactgt tggtgagaat ggctcttcaa gtgttggaat ctacctaagg tgaacacatt    1980
gtaggatttt tcttttattt aattgccatt gtataccaca ctgcagtgaa ccgcaactat    2040
gttgaccatg tcgatgaatg taagtgaacc atgaaactaa tctttctgta caatttactt    2100
acttctgagt cattgtgatg tttggttggc aggtcacctt tatttctcac actccctcca    2160
ctcatgtgat gtggttggga ttttcttttc ataagtagct ttttgtaaag aactcagtct    2220
ttctctttca aatcatggaa accttttcaa caaaagccaa atccatgtta cataagcaaa    2280
atatctgctt tcttcatctt tcctttcttt catatttgag agggaacaaa agaagaggaa    2340
gaaaatgaag caaagtaa                                                  2358
```

<210> SEQ ID NO 30
<211> LENGTH: 1213
<212> TYPE: DNA
<213> ORGANISM: artificial
<220> FEATURE:
<223> OTHER INFORMATION: modified FAD coding sequence

<400> SEQUENCE: 30

```
atgtctaaat tgataaaat atatgatgac gacaattccg gtggatcaca aaacatgggt      60
gcaggtggaa gaatgacggt tcctacttct tccaagaagt ctgaaaccga tgccttaaag    120
cgtgtgccgt gcgagaaacc gccgttcacg ctcggagaac tgaagaaagc aatcccacag    180
cattgtttca atcgctcaat ccctcgctct ttctcctacc ttatctggga catcatcata    240
gcctcttgct tctactacgt tgccaccact tacttctctc cctcccctca gcctctctct    300
tacttggctt ggcctctatt gggtctgtca aggctgtgtc ttaaccggag tctgggtcat    360
agctcacgaa tgcggccacc acgccttcag cgactaccaa tggcttgacg acacagtcgg    420
tctgatcttc cattctttcc tcctcgtccc ttacttctcc tggaaataca gccaccgccg    480
tcaccattcc aacaccggat cacttgaaaa ggacgaagtg tttgtcccta acagaaatc    540
cgccatcaaa tggtacggca agtacctcaa caaccctctg gacgcaccg tgatgttaac    600
cgtccagttc acccttggct ggcccttgta cttagccttc aacgtctcgg ggagaccct    660
cgacgggttc gcttgccact ccacccaaa cgctcccatc tacaacgacc gtgaacgcct    720
ccagatatac atctcggatg ctggtatcct cgccgtctgt tacggtctct accgttacgc    780
tgctgcacaa ggagtggcct cgatgatctg cgtctacgga gttccgcttc tgatagtcaa    840
cgggttcctc gtcttgatca catacttgca gcacacccat ccctcgttgc ctcactacga    900
ttcatccgag tgggattggt tcaggggagc tttggctacc gtagacagag actatggaat    960
cctgaacaag gtcttccaca acatcacgga cacgcacgtg gctcaccacc tgttctcgac   1020
gatgccgcat taccatgcga tggaggccac gaaggcgata aagccgatac tcggggacta   1080
ttaccagttt gatggaacac cggtcttcaa ggcgatgtgg agggaggcga aggagtgtgt   1140
ctatgtagaa ccggacagga aaggtgagaa gaaagaggga acaaaagaag aggaagaaaa   1200
tgaagcaaag taa                                                     1213
```

<210> SEQ ID NO 31
<211> LENGTH: 135
<212> TYPE: PRT
<213> ORGANISM: artificial
<220> FEATURE:
<223> OTHER INFORMATION: modified FAD polypeptide

<400> SEQUENCE: 31

```
Met Ser Lys Phe Asp Lys Ile Tyr Asp Asp Asp Asn Ser Gly Gly Ser
 1               5                  10                  15

Gln Asn Met Gly Ala Gly Gly Arg Met Thr Val Pro Thr Ser Ser Lys
            20                  25                  30

Lys Ser Glu Thr Asp Ala Leu Lys Arg Val Pro Cys Glu Lys Pro Pro
        35                  40                  45

Phe Thr Leu Gly Glu Leu Lys Lys Ala Ile Pro Gln His Cys Phe Asn
    50                  55                  60

Arg Ser Ile Pro Arg Ser Phe Ser Tyr Leu Ile Trp Asp Ile Ile Ile
65                  70                  75                  80

Ala Ser Cys Phe Tyr Tyr Val Ala Thr Thr Tyr Phe Ser Leu Leu Pro
                85                  90                  95
```

Gln Pro Leu Ser Tyr Leu Ala Trp Pro Leu Gly Leu Ser Arg Leu
            100                 105                 110

Cys Leu Asn Arg Ser Leu Gly His Ser Ser Arg Met Arg Pro Pro Arg
        115                 120                 125

Leu Gln Arg Leu Pro Met Ala
    130                 135

<210> SEQ ID NO 32
<211> LENGTH: 2331
<212> TYPE: DNA
<213> ORGANISM: artificial
<220> FEATURE:
<223> OTHER INFORMATION: modified FAD coding sequence

<400> SEQUENCE: 32

| | | | | | |
|---|---|---|---|---|---|
| atgtctaaat | ttgataaaat | atatgatgac | gacaattccg | gtggatcaca | gtttgcttca | 60 |
| tttggctttt | tttgtgtgtt | tgtcaagttg | ctattcaata | agaatttgtg | attttgattg | 120 |
| gtctcctcaa | aattctgtga | aattttagta | acaaggaaga | aattaacaaa | tcacaacaag | 180 |
| aaagagatgt | gagctgtcgt | atcaaatctt | attcgttttc | tcaacgcaat | cgttttagtt | 240 |
| ttttttaact | taacgccact | tctctgctcc | atacactcct | ttttgtccac | gtacttttca | 300 |
| tttgtggtaa | tccatttctt | cacttttggat | cttttcatctg | aacaacaatt | tcttgactca | 360 |
| atcaattacc | cccgttctt | gtgcttttgt | atagattcat | aatcttgtgt | gtttcagctt | 420 |
| ctcattgctt | tggttcttgt | tttttttct | gcagaaacat | gggtgcaggt | ggaagaatga | 480 |
| cggttcctac | ttcttccaag | aagtctgaaa | ccgatgcctt | aaagcgtgtg | ccgtgcgaga | 540 |
| aaccgccgtt | cacgctcgga | gaactgaaga | agcaatcccc | acagcattgt | tcaatcgct | 600 |
| caatccctcg | ctctttctcc | taccttatct | gggacatcat | catagcctct | tgcttctact | 660 |
| acgttgccac | cacttacttc | tctctcctcc | ctcagcctct | ctcttacttg | gcttgtctta | 720 |
| accggagtct | gggtcatagc | tcacgaatgc | ggccaccacg | ccttcagcga | ctaccaatgg | 780 |
| cttgacgaca | cagtcggtct | gatcttccat | tctttcctcc | tcgtccctta | cttctcctgg | 840 |
| aaatacagcc | accgccgtca | ccattccaac | accggatcac | ttgaaaagga | cgaagtgttt | 900 |
| gtccctaaac | agaaatccgc | catcaaatgg | tacggcaagt | acctcaacaa | ccctctggga | 960 |
| cgcaccgtga | tgttaaccgt | ccagttcacc | cttggctggc | ccttgtactt | agccttcaac | 1020 |
| gtctcgggga | gaccctacga | cgggttcgct | tgccacttcc | acccaaacgc | tcccatctac | 1080 |
| aacgaccgtg | aacgcctcca | gatatacatc | tcggatgctg | gtatcctcgc | cgtctgttac | 1140 |
| ggtctctacc | gttacgctgc | tgcacaagga | gtggcctcga | tgatctgcgt | ctacggagtt | 1200 |
| ccgcttctga | tagtcaacgg | gttcctcgtc | ttgatcacat | acttgcagca | cacccatccc | 1260 |
| tcgttgcctc | actacgattc | atccgagtgg | gattggttca | ggggagcttt | ggctaccgta | 1320 |
| gacagagact | atggaatcct | gaacaaggtc | ttccacaaca | tcacggacac | gcacgtggct | 1380 |
| caccacctgt | tctcgacgat | gccgcattac | catgcgatgg | aggccacgaa | ggcgataaag | 1440 |
| ccgatactcg | gggactatta | ccagtttgat | ggaacaccgg | tcttcaaggc | gatgtggagg | 1500 |
| gaggcgaagg | agtgtgtcta | tgtagaaccg | gacaggaaag | gtgagaagaa | aggtgtgttc | 1560 |
| tggtacaaca | acaagttgtg | aggatgatca | ggtgaaagaa | gaaggaagaa | aaatcgtcgg | 1620 |
| cctttctctt | gtcggttat | ctttgtttta | agaagatata | tgtttgtttc | aataatctta | 1680 |
| ttgtccattt | tgttgtgttc | tgacattgtg | gcttaaatta | ttatgtgatg | ttagtgtcca | 1740 |
| attgttctgc | gtctgtattg | ttcttctcat | cgctgttttg | ttgggatcgt | agaaatgtga | 1800 |

```
cttcggaca attaaactct tgtactcaag ctatcactct gttggcagca tcaaaagtgt    1860
tttcatagtt tcggtctttt ggtctctgtt tgtttgatac tgttggtgag aatggctctt    1920
caagtgttgg aatctaccta aggtgaacac attgtaggat ttttcttta tttaattgcc    1980 attgtatacc acactgcagt gaaccgcaac tatgttgacc atgtcgatga atgtaagtga    2040
accatgaaac taatctttct gtacaattta cttacttctg agtcattgtg atgtttggtt    2100
ggcaggtcac ctttatttct cacactccct ccactcatgt gatgtggttg ggattttctt    2160
ttcataagta gcttttgta aagaactcag tctttctctt tcaaatcatg gaaaccttt     2220 caacaaaagc caaatccatg ttacataagc aaaatatctg ctttcttcat ctttcctttc    2280
tttcatattt gagagggaac aaaagaagag gaagaaaatg aagcaaagta a             2331
```

<210> SEQ ID NO 33
<211> LENGTH: 1186
<212> TYPE: DNA
<213> ORGANISM: artificial
<220> FEATURE:
<223> OTHER INFORMATION: modified FAD coding sequence

<400> SEQUENCE: 33

```
atgtctaaat tgataaaat atatgatgac gacaattccg gtggatcaca aaacatgggt      60
gcaggtggaa gaatgacggt tcctacttct tccaagaagt ctgaaaccga tgccttaaag    120
cgtgtgccgt gcgagaaacc gccgttcacg ctcggagaac tgaagaaagc aatcccacag    180
cattgtttca atcgctcaat ccctcgctct ttctcctacc ttatctggga catcatcata    240
gcctcttgct tctactacgt tgccaccact tacttctctc tcctccctca gcctctctct    300
tacttggctt gtcttaaccg gagtctgggt catagctcac gaatgcggcc accacgcctt    360
cagcgactac caatggcttg acgacacagt cggtctgatc ttccattctt tcctcctcgt    420
cccttacttc tcctggaaat acagccaccg ccgtcaccat tccaacaccg gatcacttga    480
aaaggacgaa gtgtttgtcc ctaaacagaa atccgccatc aaatggtacg gcaagtacct    540
caacaaccct ctgggacgca ccgtgatgtt aaccgtccag ttcacccttg gctggccctt    600
gtacttagcc ttcaacgtct cggggagacc ctacgacggg ttcgcttgcc acttccaccc    660
aaacgctccc atctacaacg accgtgaacg cctccagata tacatctcgg atgctggtat    720
cctcgccgtc tgttacggtc tctaccgtta cgctgctgca caaggagtgg cctcgatgat    780
ctgcgtctac ggagttccgc ttctgatagt caacgggttc ctcgtcttga tcacatactt    840
gcagcacacc catccctcgt tgcctcacta cgattcatcc gagtgggatt ggttcagggg    900
agctttggct accgtagaca gagactatgg aatcctgaac aaggtcttcc acaacatcac    960
ggacacgcac gtggctcacc acctgttctc gacgatgccg cattaccatg cgatggagc    1020 cacgaaggcg ataaagccga tactcgggga ctattaccag tttgatggaa caccggtctt    1080
caaggcgatg tggagggagg cgaaggagtg tgtctatgta gaaccggaca ggaaaggtga    1140
gaagaaagag ggaacaaaag aagaggaaga aaatgaagca agtaa                   1186
```

<210> SEQ ID NO 34
<211> LENGTH: 126
<212> TYPE: PRT
<213> ORGANISM: artificial
<220> FEATURE:
<223> OTHER INFORMATION: modified FAD polypeptide

<400> SEQUENCE: 34

```
Met Ser Lys Phe Asp Lys Ile Tyr Asp Asp Asn Ser Gly Gly Ser
1               5                   10                  15

Gln Asn Met Gly Ala Gly Gly Arg Met Thr Val Pro Thr Ser Lys
            20                  25                  30

Lys Ser Glu Thr Asp Ala Leu Lys Arg Val Pro Cys Glu Lys Pro Pro
        35                  40                  45

Phe Thr Leu Gly Glu Leu Lys Lys Ala Ile Pro Gln His Cys Phe Asn
    50                  55                  60

Arg Ser Ile Pro Arg Ser Phe Ser Tyr Leu Ile Trp Asp Ile Ile Ile
65              70                  75                  80

Ala Ser Cys Phe Tyr Tyr Val Ala Thr Thr Tyr Phe Ser Leu Leu Pro
            85                  90                  95

Gln Pro Leu Ser Tyr Leu Ala Cys Leu Asn Arg Ser Leu Gly His Ser
            100                 105                 110

Ser Arg Met Arg Pro Pro Arg Leu Gln Arg Leu Pro Met Ala
            115                 120                 125
```

<210> SEQ ID NO 35
<211> LENGTH: 2361
<212> TYPE: DNA
<213> ORGANISM: artificial
<220> FEATURE:
<223> OTHER INFORMATION: modified FAD coding sequence

<400> SEQUENCE: 35

```
atgtctaaat tgataaaat atatgatgac gacaattccg gtggatcaca gtttgcttca      60
tttggctttt tttgtgtgtt tgtcaagttg ctattcaata agaatttgtg attttgattg    120
gtctcctcaa aattctgtga aattttagta acaaggaaga aattaacaaa tcacaacaag    180
aaagagatgt gagctgtcgt atcaaatctt attcgttttc tcaacgcaat cgttttagtt    240
tttttttaact taacgccact tctctgctcc atacactcct ttttgtccac gtacttttca    300
tttgtggtaa tccatttctt cactttggat ctttcatctg aacaacaatt tcttgactca    360
atcaattacc acccgttctt gtgcttttgt atagattcat aatcttgtgt gtttcagctt    420
ctcattgctt tggttcttgt ttttttttct gcagaaacat gggtgcaggt ggaagaatga    480
cggttcctac ttcttccaag aagtctgaaa ccgatgcctt aaagcgtgtg ccgtgcgaga    540
aaccgccgtt cacgctcgga gaactgaaga agcaatcccc acagcattgt ttcaatcgct    600
caatccctcg ctctttctcc taccttatct gggacatcat catagcctct tgcttctact    660
acgttgccac cacttacttc tctctcctcc ctcagcctct ctcttacttg gcttggcctc    720
tactattggg tctgtcaagg ctgtgtctta accggagtct gggtcatagc tcacgaatgc    780
ggccaccacg cctcagcga ctaccaatgg cttgacgaca cagtcggtct gatcttccat    840
tctttcctcc tcgtccctta cttctcctgg aaatacagcc accgcgtca ccattccaac    900
accggatcac ttgaaaagga cgaagtgttt gtccctaaac agaaatccgc catcaaatgg    960
tacggcaagt acctcaacaa ccctctggga cgcaccgtga tgttaaccgt ccagttcacc   1020
cttggctggc ccttgtactt agccttcaac gtctcgggga accctacga cgggttcgct   1080
tgccacttcc acccaaacgc tcccatctac aacgaccgtg aacgcctcca gatatacatc   1140
tcggatgctg gtatcctcgc cgtctgttac ggtctctacc gttacgctgc tgcacaagga   1200
gtggcctcga tgatctgcgt ctacggagtt ccgcttctga tagtcaacgg gttcctcgtc   1260
ttgatcacat acttgcagca cacccatccc tcgttgcctc actacgattc atccgagtgg   1320
gattggttca ggggagcttt ggctaccgta gacagagact atggaatcct gaacaaggtc   1380
```

```
ttccacaaca tcacggacac gcacgtggct caccacctgt tctcgacgat gccgcattac    1440
catgcgatgg aggccacgaa ggcgataaag ccgatactcg gggactatta ccagtttgat    1500
ggaacaccgg tcttcaaggc gatgtggagg gaggcgaagg agtgtgtcta tgtagaaccg    1560
gacaggaaag gtgagaagaa aggtgtgttc tggtacaaca acaagttgtg aggatgatca    1620
ggtgaaagaa aaggaagaa aaatcgtcgg cctttctctt gtctggttat ctttgtttta    1680
agaagatata tgtttgtttc aataatctta ttgtccattt tgttgtgttc tgacattgtg    1740
gcttaaatta ttatgtgatg ttagtgtcca attgttctgc gtctgtattg ttcttctcat    1800
cgctgttttg ttgggatcgt agaaatgtga ctttcggaca attaaactct tgtactcaag    1860
ctatcactct gttggcagca tcaaaagtgt tttcatagtt tcggtctttt ggtctctgtt    1920
tgtttgatac tgttggtgag aatggctctt caagtgttgg aatctaccta aggtgaacac    1980
attgtaggat ttttctttta tttaattgcc attgtatacc acactgcagt gaaccgcaac    2040
tatgttgacc atgtcgatga atgtaagtga accatgaaac taatctttct gtacaattta    2100
cttacttctg agtcattgtg atgtttggtt ggcaggtcac ctttatttct cacactccct    2160
ccactcatgt gatgtggttg ggattttctt ttcataagta gcttttttgta agaaactcag    2220 tctttctctt tcaaatcatg gaaaccttt caacaaaagc caaatccatg ttacataagc    2280
aaaatatctg ctttcttcat cttttccttc tttcatattt gagagggaac aaaagaagag    2340
gaagaaaatg aagcaaagta a                                              2361

<210> SEQ ID NO 36
<211> LENGTH: 1216
<212> TYPE: DNA
<213> ORGANISM: artificial
<220> FEATURE:
<223> OTHER INFORMATION: modified FAD coding sequence

<400> SEQUENCE: 36
atgtctaaat ttgataaaat atatgatgac gacaattccg gtggatcaca aaacatgggt      60
gcaggtggaa gaatgacggt tcctacttct tccaagaagt ctgaaaccga tgccttaaag    120
cgtgtgccgt gcgagaaacc gccgttcacg ctcggagaac tgaagaaagc aatcccacag    180
cattgtttca atcgctcaat ccctcgctct ttctcctacc ttatctggga catcatcata    240
gcctcttgct tctactacgt tgccaccact tacttctctc cctccctca gcctctctct    300 tacttggctt ggcctctact attgggtctg tcaaggctgt gtcttaaccg gagtctgggt    360
catagctcac gaatgcggcc accacgcctt cagcgactac caatggcttg acgacacagt    420
cggtctgatc ttccattctt tcctcctcgt cccttacttc tcctggaaat acagccaccg    480
ccgtcaccat tccaacaccg gatcacttga aaaggacgaa gtgttgtcc ctaaacagaa    540 atccgccatc aaatggtacg gcaagtacct caacaaccct ctgggacgca ccgtgatgtt    600
aaccgtccag ttcaccccttg gctggccctt gtacttagcc ttcaacgtct cggggagacc    660
ctacgacggg ttcgcttgcc acttccaccc aaacgctccc atctacaacg accgtgaacg    720
cctccagata tacatctcgg atgctggtat cctcgccgtc tgttacggtc tctaccgtta    780
cgctgctgca caaggagtgg cctcgatgat ctgcgtctac ggagttccgc ttctgatagt    840
caacgggttc ctcgtcttga tcacatactt gcagcacacc catccctcgt tgcctcacta    900
cgattcatcc gagtgggatt ggttcagggg agctttggct accgtagaca gagactatgg    960
aatcctgaac aaggtcttcc acaacatcac ggacacgcac gtggctcacc acctgttctc    1020
```

```
gacgatgccg cattaccatg cgatggaggc cacgaaggcg ataaagccga tactcgggga   1080
ctattaccag tttgatggaa caccggtctt caaggcgatg tggagggagg cgaaggagtg   1140
tgtctatgta gaaccggaca ggaaaggtga gaagaaagag ggaacaaaag aagaggaaga   1200
aaatgaagca aagtaa                                                  1216
```

<210> SEQ ID NO 37
<211> LENGTH: 136
<212> TYPE: PRT
<213> ORGANISM: artificial
<220> FEATURE:
<223> OTHER INFORMATION: modified FAD polypeptide

<400> SEQUENCE: 37

```
Met Ser Lys Phe Asp Lys Ile Tyr Asp Asp Asp Asn Ser Gly Gly Ser
1               5                   10                  15

Gln Asn Met Gly Ala Gly Gly Arg Met Thr Val Pro Thr Ser Ser Lys
            20                  25                  30

Lys Ser Glu Thr Asp Ala Leu Lys Arg Val Pro Cys Glu Lys Pro Pro
        35                  40                  45

Phe Thr Leu Gly Glu Leu Lys Lys Ala Ile Pro Gln His Cys Phe Asn
    50                  55                  60

Arg Ser Ile Pro Arg Ser Phe Ser Tyr Leu Ile Trp Asp Ile Ile Ile
65                  70                  75                  80

Ala Ser Cys Phe Tyr Tyr Val Ala Thr Thr Tyr Phe Ser Leu Leu Pro
                85                  90                  95

Gln Pro Leu Ser Tyr Leu Ala Trp Pro Leu Leu Leu Gly Leu Ser Arg
            100                 105                 110

Leu Cys Leu Asn Arg Ser Leu Gly His Ser Ser Arg Met Arg Pro Pro
        115                 120                 125

Arg Leu Gln Arg Leu Pro Met Ala
    130                 135
```

<210> SEQ ID NO 38
<211> LENGTH: 906
<212> TYPE: DNA
<213> ORGANISM: Thlaspi arvense

<400> SEQUENCE: 38

```
atgtcaacta aaaccgtcgt ccctctccgt cgcagatcta agccccttaa cggaaatcac    60
actaacggcg tcgccattga cggaagcctc gacgacgacc acaaccgtcg catcggatca   120
gtaaatagcc aaatggataa cattgctaag aaaacggacg acggctacgc aaacggcgga   180
ggaggaggag gaggagggaa aagcaaggcg tcgtttatga cgtggacggc gcgtgacgtt   240
gtgtacgtgc gaggtaccat tggataccg tgtttgttcg cggtcgggt tctgttcttc   300 acgggcgtgg agtacacgct ccagatgatt cccgcgaggt ctgagccgtt cgatattggg   360
tttgtggcca cgcgctctct gaatcgcgtc ttggcaaatt caccggatct taacaccgtc   420
ttagccgctc taaacacggt gttcgtaggg atgcaaacga cgtatattgt atggacatgg   480
ttaatggaag gacgaccacg agccaccatc tcggcttgct tcatgtttac ttgtcgaggc   540
attcttggtt actctactca gctccctctt cctcaggatt tctaggatc aggtgtcgat   600 tttccggtgg gaaacgtctc gttcttcctc ttctactcgg gtcacgtcgc cggttcgatg   660
atcgcatctt tggacatgag gagaatgcag aggatgagac tagcgatgct ttttgacatc   720
ctcaatgtat tacaatcgat caggctgctc gggacgagag gacactacac gattgatctc   780
```

```
gctgtcggag ttggcgctgg gattctcttt gattcattcg ccggcaagta cgaagagatg    840
ataagcaaga gacacaattt agtcaatggt tttggtttga tttcgaaaga ctcgctagtc    900
aattaa                                                                906

<210> SEQ ID NO 39
<211> LENGTH: 906
<212> TYPE: DNA
<213> ORGANISM: artificial
<220> FEATURE:
<223> OTHER INFORMATION: modified ROD coding sequence

<400> SEQUENCE: 39
atgtcaacta aaccgtcgt ccctctccgt cgcagatcta agccccttaa cggaaatcac     60
actaacggcg tcgccattga cggaagcctc gacgacgacc acaaccgtcg catcggatca   120
gtaaatagcc aaatggataa cattgctaag aaaacggacg acggctacgc aaacggcgga   180
ggaggaggag gaggagggaa aagcaaggcg tcgtttatga cgtggacggc gcgtgacgtt   240
gtgtacgtgg cgaggtacca ttggataccg tgtttgttcg cggtcggggt tctgttcttc   300
acgggcgtgg agtacacgct ccagatgatt cccgcgaggt ctgagccgtt cgatattggg   360
tttgtggcca cgcgctctct gaatcgcgtc ttggcaaatt caccggatct aacaccgtc   420 ttagccgctc taaacacggt gttcgtaggg atgcaaacga cgtatattgt atggacatgg   480
ttaatggaag gacgaccacg agccaccatc tcggcttgct tcatgtttac ttgtcgaggc   540
attcttggtt actctactca gctccctctt cctcaggatt ttctaggatc aggtgtcgat   600
tttccggtgg gaaacgtctc gttcttcctc ttctactcgg gtcacgtcgc cggttcgatg   660
atcgcatctt tggacataag gagaatgcag aggatgagac tagcgatgct ttttgacatc   720
ctcaatgtat acaatcgat caggctgctc gggacgagag gacactacac gattgatctc   780
gctgtcggag ttggcgctgg gattctcttt gattcattcg ccggcaagta cgaagagatg   840
ataagcaaga gacacaattt agtcaatggt tttggtttga tttcgaaaga ctcgctagtc   900
aattaa                                                              906

<210> SEQ ID NO 40
<211> LENGTH: 906
<212> TYPE: DNA
<213> ORGANISM: artificial
<220> FEATURE:
<223> OTHER INFORMATION: modified ROD coding sequence

<400> SEQUENCE: 40
atgtcaacta aaccgtcgt ccctctccgt cgcagatcta agccccttaa cggaaatcac     60
actaacggcg tcgccattga cggaagcctc gacgacgacc acaaccgtcg catcggatca   120
gtaaatagcc aaatggataa cattgctaag aaaacggacg acggctacgc aaacggcgga   180
ggaggaggag gaggagggaa aagcaaggcg tcgtttatga cgtggacggc gcgtgacgtt   240
gtgtacgtgg cgaggtacca ttggataccg tgtttgttcg cggtcggggt tctgttcttc   300
acgggcgtgg agtacacgct ccagatgatt cccgcgaggt ctgagccgtt cgatattggg   360
tttgtggcca cgcgctctct gaatcgcgtc ttggcaaatt caccggatct aacaccgtc   420 ttagccgctc taaacacggt gttcgtaggg atgcaaacga cgtatattgt atggacatgg   480
ttaatggaag gacgaccacg agccaccatc tcggcttgct tcatgtttac ttgtcgaggc   540
attcttggtt actctactca gctccctctt cctcaggatt ttctaggatc aggtgtcgat   600
tttccggtgg gaaacgtctc gttcttcctc ttctactcgg gtcacgtcgc cggttcgatg   660
```

```
atcgcatctt tggacatgag gagaatgcag aggatgagac tagcgatgct ttttgacatc    720
ctcaatgtat tacaatcgat caagctgctc gggacgagag gacactacac gattgatctc    780
gctgtcggag ttggcgctgg gattctcttt gattcattcg ccggcaagta cgaagagatg    840
ataagcaaga gacacaattt agtcaatggt tttggtttga tttcgaaaga ctcgctagtc    900
aattaa                                                                906

<210> SEQ ID NO 41
<211> LENGTH: 2128
<212> TYPE: DNA
<213> ORGANISM: artificial
<220> FEATURE:
<223> OTHER INFORMATION: modified ROD coding sequence

<400> SEQUENCE: 41
atgtcaacta aaccgtcgt ccctctccgt cgcagatcta agccccttaa cggaaatcac    60
actaacggcg tcgccattga cggaagcctc gacgacgacc acaaccgtcg catcggatca    120
gtaaatagcc aaatggataa cattgctaag aaaacggacg acggctgagg aggaggaggg    180
aaaagcaagg cgtcgtttat gacgtggacg gcgcgtgacg ttgtgtacgt ggcgaggtac    240
cattggatac cgtgtttgtt cgcggtcggg gttctgttct tcacgggcgt ggagtacacg    300
ctccagatga ttcccgcgag gtctgagccg ttcgatattg ggtttgtggc cacgcgctct    360
ctgaatcgcg tcttggcaaa ttcaccggat cttaacaccg tcttagccgc tctaaacacg    420
gtaatttcgt actaattaat ttagggtaaa aaatatagta tttaataatg actatcctca    480
attcctttca tgcttcacct aatatttttgt ttttttttcgt tgtcattaaa atcgtaataa    540
tatattgagt tagtcaaatg aaaaaaacaa gtggcggtag tgattggaaa caaatctcag    600
atcttttatc tgtttaataa ggtatttaat tatccagctg gaattatgct gtcaagtgtc    660
aacacagtag tagtaaacatg caatggaatt tctcaataga aaaaggtctt aattagtata    720
gataattagt ggacaaaaat gtagttaatg taatctcttt gctaagtagt tatcataatc    780 atcttttttaa caactgccat tttgtctgtg tgtttgtttt acaacgaagt agtagtagaa    840
tagatcgctt tttagctttt gaaagtttcg aacccaagga aaagggacac atgggttatg    900
agttggagac acgatcacat gcaaacagag agattggtta aattatcgac ttttttgtagt    960 acttttttaaa aaaaaactat ttatataaaa acatggtggg atggtgggga caggtgttcg   1020
tagggatgca aacgacgtat attgtatgga catggttaat ggaaggacga ccacgagcca   1080
ccatctcggc ttgcttcatg tttacttgtc gaggcattct tggttactct actcagctcc   1140
ctcttcctca ggttccaatc aacacttttc ttctatctct tttcttaatt aaaataatta   1200
ccaattaact aaatgctaat cagtcgatat atcatagttc caacgttttg gacgtgtgat   1260
ttccattggc cactaccata taaaacaaca gagtctcttt attcattatt caatatatat   1320
ttgagtattg atattattca tagggaggtt tcatttgtac tatcaataaa atttctacaa   1380
ctcttggatt ttttctgcta cattttgtag ttattttttt aattactttt aaaaacttgt   1440
gaataggaga gactaatagt agtacgtaat atgattgtat caaatgcttt aacatgtggg   1500
gtttgggtta actatcatca tttcatagat cactatttttg ttttcgtttg ttacctaact   1560
ttttgttatc tttgaaaaat aatgttccac gagttgattg actggacata aaaatcagat   1620
tctctcactc atttacgttc tacggttcta gccactcgtt tttttctttt tctttctgtg   1680
gtgtaacacg tagataatgg attttctatg tgtgtcgtct tgctcaagaa taataaatgt   1740
```

-continued

```
ggttaaaggt taaatatagc tctggaaatt aattatctcc tcttttttta ttaaccagga    1800
ttttctagga tcaggtgtcg attttccggt gggaaacgtc tcgttcttcc tcttctactc    1860
gggtcacgtc gccggttcga tgatcgcatc tttggacatg aggagaatgc agaggatgag    1920
actagcgatg cttttttgaca tcctcaatgt attacaatcg atcaggctgc tcgggacgag    1980
aggacactac acgattgatc tcgctgtcgg agttggcgct gggattctct ttgattcatt    2040
cgccggcaag tacgaagaga tgataagcaa gagacacaat ttagtcaatg gttttggttt    2100
gatttcgaaa gactcgctag tcaattaa                                      2128
```

<210> SEQ ID NO 42
<211> LENGTH: 888
<212> TYPE: DNA
<213> ORGANISM: artificial
<220> FEATURE:
<223> OTHER INFORMATION: modified ROD coding sequence

<400> SEQUENCE: 42

```
atgtcaacta aaaccgtcgt ccctctccgt cgcagatcta agccccttaa cggaaatcac      60
actaacggcg tcgccattga cggaagcctc gacgacgacc acaaccgtcg catcggatca     120
gtaaatagcc aaatggataa cattgctaag aaaacgacga acggctgagg aggaggaggg     180
aaaagcaagg cgtcgtttat gacgtggacg gcgcgtgacg ttgtgtacgt ggcgaggtac     240
cattggatac cgtgtttgtt cgcggtcggg gttctgttct tcacgggcgt ggagtacacg     300
ctccagatga ttcccgcgag gtctgagccg ttcgatattg ggtttgtggc cacgcgctct     360
ctgaatcgcg tcttggcaaa ttcaccggat cttaacaccg tcttagccgc tctaaacacg     420
gtgttcgtag ggatgcaaac gacgtatatt gtatggacat ggttaatgga aggacgacca     480
cgagccacca tctcggcttg cttcatgttt acttgtcgag gcattcttgg ttactctact     540
cagctccctc ttcctcagga ttttctagga tcaggtgtcg attttccggt gggaaacgtc     600
tcgttcttcc tcttctactc gggtcacgtc gccggttcga tgatcgcatc tttggacatg     660
aggagaatgc agaggatgag actagcgatg cttttttgaca tcctcaatgt attacaatcg     720
atcaggctgc tcgggacgag aggacactac acgattgatc tcgctgtcgg agttggcgct     780
gggattctct ttgattcatt cgccggcaag tacgaagaga tgataagcaa gagacacaat     840
ttagtcaatg gttttggttt gatttcgaaa gactcgctag tcaattaa                 888
```

<210> SEQ ID NO 43
<211> LENGTH: 55
<212> TYPE: PRT
<213> ORGANISM: artificial
<220> FEATURE:
<223> OTHER INFORMATION: modified ROD polypeptide

<400> SEQUENCE: 43

```
Met Ser Thr Lys Thr Val Val Pro Leu Arg Arg Arg Ser Lys Pro Leu
1               5                   10                  15

Asn Gly Asn His Thr Asn Gly Val Ala Ile Asp Gly Ser Leu Asp Asp
            20                  25                  30

Asp His Asn Arg Arg Ile Gly Ser Val Asn Ser Gln Met Asp Asn Ile
        35                  40                  45

Ala Lys Lys Thr Asp Asp Gly
    50                  55
```

<210> SEQ ID NO 44
<211> LENGTH: 2147

<212> TYPE: DNA
<213> ORGANISM: artificial
<220> FEATURE:
<223> OTHER INFORMATION: modified ROD coding sequence

<400> SEQUENCE: 44

```
atgtcaacta aaaccgtcgt ccctctccgt cgcagatcta agccccttaa cggaaatcac    60
actaacggcg tcgccattga cggaagcctc gacgacgacc acaaccgtcg catcggatca   120
gtaaatagcc aaatggataa cattgctaag aaaacggacg acggctacgc aaaacggcgg   180
aggaggagga ggaggaggga aaagcaaggc gtcgtttatg acgtggacgg cgcgtgacgt   240
tgtgtacgtg gcgaggtacc attggatacc gtgtttgttc gcggtcgggg ttctgttctt   300
cacgggcgtg gagtacacgc tccagatgat tcccgcgagg tctgagccgt tcgatattgg   360
gtttgtggcc acgcgctctc tgaatcgcgt cttggcaaat tcaccggatc ttaacaccgt   420
cttagccgct ctaaacacgg taatttcgta ctaattaatt tagggtaaaa aatatagtat   480
ttaataatga ctatcctcaa ttcctttcat gcttcaccta atattttgtt tttttttcgtt   540
gtcattaaaa tcgtaataat atattgagtt agtcaaatga aaaaaacaag tggcggtagt   600
gattggaaac aaatctcaga tcttttatct gtttaataag gtatttaatt atccagctgg   660
aattatgctg tcaagtgtca acacagtagt agtaacatgc aatggaattt ctcaatagaa   720
aaaggtctta attagtatag ataattagtg gacaaaatg tagttaatgt aatctctttg   780
ctaagtagtt atcataatca tcttttttaac aactgccatt ttgtctgtgt gtttgtttta   840
caacgaagta gtagtagaat agatcgcttt ttagcttttg aaagtttcga acccaaggaa   900
aagggacaca tgggttatga gttggagaca cgatcacatg caaacagaga gattggttaa   960
attatcgact ttttgtagta cttttttaaaa aaaaactatt tatataaaaa acatggtgga  1020
tggtggggac aggtgttcgt agggatgcaa acgacgtata ttgtatggac atggttaatg  1080
gaaggacgac cacgagccac catctcggct tgcttcatgt ttacttgtcg aggcattctt  1140
ggttactcta ctcagctccc tcttcctcag gttccaatca acactttct tctatctctt  1200
ttcttaatta aaataattac caattaacta aatgctaatc agtcgatata tcatagttcc  1260
aacgttttgg acgtgtgatt tccattggcc actaccatat aaaacaacag agtctcttta  1320
ttcattattc aatatatatt tgagtattga tattattcat agggaggttt catttgtact  1380
atcaataaaa tttctacaac tcttggattt tttctgctac attttgtagt tatttttta  1440
attacttta aaaacttgtg aataggagag actaatagta gtacgtaata tgattgtatc  1500
aaatgcttta acatgtgggg tttgggttaa ctatcatcat ttcatagatc actattttgt  1560
tttcgtttgt tacctaactt tttgttatct ttgaaaaata atgttccacg agttgattga  1620
ctggacataa aaatcagatt ctctcactca tttacgttct acggttctag ccactcgttt  1680
ttttctttttt ctttctgtgg tgtaacacgt agataatgga ttttctatgt gtgtcgtctt  1740
gctcaagaat aataaatgtg gttaaaggtt aaatatagct ctggaaatta attatctcct  1800
cttttttat taaccaggat tttctaggat caggtgtcga ttttccggtg ggaaacgtct  1860
cgttcttcct cttctactcg ggtcacgtcg ccggttcgat gatcgcatct ttggacatga  1920
ggagaatgca gaggatgaga ctagcgatgc ttttgacat cctcaatgta ttacaatcga  1980
tcaggctgct cgggacgaga ggacactaca cgattgatct cgctgtcgga gttggcgctg  2040
ggattctctt tgattcattc gccggcaagt acgaagagat gataagcaag agacacaatt  2100
tagtcaatgg ttttggtttg atttcgaaag actcgctagt caattaa                 2147
```

<210> SEQ ID NO 45
<211> LENGTH: 907
<212> TYPE: DNA
<213> ORGANISM: artificial
<220> FEATURE:
<223> OTHER INFORMATION: modified ROD coding sequence

<400> SEQUENCE: 45

```
atgtcaacta aaccgtcgt ccctctccgt cgcagatcta agcccttaa cggaaatcac      60
actaacggcg tcgccattga cggaagcctc gacgacgacc acaaccgtcg catcggatca     120
gtaaatagcc aaatggataa cattgctaag aaaacggacg acggctacgc aaaacggcgg    180
aggaggagga ggaggaggga aaagcaaggc gtcgtttatg acgtggacgg cgcgtgacgt     240
tgtgtacgtg gcgaggtacc attggatacc gtgtttgttc gcggtcgggg ttctgttctt    300
cacgggcgtg gagtacacgc tccagatgat tcccgcgagg tctgagccgt tcgatattgg    360
gtttgtggcc acgcgctctc tgaatcgcgt cttggcaaat tcaccggatc ttaacaccgt    420
cttagccgct ctaaacacgg tgttcgtagg gatgcaaacg acgtatattg tatggacatg    480
gttaatggaa ggacgaccac gagccaccat ctcggcttgc ttcatgttta cttgtcgagg    540
cattcttggt tactctactc agctcccctct tcctcaggat tttctaggat caggtgtcga    600
ttttccggtg ggaaacgtct cgttcttcct cttctactcg ggtcacgtcg ccggttcgat    660
gatcgcatct ttggacatga ggagaatgca gaggatgaga ctagcgatgc tttttgacat    720
cctcaatgta ttacaatcga tcaggctgct cgggacgaga ggacactaca cgattgatct    780
cgctgtcgga gttggcgctg ggattctctt tgattcattc gccggcaagt acgaagagat    840
gataagcaag agacacaatt tagtcaatgg ttttggtttg atttcgaaag actcgctagt    900
caattaa                                                              907
```

<210> SEQ ID NO 46
<211> LENGTH: 78
<212> TYPE: PRT
<213> ORGANISM: artificial
<220> FEATURE:
<223> OTHER INFORMATION: modified ROD polypeptide

<400> SEQUENCE: 46

```
Met Ser Thr Lys Thr Val Val Pro Leu Arg Arg Ser Lys Pro Leu
1               5                  10                  15

Asn Gly Asn His Thr Asn Gly Val Ala Ile Asp Gly Ser Leu Asp Asp
            20                  25                  30

Asp His Asn Arg Arg Ile Gly Ser Val Asn Ser Gln Met Asp Asn Ile
        35                  40                  45

Ala Lys Lys Thr Asp Asp Gly Tyr Ala Lys Arg Arg Arg Arg Arg
    50                  55                  60

Arg Arg Glu Lys Gln Gly Val Val Tyr Asp Val Asp Gly Ala
65                  70                  75
```

<210> SEQ ID NO 47
<211> LENGTH: 2147
<212> TYPE: DNA
<213> ORGANISM: artificial
<220> FEATURE:
<223> OTHER INFORMATION: modified ROD coding sequence

<400> SEQUENCE: 47

```
atgtcaacta aaccgtcgt ccctctccgt cgcagatcta agcccttaa cggaaatcac       60
```

| | |
|---|---|
| actaacggcg tcgccattga cggaagcctc gacgacgacc acaaccgtcg catcggatca | 120 |
| gtaaatagcc aaatggataa cattgctaag aaaacggacg acggctacgc aaatcggcgg | 180 |
| aggaggagga ggaggaggga aaagcaaggc gtcgtttatg acgtggacgg cgcgtgacgt | 240 |
| tgtgtacgtg gcgaggtacc attggatacc gtgtttgttc gcggtcgggg ttctgttctt | 300 |
| cacgggcgtg gagtacacgc tccagatgat tcccgcgagg tctgagccgt tcgatattgg | 360 |
| gtttgtggcc acgcgctctc tgaatcgcgt cttggcaaat tcaccggatc ttaacaccgt | 420 |
| cttagccgct ctaaacacgg taatttcgta ctaattaatt tagggtaaaa aatatagtat | 480 |
| ttaataatga ctatcctcaa ttcctttcat gcttcaccta atattttgtt tttttttcgtt | 540 |
| gtcattaaaa tcgtaataat atattgagtt agtcaaatga aaaaaacaag tggcggtagt | 600 |
| gattggaaac aaatctcaga tcttttatct gtttaataag gtatttaatt atccagctgg | 660 |
| aattatgctg tcaagtgtca acacagtagt agtaacatgc aatggaattt ctcaatagaa | 720 |
| aaaggtctta attagtatag ataattagtg gacaaaaatg tagttaatgt aatctctttg | 780 |
| ctaagtagtt atcataatca tcttttttaac aactgccatt ttgtctgtgt gtttgtttta | 840 |
| caacgaagta gtagtagaat agatcgcttt ttagcttttg aaagtttcga acccaaggaa | 900 |
| aagggacaca tgggttatga gttggagaca cgatcacatg caaacagaga gattggttaa | 960 |
| attatcgact ttttgtagta cttttttaaaa aaaaactatt tatataaaaa acatggtgga | 1020 |
| tggtggggac aggtgttcgt agggatgcaa acgacgtata ttgtatggac atggttaatg | 1080 |
| gaaggacgac cacgagccac catctcggct tgcttcatgt ttacttgtcg aggcattctt | 1140 |
| ggttactcta ctcagctccc tcttcctcag gttccaatca acactttttct tctatctctt | 1200 |
| ttcttaatta aaataattac caattaacta aatgctaatc agtcgatata tcatagttcc | 1260 |
| aacgttttgg acgtgtgatt tccattggcc actaccatat aaaacaacag agtctcttta | 1320 |
| ttcattattc aatatatatt tgagtattga tattattcat agggaggttt catttgtact | 1380 |
| atcaataaaa tttctacaac tcttggattt tttctgctac attttgtagt tattttttta | 1440 |
| attacttttta aaaacttgtg aataggagag actaatagta gtacgtaata tgattgtatc | 1500 |
| aaatgctttta acatgtgggg tttgggttaa ctatcatcat ttcatagatc actatttttgt | 1560 |
| tttcgtttgt tacctaactt tttgttatct ttgaaaaata atgttccacg agttgattga | 1620 |
| ctggacataa aaatcagatt ctctcactca tttacgttct acggttctag ccactcgttt | 1680 |
| ttttctttttt ctttctgtgg tgtaacacgt agataatgga ttttctatgt gtgtcgtctt | 1740 |
| gctcaagaat aataaatgtg gttaaaggtt aaatatagtc ctggaaatta attatctcct | 1800 |
| cttttttttat taaccaggat tttctaggat caggtgtcga ttttccggtg ggaaacgtct | 1860 |
| cgttcttcct cttctactcg ggtcacgtcg ccggttcgat gatcgcatct ttggacatga | 1920 |
| ggagaatgca gaggatgaga ctagcgatgc ttttttgacat cctcaatgta ttacaatcga | 1980 |
| tcaggctgct cgggacgaga ggacactaca cgattgatct cgctgtcgga gttggcgctg | 2040 |
| ggattctctt tgattcattc gccggcaagt acgaagagat gataagcaag agacacaatt | 2100 |
| tagtcaatgg ttttggtttg atttcgaaag actcgctagt caattaa | 2147 |

<210> SEQ ID NO 48
<211> LENGTH: 907
<212> TYPE: DNA
<213> ORGANISM: artificial
<220> FEATURE:
<223> OTHER INFORMATION: modified ROD coding sequence

<400> SEQUENCE: 48

```
atgtcaacta aaaccgtcgt ccctctccgt cgcagatcta agccccttaa cggaaatcac    60
actaacggcg tcgccattga cggaagcctc gacgacgacc acaaccgtcg catcggatca   120
gtaaatagcc aaatggataa cattgctaag aaaacggacg acggctacgc aaatcggcgg   180
aggaggagga ggaggaggga aaagcaaggc gtcgtttatg acgtggacgg cgcgtgacgt   240
tgtgtacgtg gcgaggtacc attggatacc gtgtttgttc gcggtcgggg ttctgttctt   300
cacgggcgtg gagtacacgc tccagatgat tcccgcgagg tctgagccgt tcgatattgg   360
gtttgtggcc acgcgctctc tgaatcgcgt cttggcaaat tcaccggatc ttaacaccgt   420
cttagccgct ctaaacacgg tgttcgtagg gatgcaaacg acgtatattg tatggacatg   480
gttaatggaa ggacgaccac gagccaccat ctcggcttgc ttcatgttta cttgtcgagg   540
cattcttggt tactctactc agctccctct tcctcaggat tttctaggat caggtgtcga   600
ttttccggtg ggaaacgtct cgttcttcct cttctactcg ggtcacgtcg ccggttcgat   660
gatcgcatct ttggacatga ggagaatgca gaggatgaga ctagcgatgc ttttgacat   720
cctcaatgta ttacaatcga tcaggctgct cgggacgaga ggacactaca cgattgatct   780
cgctgtcgga gttggcgctg ggattctctt tgattcattc gccggcaagt acgaagagat   840
gataagcaag agacacaatt tagtcaatgg ttttggtttg atttcgaaag actcgctagt   900
caattaa                                                              907

<210> SEQ ID NO 49
<211> LENGTH: 78
<212> TYPE: PRT
<213> ORGANISM: artificial
<220> FEATURE:
<223> OTHER INFORMATION: modified ROD polypeptide

<400> SEQUENCE: 49

Met Ser Thr Lys Thr Val Val Pro Leu Arg Arg Arg Ser Lys Pro Leu
1               5                   10                  15

Asn Gly Asn His Thr Asn Gly Val Ala Ile Asp Gly Ser Leu Asp Asp
            20                  25                  30

Asp His Asn Arg Arg Ile Gly Ser Val Asn Ser Gln Met Asp Asn Ile
        35                  40                  45

Ala Lys Lys Thr Asp Asp Gly Tyr Ala Asn Arg Arg Arg Arg Arg Arg
    50                  55                  60

Arg Arg Glu Lys Gln Gly Val Val Tyr Asp Val Asp Gly Ala
65                  70                  75

<210> SEQ ID NO 50
<211> LENGTH: 1521
<212> TYPE: DNA
<213> ORGANISM: artificial
<220> FEATURE:
<223> OTHER INFORMATION: modified FAE coding sequence

<400> SEQUENCE: 50
atgacgtccg ttaacgttaa gctcctttac cattacgtca tcaccaactt tttcaacctt    60
tgcttcttcc cgttagcggc gatcgttgcc ggaaaagcct ctcggcttac acaaacgat   120
cttcaccact tctactattc ctatctccaa cacaacctaa taccatatc tctactcttt   180
gccttcaccg ttttcggttt ggctctctac atcgtaaccc ggcccaaacc ggtttacctc   240
gttgaccatt cctgctacct tccaccatcg catcttagaa gcagtatctc taaggtcatg   300
gatatcttct atcaagtaag attagccgat cctttacgga acgcggcaag cgatgattcg   360
```

```
tcctggcttg atttcttgag gaagattcag gagcggtctg gtctaggcga tgaaacccac    420
ggccccgagg gactgcttca ggtccctcca cggaagactt tgccgcggc gcgtgaagaa     480 acagagcaag tgatcatcgg tgcgctcgaa aaactattcg agaacaccaa agttaaccct    540
aaagagattg gtatacttgt ggtgaactca agcatgttta tccgactcc ttcgctctcg     600 gcgatggttg ttaatacttt caagctccga agcaacatca gaagctttaa tcttggagga    660
atgggttgta gtgccggcgt tatagccatt gatctggcta aggacttgtt gcatgtccat    720
aaaaacactt atgctcttgt ggtgagcaca gagaacatca cttacaacat ttatgctggt    780
gataacagat ccatgatggt ttcgaattgc ttgttccgtg ttggtggggc cgcgattttg    840
ctctccaaca gccgaggga ccggagacgg tccaagtacc agctacttca cacggttcgg    900
acgcataccg gagctgacga caagtctttc cgatgtgtgc aacaagaaga cgacgagagc    960
ggtaaaaccg gggtgtgttt gtccaaggac ataaccggtg ttgccgggag aactgtttag   1020
aaaaacataa caacattggg tccgttggtt cttccttta gcgagaaatt tctttttttc    1080
gttaccttca tcgccaagaa actctttaaa gacaagatca acattacta cgtcccggat    1140 ttcaagcttg ctatcgacca tttttgtatt catgccggag gcagagccgt gatcgatgtg    1200
ctacagaaga acttaggtct attgccgatc gatgtggagg catctaggtc aacgttacat    1260
agatttggga acacttcgtc tagctcaatt tggtatgaat tggcgtacat agaggcaaaa    1320
ggaaggatga agagagggaa caaagtttag cagattgctt tagggtcagg gtttaagtgt    1380
aatagtgcgg tttgggtggc tctacgcaat gtcaaggctt cgacaaatag tccttgggaa    1440
cattgcattg atagatatcc agatgcaatt gattctgatt cgggtaagtc agagactcgt    1500
gtccaaaacg gtcggtccta a                                              1521
```

<210> SEQ ID NO 51
<211> LENGTH: 449
<212> TYPE: PRT
<213> ORGANISM: artificial
<220> FEATURE:
<223> OTHER INFORMATION: modified FAE polypeptide

<400> SEQUENCE: 51

```
Met Thr Ser Val Asn Val Lys Leu Leu Tyr His Tyr Val Ile Thr Asn
1               5                   10                  15

Phe Phe Asn Leu Cys Phe Phe Pro Leu Ala Ala Ile Val Ala Gly Lys
                20                  25                  30

Ala Ser Arg Leu Thr Thr Asn Asp Leu His His Phe Tyr Tyr Ser Tyr
        35                  40                  45

Leu Gln His Asn Leu Ile Thr Ile Ser Leu Leu Phe Ala Phe Thr Val
    50                  55                  60

Phe Gly Leu Ala Leu Tyr Ile Val Thr Arg Pro Lys Pro Val Tyr Leu
65                  70                  75                  80

Val Asp His Ser Cys Tyr Leu Pro Pro Ser His Leu Arg Ser Ile
                85                  90                  95

Ser Lys Val Met Asp Ile Phe Tyr Gln Val Arg Leu Ala Asp Pro Leu
                100                 105                 110

Arg Asn Ala Ala Ser Asp Asp Ser Ser Trp Leu Asp Phe Leu Arg Lys
            115                 120                 125

Ile Gln Glu Arg Ser Gly Leu Gly Asp Glu Thr His Gly Pro Glu Gly
    130                 135                 140

Leu Leu Gln Val Pro Pro Arg Lys Thr Phe Ala Ala Ala Arg Glu Glu
```

```
            145                 150                 155                 160
Thr Glu Gln Val Ile Ile Gly Ala Leu Glu Lys Leu Phe Glu Asn Thr
                    165                 170                 175

Lys Val Asn Pro Lys Glu Ile Gly Ile Leu Val Val Asn Ser Ser Met
                180                 185                 190

Phe Asn Pro Thr Pro Ser Leu Ser Ala Met Val Val Asn Thr Phe Lys
            195                 200                 205

Leu Arg Ser Asn Ile Arg Ser Phe Asn Leu Gly Gly Met Gly Cys Ser
        210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                    245                 250                 255

Ile Tyr Ala Gly Asp Asn Arg Ser Met Met Val Ser Asn Cys Leu Phe
                260                 265                 270

Arg Val Gly Gly Ala Ala Ile Leu Leu Ser Asn Lys Pro Arg Asp Arg
            275                 280                 285

Arg Arg Ser Lys Tyr Gln Leu Leu His Thr Val Arg Thr His Thr Gly
        290                 295                 300

Ala Asp Asp Lys Ser Phe Arg Cys Val Gln Gln Glu Asp Glu Ser
305                 310                 315                 320

Gly Lys Thr Gly Val Cys Leu Ser Lys Asp Ile Thr Gly Val Ala Gly
                    325                 330                 335

Arg Thr Val Gln Lys Asn Ile Thr Thr Leu Gly Pro Leu Val Leu Pro
                340                 345                 350

Phe Ser Glu Lys Phe Leu Phe Phe Val Thr Phe Ile Ala Lys Lys Leu
            355                 360                 365

Phe Lys Asp Lys Ile Lys His Tyr Tyr Val Pro Asp Phe Lys Leu Ala
        370                 375                 380

Ile Asp His Phe Cys Ile His Ala Gly Gly Arg Ala Val Ile Asp Val
385                 390                 395                 400

Leu Gln Lys Asn Leu Gly Leu Leu Pro Ile Asp Val Glu Ala Ser Arg
                    405                 410                 415

Ser Thr Leu His Arg Phe Gly Asn Thr Ser Ser Ser Ile Trp Tyr
                420                 425                 430

Glu Leu Ala Tyr Ile Glu Ala Lys Gly Arg Met Lys Arg Gly Asn Lys
            435                 440                 445

Val

<210> SEQ ID NO 52
<211> LENGTH: 1517
<212> TYPE: DNA
<213> ORGANISM: artificial
<220> FEATURE:
<223> OTHER INFORMATION: modified FAE coding sequence

<400> SEQUENCE: 52
atgacgtccg ttaacgttaa gctcctttac cattacgtca tcaccaactt tttcaacctt      60
tgcttcttcc cgttagcggc gatcgttgcc ggaaaagcct ctcggcttac cacaaacgat     120
cttcaccact tctactattc ctatctccaa cacaacctaa taccatatc tctactcttt     180 gccttcaccg ttttcggttt ggctctctac atacccggcc caaaccggtt tacctcgttg     240
accattcctg ctaccttcca ccatcgcatc ttagaagcag tatctctaag gtcatggata     300
tcttctatca agtaagatta gccgatcctt acggaacgc ggcaagcgat gattcgtcct     360
```

```
ggcttgattt cttgaggaag attcaggagc ggtctggtct aggcgatgaa acccacggcc      420
ccgagggact gcttcaggtc cctccacgga agacttttgc cgcggcgcgt gaagaaacag      480
agcaagtgat catcggtgcg ctcgaaaaac tattcgagaa caccaaagtt aaccctaaag      540
agattggtat acttgtggtg aactcaagca tgtttaatcc gactccttcg ctctcggcga      600
tggttgttaa tactttcaag ctccgaagca acatcagaag ctttaatctt ggaggaatgg      660
gttgtagtgc cggcgttata gccattgatc tggctaagga cttgttgcat gtccataaaa      720
acacttatgc tcttgtggtg agcacagaga acatcactta caacatttat gctggtgata      780
acagatccat gatggtttcg aattgcttgt tccgtgttgg tggggccgcg attttgctct      840
ccaacaagcc gagggaccgg agacggtcca gtaccagct acttcacacg ttcggacgc       900 ataccggagc tgacgacaag tctttccgat gtgtgcaaca agaagacgac gagagcggta      960
aaaccggggt gtgtttgtcc aaggacataa ccggtgttgc cgggagaact gtttagaaaa     1020
acataacaac attgggtccg ttggttcttc cttttagcga gaaatttctt tttttcgtta     1080
ccttcatcgc caagaaactc tttaaagaca agatcaaaca ttactacgtc ccggatttca     1140
agcttgctat cgaccatttt tgtattcatg ccggaggcag agccgtgatc gatgtgctac     1200
agaagaactt aggtctattg ccgatcgatg tggaggcatc taggtcaacg ttacatagat     1260
ttgggaacac ttcgtctagc tcaatttggt atgaattggc gtacatagag gcaaaaggaa     1320
ggatgaagag agggaacaaa gtttggcaga ttgctttagg gtcagggttt aagtgtaata     1380
gtgcggtttg ggtggctcta cgcaatgtca aggcttcgac aaatagtcct tgggaacatt     1440
gcattgatag atatccagat gcaattgatt ctgattcggg taagtcagag actcgtgtcc     1500
aaaacggtcg gtcctaa                                                    1517
```

<210> SEQ ID NO 53
<211> LENGTH: 104
<212> TYPE: PRT
<213> ORGANISM: artificial
<220> FEATURE:
<223> OTHER INFORMATION: modified FAE polypeptide

<400> SEQUENCE: 53

```
Met Thr Ser Val Asn Val Lys Leu Leu Tyr His Tyr Val Ile Thr Asn
1               5                   10                  15

Phe Phe Asn Leu Cys Phe Phe Pro Leu Ala Ala Ile Val Ala Gly Lys
                20                  25                  30

Ala Ser Arg Leu Thr Thr Asn Asp Leu His His Phe Tyr Tyr Ser Tyr
            35                  40                  45

Leu Gln His Asn Leu Ile Thr Ile Ser Leu Leu Phe Ala Phe Thr Val
        50                  55                  60

Phe Gly Leu Ala Leu Tyr Ile Pro Gly Pro Asn Arg Phe Thr Ser Leu
65                  70                  75                  80

Thr Ile Pro Ala Thr Phe His His Arg Ile Leu Glu Ala Val Ser Leu
                85                  90                  95

Arg Ser Trp Ile Ser Ser Ile Lys
            100
```

<210> SEQ ID NO 54
<211> LENGTH: 506
<212> TYPE: PRT
<213> ORGANISM: Arabidopsis thaliana

<400> SEQUENCE: 54

```
Met Thr Ser Val Asn Val Lys Leu Leu Tyr Arg Tyr Val Leu Thr Asn
1               5                   10                  15

Phe Phe Asn Leu Cys Leu Phe Pro Leu Thr Ala Phe Leu Ala Gly Lys
            20                  25                  30

Ala Ser Arg Leu Thr Ile Asn Asp Leu His Asn Phe Leu Ser Tyr Leu
            35                  40                  45

Gln His Asn Leu Ile Thr Val Thr Leu Leu Phe Ala Phe Thr Val Phe
    50                  55                  60

Gly Leu Val Leu Tyr Ile Val Thr Arg Pro Asn Pro Val Tyr Leu Val
65                  70                  75                  80

Asp Tyr Ser Cys Tyr Leu Pro Pro His Leu Lys Val Ser Val Ser
                85                  90                  95

Lys Val Met Asp Ile Phe Tyr Gln Ile Arg Lys Ala Asp Thr Ser Ser
            100                 105                 110

Arg Asn Val Ala Cys Asp Asp Pro Ser Ser Leu Asp Phe Leu Arg Lys
            115                 120                 125

Ile Gln Glu Arg Ser Gly Leu Gly Asp Glu Thr Tyr Ser Pro Glu Gly
    130                 135                 140

Leu Ile His Val Pro Pro Arg Lys Thr Phe Ala Ala Ser Arg Glu Glu
145                 150                 155                 160

Thr Glu Lys Val Ile Ile Gly Ala Leu Glu Asn Leu Phe Glu Asn Thr
                165                 170                 175

Lys Val Asn Pro Arg Glu Ile Gly Ile Leu Val Val Asn Ser Ser Met
            180                 185                 190

Phe Asn Pro Thr Pro Ser Leu Ser Ala Met Val Val Asn Thr Phe Lys
            195                 200                 205

Leu Arg Ser Asn Ile Lys Ser Phe Asn Leu Gly Gly Met Gly Cys Ser
210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Gln Gly
            245                 250                 255

Ile Tyr Ala Gly Glu Asn Arg Ser Met Met Val Ser Asn Cys Leu Phe
            260                 265                 270

Arg Val Gly Gly Ala Ala Ile Leu Leu Ser Asn Lys Ser Gly Asp Arg
            275                 280                 285

Arg Arg Ser Lys Tyr Lys Leu Val His Thr Val Arg Thr His Thr Gly
            290                 295                 300

Ala Asp Asp Lys Ser Phe Arg Cys Val Gln Gln Glu Asp Asp Glu Ser
305                 310                 315                 320

Gly Lys Ile Gly Val Cys Leu Ser Lys Asp Ile Thr Asn Val Ala Gly
                325                 330                 335

Thr Thr Leu Thr Lys Asn Ile Ala Thr Leu Gly Pro Leu Ile Leu Pro
            340                 345                 350

Leu Ser Glu Lys Phe Leu Phe Phe Ala Thr Phe Val Ala Lys Lys Leu
        355                 360                 365

Leu Lys Asp Lys Ile Lys His Tyr Tyr Val Pro Asp Phe Lys Leu Ala
        370                 375                 380

Val Asp His Phe Cys Ile His Ala Gly Gly Arg Ala Val Ile Asp Glu
385                 390                 395                 400

Leu Glu Lys Asn Leu Gly Leu Ser Pro Ile Asp Val Glu Ala Ser Arg
                405                 410                 415
```

```
Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
        435                 440                 445

Ala Trp Gln Ile Ala Leu Gly Ser Gly Phe Lys Cys Asn Ser Ala Val
    450                 455                 460

Trp Val Ala Leu Arg Asn Val Lys Ala Ser Ala Asn Ser Pro Trp Gln
465                 470                 475                 480

His Cys Ile Asp Arg Tyr Pro Val Lys Ile Asp Ser Asp Leu Ser Lys
                485                 490                 495

Ser Lys Thr His Val Gln Asn Gly Arg Ser
                500                 505

<210> SEQ ID NO 55
<211> LENGTH: 514
<212> TYPE: PRT
<213> ORGANISM: Oryza sativa

<400> SEQUENCE: 55

Met Asn Gly Gly Asp Ala Ala Ala Ala Thr Pro Ser His Arg
1               5                   10                  15

Arg Leu Pro Asp Phe Leu Gln Ser Val Asn Leu Lys Tyr Val Lys Leu
            20                  25                  30

Gly Tyr His Tyr Leu Ile Thr His Leu Leu Thr Leu Leu Leu Leu Pro
        35                  40                  45

Leu Met Ala Val Ile Val Leu Glu Ala Gly Arg Thr Asp Pro Asp Asp
    50                  55                  60

Leu Arg Gln Leu Trp Leu His Leu Gln Tyr Asn Leu Val Ser Val Leu
65              70                  75                  80

Val Leu Ser Ala Val Leu Val Phe Gly Ala Thr Val Tyr Val Leu Thr
                85                  90                  95

Arg Pro Arg Pro Val Tyr Leu Val Asp Phe Ala Cys Tyr Lys Pro Pro
            100                 105                 110

Asp Lys Leu Lys Val Arg Phe Asp Glu Phe Leu His His Ser Lys Leu
        115                 120                 125

Cys Gly Phe Ser Asp Asp Cys Leu Glu Phe Gln Arg Lys Ile Leu Glu
    130                 135                 140

Arg Ser Gly Leu Ser Glu Glu Thr Tyr Val Pro Glu Ala Met His Leu
145                 150                 155                 160

Ile Pro Pro Glu Pro Thr Met Ala Asn Ala Arg Ala Glu Ala Glu Ser
                165                 170                 175

Val Met Phe Gly Ala Leu Asp Lys Leu Phe Lys Phe Thr Gly Val Lys
            180                 185                 190

Pro Lys Asp Val Gly Val Leu Val Asn Cys Ser Leu Phe Asn Pro
        195                 200                 205

Thr Pro Ser Leu Ser Ala Met Ile Val Asn Lys Tyr Lys Leu Arg Gly
    210                 215                 220

Asn Ile Lys Ser Phe Asn Leu Gly Gly Met Gly Cys Ser Ala Gly Val
225                 230                 235                 240

Ile Ala Val Asp Leu Ala Arg Asp Met Leu Gln Val His Arg Asn Thr
                245                 250                 255

Tyr Ala Val Val Val Ser Thr Glu Asn Ile Thr Gln Asn Trp Tyr Phe
            260                 265                 270

Gly Asn Arg Lys Ser Met Leu Ile Pro Asn Cys Leu Phe Arg Val Gly
        275                 280                 285
```

```
Gly Ala Ala Val Leu Leu Ser Asn Arg Gly Ala Asp Arg Arg Ala
            290                 295                 300

Lys Tyr Ala Leu Lys His Val Val Arg Thr His Lys Gly Ala Asp Asn
305                 310                 315                 320

Lys Ala Phe Asn Cys Val Tyr Gln Glu Gln Asp Asp Glu Gly Lys Thr
                325                 330                 335

Gly Val Ser Leu Ser Lys Asp Leu Met Ala Ile Ala Gly Gly Ala Leu
                340                 345                 350

Lys Thr Asn Ile Thr Thr Leu Gly Pro Leu Val Leu Pro Phe Ser Glu
                355                 360                 365

Gln Leu Leu Phe Phe Ala Thr Leu Val Ala Lys Lys Leu Phe Asn Ala
            370                 375                 380

Lys Ile Lys Pro Tyr Ile Pro Asp Phe Lys Leu Ala Phe Glu His Phe
385                 390                 395                 400

Cys Ile His Ala Gly Gly Arg Ala Val Ile Asp Glu Leu Glu Lys Asn
                405                 410                 415

Leu Gln Leu Gln Pro Val His Val Glu Ala Ser Arg Met Thr Leu His
            420                 425                 430

Arg Phe Gly Asn Thr Ser Ser Ser Ile Trp Tyr Glu Leu Ala Tyr
            435                 440                 445

Met Glu Ala Lys Gly Arg Val Arg Arg Gly His Arg Ile Trp Gln Ile
450                 455                 460

Ala Phe Gly Ser Gly Phe Lys Cys Asn Ser Ala Val Trp His Ala Leu
465                 470                 475                 480

Arg Asn Val Asn Pro Ser Pro Glu Ser Pro Trp Glu Asp Cys Ile Asp
                485                 490                 495

Arg Tyr Pro Val Glu Leu Val Asp Gly Phe Ala Thr His Asn Asn Thr
                500                 505                 510

Gln Gln

<210> SEQ ID NO 56
<211> LENGTH: 457
<212> TYPE: PRT
<213> ORGANISM: Glycine max

<400> SEQUENCE: 56

Val Pro Leu Ile Leu Val Thr Leu Ile Gln Val Ser Gln Thr Thr Asp
1               5                   10                  15

Leu Arg His Leu Trp Leu His Leu Gln Tyr Asn Leu Leu Thr Ile Leu
            20                  25                  30

Thr Cys Ser Ala Val Leu Val Phe Gly Leu Thr Leu Tyr Ala Val Thr
                35                  40                  45

Cys Pro Arg Pro Val Tyr Leu Leu Asp Ser Ala Cys Phe Arg Pro Ala
        50                  55                  60

Asp His Leu Lys Ala Pro Phe Arg Ser Phe Met Asp His Ser Arg Leu
65                  70                  75                  80

Thr Gly Asp Phe Glu Glu Ser Ser Leu Glu Phe Gln Arg Lys Ile Leu
                85                  90                  95

Glu Arg Ser Gly Leu Gly Glu Gly Thr Tyr Val Pro Ala Met His
                100                 105                 110

Ser Ile Pro Pro Gln Pro Ser Met Ala Ala Arg Ala Glu Ala Glu
            115                 120                 125

Gln Val Met Phe Gly Ala Leu Asp Asn Leu Phe Gln Ser Thr Asn Ile
            130                 135                 140
```

```
Lys Pro Lys Asp Ile Gly Ile Leu Ile Val Asn Cys Ser Leu Phe Asn
145                 150                 155                 160

Pro Thr Pro Ser Leu Ser Ser Met Ile Val Asn Lys Tyr Lys Leu Arg
            165                 170                 175

Gly Asn Ile Arg Ser Phe Asn Leu Gly Gly Met Gly Cys Ser Ala Gly
        180                 185                 190

Val Ile Ala Val Asp Leu Ala Lys Asp Leu Leu Gln Val His Arg Asn
    195                 200                 205

Thr Tyr Ala Val Val Ser Thr Glu Asn Ile Thr Gln Asn Trp Tyr
210                 215                 220

Phe Gly Asn Lys Lys Ser Met Leu Ile Pro Asn Cys Leu Phe Arg Val
225                 230                 235                 240

Gly Cys Ser Val Leu Leu Leu Ser Asn Lys Pro Ala Asp Arg Arg
            245                 250                 255

Ala Lys Tyr Arg Leu Val His Val Val Arg Thr His Arg Gly Ala Asp
            260                 265                 270

Asp Lys Ala Phe Arg Cys Val Tyr Gln Glu Gln Asp Ala Gly Lys
        275                 280                 285

Thr Gly Val Ser Leu Ser Lys Asp Leu Met Ala Ile Ala Gly Gly Ala
    290                 295                 300

Leu Lys Thr Asn Ile Thr Thr Leu Gly Pro Leu Val Leu Pro Ile Ser
305                 310                 315                 320

Glu Gln Leu Leu Phe Phe Val Thr Leu Leu Met Lys Lys Leu Phe Lys
                325                 330                 335

Ala Asp Val Lys Pro Tyr Ile Pro Asp Phe Lys Leu Ala Phe Asp His
        340                 345                 350

Phe Cys Ile His Ala Gly Gly Arg Ala Val Ile Asp Glu Leu Glu Lys
        355                 360                 365

Asn Leu Gln Leu Leu Pro Glu His Val Glu Ala Ser Arg Met Thr Leu
370                 375                 380

His Arg Phe Gly Asn Thr Ser Ser Ser Ile Trp Tyr Glu Leu Ala
385                 390                 395                 400

Tyr Ile Glu Ala Lys Gly Arg Ile Lys Lys Gly Asn Arg Ile Trp Gln
                405                 410                 415

Ile Ala Phe Gly Ser Gly Phe Lys Cys Asn Ser Ala Val Trp Gln Ala
            420                 425                 430

Leu Arg Asn Val Arg Pro Ser Pro Asn Gly Pro Trp Glu Asp Cys Ile
        435                 440                 445

Asp Lys Tyr Pro Val Glu Ile Val Ser
        450                 455

<210> SEQ ID NO 57
<211> LENGTH: 517
<212> TYPE: PRT
<213> ORGANISM: Solanum lycopersicum

<400> SEQUENCE: 57

Met Asn Gly Ala Thr Gly Thr Gln Val Asn Thr Ala Asn Gly Gly Gly
1               5                   10                  15

Gly Glu Pro Val Gly Val Gln Ile Gln Gln Ser Arg Arg Leu Pro Asp
            20                  25                  30

Phe Leu Gln Ser Val Asn Leu Lys Tyr Val Lys Leu Gly Tyr His Tyr
        35                  40                  45

Leu Ile Ser His Leu Leu Thr Leu Cys Leu Ile Pro Val Met Ala Val
```

-continued

```
            50                  55                  60
Ile Leu Ile Glu Ala Ser Gln Met Asn Pro Asp Asp Ile Arg Gln Leu
 65                  70                  75                  80

Trp Leu His Leu Gln Tyr Asn Leu Val Ser Val Ile Cys Ser Ala
                 85                  90                  95

Val Leu Val Phe Gly Ser Thr Val Tyr Ile Met Thr Arg Pro Arg Pro
                100                 105                 110

Val Tyr Leu Ile Asp Tyr Ser Cys Tyr Lys Ala Pro Glu His Leu Lys
                115                 120                 125

Ala Pro Tyr Glu Arg Phe Met Gln His Ser Arg Leu Thr Gly Asp Phe
130                 135                 140

Asp Glu Ser Ser Leu Glu Phe Gln Arg Lys Ile Leu Glu Arg Ser Gly
145                 150                 155                 160

Leu Gly Asp Glu Thr Tyr Val Pro Glu Ala Met His Gln Leu Pro Pro
                165                 170                 175

Gln Pro Ser Met Gln Ala Ala Arg Glu Glu Ala Glu Gln Val Met Phe
                180                 185                 190

Gly Ala Leu Asp Lys Leu Phe Ala Asn Thr Ser Val Lys Pro Lys Lys
                195                 200                 205

Ile Gly Val Leu Val Asn Cys Ser Leu Phe Asn Pro Thr Pro Ser
                210                 215                 220

Leu Ser Ala Met Ile Val Asn Lys Tyr Lys Leu Arg Gly Asn Ile Arg
225                 230                 235                 240

Ser Phe Asn Leu Gly Gly Met Gly Cys Ser Ala Gly Val Ile Ala Val
                245                 250                 255

Asp Leu Ala Lys Asp Met Leu Gln Val His Arg Asn Thr Tyr Ala Val
                260                 265                 270

Val Val Ser Thr Glu Asn Ile Thr Gln Asn Trp Tyr Phe Gly Asn Lys
                275                 280                 285

Lys Ser Met Leu Ile Pro Asn Cys Leu Phe Arg Val Gly Gly Ser Ala
                290                 295                 300

Val Leu Leu Ser Asn Lys Ser Val Asp Arg Arg Ala Lys Tyr Lys
305                 310                 315                 320

Leu Val His Val Val Arg Thr His Arg Gly Ala Asp Asp Lys Ala Phe
                325                 330                 335

Arg Cys Val Tyr Gln Glu Gln Asp Asp Ala Gly Lys Thr Gly Val Ser
                340                 345                 350

Leu Ser Lys Asp Leu Met Ala Ile Ala Gly Gly Ala Leu Lys Thr Asn
                355                 360                 365

Ile Thr Thr Leu Gly Pro Leu Val Leu Pro Ile Ser Glu Gln Leu Leu
370                 375                 380

Phe Phe Gly Ser Leu Ile Ile Lys Lys Ile Phe Asn Lys His Ile Lys
385                 390                 395                 400

Pro Tyr Ile Pro Asp Phe Lys Leu Ala Phe Asp His Phe Cys Ile His
                405                 410                 415

Ala Gly Gly Arg Ala Val Ile Asp Glu Leu Glu Lys Asn Leu Gln Leu
                420                 425                 430

Thr Gln Val His Val Glu Ala Ser Arg Met Thr Leu His Arg Phe Gly
                435                 440                 445

Asn Thr Ser Ser Ser Ile Trp Tyr Glu Leu Ala Tyr Ile Glu Ala
450                 455                 460

Lys Gly Arg Met Lys Lys Gly Asn Lys Val Trp Gln Ile Ala Phe Gly
465                 470                 475                 480
```

Ser Gly Phe Lys Cys Asn Ser Ala Val Trp Gln Ala Leu Arg Asn Val
            485                 490                 495

Lys Pro Ser Pro Asp Gly Pro Trp Glu Asp Cys Ile Asp Arg Tyr Pro
            500                 505                 510

Val Lys Val Val Ser
            515

<210> SEQ ID NO 58
<211> LENGTH: 383
<212> TYPE: PRT
<213> ORGANISM: Solanum lycopersicum

<400> SEQUENCE: 58

Met Gly Ala Gly Gly Arg Met Ser Ala Pro Asn Gly Gly Thr Glu Val
1               5                   10                  15

Lys Lys Asn Pro Leu Gln Lys Val Pro Thr Ser Lys Pro Pro Phe Thr
            20                  25                  30

Val Gly Asp Ile Lys Lys Ala Ile Pro Pro His Cys Phe Gln Arg Ser
            35                  40                  45

Leu Ile Arg Ser Phe Ser Tyr Val Val Tyr Asp Leu Ile Leu Val Ser
    50                  55                  60

Ile Met Tyr Tyr Val Ala Asn Thr Tyr Phe His Leu Ile Pro Ser Pro
65              70                  75                  80

Tyr Cys Tyr Ile Ala Trp Pro Ile Tyr Trp Ile Cys Gln Gly Cys Val
                85                  90                  95

Cys Thr Gly Ile Trp Val Asn Ala His Glu Cys Gly His His Ala Phe
            100                 105                 110

Ser Asp Tyr Gln Leu Val Asp Asp Thr Val Gly Leu Ile Leu His Ser
            115                 120                 125

Ala Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Ser Lys Ser Gln Leu Gly Trp Tyr Ser Lys Tyr Leu Asn Asn Pro Leu
                165                 170                 175

Gly Arg Val Ile Thr Leu Thr Val Thr Leu Thr Leu Gly Trp Pro Leu
            180                 185                 190

Tyr Leu Ala Phe Asn Val Ser Gly Arg Pro Tyr Asp Arg Phe Ala Cys
            195                 200                 205

His Tyr Asp Pro Tyr Gly Pro Ile Tyr Asn Asn Arg Glu Arg Leu Gln
210                 215                 220

Ile Phe Leu Ser Asp Ala Gly Val Leu Gly Ala Cys Tyr Leu Leu Tyr
225                 230                 235                 240

Arg Val Ala Leu Val Lys Gly Leu Ala Trp Leu Val Cys Ile Tyr Gly
                245                 250                 255

Val Pro Leu Leu Val Val Asn Gly Phe Leu Val Leu Ile Thr Tyr Leu
            260                 265                 270

Gln His Thr His Pro Ser Leu Pro His Tyr Asp Ser Thr Glu Trp Asp
            275                 280                 285

Trp Leu Arg Gly Ala Leu Ala Thr Cys Asp Arg Asp Tyr Gly Val Leu
            290                 295                 300

Asn Lys Val Phe His Asn Ile Thr Asp Thr His Val Val His His Leu
305                 310                 315                 320

Phe Ser Ala Met Pro His Tyr Asn Ala Met Glu Ala Thr Lys Ala Val

```
                        325                 330                 335
Lys Pro Leu Leu Gly Asp Tyr Tyr Gln Phe Asp Gly Thr Pro Ile Phe
                    340                 345                 350
Lys Ala Met Trp Arg Glu Ala Lys Glu Cys Leu Tyr Val Glu Lys Asp
                355                 360                 365
Glu Ser Ser Gln Gly Lys Gly Val Phe Trp Tyr Lys Asn Lys Leu
            370                 375                 380

<210> SEQ ID NO 59
<211> LENGTH: 293
<212> TYPE: PRT
<213> ORGANISM: Solanum lycopersicum

<400> SEQUENCE: 59

Met Asn Gly Asp Thr Phe His Ser Arg Asn Ser Ser Ser Thr Leu
1               5                   10                  15

Ser Lys Arg Asn Thr Thr Glu Arg Lys Val Asp Val Thr Glu Met Lys
                20                  25                  30

Lys Lys Ser Ala Ser Ala Thr Gly Thr Glu Val Gly Gly Tyr Gly Trp
            35                  40                  45

Trp Leu Gly Asn Ala Tyr Phe Met Lys Trp Arg Met Glu Asp Val Phe
50                  55                  60

Gly Val Val Lys Tyr His Pro Ile Pro Cys Ile Phe Ala Ala Ser Leu
65                  70                  75                  80

Leu Phe Phe Met Gly Val Glu Tyr Thr Leu His Met Ile Pro Ala Ser
                85                  90                  95

Ala Pro Pro Phe Asp Leu Gly Phe Ile Val Thr Val Pro Leu Asn Arg
            100                 105                 110

Leu Leu Ala Ala Lys Pro Ala Leu Asn Thr Leu Phe Ala Gly Leu Asn
        115                 120                 125

Thr Val Phe Val Ala Met Gln Thr Ala Tyr Ile Leu Gly Thr Phe Leu
130                 135                 140

Ile Glu Gly Arg Pro Arg Ala Thr Ile Ser Ala Leu Phe Met Phe Thr
145                 150                 155                 160

Phe Arg Gly Ile Leu Gly Tyr Ala Thr Gln Leu Pro Leu Pro Glu Asp
                165                 170                 175

Phe Leu Gly Ser Gly Val Asp Phe Pro Val Gly Asn Val Ser Phe Phe
            180                 185                 190

Leu Phe Tyr Ser Gly His Val Ala Ala Ser Val Ile Ala Ser Leu Asp
        195                 200                 205

Met Lys Arg Met Gln Arg Trp Glu Met Ala Arg Val Phe Asp Ala Leu
210                 215                 220

Asn Val Leu Gln Val Val Arg Leu Leu Ser Thr Arg Gly His Tyr Thr
225                 230                 235                 240

Ile Asp Leu Ala Val Gly Ile Gly Ala Gly Ile Leu Phe Asp Ser Met
                245                 250                 255

Ala Gly Asn Tyr Val Glu Thr Arg Thr Lys Leu Ser Ala Thr Asn Gly
            260                 265                 270

Ile Gly Val Glu Tyr Ser Pro Lys His Glu Asn Gly Val Lys Tyr Gln
        275                 280                 285

Ser Val Ser Ser Asp
        290

<210> SEQ ID NO 60
<211> LENGTH: 20
```

```
<212> TYPE: DNA
<213> ORGANISM: artificial
<220> FEATURE:
<223> OTHER INFORMATION: protospacer sequence

<400> SEQUENCE: 60
tacttggctt ggcctctcta                                              20

<210> SEQ ID NO 61
<211> LENGTH: 20
<212> TYPE: DNA
<213> ORGANISM: artificial
<220> FEATURE:
<223> OTHER INFORMATION: protospacer sequence

<400> SEQUENCE: 61
gacgacggct acgcaaacgg                                              20

<210> SEQ ID NO 62
<211> LENGTH: 24
<212> TYPE: DNA
<213> ORGANISM: artificial
<220> FEATURE:
<223> OTHER INFORMATION: synthetic oligonucleotide primer

<400> SEQUENCE: 62
attgtacttg gcttggcctc tcta                                         24

<210> SEQ ID NO 63
<211> LENGTH: 24
<212> TYPE: DNA
<213> ORGANISM: artificial
<220> FEATURE:
<223> OTHER INFORMATION: synthetic oligonucleotide primer

<400> SEQUENCE: 63
aaactagaga ggccaagcca agta                                         24

<210> SEQ ID NO 64
<211> LENGTH: 24
<212> TYPE: DNA
<213> ORGANISM: artificial
<220> FEATURE:
<223> OTHER INFORMATION: synthetic oligonucleotide primer

<400> SEQUENCE: 64
attggacgac ggctacgcaa acgg                                         24

<210> SEQ ID NO 65
<211> LENGTH: 24
<212> TYPE: DNA
<213> ORGANISM: artificial
<220> FEATURE:
<223> OTHER INFORMATION: synthetic oligonucleotide primer

<400> SEQUENCE: 65
aaacccgttt gcgtagccgt cgtc                                         24

<210> SEQ ID NO 66
<211> LENGTH: 21
<212> TYPE: DNA
<213> ORGANISM: artificial
<220> FEATURE:
<223> OTHER INFORMATION: synthetic oligonucleotide primer

<400> SEQUENCE: 66
```

```
aattaccacc cgttcttgtg c                                                   21

<210> SEQ ID NO 67
<211> LENGTH: 22
<212> TYPE: DNA
<213> ORGANISM: artificial
<220> FEATURE:
<223> OTHER INFORMATION: synthetic oligonucleotide primer

<400> SEQUENCE: 67
tctacgatcc caacaaaaca gc                                                  22

<210> SEQ ID NO 68
<211> LENGTH: 21
<212> TYPE: DNA
<213> ORGANISM: artificial
<220> FEATURE:
<223> OTHER INFORMATION: synthetic oligonucleotide primer

<400> SEQUENCE: 68
ttcttccttc gaaatctccg c                                                   21

<210> SEQ ID NO 69
<211> LENGTH: 22
<212> TYPE: DNA
<213> ORGANISM: artificial
<220> FEATURE:
<223> OTHER INFORMATION: synthetic oligonucleotide primer

<400> SEQUENCE: 69
aagaccataa gaagtacacg cc                                                  22
```

PLANTS HAVING INCREASED OIL QUALITY

CROSS-REFERENCE TO RELATED APPLICATIONS

This application is a National Stage application under 35 U.S.C. § 371 of International Application No. PCT/US2019/017660, having an International Filing Date of Feb. 12, 2019, which claims the benefit of U.S. Patent Application Ser. No. 62/629,387, filed on Feb. 12, 2018. The disclosure of the prior applications are considered part of (and are incorporated by reference in) the disclosure of this application.

STATEMENT REGARDING FEDERAL FUNDING

This invention was made with government support under 2014-67009-22305 awarded by the United States Department of Agriculture. The government has certain rights in the invention.

INCORPORATION BY REFERENCE

This application contains a Sequence Listing that has been submitted electronically as an ASCII text file named "09531-0412US1 SL_ST25.txt." The ASCII text file, created on Jun. 6, 2024, is 151,460 bytes in size. The material in the ASCII text file is hereby incorporated by reference in its entirety.

BACKGROUND

1. Technical Field

This document relates to methods and materials for generating oilseed (e.g., pennycress) plants that have oil with reduced levels of polyunsaturated fatty acids (PUFAs) and/or increased levels of oleic acid. For example, this document provides oilseed plants having reduced expression levels of one or more polypeptides involved in fatty acid biosynthesis (e.g., fatty acid desaturase 2 (FAD2) and reduced oleate desaturation 1 (ROD1)), as well as methods and materials for making and using oilseed plants having oil with reduced levels of polyunsaturated fatty acids and/or increased levels of oleic acid.

2. Background Information

Oilseed crops are sources of oils and seed meal having a multitude of uses. Winter annual varieties of pennycress (*Thlaspi arvense* L.) have been developed into a crop species that can be grown on the fallow land available between the harvest of corn and the sowing of soybeans the following year (Phippen et al., 2012 *Crop Science*, 52:2767-2773). There are over eighty million acres of land undergoing the corn/soybean rotation (e.g., in the United States, Argentina, and elsewhere) that could be used for double cropping pennycress. Pennycress can yield over 2000 pounds per acre of oilseeds that naturally contain up to 35% oil (Boateng et al., 2010 *Energy & Fuels*, 24:6624-6632; and Warwick et al., 2002 *Canadian Journal of Plant Science*, 82:803-823). The extracted oil can be easily converted into a variety of biofuels including biodiesel and jet fuel (Moser et al., 2009 *Energy & Fuels*, 23:4149-4155). However, natural fatty acid profiles of wild pennycress strains make pennycress oil inedible for humans (Bell, 1993 *Canadian Journal of Animal Science*, 73:679-697), and render pennycress oil of suboptimal quality for both biofuel and food production.

SUMMARY

This document provides methods and materials for generating oilseed crops (e.g., pennycress) with reduced levels of PUFAs and/or increased levels of oleic acid. For example, this document provides pennycress plants having reduced expression levels of one or more polypeptides involved in fatty acid biosynthesis (e.g., FAD2 polypeptides and/or ROD1 polypeptides) and/or reduced polypeptide activity of one or more polypeptides involved in fatty acid biosynthesis (e.g., FAD2 polypeptides and/or ROD1 polypeptides), as compared to corresponding wild type pennycress plants, as well as methods and materials for making and using oilseed plants having oil with reduced levels of polyunsaturated fatty acids and/or increased levels of oleic acid.

As demonstrated herein, pennycress plants having one or more loss-of-function modifications in the FAD2 gene (e.g., a single base-pair substitution) and pennycress plants having one or more loss-of-function modifications in the ROD1 gene (e.g., a single base-pair substitution) produced oils having reduced levels of PUFAs (e.g., reduced levels of linoleic acid and reduced levels of linolenic acids) and having increased levels of oleic acid, as compared to corresponding wild type pennycress plants. Also as demonstrated herein, pennycress plants having one or more loss-of-function modifications in the FAD2 gene and one or more loss-of-function modifications in the fatty acid elongase 1 (FAE1) gene, and pennycress plants having one or more loss-of-function modifications in the ROD1 gene and one or more loss-of-function modifications in the FAE1 gene, produced oils having reduced levels of PUFAs and having increased levels of oleic acid, as compared to corresponding wild type pennycress plants and as compared to pennycress plants having one or more modifications in only a single gene.

Having the ability to design oilseed (e.g., pennycress) plants having reduced levels of polyunsaturated fatty acids and/or increased levels of oleic acid provides a unique and unrealized opportunity to grow plants having improved oil quality without displacing other crops. For example, the oilseed plants provided herein can be grown in the interval between the harvest of summer crops (e.g., corn) and the establishment of the following spring crops (e.g., soybean) in the Midwestern United States, thereby maximizing potential production from land already in use. PUFAs make oils much less stable and prone to oxidation. Oil with reduced PUFAs enhances the value of the oil by increasing the stability of the oil (e.g., to extend the shelf life of products made using reduced PUFA oils), and by extending the temperature range at which the oil can be used. For example, reduced PUFA oil can be used at increased temperatures (e.g., in a food fryer or as a lubricant for mechanical systems). In addition, high levels of oleic acid are desirable in food sources (e.g., for human consumption and as a feedstock) and for the production of many bio-based products. The plants described herein can provide a new source of oilseeds that can be used for the production of, for example, biofuels (e.g., biodiesel and bio jet fuel), bioproducts (e.g., biopolymers used for the production of bioplastics), animal feed supplements, and/or edible oil.

In general, one aspect of this document features pennycress plants having reduced level of a PUFA and/or an increased level of oleic acid, as compared to a corresponding wild type pennycress plant, where the pennycress plant includes a modification in a nucleotide sequence encoding a polypeptide involved in fatty acid biosynthesis, and where the modification can be effective to reduce expression levels and/or polypeptide activity of said polypeptide. The modification can be a substitution, an insertion, or a deletion. The nucleotide sequence encoding a polypeptide involved in fatty acid biosynthesis can be a FAD2 coding sequence or a ROD1 coding sequence. The modification can be in a FAD2 coding sequence, where the FAD2 coding sequence containing the modification can be as set forth in SEQ ID NO:3 or SEQ ID NO:26. A FAD2 coding sequence containing a modification (e.g., a modification as set forth in SEQ ID NO:3 or SEQ ID NO:26) can encode a FAD2 polypeptide as set forth in SEQ ID NO:4. The modification can be in a FAD2 coding sequence, where the FAD2 coding sequence containing the modification can be as set forth in SEQ ID NO:5 or SEQ ID NO:27. A FAD2 coding sequence containing a modification (e.g., a modification as set forth in SEQ ID NO:5 or SEQ ID NO:27) can encode a FAD2 polypeptide as set forth in SEQ ID NO:6. The modification can be in a FAD2 coding sequence, where the FAD2 coding sequence containing the modification can be set forth in SEQ ID NO:7 or SEQ ID NO:28. A FAD2 coding sequence containing a modification (e.g., a modification as set forth in SEQ ID NO:7 or SEQ ID NO:28) can encode a FAD2 polypeptide as set forth in SEQ ID NO:8. The modification can be in a FAD2 coding sequence, where the modified FAD2 coding sequence containing the modification can be as set forth in SEQ ID NO:29 or SEQ ID NO:30. A FAD2 coding sequence containing a modification (e.g., a modification as set forth in SEQ ID NO:29 or SEQ ID NO:30) can encode a FAD2 polypeptide as set forth in SEQ ID NO:31. The modification can be in a FAD2 coding sequence, where the FAD2 coding sequence containing the modification can be as set forth in SEQ ID NO:32 or SEQ ID NO:33. A FAD2 coding sequence containing a modification (e.g., a modification as set forth in SEQ ID NO:32 or SEQ ID NO:33) can encode a FAD2 polypeptide as set forth in SEQ ID NO:34. The modification can be in a FAD2 coding sequence, where the FAD2 coding sequence containing the modification can be as set forth in SEQ ID NO:35 or SEQ ID NO:36. A FAD2 coding sequence containing a modification (e.g., a modification as set forth in SEQ ID NO:35 or SEQ ID NO:36) can encode a FAD2 polypeptide set forth in SEQ ID NO:37. The modification can be in a ROD1 coding sequence, where the ROD1 coding sequence containing the modification can be as set forth in SEQ ID NO: 11 or SEQ ID NO:39. A ROD1 coding sequence containing a modification (e.g., a modification as set forth in SEQ ID NO: 11 or SEQ ID NO:3) can encode a ROD1 polypeptide as set forth in SEQ ID NO:12. The modification can be in a ROD1 coding sequence, where the ROD1 coding sequence containing the modification can be as set forth in SEQ ID NO: 13 or SEQ ID NO:40. A ROD1 coding sequence containing a modification (e.g., a modification as set forth in SEQ ID NO: 13 or SEQ ID NO:40) can encode a ROD1 polypeptide as set forth in SEQ ID NO:14. The modification can be in a ROD1 coding sequence, where the ROD1 coding sequence containing the modification can be as set forth in SEQ ID NO:41 or SEQ ID NO:42. A ROD1 coding sequence containing a modification (e.g., a modification as set forth in SEQ ID NO: 41 or SEQ ID NO:42) can encode a ROD1 polypeptide set forth in SEQ ID NO:43. The modification can be in a ROD1 coding sequence, where the ROD1 coding sequence containing the modification can be as set forth in SEQ ID NO:44 or SEQ ID NO:45. A ROD1 coding sequence containing a modification (e.g., a modification as set forth in SEQ ID NO: 44 or SEQ ID NO:45) can encode a ROD1 polypeptide set forth in SEQ ID NO:46. The modification can be in a ROD1 coding sequence, where the ROD1 coding sequence containing the modification can be as set forth in SEQ ID NO:47 or SEQ ID NO:48. A ROD1 coding sequence containing a modification (e.g., a modification as set forth in SEQ ID NO: 47 or SEQ ID NO:48) can encode a ROD1 polypeptide set forth in SEQ ID NO:49. The pennycress plant also can include a modification in a FAE1 coding sequence, where modification can be effective to reduce expression levels and/or to reduced FAE1 polypeptide activity. The FAE1 coding sequence containing a modification can be as set forth in SEQ ID NO:17, SEQ ID NO:50, or SEQ ID NO:52. The FAE1 coding sequence containing a modification can encode a FAE1 polypeptide set forth in SEQ ID NO:18, SEQ ID NO: 51, or SEQ ID NO:53. The PUFAs can include one or more of linoleic acid (18:2) and linolenic acid (18:3). The PUFA can be linoleic acid, and the reduced level of linoleic acid can include about 1 mole % to about 15 mole % linoleic acid. The PUFA can be linoleic acid, and the reduced level of linoleic acid can include less than about 18 mole % linoleic acid. The PUFA can be linolenic acid, and the reduced level of linolenic acid can include about 1 mole % to about 11 mole % linoleic acid. The PUFA can be linolenic acid, and the reduced level of linolenic acid can include less than about 13 mole % linoleic acid. The increased levels of oleic acid can include from about 12 mole % to about 90 mole % oleic acid. The increased levels of oleic acid can include greater than about 12 mole % oleic acid.

In another aspect, this document features seed produced by pennycress plants having reduced level of a PUFA and/or an increased level of oleic acid, as compared to a corresponding wild type pennycress plant, where the pennycress plant includes a modification in a nucleotide sequence encoding a polypeptide involved in fatty acid biosynthesis, and where the modification can be effective to reduce expression levels and/or polypeptide activity of said polypeptide.

In another aspect, this document features pennycress plants having a reduced level of PUFAs and/or an increased level of oleic acid, as compared to a corresponding wild type pennycress plant, a pennycress plant having a genome edited in a site-specific manner to modify the coding sequence of the FAD2 gene, where the modified FAD2 coding sequence can be effective to reduce expression levels of FAD2 polypeptides and/or to reduced FAD2 polypeptide activity, and where the modified FAD2 coding sequence can be effective to reduce levels of PUFAs and/or increase levels of oleic acid in the plant. The modified FAD2 coding sequence can be as set forth in SEQ ID NO:3 or SEQ ID NO:26, and modified FAD2 coding sequence can encode a FAD2 polypeptide as set forth in SEQ ID NO:4. The modified FAD2 coding sequence can be as set forth in SEQ ID NO:5 or SEQ ID NO:27, and the modified FAD2 coding sequence can encode a FAD2 polypeptide as set forth in SEQ ID NO: 6. The modified FAD2 gene can be as set forth in SEQ ID NO:7 or SEQ ID NO:28, and the modified FAD2 coding sequence can encode a FAD2 polypeptide as set forth in SEQ ID NO: 8. The modified FAD2 coding sequence can be as set forth in SEQ ID NO:29 or SEQ ID NO: 30, and the modified FAD2 coding sequence can encode a FAD2 polypeptide as set forth in SEQ ID NO:31. The pennycress plant of claim 29, wherein modified FAD2 coding sequence can be as set forth in SEQ ID NO:32 or SEQ ID NO:33, and the modified FAD2 coding sequence can encode a FAD2 polypeptide as set forth in SEQ ID NO:34. The modified FAD2 coding sequence can be as set forth in SEQ ID NO:35 or SEQ ID NO:36, and the modified FAD2 coding sequence can encode a FAD2 polypeptide as set forth in SEQ ID NO: 37. The genome of the pennycress plant also can be edited in a site-specific manner to modify the coding sequence of the FAE1 gene, wherein the modified FAE1 coding sequence can be effective to reduce expression levels of FAE1 polypeptides and/or to reduced FAE1 polypeptide activity. The modified FAE1 coding sequence can be as set forth in SEQ ID NO: 17, SEQ ID NO:50, or SEQ ID NO:52. The modified FAE1 coding sequence can encode a FAE1 polypeptide as set forth in SEQ ID NO: 18, SEQ ID NO:51, or SEQ ID NO:53. The PUFAs can include one or more of linoleic acid (18:2) and linolenic acid (18:3). The PUFA can be linoleic acid, and the reduced level of linoleic acid can include about 1 mole % to about 15 mole % linoleic acid. The PUFA can be linoleic acid, and the reduced level of linoleic acid can include less than about 18 mole % linoleic acid. The PUFA can be linolenic acid, and the reduced level of linolenic acid can include about 1 mole % to about 11 mole % linoleic acid. The PUFA can be linolenic acid, and the reduced level of linolenic acid can include less than about 13 mole % linoleic acid. The increased levels of oleic acid can include from about 12 mole % to about 90 mole % oleic acid. The increased levels of oleic acid can include greater than about 12 mole % oleic acid.

In another aspect, this document features seed produced by pennycress plants having a reduced level of PUFAs and/or an increased level of oleic acid, as compared to a corresponding wild type pennycress plant, a pennycress plant having a genome edited in a site-specific manner to modify the coding sequence of the FAD2 gene, where the modified FAD2 coding sequence can be effective to reduce expression levels of FAD2 polypeptides and/or to reduced FAD2 polypeptide activity, and where the modified FAD2 coding sequence can be effective to reduce levels of PUFAs and/or increase levels of oleic acid in the plant.

In another aspect, this document features pennycress plants having reduced levels of PUFAs and/or increased levels of oleic acid, as compared to a corresponding wild type pennycress plant, a pennycress plant having a genome edited in a site-specific manner to modify the coding sequence of the ROD1 gene, where the modified ROD1 coding sequence can be effective to reduce expression levels of ROD1 polypeptides and/or to reduced ROD1 polypeptide activity, and where the modified ROD1 coding sequence can be effective to reduce levels of PUFAs and/or increase levels of oleic acid in the plant. The modified ROD1 coding sequence can be as set forth in SEQ ID NO: 11 or SEQ ID NO:39, and the modified ROD1 coding sequence can encode a ROD1 polypeptide as set forth in SEQ ID NO:12. The modified ROD1 coding sequence can be as set forth in SEQ ID NO: 13 or SEQ ID NO:40, and the modified ROD1 coding sequence can encode a ROD1 polypeptide as set forth in SEQ ID NO: 14. The modified ROD1 coding sequence can be as set forth in SEQ ID NO:41 or SEQ ID NO:42, and the modified ROD1 coding sequence can encode a ROD1 polypeptide as set forth in SEQ ID NO:43. The modified ROD1 coding sequence can be as set forth in SEQ ID NO:44 or SEQ ID NO:45, and the modified ROD1 coding sequence can encode a ROD1 polypeptide as set forth in SEQ ID NO:46. The modified ROD1 coding sequence can be as set forth in SEQ ID NO:47 or SEQ ID NO:48, and the modified ROD1 coding sequence can encode a ROD1 polypeptide as set forth in SEQ ID NO:49. The genome of the pennycress plant also can be edited in a site-specific manner to modify the coding sequence of the FAE1 gene, where the modified FAE1 coding sequence can be effective to reduce expression levels of FAE1 polypeptides and/or to reduced FAE1 polypeptide activity. The modified FAE1 coding sequence can be as set forth in SEQ ID NO:17, SEQ ID NO:50, or SEQ ID NO:52. The modified FAE1 coding sequence can encode a FAE1 polypeptide as set forth in SEQ ID NO: 18, SEQ ID NO:51, or SEQ ID NO:53. The PUFAs can include one or more of linoleic acid (18:2) and linolenic acid (18:3). The PUFA can be linoleic acid, and the reduced level of linoleic acid can include about 1 mole % to about 15 mole % linoleic acid. The PUFA can be linoleic acid, and the reduced level of linoleic acid can include less than about 18 mole % linoleic acid. The PUFA can be linolenic acid, and the reduced level of linolenic acid can include about 1 mole % to about 11 mole % linoleic acid. The PUFA can be linolenic acid, and the reduced level of linolenic acid can include less than about 13 mole % linoleic acid. The increased levels of oleic acid can include from about 12 mole % to about 90 mole % oleic acid. The increased levels of oleic acid can include greater than about 12 mole % oleic acid.

In another aspect, this document features seed produced by pennycress plants having reduced levels of PUFAs and/or increased levels of oleic acid, as compared to a corresponding wild type pennycress plant, a pennycress plant having a genome edited in a site-specific manner to modify the coding sequence of the ROD1 gene, where the modified ROD1 coding sequence can be effective to reduce expression levels of ROD1 polypeptides and/or to reduced ROD1 polypeptide activity, and where the modified ROD1 coding sequence can be effective to reduce levels of PUFAs and/or increase levels of oleic acid in the plant.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 3 contains an amino acid alignment including a wild type *Oryza sativa* FAD2 sequence (XP_015625626.1; SEQ ID NO: 19), a wild type *Glycine max* FAD2 sequence (NP 001347010.1; SEQ ID NO:20), a wild type *Arabidopsis thaliana* FAD2 sequence (NP_187819.1; SEQ ID NO:21), a mutant pennycress FAD2 sequence (Tafad2-1; SEQ ID NO: 4), a mutant pennycress FAD2 sequence (Tafad2-2; SEQ ID NO:6), a mutant pennycress FAD2 sequence (Tafad2-3; SEQ ID NO:8), and a wild type pennycress FAD2 sequence (TaFAD2; SEQ ID NO:2). Changes in pennycress mutant sequences relative to wild type pennycress TaFAD2 are shown in bold font.

FIG. 5 contains an amino acid alignment including a wild type *Oryza sativa* ROD1 sequence (XP_015644243.1; SEQ ID NO:22), a wild type *Glycine max* ROD1 sequence (XP_003531718.1; SEQ ID NO:23), a wild type *Arabidopsis thaliana* ROD1 sequence (NP_566527.1; SEQ ID NO:24), a mutant pennycress ROD1 sequence (Tarod1-2; SEQ ID NO: 14), a wild type pennycress ROD1 sequence (TaROD1; SEQ ID NO:10), and a mutant pennycress ROD1 sequence (Tarod1-1; SEQ ID NO:12). Changes in pennycress mutant sequences relative to wild type pennycress TaROD1 are shown in bold font.

FIG. 11 contains an amino acid alignment of pennycress FAE1 EMS and CRISPR-Cas9 generated alleles with wild type FAE1 amino acid sequences. Sequences shown include a wild type *Arabidopsis thaliana* (At) FAE1 (SEQ ID NO:54), a wild type pennycress (Ta) FAE1 (SEQ ID NO:16), a mutant pennycress FAE1 sequence (Ta-fae1-1; SEQ ID NO:18), a mutant pennycress FAE1 sequence (Ta-fae1-2; SEQ ID NO:51), a mutant pennycress FAE1 sequence (Ta-fae1-3; SEQ ID NO:53), a wild type *Oryza sativa* (Os) FAE1 (SEQ ID NO:55), a wild type *Glycine max* (Gm) FAE1 (SEQ ID NO:56), and a wild type *Solanum lycopersicum* (Sl) FAE1 (SEQ ID NO:57). Changes in pennycress mutant sequences relative to wild type pennycress TaFAE1 are highlighted.

FIG. 13 contains an amino acid alignment of pennycress FAD2 EMS and CRISPR-Cas9 generated alleles with wild type FAD2 amino acid sequences. Sequences shown include a wild type *Arabidopsis thaliana* (At) FAD2 (SEQ ID NO:21), a wild type pennycress (Ta) FAD2 (SEQ ID NO:2), a mutant pennycress FAD2 sequence (Ta-fad2-1; SEQ ID NO:4), a mutant pennycress FAD2 sequence (Ta-fad2-2; SEQ ID NO:6), a mutant pennycress FAD2 sequence (Ta-fad2-3; SEQ ID NO:8), a mutant pennycress FAD2 sequence (Ta-fad2-4; SEQ ID NO:31), a mutant pennycress FAD2 sequence (Ta-fad2-5; SEQ ID NO:34), a mutant pennycress FAD2 sequence (Ta-fad2-6; SEQ ID NO:37), a wild type *Oryza sativa* (Os) FAD2 (SEQ ID NO:19), a wild type *Glycine max* (Gm) FAD2 (SEQ ID NO: 20), and a wild type *Solanum lycopersicum* (Sl) FAD2 (SEQ ID NO:58). Changes in pennycress mutant sequences relative to wild type pennycress TaFAD2 are highlighted.

FIG. 15 contains an amino acid alignment of pennycress ROD1 EMS and CRISPR-Cas9 generated alleles with wild type ROD1 amino acid sequences. Sequences shown include a wild type *Arabidopsis thaliana* (At) ROD1 (SEQ ID NO:24), a wild type pennycress (Ta) ROD1 (SEQ ID NO: 10), a mutant pennycress ROD1 sequence (Ta-rod1-1; SEQ ID NO: 12), a mutant pennycress ROD1 sequence (Ta-rod1-2; SEQ ID NO:14), a mutant pennycress ROD1 sequence (Ta-rod1-3; SEQ ID NO:43), a mutant pennycress ROD1 sequence (Ta-rod1-4; SEQ ID NO:46), a mutant pennycress ROD1 sequence (Ta-rod1-5; SEQ ID NO:49), a wild type *Oryza sativa* (Os) ROD1 (SEQ ID NO:22), a wild type *Glycine max* (Gm) ROD1 (SEQ ID NO:23), and a wild type *Solanum lycopersicum* (Sl) ROD1 (SEQ ID NO: 59). Changes in pennycress mutant sequences relative to wild type pennycress TaROD1 are highlighted.

Figure 20:
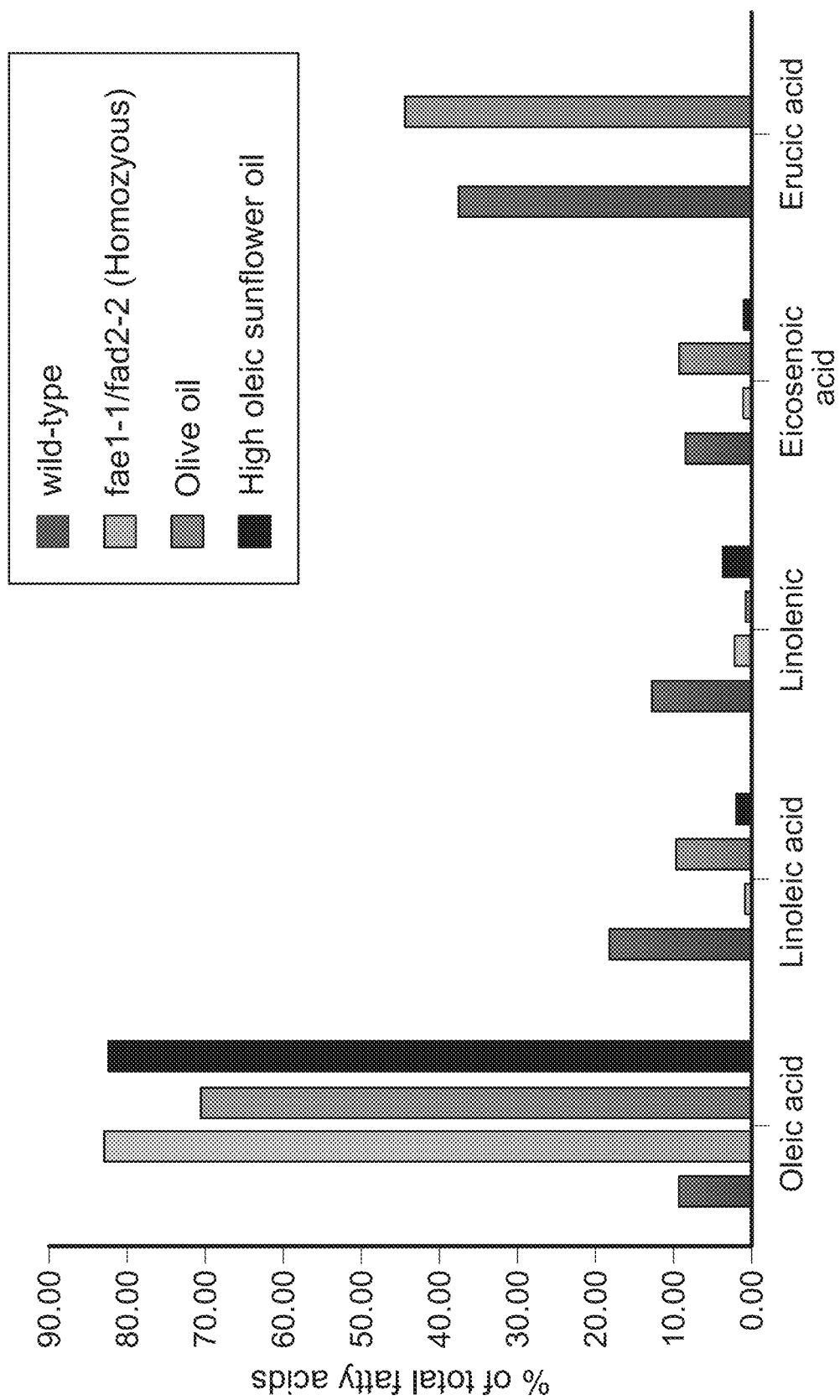

FIG. 20 contains a graph showing that Tafae1/Tafad2 oil is very similar in fatty acid composition to olive oil and high oleic sunflower.

Figure 21:
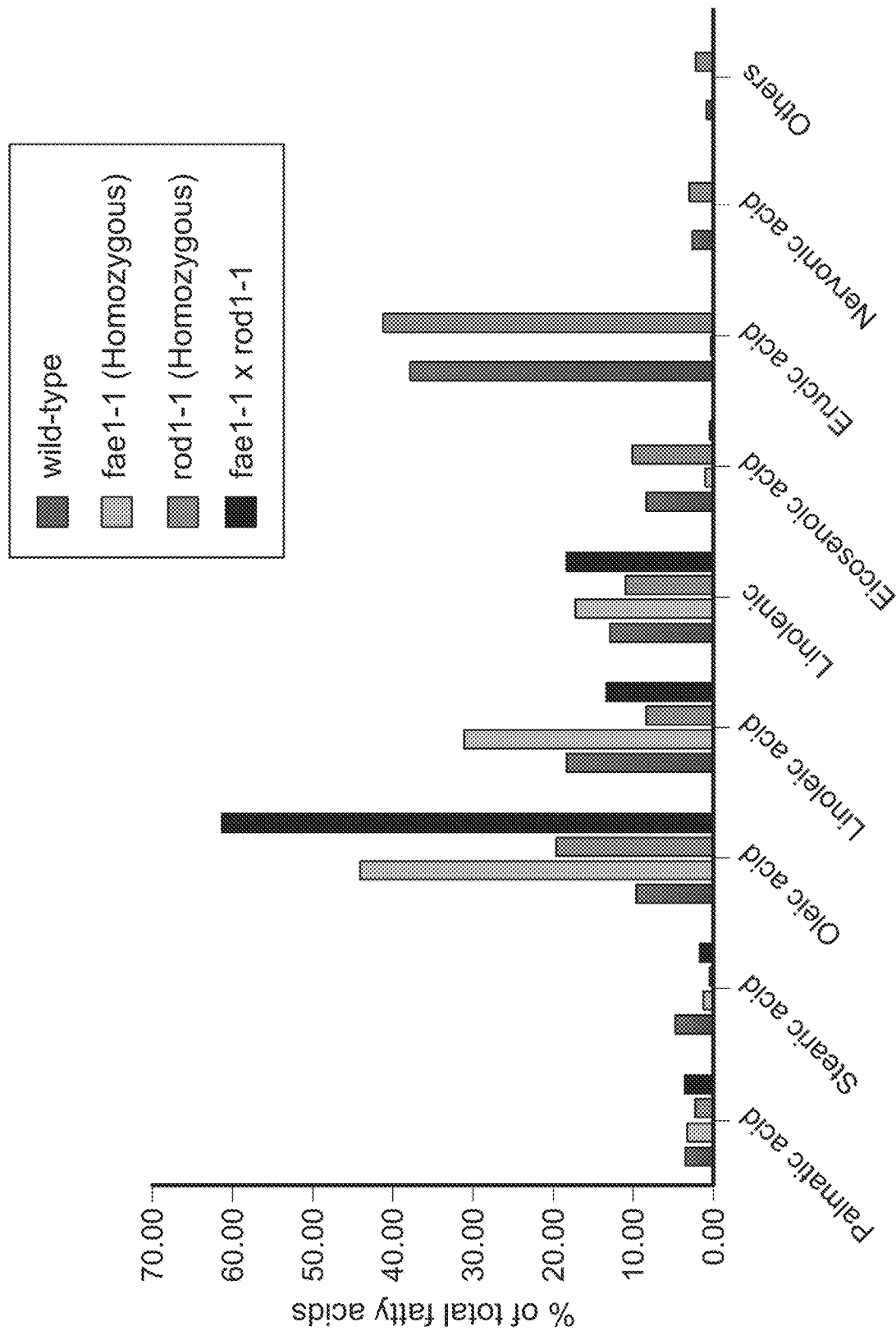

FIG. 21 contains a graph showing that combining Tafae1 and Tarod1 mutations results in great increase in oleic acid. The Tarod1-1 and Tafae1-1 mutants were crossed. The resulting F1 plants were allowed to self fertilize. F2 seeds were scored for the homozygosity for both Tarod1-1 and Tafae1-1 using PCR based DNA markers that used the mutations in the respective genes as markers to assess the genotypes of the seeds. Oil was extracted from seeds that were homozygous for both Tarod1-1 and Tafae1-1and subjected to GC analysis. The double mutant seed contained ~55 mol % of oleic acid while maintaining lower levels of the PUFAs linoleic and linolenic along with near zero erucic acid.

Figure 22:
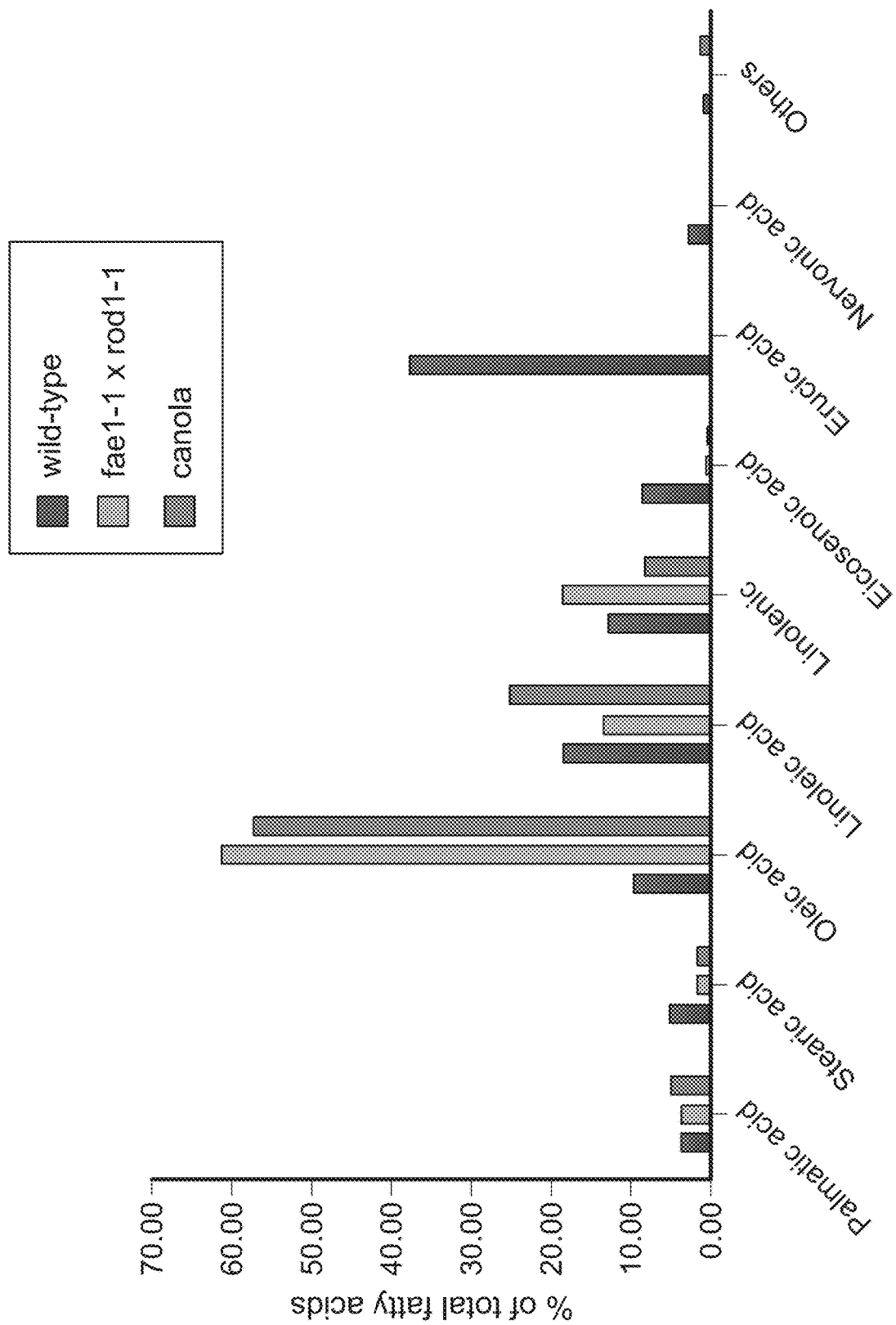

FIG. 22 contains a graph showing Tafae1×Tarod1 double mutant seed oil is very similar in fatty acid composition to canola oil.

DETAILED DESCRIPTION

This document provides oilseed (e.g., pennycress) plants. For example, this document provides oilseed plants having reduced levels of PUFAs and/or increased levels of oleic acid. In some cases, this document provides oilseed plants having reduced expression levels of one or more polypeptides involved in fatty acid biosynthesis (e.g., FAD2 polypeptides and/or ROD1 polypeptides) and/or reduced polypeptide activity of one or more polypeptides involved in fatty acid biosynthesis (e.g., FAD2 polypeptides and/or ROD1 polypeptides), as compared to corresponding wild type plants. For example, an oilseed plant having reduced levels of PUFAs and/or increased levels of oleic acid can have one or more modifications in a FAD2 gene effective to reduce FAD2 polypeptide expression and/or reduce FAD2 polypeptide function. For example, an oilseed plant having reduced levels of PUFAs and/or increased levels of oleic acid can have a one or more modifications in a ROD1 gene effective to reduce ROD1 polypeptide expression and/or reduce ROD1 polypeptide function.

This document also provides methods and materials for making and using oilseed plants having reduced levels of PUFAs and/or increased levels of oleic acid. In some cases, site-specific gene editing can be used to modify an FAD2 gene and/or a ROD1 gene. For example, site-specific editing can be used to modify the FAD2 gene in an oilseed plant genome to reduce FAD2 polypeptide expression and/or reduce FAD2 polypeptide function. For example, site-specific editing can be used to modify the ROD1 gene in an oilseed plant genome to reduce ROD1 polypeptide expression and/or reduce ROD1 polypeptide function. In some cases, oilseed (e.g. pennycress) plants described herein (e.g., having reduced levels of PUFAs and/or increased levels of oleic acid) can produce oil containing erucic acid (e.g., having any detectable level of erucic acid or having about 0.5% or greater mole % erucic acid). In some cases, oilseed (e.g., pennycress) plants provided herein can produce oil not containing erucic acid (e.g., having non-detectable levels of erucic acid or having zero mole % erucic acid).

In some cases, oilseed (e.g. pennycress) plants described herein (e.g., having reduced levels of PUFAs and/or increased levels of oleic acid) can produce oil similar in fatty acid composition to olive oil. The fatty acid profile of olive oil can be as described elsewhere (see, e.g., Montero de Espinosa et al., 2011 European Polymer Journal 47:837-852).

In some cases, oilseed (e.g. pennycress) plants described herein (e.g., having reduced levels of PUFAs and/or increased levels of oleic acid) can produce oil similar in fatty acid composition to sunflower oil. The fatty acid profile of sunflower oil can be as described elsewhere (see, e.g., Montero de Espinosa et al., 2011 European Polymer Journal 47:837-852).

In some cases, oilseed (e.g. pennycress) plants described herein (e.g., having reduced levels of PUFAs and/or increased levels of oleic acid) can produce oil similar in fatty acid composition to canola oil. The fatty acid profile of canola oil can be as described elsewhere (see, e.g., Montero de Espinosa et al., 2011 European Polymer Journal 47:837-852).

The oilseed (e.g. pennycress) plants described herein (e.g., having reduced levels of PUFAs and/or increased levels of oleic acid) can be derived from any appropriate species of oilseed plant. An oilseed plant can be a monocotyledonous oilseed plant. An oilseed plant can be a dicotyledonous oilseed plant. An oilseed plant can be a member of the family Brassicaceae (e.g., the mustard family). For example, an oilseed plant can be a member of the genus *Brassica*. Examples of oilseed plants include, without limitation, pennycress, rapeseed, soybean, sunflower, canola, flax, camelina, *carinata, crambe*, and *lepidium* plants. In some cases, an oilseed plant having reduced levels of PUFAs and/or increased levels of oleic acid as described herein can be a pennycress plant.

The oilseed (e.g. pennycress) plants described herein (e.g., having reduced levels of PUFAs and/or increased levels of oleic acid) can have reduced levels of any appropriate PUFA. In some cases, an oilseed plant having reduced levels of PUFAs as described herein can have reduced levels of one or more (e.g., one, two, three, four, or more) PUFAs. In some cases, a PUFA can be an Omega 3 fatty acid. In some cases, a PUFA can be an Omega 6 fatty acid. In some cases, a PUFA can be an Omega 9 fatty acid. Examples of PUFAs include, without limitation, linoleic acid (18:2) and linolenic acid (18:3). For example, a pennycress plant having reduced levels of PUFAs can have reduced levels of linoleic acid, and can have reduced levels of linolenic acid.

The oilseed (e.g. pennycress) plants described herein (e.g., having reduced levels of PUFAs and/or increased levels of oleic acid) can have reduced levels of PUFAs in one or more plant tissues. In some cases, an oilseed plant having reduced levels of PUFAs and/or increased levels of oleic acid as described herein can have reduced levels of PUFAs and/or increased levels of oleic acid in the seeds. In other cases, an oilseed plant (or any plant) can have reduced levels of PUFAs and/or increased levels of oleic acid in vegetative and storage tissues (e.g., natural and/or man-made) including stems, leaves, roots, and tubers.

The term "reduced level" as used herein with respect to a level of PUFAs in the oil obtained from an oilseed (e.g., pennycress) plant refers to any level that is lower than a reference level of PUFAs. The term "reference level" as used herein with respect to PUFAs refers to the level of PUFAs typically observed in the oil obtained from a wild type oilseed plant. It will be appreciated that levels of PUF As in the oil obtained from comparable oilseed plants are used when determining whether or not the level of PUF As in the oil obtained from a particular oilseed plant is a reduced level. For example, a wild type pennycress plant typically produces oil having about 26 mole % to about 35 mole % PUFAs (see, e.g., Moser et al., 2009 *Energy and Fuels*, 23:4149-4155).

In some cases, an oilseed plant having reduced levels of PUFAs as described herein can have a reduced level of linoleic acid (18:2). For example, a pennycress plant having reduced levels of linoleic acid can have from less than about 1 mole % (e.g., about 0.5 mole %) to about 15 mole % (e.g., from about 1 mole % to about 13 mole %, from about 1 mole % to about 12 mole %, from about 1 mole % to about 11 mole %, from about 1 mole % to about 10 mole %, from about 1 mole % to about 8 mole %, from about 1 mole % to about 5 mole %, from about 1 mole % to about 3 mole %, from about 2 mole % to about 15 mole %, from about 3 mole % to about 15 mole %, from about 5 mole % to about 15 mole %, from about 7 mole % to about 15 mole %, from about 10 mole % to about 15 mole %, from about 12 mole % to about 15 mole %, from about 2 mole % to about 12 mole %, from about 5 mole % to about 10 mole %, or from about 7 mole % to about 9 mole %) linoleic acid, as compared to corresponding wild type plants. For example, a pennycress plant having reduced levels of linoleic acid can have less than about 18 mole % (e.g., less than about 17 mole %, less than about 16 mole %, less than about 15 mole %, less than about 14 mole %, less than about 13 mole %, less than about 12 mole %, less than about 11 mole %, less than about 10 mole %, less than about 9 mole %, less than about 8 mole %, less than about 7 mole %, less than about 6 mole %, less than about 5 mole %, less than about 4 mole %, less than about 3 mole %, less than about 2 mole %, less than about 1 mole %, or less than about 0.5 mole %) linoleic acid, as compared to corresponding wild type plants.

In some cases, an oilseed plant having reduced levels of PUFAs as described herein can have a reduced level of linolenic acid (18:3). For example, a pennycress plant having reduced levels of linolenic acid can have from about 1 mole % to about 11 mole % (e.g., from about 1 mole % to about 10 mole %, from about 1 mole % to about 8 mole %, from about 1 mole % to about 6 mole %, from about 1 mole % to about 5 mole %, from about 1 mole % to about 3 mole %, from about 3 mole % to about 11 mole %, from about 5 mole % to about 11 mole %, from about 7 mole % to about 11 mole %, from about 9 mole % to about 11 mole %, from about 2 mole % to about 10 mole %, from about 4 mole % to about 9 mole %, or from about 6 mole % to about 8 mole %) linolenic acid, as compared to corresponding wild type plants. For example, a pennycress plant having reduced levels of linolenic acid can have less than about 13 mole % (e.g., less than about 12 mole %, less than about 11 mole %, less than about 10 mole %, less than about 9 mole %, less than about 8 mole %, less than about 7 mole %, less than about 6 mole %, less than about 5 mole %, less than about 4 mole %, less than about 3 mole %, less than about 2 mole %, less than about 1 mole %, or less than about 0.5 mole %) linolenic acid, as compared to corresponding wild type plants.

The oilseed (e.g. pennycress) plants described herein (e.g., having reduced levels of PUFAs and/or increased levels of oleic acid) can have increased levels of oleic acid in one or more plant tissues. In some cases, an oilseed plant having increased levels of oleic acid as described herein can have increased levels of oleic acid in the seeds. In other cases, an oilseed plant (or any plant) can have increased levels of oleic acid in vegetative and storage tissues (e.g., natural and/or man-made) including stems, leaves, roots, and tubers.

The term "increased level" as used herein with respect to a level of oleic acid in the oil obtained from an oilseed (e.g., pennycress) plant refers to any level that is lower than a reference level of oleic acid. The term "reference level" as used herein with respect to oleic acid refers to the level of oleic acid typically observed in the oil obtained from a wild type oilseed plant. It will be appreciated that levels of oleic acid in the oil obtained from comparable oilseed plants are used when determining whether or not the level of oleic acid in the oil obtained from a particular oilseed plant is an increased level. For example, a wild type pennycress plant typically produces oil having about 12 mole % to about 13 mole % oleic acid (see, e.g., Moser et al., 2009 *Energy and Fuels,* 23:4149-4155).

In some cases, an oilseed plant having increased levels of oleic acid as described herein can have from about 12 mole % to about 90 mole % (e.g., from about 15 mole % to about 90 mole %, from about 18 mole % to about 90 mole %, from about 20 mole % to about 90 mole %, from about 25 mole % to about 90 mole %, from about 30 mole % to about 90 mole %, from about 35 mole % to about 90 mole %, from about 40 mole % to about 90 mole %, from about 50 mole % to about 90 mole %, from about 75 mole % to about 90 mole %, from about 12 mole % to about 80 mole %, from about 12 mole % to about 60 mole %, from about 12 mole % to about 50 mole %, from about 12 mole % to about 40 mole %, from about 12 mole % to about 30 mole %, from about 12 mole % to about 20 mole %, from about 12 mole % to about 15 mole %, from about 15 mole % to about 80 mole %, from about 20 mole % to about 70 mole %, from about 25 mole % to about 60 mole %, from about 30 mole % to about 50 mole %, or from about 35 mole % to about 40 mole %) oleic acid, as compared to corresponding wild type plants. For example, a pennycress plant having increased levels of oleic acid can have greater than about 12 mole % (e.g., greater than about 13 mole %, greater than about 14 mole %, greater than about 15 mole %, greater than about 16 mole %, greater than about 17 mole %, greater than about 18 mole %, greater than about 19 mole %, greater than about 20 mole %, greater than about 22 mole %, greater than about 25 mole %, greater than about 30 mole %, greater than about 32 mole %, greater than about 35 mole %, or greater than about 40 mole %) oleic acid, as compared to corresponding wild type plants.

In some cases, the oilseed (e.g. pennycress) plants described herein (e.g., having reduced levels of PUFAs and/or increased levels of oleic acid) can be as described in the Examples. For example, the oilseed plants described herein can be from the Tafad2-1 line, the Tafad2-2 line, the Tafad2-3 line, the D0422 Tarod1-1 line, or the E2014 Tarod1-2 line as described, for example, in Example 1, or can be progeny derived from those lines. For example, the oilseed plants described herein can be from the Tafae1-1 Tarod1-1 line or the Tafae1-1 Tafad2-2 line as described, for example, in Example 2, or can be progeny derived from those lines. For example, the oilseed plants described herein can be from the E5 398P5 Tafad2-1 line, the E2790 Tafad2-2 line, the E5 199P5 Tafad2-3 line, the D0422 Tarod1-1 line, the E2014 Tarod1-2, the Ta-fae1-3 line 745D1, the Ta-fad2-4 line 1791D1, the Ta-fad2-4 line 1791D2, the Ta-fad2-4 line 1791D3, the Ta-fad2-4 line 1791A6D, the Ta-fad2-5 line 1791A6E, the Ta-fad2-6 line 1791A6P, the Ta-fad2-6 line 1791A6P, the Ta-rod1-3 line 2B2K, the Ta-rod1-4 line 5B3E, the Ta-rod1-5 line 6C2B, as described, for example, in Example 3, or can be progeny from those lines.

The oilseed (e.g., pennycress) plants described herein (e.g., having reduced levels of PUFAs and/or increased levels of oleic acid) can include one or more modifications in a gene that encodes a polypeptide involved in fatty acid biosynthesis. In some cases, the one or more modification in a gene that encodes a polypeptide involved in fatty acid biosynthesis can be in the coding sequence. Polypeptides involved in fatty acid biosynthesis include, without limitation, FAD2 polypeptides, ROD1 polypeptides, and FAE1 polypeptides.

In some cases, the oilseed (e.g., pennycress) plants described herein (e.g., having reduced levels of PUFAs and/or increased levels of oleic acid) can include one or more modifications in a FAD2 gene. A representative nucleotide sequence for a WT pennycress FAD2 gene is as follows (SEQ ID NO:1), with upper case letters representing the FAD2 coding sequence and the lower case letters representing introns:

ATGTCTAAATTTGATAAAATATATGATGACGACAATTCCGGTGGATCACA gtttgcttcatttggctttttttgtgtgtttgtcaagttgctattcaata agaatttgtgattttgattggtctcctcaaaattctgtgaaattttagta acaaggaagaaattaacaaatcacaacaagaaagagatgtgagctgtcgt atcaaatcttattcgttttctcaacgcaatcgttttagttttttttaact taacgccacttctctgctccatacactccttttttgtccacgtacttttca tttgtggtaatccatttcttcactttggatctttcatctgaacaacaatt tcttgactcaatcaattaccacccgttcttgtgcttttgtatagattcat aatcttgtgtgtttcagcttctcattgctttggttcttgttttttttct gcagAAACATGGGTGCAGGTGGAAGAATGACGGTTCCTACTTCTTCCAAG

AAGTCTGAAACCGATGCCTTAAAGCGTGTGCCGTGCGAGAAACCGCCGTT

CACGCTCGGAGAACTGAAGAAAGCAATCCCACAGCATIGTTICAATCGCT

CAATCCCTCGCTCTITCTCCTACCTTATCTGGGACATCATCATAGCCTCT

TGCTTCTACTACGTTGCCACCACTTACTTCTCTCTCCTCCCTCAGCCTCT

CTCTTACTTGGCTTGGCCTCTCTATTGGGTCTGTCAAGGCTGTGTCTTAA

CCGGAGTCTGGGTCATAGCTCACGAATGCGGCCACCACGCCTTCAGCGAC

TACCAATGGCTTGACGACACAGTCGGTCTGATCTTCCATTCTTTCCTCCT

CGTCCCTTACTTCTCCTGGAAATACAGCCACCGCCGTCACCATTCCAACA

CCGGATCACTTGAAAAGGACGAAGTGTTTGTCCCTAAACAGAAATCCGCC

ATCAAATGGTACGGCAAGTACCTCAACAACCCTCTGGGACGCACCGTGAT

GTTAACCGTCCAGTTCACCCTTGGCTGGCCCTTGTACTTAGCCTTCAACG

TCTCGGGGAGACCCTACGACGGGTTCGCTTGCCACTTCCACCCAAACGCT

CCCATCTACAACGACCGTGAACGCCTCCAGATATACATCTCGGATGCTGG

TATCCTCGCCGTCTGTTACGGTCTCTACCGTTACGCTGCTGCACAAGGAG

TGGCCTCGATGATCTGCGTCTACGGAGTTCCGCTTCTGATAGTCAACGGG

TTCCTCGTCTTGATCACATACTTGCAGCACACCCATCCCTCGTTGCCTCA

CTACGATTCATCCGAGTGGGATTGGTTCAGGGGAGCTTTGGCTACCGTAG

ACAGAGACTATGGAATCCTGAACAAGGTCTTCCACAACATCACGGACACG

CACGTGGCTCACCACCTGTTCTCGACGATGCCGCATTACCATGCGATGGA

GGCCACGAAGGCGATAAAGCCGATACTCGGGGACTATTACCAGTTTGATG

GAACACCGGTCTTCAAGGCGATGTGGAGGGAGGCGAAGGAGTGTGTCTAT

GTAGAACCGGACAGGAAAGGTGAGAAGAAAGgtgtgttctggtacaacaa caagttgtgaggatgatcaggtgaaagaagaaggaagaaaaatcgtcggc ctttctcttgtctggttatctttgttttaagaagatatatgtttgtttca ataatcttattgtccattttgttgtgttctgacattgtggcttaaattat tatgtgatgttagtgtccaattgttctgcgtctgtattgttcttctcatc gctgttttgttgggatcgtagaaatgtgactttcggacaattaaactctt gtactcaagctatcactctgttggcagcatcaaaagtgttttcatagttt cggtcttttggtctctgtttgtttgatactgttggtgagaatggctcttc aagtgttggaatctacctaaggtgaacacattgtaggattttttctttat ttaattgccattgtataccacactgcagtgaaccgcaactatgttgacca tgtcgatgaatgtaagtgaaccatgaaactaatctttctgtacaatttac ttacttctgagtcattgtgatgtttggttggcaggtcacctttatttctc acactccctccactcatgtgatgtggttgggattttcttttcataagtag cttttttgtaaagaactcagtctttctctttcaaatcatggaaacctttc aacaaaagccaaatccatgttacataagcaaaatatctgctttcttcatc tttcctttctttcatatttgagAGGGAACAAAAGAAGAGGAAGAAAATGA

AGCAAAGTAA

Another representative nucleotide sequence for a WT pennycress IA1) 2 coding sequence is as follows (SEQ ID NO:25):

ATGTCTAAATTTGATAAAATATATGATGACGACAATTCCGGTGGATCACA

AAACATGGGTGCAGGTGGAAGAATGACGGTTCCTACTTCTTCCAAGAAGT

CTGAAACCGATGCCTTAAAGCGTGTGCCGTGCGAGAAACCGCCGTTCACG

CTCGGAGAACTGAAGAAAGCAATCCCACAGCATTGTTTCAATCGCTCAAT

CCCTCGCTCTTTCTCCTACCTTATCTGGGACATCATCATAGCCTCTTGCT

TCTACTACGTTGCCACCACTTACTTCTCTCTCCTCCCTCAGCCTCTCTCT

TACTTGGCTTGGCCTCTCTATTGGGTCTGTCAAGGCTGTGTCTTAACCGG

AGTCTGGGTCATAGCTCACGAATGCGGCCACCACGCCTTCAGCGACTACC

AATGGCTTGACGACACAGTCGGTCTGATCTTCCATTCTTTCCTCCTCGTC

CCTTACTTCTCCTGGAAATACAGCCACCGCCGTCACCATTCCAACACCGG

ATCACTTGAAAAGGACGAAGIGTTTGTCCCTAAACAGAAATCCGCCATCA

AATGGTACGGCAAGTACCTCAACAACCCTCTGGGACGCACCGTGATGTTA

ACCGTCCAGTTCACCCTTGGCTGGCCCTTGTACTTAGCCTTCAACGTCTC

GGGGAGACCCTACGACGGGTTCGCTTGCCACTTCCACCCAAACGCTCCCA

TCTACAACGACCGTGAACGCCTCCAGATATACATCTCGGATGCTGGTATC

CTCGCCGTCTGTTACGGTCTCTACCGTTACGCTGCTGCACAAGGAGTGGC

CTCGATGATCTGCGTCTACGGAGTTCCGCTTCTGATAGTCAACGGGTTCC

TCGTCTTGATCACATACTTGCAGCACACCCATCCCTCGTTGCCTCACTAC

GATTCATCCGAGTGGGATTGGTTCAGGGGAGCTTTGGCTACCGTAGACAG

AGACTATGGAATCCTGAACAAGGTCTTCCACAACATCACGGACACGCACG

-continued

TGGCTCACCACCTGTTCTCGACGATGCCGCATTACCATGCGATGGAGGCC

ACGAAGGCGATAAAGCCGATACTCGGGGACTATTACCAGTTTGATGGAAC

ACCGGTCTTCAAGGCGATGTGGAGGGAGGCGAAGGAGTGTGTCTATGTAG

AACCGGACAGGAAAGGTGAGAAGAAAGAGGGAACAAAAGAAGAGGAAGAA

AATGAAGCAAAGTAA

In some cases, a WT pennycress FAD2 gene can have a sequence that deviates from a representative nucleotide sequence as set forth above (SEQ ID NO:1 or SEQ ID NO:25), sometimes referred to as a variant sequence, provided that the variant sequence encodes a WT pennycress FAD2 polypeptide. A representative polypeptide sequence for a WT pennycress FAD2 polypeptide is as follows (SEQ ID NO:2):

MSKFDKIYDDDNSGGSQNMGAGGRMTVPTSSKKSETDALKRVPCEKPPFT

LGELKKAIPQHCFNRSIPRSFSYLIWDIIIASCFYYVATTYFSLLPQPLS

YLAWPLYWVCQGCVLTGVWVIAHECGHHAFSDYQWLDDTVGLIFHSFLLV

PYFSWKYSHRRHHSNTGSLEKDEVFVPKQKSAIKWYGKYLNNPLGRTVML

TVQFTLGWPLYLAFNVSGRPYDGFACHFHPNAPIYNDRERLQIYISDAGI

LAVCYGLYRYAAAQGVASMICVYGVPLLIVNGFLVLITYLQHTHPSLPHY

DSSEWDWFRGALATVDRDYGILNKVFHNITDTHVAHHLFSTMPHYHAMEA

TKAIKPILGDYYQFDGTPVFKAMWREAKECVYVEPDRKGEKKEGTKEEEE

NEAK

In some cases, a WT pennycress FAD2 polypeptide can have a sequence that deviates from the polypeptide sequence set forth above (SEQ ID NO:2), sometimes referred to as a variant sequence, provided that the polypeptide maintains its WT function (e.g., its level of WT function). For example, a FAD2 polypeptide can have at least 80 (e.g., at least 85, at least 90, at least 95, at least 98, or at least 99) percent sequence identity to SEQ ID NO:2. A FAD2 polypeptide can have one or more (e.g., 2, 3, 4, 5, 6, 7, 8, 9, or 10) amino acid modifications (e.g., substitutions) relative to SEQ ID NO:2.

In some cases, oilseed (e.g., pennycress) plants described herein (e.g., having reduced levels of PUFAs and/or increased levels of oleic acid) can include a loss-of-function modification in an FAD2 gene (e.g., in an FAD2 coding sequence). As used herein, a loss-of-function modification in an FAD2 gene can be any modification that is effective to reduce FAD2 polypeptide expression or FAD2 polypeptide function. In some cases, reduced FAD2 polypeptide expression or reduced FAD2 polypeptide function can be eliminated FAD2 polypeptide expression or eliminated FAD2 polypeptide function. Examples of genetic modifications include, without limitation, deletions, insertions, substitutions, frameshifts, duplications, and rearrangements.

In some cases, oilseed (e.g., pennycress) plants described herein (e.g., having reduced levels of PUFAs and/or increased levels of oleic acid) can include a substitution (e.g., a single base-pair insertion) relative to a nucleotide sequence of a WT pennycress FAD2 coding sequence (e.g., SEQ ID NO:1 or SEQ ID NO:25). The single base-pair substitution can be a substitution of any appropriate nucleotide. For example, a modified FAD2 coding sequence can include a G to A substitution at nucleotide residue 513 in a WT pennycress FAD2 coding sequence (e.g., SEQ ID NO:1). A representative modified nucleotide sequence of a pennycress FAD2 coding sequence having a loss-of-function G to A substitution at nucleotide residue 513 (e.g., nucleotide residue 513 as corresponding to the numbering of a genomic FAD2 coding sequence such as the sequence set forth in SEQ ID NO: 1) is as follows (SEQ ID NO: 3):

ATGTCTAAATTTGATAAAATATATGATGACGACAATTCCGGTGGATCACA

GTTTGCTTCATTTGGCTTTTTTTGTGTGTTTGTCAAGTTGCTATTCAATA

AGAATTTGTGATTTTGATTGGTCTCCTCAAAATTCTGTGAAATTTTAGTA

ACAAGGAAGAAATTAACAAATCACAACAAGAAAGAGATGTGAGCTGTCGT

ATCAAATCTTATTCGTTTTCTCAACGCAATCGTTTTAGTTTTTTTTAACT

TAACGCCACTTCTCTGCTCCATACACTCCTTTTTGTCCACGTACTTTTCA

TTTGTGGTAATCCATTTCTTCACTTTGGATCTTTCATCTGAACAACAATT

TCTTGACTCAATCAATTACCACCCGTTCTTGTGCTTTTGTATAGATTCAT

AATCTTGTGTGTTTCAGCTTCTCATTGCTTTGGTTCTTGTTTTTTTTTCT

GCAGAAACATGGGTGCAGGTGGAAGAATGACGGTTCCTACTTCTTCCAAG

AAGTCTGAAACC*ATGCCTTAAAGCGTGTGCCGTGCGAGAAACCGCCGTT

CACGCTCGGAGAACTGAAGAAAGCAATCCCACAGCATTGTTTCAATCGCT

CAATCCCTCGCTCTTTCTCCTACCTTATCTGGGACATCATCATAGCCTCT

TGCTTCTACTACGTTGCCACCACTTACTTCTCTCTCCTCCCTCAGCCTCT

CTCTTACTTGGCTTGGCCTCTCTATTGGGTCTGTCAAGGCTGTGTCTTAA

CCGGAGTCTGGGTCATAGCTCACGAATGCGGCCACCACGCCTTCAGCGAC

TACCAATGGCTTGACGACACAGTCGGTCTGATCTTCCATTCTTTCCTCCT

CGTCCCTTACTTCTCCTGGAAATACAGCCACCGCCGTCACCATTCCAACA

CCGGATCACTTGAAAAGGACGAAGTGTTTGTCCCTAAACAGAAATCCGCC

ATCAAATGGTACGGCAAGTACCTCAACAACCCTCTGGGACGCACCGTGAT

GTTAACCGTCCAGTTCACCCTTGGCTGGCCCTTGTACTTAGCCTTCAACG

TCTCGGGGAGACCCTACGACGGGTTCGCTTGCCACTTCCACCCAAACGCT

CCCATCTACAACGACCGTGAACGCCTCCAGATATACATCTCGGATGCTGG

TATCCTCGCCGTCTGTTACGGTCTCTACCGTTACGCTGCTGCACAAGGAG

TGGCCTCGATGATCTGCGTCTACGGAGTTCCGCTTCTGATAGTCAACGGG

TTCCTCGTCTTGATCACATACTTGCAGCACACCCATCCCTCGTTGCCTCA

CTACGATTCATCCGAGTGGGATTGGTTCAGGGGAGCTTTGGCTACCGTAG

ACAGAGACTATGGAATCCTGAACAAGGTCTTCCACAACATCACGGACACG

CACGTGGCTCACCACCTGTTCTCGACGATGCCGCATTACCATGCGATGGA

GGCCACGAAGGCGATAAAGCCGATACTCGGGGACTATTACCAGTTTGATG

GAACACCGGTCTTCAAGGCGATGTGGAGGGAGGCGAAGGAGTGTGTCTAT

GTAGAACCGGACAGGAAAGGTGAGAAGAAAGGTGTGTTCTGGTACAACAA

CAAGTTGTGAGGATGATCAGGTGAAAGAAGAAGGAAGAAAAATCGTCGGC

CTTTCTCTTGTCTGGTTATCTTTGTTTTAAGAAGATATATGTTTGTTTCA

ATAATCTTATTGTCCATTTTGTTGTGTTCTGACATTGTGGCTTAAATTAT

TATGTGATGTTAGTGTCCAATTGTTCTGCGTCTGTATTGTTCTTCTCATC

GCTGTTTTGTTGGGATCGTAGAAATGTGACTTTCGGACAATTAAACTCTT

GTACTCAAGCTATCACTCTGTTGGCAGCATCAAAAGTGTTTTCATAGTTT

-continued

```
CGGTCTTTTGGTCTCTGTTTGTTTGATACTGTTGGTGAGAATGGCTCTTC

AAGTGTTGGAATCTACCTAAGGTGAACACATTGTAGGATTTTTCTTTTAT

TTAATTGCCATTGTATACCACACTGCAGTGAACCGCAACTATGTTGACCA

TGTCGATGAATGTAAGTGAACCATGAAACTAATCTTTCTGTACAATTTAC

TTACTTCTGAGTCATTGTGATGTTTGGTTGGCAGGTCACCTTTATTTCTC

ACACTCCCTCCACTCATGTGATGTGGTTGGGATTTTCTTTTCATAAGTAG

CTTTTTGTAAAGAACTCAGTCTTTCTCTTTCAAATCATGGAAACCTTTTC

AACAAAAGCCAAATCCATGTTACATAAGCAAAATATCTGCTTTCTTCATC

TTTCCTTTCTTTCATATTTGAGAGGGAACAAAAGAAGAGGAAGAAAATGA

AGCAAAGTAA
```

Another representative nucleotide sequence of a modified pennycress FAD2 coding sequence having a loss-of-function G to A substitution at nucleotide residue 513 (e.g., nucleotide residue 513 as corresponding to the numbering of a genomic FAD2 coding sequence such as the sequence set forth in SEQ ID NO:1) is as follows (SEQ ID NO:26):

```
ATGTCTAAATTTGATAAAATATATGATGACGACAATTCCGGTGGATCACA

AAACATGGGTGCAGGTGGAAGAATGACGGTTCCTACTTCTTCCAAGAAGT

CTGAAACCAATGCCTTAAAGCGTGTGCCGTGCGAGAAACCGCCGTTCACG

CTCGGAGAACTGAAGAAAGCAATCCCACAGCATTGTTTCAATCGCTCAAT

CCCTCGCTCTTTCTCCTACCTTATCTGGGACATCATCATAGCCTCTTGCT

TCTACTACGTTGCCACCACTTACTTCTCTCTCCTCCCTCAGCCTCTCTCT

TACTTGGCTTGGCCTCTCTATTGGGTCTGTCAAGGCTGTGTCTTAACCGG

AGTCTGGGTCATAGCTCACGAATGCGGCCACCACGCCTTCAGCGACTACC

AATGGCTTGACGACACAGTCGGTCTGATCTTCCATTCTTTCCTCCTCGTC

CCTTACTTCTCCTGGAAATACAGCCACCGCCGTCACCATTCCAACACCGG

ATCACTTGAAAAGGACGAAGTGTTTGTCCCTAAACAGAAATCCGCCATCA

AATGGTACGGCAAGTACCTCAACAACCCTCTGGGACGCACCGTGATGTTA

ACCGTCCAGTTCACCCTTGGCTGGCCCTTGTACTTAGCCTTCAACGTCTC

GGGGAGACCCTACGACGGGTTCGCTTGCCACTTCCACCCAAACGCTCCCA

TCTACAACGACCGTGAACGCCTCCAGATATACATCTCGGATGCTGGTATC

CTCGCCGTCTGTTACGGTCTCTACCGTTACGCTGCTGCACAAGGAGTGGC

CTCGATGATCTGCGTCTACGGAGTTCCGCTTCTGATAGTCAACGGGTTCC

TCGTCTTGATCACATACTTGCAGCACACCCATCCCTCGTTGCCTCACTAC

GATTCATCCGAGTGGGATTGGTTCAGGGGAGCTTTGGCTACCGTAGACAG

AGACTATGGAATCCTGAACAAGGTCTTCCACAACATCACGGACACGCACG

TGGCTCACCACCTGTTCTCGACGATGCCGCATTACCATGCGATGGAGGCC

ACGAAGGCGATAAAGCCGATACTCGGGGACTATTACCAGTTTGATGGAAC

ACCGGTCTTCAAGGCGATGTGGAGGGAGGCGAAGGAGTGTGTCTATGTAG

AACCGGACAGGAAAGGTGAGAAGAAAGAGGGAACAAAAGAAGAGGAAGAA

AATGAAGCAAAGTAA
```

A modified pennycress FAD2 coding sequence having a G to A substitution at nucleotide residue 513 in a WT pennycress FAD2 coding sequence (e.g., SEQ ID NO:3 or SEQ ID NO: 26) can result in a FAD2 polypeptide having an amino acid substitution. For example, a modified pennycress FAD2 coding sequence having a G to A substitution at nucleotide residue 513 in a WT pennycress FAD2 coding sequence (e.g., SEQ ID NO:3 or SEQ ID NO: 26) can encode a FAD2 polypeptide having a D to N amino acid substitution at amino acid residue 37. A representative polypeptide sequence of a pennycress FAD2 polypeptide having a D to N amino acid substitution at amino acid residue 37 (e.g., amino acid residue 37 as corresponding to the numbering of a WT FAD2 polypeptide such as the sequence set forth in SEQ ID NO:2) is as follows (SEQ ID NO:4):

```
MSKFDKIYDDDNSGGSQNMGAGGRMTVPTSSKKSETNALKRVPCEKPPFT

LGELKKAIPQHCFNRSIPRSFSYLIWDIIIASCFYYVATTYFSLLPQPLS

YLAWPLYWVCQGCVLTGVWVIAHECGHHAFSDYQWLDDTVGLIFHSFLLV

PYFSWKYSHRRHHSNTGSLEKDEVFVPKQKSAIKWYGKYLNNPLGRTVML

TVQFTLGWPLYLAFNVSGRPYDGFACHFHPNAPIYNDRERLQIYISDAGI

LAVCYGLYRYAAAQGVASMICVYGVPLLIVNGFLVLITYLQHTHPSLPHY

DSSEWDWFRGALATVDRDYGILNKVFHNITDTHVAHHLFSTMPHYHAMEA

TKAIKPILGDYYQFDGTPVFKAMWREAKECVYVEPDRKGEKKEGTKEEEE

NEAK
```

For example, a modified FAD2 coding sequence can include a G to A substitution at nucleotide residue 826 in a WT pennycress FAD2 coding sequence (e.g., SEQ ID NO:1). A representative nucleotide sequence of a modified pennycress FAD2 coding sequence having a loss-of-function G to A substitution at nucleotide residue 826 (e.g., nucleotide residue 826 as corresponding to the numbering of a genomic FAD2 coding sequence such as the sequence set forth in SEQ ID NO:1) is as follows (SEQ ID NO:5):

```
ATGTCTAAATTTGATAAAATATATGATGACGACAATTCCGGTGGATCACA

GTTTGCTTCATTTGGCTTTTTTTGTGTGTTTGTCAAGTTGCTATTCAATA

AGAAATTTGTGATTTTGATTGGTCTCCTCAAAATTCTGTGAAATTTTAGTA

ACAAGGAAGAAATTAACAAATCACAACAAGAAAGAGATGTGAGCTGTCGT

ATCAAATCTTATTCGTTTTCTCAACGCAATCGTTTTAGTTTTTTTTAACT

TAACGCCACTTCTCTGCTCCATACACTCCTTTTTGTCCACGTACTTTTCA

TTTGTGGTAATCCATTTCTTCACTTTGGATCTTTCATCTGAACAACAATT

TCTTGACTCAATCAATTACCACCCGTTCTTGTGCTTTTGTATAGATTCAT

AATCTTGTGTGTTTCAGCTTCTCATTGCTTTGGTTCTTGTTTTTTTTTCT

GCAGAAACATGGGTGCAGGTGGAAGAATGACGGTTCCTACTTCTTCCAAG

AAGTCTGAAACCGATGCCTTAAAGCGTGTGCCGTGCGAGAAACCGCCGTT

CACGCTCGGAGAACTGAAGAAAGCAATCCCACAGCATTGTTTCAATCGCT

CAATCCCTCGCTCTTTCTCCTACCTTATCTGGGACATCATCATAGCCTCT

TGCTTCTACTACGTTGCCACCACTTACTTCTCTCTCCTCCCTCAGCCTCT
```

```
CTCTTACTTGGCTTGGCCTCTCTATTGGGTCTGTCAAGGCTGTGTCTTAA

CCGGAGTCTGGGTCATAGCTCACGAATGCGGCCACCACGCCTTCAGCGAC

TACCAATGGCTTGACGACACAGTCGXTCTGATCTTCCATTCTTTCCTCCT

CGTCCCTTACTTCTCCTGGAAATACAGCCACCGCCGTCACCATTCCAACA

CCGGATCACTTGAAAAGGACGAAGTGTTTGTCCCTAAACAGAAATCCGCC

ATCAAATGGTACGGCAAGTACCTCAACAACCCTCTGGGACGCACCGTGAT

GTTAACCGTCCAGTTCACCCTTGGCTGGCCCTTGTACTTAGCCTTCAACG

TCTCGGGGAGACCCTACGACGGGTTCGCTTGCCACTTCCACCCAAACGCT

CCCATCTACAACGACCGTGAACGCCTCCAGATATACATCTCGGATGCTGG

TATCCTCGCCGTCTGTTACGGTCTCTACCGTTACGCTGCTGCACAAGGAG

TGGCCTCGATGATCTGCGTCTACGGAGTTCCGCTTCTGATAGTCAACGGG

TTCCTCGTCTTGATCACATACTTGCAGCACACCCATCCCTCGTTGCCTCA

CTACGATTCATCCGAGTGGGATTGGTTCAGGGGAGCTTTGGCTACCGTAG

ACAGAGACTATGGAATCCTGAACAAGGTCTTCCACAACATCACGGACACG

CACGTGGCTCACCACCTGTTCTCGACGATGCCGCATTACCATGCGATGGA

GGCCACGAAGGCGATAAAGCCGATACTCGGGGACTATTACCAGTTTGATG

GAACACCGGTCTTCAAGGCGATGTGGAGGGAGGCGAAGGAGTGTGTCTAT

GTAGAACCGGACAGGAAAGGTGAGAAGAAAGGTGTGTTCTGGTACAACAA

CAAGTTGTGAGGATGATCAGGTGAAAGAAGAAGGAAGAAAAATCGTCGGC

CTTTCTCTTGTCTGGTTATCTTTGTTTTAAGAAGATATATGTTTGTTTCA

ATAATCTTATTGTCCATTTTGTTGTGTTCTGACATTGTGGCTTAAATTAT

TATGTGATGTTAGTGTCCAATTGTTCTGCGTCTGTATTGTTCTTCTCATC

GCTGTTTTGTTGGGATCGTAGAAATGTGACTTTCGGACAATTAAACTCTT

GTACTCAAGCTATCACTCTGTTGGCAGCATCAAAAGTGTTTTCATAGTTT

CGGTCTTTTGGTCTCTGTTTGTTTGATACTGTTGGTGAGAATGGCTCTTC

AAGTGTTGGAATCTACCTAAGGTGAACACATTGTAGGATTTTTCTTTTAT

TTAATTGCCATTGTATACCACACTGCAGTGAACCGCAACTATGTTGACCA

TGTCGATGAATGTAAGTGAACCATGAAACTAATCTTTCTGTACAATTTAC

TTACTTCTGAGTCATTGTGATGTTTGGTTGGCAGGTCACCTTTATTTCTC

ACACTCCCTCCACTCATGTGATGTGGTTGGGATTTTCTTTTCATAAGTAG

CTTTTTGTAAAGAACTCAGTCTTTCTCTTTCAAATCATGGAAACCTTTTC

AACAAAAGCCAAATCCATGTTACATAAGCAAAATATCTGCTTTCTTCATC

TTTCCTTTCTTTCATATTTGAGAGGGAACAAAAGAAGAGGAAGAAAATGA

AGCAAAGTAA
```

Another representative nucleotide sequence of a modified pennycress FAD2 coding sequence having a loss-of-function G to A substitution at nucleotide residue 826 (e.g., nucleotide residue 826 as corresponding to the numbering of a genomic FAD2 coding sequence such as the sequence set forth in SEQ ID NO:1) is as follows (SEQ ID NO:27):

```
ATGTCTAAATTTGATAAAATATATGATGACGACAATTCCGGTGGATCACA

AAACATGGGTGCAGGTGGAAGAATGACGGTTCCTACTTCTTCCAAGAAGT

CTGAAACCGATGCCTTAAAGCGTGTGCCGTGCGAGAAACCGCCGTTCACG

CTCGGAGAACTGAAGAAAGCAATCCCACAGCATTGTTTCAATCGCTCAAT

CCCTCGCTCTTTCTCCTACCTTATCTGGGACATCATCATAGCCTCTTGCT

TCTACTACGTTGCCACCACTTACTTCTCTCTCCTCCCTCAGCCTCTCTCT

TACTTGGCTTGGCCTCTCTATTGGGTCTGTCAAGGCTGTGTCTTAACCGG

AGTCTGGGTCATAGCTCACGAATGCGGCCACCACGCCTTCAGCGACTACC

AATGGCTTGACGACACAGTCGXTCTGATCTTCCATTCTTTCCTCCTCGTC

CCTTACTTCTCCTGGAAATACAGCCACCGCCGTCACCATTCCAACACCGG

ATCACTTGAAAAGGACGAAGTGTTTGTCCCTAAACAGAAATCCGCCATCA

AATGGTACGGCAAGTACCTCAACAACCCTCTGGGACGCACCGTGATGTTA

ACCGTCCAGTTCACCCTTGGCTGGCCCTTGTACTTAGCCTTCAACGTCTC

GGGGAGACCCTACGACGGGTTCGCTTGCCACTTCCACCCAAACGCTCCCA

TCTACAACGACCGTGAACGCCTCCAGATATACATCTCGGATGCTGGTATC

CTCGCCGTCTGTTACGGTCTCTACCGTTACGCTGCTGCACAAGGAGTGGC

CTCGATGATCTGCGTCTACGGAGTTCCGCTTCTGATAGTCAACGGGTTCC

TCGTCTTGATCACATACTTGCAGCACACCCATCCCTCGTTGCCTCACTAC

GATTCATCCGAGTGGGATTGGTTCAGGGGAGCTTTGGCTACCGTAGACAG

AGACTATGGAATCCTGAACAAGGTCTTCCACAACATCACGGACACGCACG

TGGCTCACCACCTGTTCTCGACGATGCCGCATTACCATGCGATGGAGGCC

ACGAAGGCGATAAAGCCGATACTCGGGGACTATTACCAGTTTGATGGAAC

ACCGGTCTTCAAGGCGATGTGGAGGGAGGCGAAGGAGTGTGTCTATGTAG

AACCGGACAGGAAAGGTGAGAAGAAAGAGGGAACAAAAGAAGAGGAAGAA

AATGAAGCAAAGTAA
```

A modified pennycress FAD2 coding sequence having a G to A substitution at nucleotide residue 826 in a WT pennycress FAD2 coding sequence (e.g., SEQ ID NO:5 or SEQ ID NO: 27) can result in a FAD2 polypeptide having an amino acid substitution. For example, a modified pennycress FAD2 coding sequence having a G to A substitution at nucleotide residue 826 in a WT pennycress FAD2 coding sequence (e.g., SEQ ID NO:5 or SEQ ID NO: 27) can encode a FAD2 polypeptide having a G to D amino acid substitution at amino acid residue 141. A representative polypeptide sequence of a pennycress FAD2 polypeptide having a G to D amino acid substitution at amino acid residue 141 (e.g., amino acid residue 141 as corresponding to the numbering of a WT FAD2 polypeptide such as the sequence set forth in SEQ ID NO:2) is as follows (SEQ ID NO:6):

```
MSKFDKIYDDDNSGGSQNMGAGGRMTVPTSSKKSETDALKRVPCEKPPFT

LGELKKAIPQHCFNRSIPRSFSYLIWDIIIASCFYYVATTYFSLLPQPLS

YLAWPLYWVCQGCVLTGVWVIAHECGHHAFSDYQWLDDTVXLIFHSFLLV

PYFSWKYSHRRHHSNTGSLEKDEVFVPKQKSAIKWYGKYLNNPLGRTVML

TVQFTLGWPLYLAFNVSGRPYDGFACHFHPNAPIYNDRERLQIYISDAGI

LAVCYGLYRYAAAQGVASMICVYGVPLLIVNGFLVLITYLQHTHPSLPHY
```

DSSEWDWFRGALATVDRDYGILNKVFHNITDTHVAHHLFSTMPHYHAMEA

TKAIKPILGDYYQFDGTPVFKAMWREAKECVYVEPDRKGEKKEGTKEEEE

NEAK

For example, a modified FAD2 coding sequence can include a C to T substitution at nucleotide residue 1299 in a WT pennycress FAD2 coding sequence (e.g., SEQ ID NO:1). A representative nucleotide sequence of a modified pennycress FAD2 coding sequence having a loss-of-function C to T substitution at nucleotide residue 1299 (e.g., nucleotide residue 1299 as corresponding to the numbering of a genomic FAD2 coding sequence such as the sequence set forth in SEQ ID NO:1) is as follows (SEQ ID NO:7):

ATGTCTAAATTTGATAAAATATATGATGACGACAATTCCGGTGGATCACA

GTTTGCTTCATTTGGCTTTTTTTGTGTGTTTGTCAAGTTGCTATTCAATA

AGAATTTGTGATTTTGATTGGTCTCCTCAAAATTCTGTGAAATTTTAGTA

ACAAGGAAGAAATTAACAAATCACAACAAGAAAGAGATGTGAGCTGTCGT

ATCAAATCTTATTCGTTTTCTCAACGCAATCGTTTTAGTTTTTTTTAACT

TAACGCCACTTCTCTGCTCCATACACTCCTTTTTGTCCACGTACTTTTCA

TTTGTGGTAATCCATTTCTTCACTTTGGATCTTTCATCTGAACAACAATT

TCTTGACTCAATCAATTACCACCCGTTCTTGTGCTTTTGTATAGATTCAT

AATCTTGTGTGTTTCAGCTTCTCATTGCTTTGGTTCTTGTTTTTTTTTCT

GCAGAAACATGGGTGCAGGTGGAAGAATGACGGTTCCTACTTCTTCCAAG

AAGTCTGAAACCGATGCCTTAAAGCGTGTGCCGTGCGAGAAACCGCCGTT

CACGCTCGGAGAACTGAAGAAAGCAATCCCACAGCATTGTTTCAATCGCT

CAATCCCTCGCTCTTTCTCCTACCTTATCTGGGACATCATCATAGCCTCT

TGCTTCTACTACGTTGCCACCACTTACTTCTCTCTCCTCCCTCAGCCTCT

CTCTTACTTGGCTTGGCCTCTCTATTGGGTCTGTCAAGGCTGTGTCTTAA

CCGGAGTCTGGGTCATAGCTCACGAATGCGGCCACCACGCCTTCAGCGAC

TACCAATGGCTTGACGACACAGTCGGTCTGATCTTCCATTCTTTCCTCCT

CGTCCCTTACTTCTCCTGGAAATACAGCCACCGCCGTCACCATTCCAACA

CCGGATCACTTGAAAAGGACGAAGTGTTTGTCCCTAAACAGAAATCCGCC

ATCAAATGGTACGGCAAGTACCTCAACAACCCTCTGGGACGCACCGTGAT

GTTAACCGTCCAGTTCACCCTTGGCTGGCCCTTGTACTTAGCCTTCAACG

TCTCGGGGAGACCCTACGACGGGTTCGCTTGCCACTTCCACCCAAACGCT

CCCATCTACAACGACCGTGAACGCCTCCAGATATACATCTCGGATGCTGG

TATCCTCGCCGTCTGTTACGGTCTCTACCGTTACGCTGCTGCACAAGGAG

TGGCCTCGATGATCTGCGTCTACGGAGTTCCGCTTCTGATAGTCAACGGG

TTCCTCGTCTTGATCACATACTTGCAGCACACCCATCCCTCGTTGCCTCA

CTACGATTCATCCGAGTGGGATTGGTTCAGGGGAGCTTTGGCTACCGTAG

ACAGAGACTATGGAATCCTGAACAAGGTCTTCCACAACATCACGGACACG

CACGTGGCTCACCACCTGTTCTCGACGATGCCGCATTACCATGCGATGGA

GGCCACGAAGGCGATAAAGCCGATACTCGGGGACTATTACCAGTTTGATG

GAACACCGGTCTTCAAGGCGATGTGGAGGGAGGCGAAGGAGTGTGTCTAT

GTAGAACCGGACAGGAAAGGTGAGAAGAAAGGTGTGTTCTGGTACAACAA

CAAGTTGTGAGGATGATCAGGTGAAAGAAGAAGGAAGAAAAATCGTCGGC

CTTTCTCTTGTCTGGTTATCTTTGTTTTAAGAAGATATATGTTTGTTTCA

ATAATCTTATTGTCCATTTTGTTGTGTTCTGACATTGTGGCTTAAATTAT

TATGTGATGTTAGTGTCCAATTGTTCTGCGTCTGTATTGTTCTTCTCATC

GCTGTTTTGTTGGGATCGTAGAAATGTGACTTTCGGACAATTAAACTCTT

GTACTCAAGCTATCACTCTGTTGGCAGCATCAAAAGTGTTTTCATAGTTT

CGGTCTTTTGGTCTCTGTTTGTTTGATACTGTTGGTGAGAATGGCTCTTC

AAGTGTTGGAATCTACCTAAGGTGAACACATTGTAGGATTTTTCTTTTAT

TTAATTGCCATTGTATACCACACTGCAGTGAACCGCAACTATGTTGACCA

TGTCGATGAATGTAAGTGAACCATGAAACTAATCTTTCTGTACAATTTAC

TTACTTCTGAGTCATTGTGATGTTTGGTTGGCAGGTCACCTTTATTTCTC

ACACTCCCTCCACTCATGTGATGTGGTTGGGATTTTCTTTTCATAAGTAG

CTTTTTGTAAAGAACTCAGTCTTTCTCTTTCAAATCATGGAAACCTTTTC

AACAAAAGCCAAATCCATGTTACATAAGCAAAATATCTGCTTTCTTCATC

TTTCCTTTCTTTCATATTTGAGAGGGAACAAAAGAAGAGGAAGAAAATGA

AGCAAAGTAA

Another representative nucleotide sequence of a modified pennycress FAD2 coding sequence having a loss-of-function C to T substitution at nucleotide residue 1299 (e.g., nucleotide residue 1299 as corresponding to the numbering of a genomic FAD2 coding sequence such as the sequence set forth in SEQ ID NO:1) is as follows (SEQ ID NO:28):

ATGTCTAAATTTGATAAAATATATGATGACGACAATTCCGGTGGATCACA

AAACATGGGTGCAGGTGGAAGAATGACGGTTCCTACTTCTTCCAAGAAGT

CTGAAACCGATGCCTTAAAGCGTGTGCCGTGCGAGAAACCGCCGTTCACG

CTCGGAGAACTGAAGAAAGCAATCCCACAGCATTGTTTCAATCGCTCAAT

CCCTCGCTCTTTCTCCTACCTTATCTGGGACATCATCATAGCCTCTTGCT

TCTACTACGTTGCCACCACTTACTTCTCTCTCCTCCCTCAGCCTCTCTCT

TACTTGGCTTGGCCTCTCTATTGGGTCTGTCAAGGCTGTGTCTTAACCGG

AGTCTGGGTCATAGCTCACGAATGCGGCCACCACGCCTTCAGCGACTACC

AATGGCTTGACGACACAGTCGGTCTGATCTTCCATTCTTTCCTCCTCGTC

CCTTACTTCTCCTGGAAATACAGCCACCGCCGTCACCATTCCAACACCGG

ATCACTTGAAAAGGACGAAGTGTTTGTCCCTAAACAGAAATCCGCCATCA

AATGGTACGGCAAGTACCTCAACAACCCTCTGGGACGCACCGTGATGTTA

ACCGTCCAGTTCACCCTTGGCTGGCCCTTGTACTTAGCCTTCAACGTCTC

GGGGAGACCCTACGACGGGTTCGCTTGCCACTTCCACCCAAACGCTCCCA

TCTACAACGACCGTGAACGCCTCCAGATATACATCTCGGATGCTGGTATC

CTCGCCGTCTGTTACGGTCTCTACCGTTACGCTGCTGCACAAGGAGTGGC

CTCGATGATCTGCGTCTACGGAGTTCCGCTTCTGATAGTCAACGGGTTCC

TCGTCTTGATCACATACTTGCAGCACACCCATCCCTCGTTGCCTCACTAC

-continued

GATTCATCCGAGTGGGATTGGTTCAGGGGAGCTTTGGCTACCGTAGACAG

AGACTATGGAATCCTGAACAAGGTCTTCCACAACATCACGGACACGCACG

TGGCTCACCACCTGTTCTCGACGATGCCGCATTACCATGCGATGGAGGCC

ACGAAGGCGATAAAGCCGATACTCGGGGACTATTACCAGTTTGATGGAAC

ACCGGTCTTCAAGGCGATGTGGAGGGAGGCGAAGGAGTGTGTCTATGTAG

AACCGGACAGGAAAGGTGAGAAGAAAGAGGGAACAAAAGAAGAGGAAGAA

AATGAAGCAAAGTAA

A modified pennycress FAD2 coding sequence having a C to T substitution at nucleotide residue 1299 in a WT pennycress FAD2 coding sequence (e.g., SEQ ID NO:7 or SEQ ID NO: 28) can result in a FAD2 polypeptide having an amino acid substitution. For example, a modified pennycress FAD2 coding sequence having a C to T substitution at nucleotide residue 1299 in a WT pennycress FAD2 coding sequence (e.g., SEQ ID NO:7 or SEQ ID NO: 28) can encode a FAD2 polypeptide having a H to Y amino acid substitution at amino acid residue 299. A representative polypeptide sequence of pennycress FAD2 polypeptide having a H to Y amino acid substitution at amino acid residue 299 (e.g., amino acid residue 299 as corresponding to the numbering of a WT FAD2 polypeptide such as the sequence set forth in SEQ ID NO:2) is as follows (SEQ ID NO:8):

MSKFDKIYDDDNSGGSQNMGAGGRMTVPTSSKKSETDALKRVPCEKPPFT

LGELKKAIPQHCFNRSIPRSFSYLIWDIIIASCFYYVATTYFSLLPQPLS

YLAWPLYWVCQGCVLTGVWVIAHECGHHAFSDYQWLDDTVGLIFHSFLLV

PYFSWKYSHRRHHSNTGSLEKDEVFVPKQKSAIKWYGKYLNNPLGRTVML

TVQFTLGWPLYLAFNVSGRPYDGFACHFHPNAPIYNDRERLQIYISDAGI

LAVCYGLYRYAAAQGVASMICVYGVPLLIVNGFLVLITYLQHTHPSLFÿY

DSSEWDWFRGALATVDRDYGILNKVFHNITDTHVAHHLFSTMPHYHAMEA

TKAIKPILGDYYQFDGTPVFKAMWREAKECVYVEPDRKGEKKEGTKEEEE

NEAK

In some cases, oilseed (e.g., pennycress) plants described herein (e.g., having reduced levels of PUFAs and/or increased levels of oleic acid) can include a deletion relative to the WT pennycress FAD2 coding sequence (e.g., SEQ ID NO:1). A deletion can include any number of nucleotides. For example, a deletion can include the entire length of the gene and/or regulatory sequences. For example, a deletion can include from about 1 nucleotide to about 50 nucleotides (e.g., about 2 nucleotides such as a 2 bp deletion, about 29 nucleotides such as a 29 bp deletion). In some cases, a modified FAD2 coding sequence can include a 2 bp deletion in a WT pennycress FAD2 coding sequence (e.g., SEQ ID NO:1). A deletion can include any appropriate nucleotides within a FAD2 coding sequence. In some cases, a modified FAD2 coding sequence having a 2 bp deletion in a WT pennycress FAD2 coding sequence (e.g., SEQ ID NO:1), can have a 2 bp deletion of nucleotide residues 718 and 719 in a WT pennycress FAD2 coding sequence (e.g., SEQ ID NO:1). A representative nucleotide sequence of a modified pennycress FAD2 coding sequence having a 2 bp deletion of nucleotide residues 718 and 719 (e.g., nucleotide residues 718 and 719 as corresponding to the numbering of a genomic FAD2 coding sequence such as the sequence set forth in SEQ ID NO: 1) is as follows, with the deleted nucleotide residues (SEQ ID NO:29):

ATGTCTAAATTTGATAAAATATATGATGACGACAATTCCGGTGGATCACA gtttgcttcatttggcttttttttgtgtgtttgtcaagttgctattcaata agaatttgtgattttgattggtctcctcaaaattctgtgaaattttagta acaaggaagaaattaacaaatcacaacaagaaagagatgtgagctgtcgt atcaaatcttattcgttttctcaacgcaatcgttttagttttttttaact taacgccacttctctgctccatacactccttttttgtccacgtactttca tttgtggtaatccatttcttcactttggatctttcatctgaacaacaatt tcttgactcaatcaattaccacccgttcttgtgcttttgtatagattcat aatcttgtgtgtttcagcttctcattgctttggttcttgttttttttttct gcagAAACATGGGTGCAGGTGGAAGAATGACGGTTCCTACTTCTTCCAAG

AAGTCTGAAACCGATGCCTTAAAGCGTGTGCCGTGCGAGAAACCGCCGTT

CACGCTCGGAGAACTGAAGAAAGCAATCCCACAGCATTGTTTCAATCGCT

CAATCCCTCGCTCTTTCTCCTACCTTATCTGGGACATCATCATAGCCTCT

TGCTTCTACTACGTTGCCACCACTTACTTCTCTCTCCTCCCTCAGCCTCT

CTCTTACTTGGCTTGG[ct]CTCTATTGGGTCTGTCAAGGCTGTGTC

TTAACCGGAGTCTGGGTCATAGCTCACGAATGCGGCCACCACGCCTTCAG

CGACTACCAATGGCTTGACGACACAGTCGGTCTGATCTTCCATTCTTTCC

TCCTCGTCCCTTACTTCTCCTGGAAATACAGCCACCGCCGTCACCATTCC

AACACCGGATCACTTGAAAAGGACGAAGTGTTTGTCCCTAAACAGAAATC

CGCCATCAAATGGTACGGCAAGTACCTCAACAACCCTCTGGGACGCACCG

TGATGTTAACCGTCCAGTTCACCCTTGGCTGGCCCTTGTACTTAGCCTTC

AACGTCTCGGGGAGACCCTACGACGGGTTCGCTTGCCACTTCCACCCAAA

CGCTCCCATCTACAACGACCGTGAACGCCTCCAGATATACATCTCGGATG

CTGGTATCCTCGCCGTCTGTTACGGTCTCTACCGTTACGCTGCTGCACAA

GGAGTGGCCTCGATGATCTGCGTCTACGGAGTTCCGCTTCTGATAGTCAA

CGGGTTCCTCGTCTTGATCACATACTTGCAGCACACCCATCCCTCGTTGC

CTCACTACGATTCATCCGAGTGGGATTGGTTCAGGGGAGCTTTGGCTACC

GTAGACAGAGACTATGGAATCCTGAACAAGGTCTTCCACAACATCACGGA

CACGCACGTGGCTCACCACCTGTTCTCGACGATGCCGCATTACCATGCGA

TGGAGGCCACGAAGGCGATAAAGCCGATACTCGGGGACTATTACCAGTTT

GATGGAACACCGGTCTTCAAGGCGATGTGGAGGGAGGCGAAGGAGTGTGT

CTATGTAGAACCGGACAGGAAAGGTGAGAAGAAAGgtgtgttctggtaca acaacaagttgtgaggatgatcaggtgaaagaagaaggaagaaaaatcgt cggcctttctcttgtctggttatctttgttttaagaagatatatgtttgt ttcaataatcttattgtccattttgttgtgttctgacattgtggcttaaa ttattatgtgatgttagtgtccaattgttctgcgtctgtattgttcttct catcgctgttttgttgggatcgtagaaatgtgactttcggacaattaaac tcttgtactcaagctatcactctgttggcagcatcaaaagtgttttcata -continued
```
gtttcggtcttttggtctctgtttgtttgatactgttggtgagaatggct cttcaagtgttggaatctacctaaggtgaacacattgtaggattttctt ttatttaattgccattgtataccacactgcagtgaaccgcaactatgttg accatgtcgatgaatgtaagtgaaccatgaaactaatctttctgtacaat ttacttacttctgagtcattgtgatgtttggttggcaggtcacctttatt tctcacactccctccactcatgtgatgtggttgggattttcttttcataa gtagcttttgtaaagaactcagtctttctctttcaaatcatggaaacct tttcaacaaaagccaaatccatgttacataagcaaaatatctgctttctt catctttcctttctttcatatttgagAGGGAACAAAAGAAGAGGAAGAAA

ATGAAGCAAAGTAA
```

Another representative nucleotide sequence of a modified pennycress FAD2 coding sequence having a 2 bp deletion of nucleotide residues 718 and 719 (e.g., nucleotide residues 718 and 719 as corresponding to the numbering of a genomic FAD2 coding sequence such as the sequence set forth in SEQ ID NO:1) is as follows, with the deleted nucleotide residues (SEQ ID NO:30):

```
ATGTCTAAATTTGATAAAATATATGATGACGACAATTCCGGTGGATCACA

AAACATGGGTGCAGGTGGAAGAATGACGGTTCCTACTTCTTCCAAGAAGT

CTGAAACCGATGCCTTAAAGCGTGTGCCGTGCGAGAAACCGCCGTTCACG

CTCGGAGAACTGAAGAAAGCAATCCCACAGCATTGTTTCAATCGCTCAAT

CCCTCGCTCTTTCTCCTACCTTATCTGGGACATCATCATAGCCTCTTGCT

TCTACTACGTTGCCACCACTTACTTCTCTCTCCTCCCTCAGCCTCTCTCT

TACTTGGCTTGGC[ct]CTCTATTGGGTCTGTCAAGGCTGTGTCTTAA

CCGGAGTCTGGGTCATAGCTCACGAATGCGGCCACCACGCCTTCAGCGAC

TACCAATGGCTTGACGACACAGTCGGTCTGATCTTCCATTCTTTCCTCCT

CGTCCCTTACTTCTCCTGGAAATACAGCCACCGCCGTCACCATTCCAACA

CCGGATCACTTGAAAAGGACGAAGTGTTTGTCCCTAAACAGAAATCCGCC

ATCAAATGGTACGGCAAGTACCTCAACAACCCTCTGGGACGCACCGTGAT

GTTAACCGTCCAGTTCACCCTTGGCTGGCCCTTGTACTTAGCCTTCAACG

TCTCGGGGAGACCCTACGACGGGTTCGCTTGCCACTTCCACCCAAACGCT

CCCATCTACAACGACCGTGAACGCCTCCAGATATACATCTCGGATGCTGG

TATCCTCGCCGTCTGTTACGGTCTCTACCGTTACGCTGCTGCACAAGGAG

TGGCCTCGATGATCTGCGTCTACGGAGTTCCGCTTCTGATAGTCAACGGG

TTCCTCGTCTTGATCACATACTTGCAGCACACCCATCCCTCGTTGCCTCA

CTACGATTCATCCGAGTGGGATTGGTTCAGGGGAGCTTTGGCTACCGTAG

ACAGAGACTATGGAATCCTGAACAAGGTCTTCCAACATCACGGACACG

CACGTGGCTCACCACCTGTTCTCGACGATGCCGCATTACCATGCGATGGA

GGCCACGAAGGCGATAAAGCCGATACTCGGGGACTATTACCAGTTTGATG

GAACACCGGTCTTCAAGGCGATGTGGAGGGAGGCGAAGGAGTGTGTCTAT

GTAGAACCGGACAGGAAAGGTGAGAAGAAAGAGGGAACAAAAGAAGAGGA

AGAAAATGAAGCAAAGTAA
```

A modified pennycress FAD2 coding sequence having a 2 bp deletion of nucleotide residues 718 and 719 in a WT pennycress FAD2 coding sequence (e.g., SEQ ID NO:29 or SEQ ID NO: 30) can result in a frameshift of the codons in the coding sequence and a modified polypeptide. For example, a modified pennycress FAD2 coding sequence having a 2 bp deletion of nucleotide residues 718 and 719 in a WT pennycress FAD2 coding sequence (e.g., SEQ ID NO:29 or SEQ ID NO:30) can encode a FAD2 polypeptide having a substituted C-terminal end. A representative polypeptide sequence of a pennycress FAD2 polypeptide having a substituted C-terminal end is as follows, with the substituted sequence highlighted (SEQ ID NO:31):

```
MSKFDKIYDDDNSGGSQNMGAGGRMTVPTSSKKSETDALKRVPCEKPPFT

LGELKKAIPQHCFNRSIPRSFSYLIWDIIIASCFYYVATTYFSLLPQPLS

YLAWPLLGLSRLCLNRSLGHSSRMPPPRLQRLPMA
```

In some cases, a modified FAD2 coding sequence can include a 29 bp deletion in a WT pennycress FAD2 coding sequence (e.g., SEQ ID NO:1). For example, a modified FAD2 coding sequence can have a 29 bp deletion of nucleotide residues 714-742 in a WT pennycress FAD2 coding sequence (e.g., SEQ ID NO:1). A representative nucleotide sequence of a modified pennycress FAD2 coding sequence having a 29 bp deletion of nucleotide residues 714-742 (e.g., nucleotide residues 714-742 as corresponding to the numbering of a genomic FAD2 coding sequence such as the sequence set forth in SEQ ID NO: 1) is as follows, with the deleted nucleotide residues [bracketed] (SEQ ID NO:32):

```
ATGTCTAAATTTGATAAAATATATGATGACGACAATTCCGGTGGATCACA gtttgcttcatttggctttttttgtgtgtttgtcaagttgctattcaata agaatttgtgattttgattggtctcctcaaaattctgtgaaattttagta acaaggaagaaattaacaaatcacaacaagaaagagatgtgagctgtcgt atcaaatcttattcgttttctcaacgcaatcgttttagttttttttaact taacgccacttctctgctccatacactccttttttgtccacgtactttca tttgtggtaatccatttcttcactttggatctttcatctgaacaacaatt tcttgactcaatcaattaccaccgttcttgtgcttttgtatagattcat aatcttgtgtgtttcagcttctcattgctttggttcttgtttttttttct gcagAAACATGGGTGCAGGTGGAAGAATGACGGTTCCTACTTCTTCCAAG

AAGTCTGAAACCGATGCCTTAAAGCGTGTGCCGTGCGAGAAACCGCCGTT

CACGCTCGGAGAACTGAAGAAAGCAATCCCACAGCATTGTTTCAATCGCT

CAATCCCTCGCTCTTTCTCCTACCTTATCTGGGACATCATCATAGCCTCT

TGCTTCTACTACGTTGCCACCACTTACTTCTCTCTCCTCCCTCAGCCTCT

CTCTTACTTGGCT[tggcctctctattgggtctgtcaaggctg]]

TGTCTTAACCGGAGTCTGGGTCATAGCTCACGAATGCGGCCACCACGCCT

TCAGCGACTACCAATGGCTTGACGACACAGTCGGTCTGATCTTCCATTCT

TTCCTCCTCGTCCCTTACTTCTCCTGGAAATACAGCCACCGCCGTCACCA

TTCCAACACCGGATCACTTGAAAAGGACGAAGTGTTTGTCCCTAAACAGA
```

```
AATCCGCCATCAAATGGTACGGCAAGTACCTCAACAACCCTCTGGGACGC

ACCGTGATGTTAACCGTCCAGTTCACCCTTGGCTGGCCCTTGTACTTAGC

CTTCAACGTCTCGGGGAGACCCTACGACGGGTTCGCTTGCCACTTCCACC

CAAACGCTCCCATCTACAACGACCGTGAACGCCTCCAGATATACATCTCG

GATGCTGGTATCCTCGCCGTCTGTTACGGTCTCTACCGTTACGCTGCTGC

ACAAGGAGTGGCCTCGATGATCTGCGTCTACGGAGTTCCGCTTCTGATAG

TCAACGGGTTCCTCGTCTTGATCACATACTTGCAGCACACCCATCCCTCG

TTGCCTCACTACGATTCATCCGAGTGGGATTGGTTCAGGGGAGCTTTGGC

TACCGTAGACAGAGACTATGGAATCCTGAACAAGGTCTTCCACAACATCA

CGGACACGCACGTGGCTCACCACCTGTTCTCGACGATGCCGCATTACCAT

GCGATGGAGGCCACGAAGGCGATAAAGCCGATACTCGGGGACTATTACCA

GTTTGATGGAACACCGGTCTTCAAGGCGATGTGGAGGGAGGCGAAGGAGT

GTGTCTATGTAGAACCGGACAGGAAAGGTGAGAAGAAAGgtgtgttctgg tacaacaacaagttgtgaggatgatcaggtgaaagaagaaggaagaaaaa tcgtcggcctttctcttgtctggttatctttgttttaagaagatatatgt ttgtttcaataatcttattgtccattttgttgtgttctgacattgtggct taaattattatgtgatgttagtgtccaattgttctgcgtctgtattgttc ttctcatcgctgttttgttgggatcgtagaaatgtgactttcggacaatt aaactcttgtactcaagctatcactctgttggcagcatcaaaagtgtttt catagtttcggtcttttggtctctgtttgtttgatactgttggtgagaat ggctcttcaagtgttggaatctacctaaggtgaacacattgtaggatttt tcttttatttaattgccattgtataccacactgcagtgaaccgcaactat gttgaccatgtcgatgaatgtaagtgaaccatgaaactaatctttctgta caatttacttacttctgagtcattgtgatgtttggttggcaggtcacctt tatttctcacactccctccactcatgtgatgtggttgggattttctttc ataagtagcttttgtaaagaactcagtctttctctttcaaatcatggaa acctttcaacaaaagccaaatccatgttacataagcaaaatatctgctt tcttcatctttcctttctttcatatttgagAGGGAACAAAAGAAGAGGAA

GAAAATGAAGCAAAGTAA
```

Another representative nucleotide sequence of a modified pennycress FAD2 coding sequence having a 29 bp deletion of nucleotide residues 714-742 (e.g., nucleotide residues 714-742 as corresponding to the numbering of a genomic FAD2 coding sequence such as the sequence set forth in SEQ ID NO:1) is as follows, with the deleted nucleotide residues [[bracketed]] (SEQ ID NO: 33):

```
ATGTCTAAATTTGATAAAATATATGATGACGACAATTCCGGTGGATCACA

AAACATGGGTGCAGGTGGAAGAATGACGGTTCCTACTTCTTCCAAGAAGT

CTGAAACCGATGCCTTAAAGCGTGTGCCGTGCGAGAAACCGCCGTTCACG

CTCGGAGAACTGAAGAAAGCAATCCCACAGCATTGTTTCAATCGCTCAAT

CCCTCGCTCTTTCTCCTACCTTATCTGGGACATCATCATAGCCTCTTGCT

TCTACTACGTTGCCACCACTTACTTCTCTCTCCTCCCTCAGCCTCTCTCT

TACTTGGCT[[tggcctctctattgggtctgtcaaggctg]]

TGTCTTAACCGGAGTCTGGGTCATAGCTCACGAATGCGGCCACCACGCCT

TCAGCGACTACCAATGGCTTGACGACACAGTCGGTCTGATCTTCCATTCT

TTCCTCCTCGTCCCTTACTTCTCCTGGAAATACAGCCACCGCCGTCACCA

TTCCAACACCGGATCACTTGAAAAGGACGAAGTGTTTGTCCCTAAACAGA

AATCCGCCATCAAATGGTACGGCAAGTACCTCAACAACCCTCTGGGACGC

ACCGTGATGTTAACCGTCCAGTTCACCCTTGGCTGGCCCTTGTACTTAGC

CTTCAACGTCTCGGGGAGACCCTACGACGGGTTCGCTTGCCACTTCCACC

CAAACGCTCCCATCTACAACGACCGTGAACGCCTCCAGATATACATCTCG

GATGCTGGTATCCTCGCCGTCTGTTACGGTCTCTACCGTTACGCTGCTGC

ACAAGGAGTGGCCTCGATGATCTGCGTCTACGGAGTTCCGCTTCTGATAG

TCAACGGGTTCCTCGTCTTGATCACATACTTGCAGCACACCCATCCCTCG

TTGCCTCACTACGATTCATCCGAGTGGGATTGGTTCAGGGGAGCTTTGGC

TACCGTAGACAGAGACTATGGAATCCTGAACAAGGTCTTCCACAACATCA

CGGACACGCACGTGGCTCACCACCTGTTCTCGACGATGCCGCATTACCAT

GCGATGGAGGCCACGAAGGCGATAAAGCCGATACTCGGGGACTATTACCA

GTTTGATGGAACACCGGTCTTCAAGGCGATGTGGAGGGAGGCGAAGGAGT

GTGTCTATGTAGAACCGGACAGGAAAGGTGAGAAGAAAGAGGGAACAAAA

GAAGAGGAAGAAAATGAAGCAAAGTAA
```

A modified pennycress FAD2 coding sequence having a 29 bp deletion of nucleotide residues 714-742 in a WT pennycress FAD2 coding sequence (e.g., SEQ ID NO:32 or SEQ ID NO: 33) can result in a frameshift of the codons in the coding sequence and a modified polypeptide. For example, a modified pennycress FAD2 coding sequence having a 29 bp deletion of nucleotide residues 714-742 in a WT pennycress FAD2 coding sequence (e.g., SEQ ID NO:32 or SEQ ID NO:33) can encode a FAD2 polypeptide having a substituted C-terminal end. A representative polypeptide sequence of a pennycress FAD2 polypeptide having a substituted C-terminal end is as follows, with the substituted sequence highlighted (SEQ ID NO:34):

```
MSKFDKIYDDDNSGGSQNMGAGGRMTVPTSSKKSETDALKRVPCEKPPFT

LGELKKAIPQHCFNRSIPRSFSYLIWDIIIASCFYYVATTYFSLLPQPLS

YLACLNRSLGHSSRMRPPRLQRLPMA
```

In some cases, oilseed (e.g., pennycress) plants described herein (e.g., having reduced levels of PUFAs and/or increased levels of oleic acid) can include an insertion relative to the WT pennycress FAD2 coding sequence (e.g., SEQ ID NO:1). An insertion can include any number of nucleotides. For example, a deletion can include the entire length of the gene and/or regulatory sequences. For example, an insertion can include from about 1 nucleotide to about 50 nucleotides (e.g., about 1 nucleotide such as a single base-pair insertion). In some cases, a modified FAD2 coding sequence can include a single base-pair insertion in a WT pennycress FAD2 coding sequence (e.g., SEQ ID NO:1). An insertion can be an insertion of any appropriate nucleotide(s) (e.g., A, T, G, C, and any combinations thereof). In some cases, a single base-pair insertion can be an insertion of an A nucleotide. An insertion can be in any location within a FAD2 coding sequence. In some cases, a modified FAD2 coding sequence having a single base-pair insertion in a WT pennycress FAD2 coding sequence (e.g., SEQ ID NO:1), can have a single base-pair insertion following nucleotide residue 721 in a WT pennycress FAD2 coding sequence (e.g., SEQ ID NO:1). For example, a modified FAD2 coding sequence can include a single bp of an A nucleotide following nucleotide residue 721 in a WT pennycress FAD2 coding sequence (e.g., SEQ ID NO:1). A representative nucleotide sequence of a modified pennycress FAD2 coding sequence having a single bp insertion of an A nucleotide following nucleotide residue 721 (e.g., nucleotide residue 721 as corresponding to the numbering of a genomic FAD2 coding sequence such as the sequence set forth in SEQ ID NO: 1) is as follows, with the inserted nucleotide residue highlighted (SEQ ID NO:35):

```
ATGTCTAAATTTGATAAAATATATGATGACGACAATTCCGGTGGATCACA
gtttgcttcatttggctttttttgtgtgtttgtcaagttgctattcaata
agaatttgtgattttgattggtctcctcaaaattctgtgaaattttagta
acaaggaagaaattaacaaatcacaacaagaaagagatgtgagctgtcgt
atcaaatcttattcgttttctcaacgcaatcgttttagttttttttaact
taacgccacttctctgctccatacactccttttttgtccacgtactttttca
tttgtggtaatccatttcttcactttggatctttcatctgaacaacaatt
tcttgactcaatcaattaccacccgttcttgtgcttttgtatagattcat
aatcttgtgtgtttcagcttctcattgctttggttcttgtttttttttct
gcagAAACATGGGTGCAGGTGGAAGAATGACGGTTCCTACTTCTTCCAAG
AAGTCTGAAACCGATGCCTTAAAGCGTGTGCCGTGCGAGAAACCGCCGTT
CACGCTCGGAGAACTGAAGAAAGCAATCCCACAGCATTGTTTCAATCGCT
CAATCCCTCGCTCTTTCTCCTACCTTATCTGGGACATCATCATAGCCTCT
TGCTTCTACTACGTTGCCACCACTTACTTCTCTCCTCCCTCAGCCTCT
CTCTTACTTGGCTTGGCCTCTACTATTGGGTCTGTCAAGGCTGTGTCTTA
ACCGGAGTCTGGGTCATAGCTCACGAATGCGGCCACCACGCCTTCAGCGA
CTACCAATGGCTTGACGACACAGTCGGTCTGATCTTCCATTCTTTCCTCC
TCGTCCCTTACTTCTCCTGGAAATACAGCCACCGCCGTCACCATTCCAAC
ACCGGATCACTTGAAAAGGACGAAGTGTTTGTCCCTAAACAGAAATCCGC
CATCAAATGGTACGGCAAGTACCTCAACAACCCTCTGGGACGCACCGTGA
TGTTAACCGTCCAGTTCACCCTTGGCTGGCCCTTGTACTTAGCCTTCAAC
GTCTCGGGGAGACCCTACGACGGGTTCGCTTGCCACTTCCACCCAAACGC
TCCCATCTACAACGACCGTGAACGCCTCCAGATATACATCTCGGATGCTG
GTATCCTCGCCGTCTGTTACGGTCTCTACCGTTACGCTGCTGCACAAGGA
GTGGCCTCGATGATCTGCGTCTACGGAGTTCCGCTTCTGATAGTCAACGG
GTTCCTCGTCTTGATCACATACTTGCAGCACACCCATCCCTCGTTGCCTC
ACTACGATTCATCCGAGTGGGATTGGTTCAGGGGAGCTTTGGCTACCGTA
GACAGAGACTATGGAATCCTGAACAAGGTCTTCCACAACATCACGGACAC
GCACGTGGCTCACCACCTGTTCTCGACGATGCCGCATTACCATGCGATGG
AGGCCACGAAGGCGATAAAGCCGATACTCGGGGACTATTACCAGTTTGAT
GGAACACCGGTCTTCAAGGCGATGTGGAGGGAGGCGAAGGAGTGTGTCTA
TGTAGAACCGGACAGGAAAGGTGAGAAGAAAGgtgtgttctggtacaaca
acaagttgtgaggatgatcaggtgaaagaagaaggaagaaaaatcgtcgg
cctttctcttgtctggttatctttgttttaagaagatatatgtttgtttc
aataatcttattgtccattttgttgtgttctgacattgtggcttaaatta
ttatgtgatgttagtgtccaattgttctgcgtctgtattgttcttctcat
cgctgttttgtgggatcgtagaaatgtgactttcggacaattaaactct
tgtactcaagctatcactctgttggcagcatcaaaagtgttttcatagtt
tcggtcttttggtctctgtttgtttgatactgttggtgagaatggctctt
caagtgttggaatctacctaaggtgaacacattgtaggattttttctttta
tttaattgccattgtataccacactgcagtgaaccgcaactatgttgacc
atgtcgatgaatgtaagtgaaccatgaaactaatctttctgtacaattta
cttacttctgagtcattgtgatgtttggttggcaggtcaccttttatttct
cacactccctccactcatgtgatgtggttgggattttcttttcataagta
gcttttgtaaagaactcagtctttctctttcaaatcatggaaaccttt
caacaaaagccaaatccatgttacataagcaaaatatctgctttcttcat
ctttcctttctttcatatttgagAGGGAACAAAAGAAGAGGAAGAAAATG
AAGCAAAGTAA
```

Another representative nucleotide sequence of a modified pennycress FAD2 coding sequence having a single bp insertion of an A nucleotide following nucleotide residue 721 (e.g., nucleotide residue 721 as corresponding to the numbering of a genomic FAD2 coding sequence such as the sequence set forth in SEQ ID NO:1) is as follows, with the inserted nucleotide residue highlighted (SEQ ID NO:36):

```
ATGTCTAAATTTGATAAAATATATGATGACGACAATTCCGGTGGATCACA
AAACATGGGTGCAGGTGGAAGAATGACGGTTCCTACTTCTTCCAAGAAGT
CTGAAACCGATGCCTTAAAGCGTGTGCCGTGCGAGAAACCGCCGTTCACG
CTCGGAGAACTGAAGAAAGCAATCCCACAGCATTGTTTCAATCGCTCAAT
CCCTCGCTCTTTCTCCTACCTTATCTGGGACATCATCATAGCCTCTTGCT
TCTACTACGTTGCCACCACTTACTTCTCTCTCCTCCCTCAGCCTCTCTCT
TACTTGGCTTGGCCTCTACTATTGGGTCTGTCAAGGCTGTGTCTTAACCG
GAGTCTGGGTCATAGCTCACGAATGCGGCCACCACGCCTTCAGCGACTAC
CAATGGCTTGACGACACAGTCGGTCTGATCTTCCATTCTTTCCTCCTCGT
CCCTTACTTCTCCTGGAAATACAGCCACCGCCGTCACCATTCCAACACCG
GATCACTTGAAAAGGACGAAGTGTTTGTCCCTAAACAGAAATCCGCCATC
AAATGGTACGGCAAGTACCTCAACAACCCTCTGGGACGCACCGTGATGTT
AACCGTCCAGTTCACCCTTGGCTGGCCCTTGTACTTAGCCTTCAACGTCT
CGGGGAGACCCTACGACGGGTTCGCTTGCCACTTCCACCCAAACGCTCCC
ATCTACAACGACCGTGAACGCCTCCAGATATACATCTCGGATGCTGGTAT
CCTCGCCGTCTGTTACGGTCTCTACCGTTACGCTGCTGCACAAGGAGTGG
```

CCTCGATGATCTGCGTCTACGGAGTTCCGCTTCTGATAGTCAACGGGTTC

CTCGTCTTGATCACATACTTGCAGCACACCCATCCCTCGTTGCCTCACTA

CGATTCATCCGAGTGGGATTGGTTCAGGGGAGCTTTGGCTACCGTAGACA

GAGACTATGGAATCCTGAACAAGGTCTTCCACAACATCACGGACACGCAC

GTGGCTCACCACCTGTTCTCGACGATGCCGCATTACCATGCGATGGAGGC

CACGAAGGCGATAAAGCCGATACTCGGGGACTATTACCAGTTTGATGGAA

CACCGGTCTTCAAGGCGATGTGGAGGGAGGCGAAGGAGTGTGTCTATGTA

GAACCGGACAGGAAAGGTGAGAAGAAAGAGGGAACAAAAGAAGAGGAAGA

AAATGAAGCAAAGTAA

A modified pennycress FAD2 coding sequence having a single bp insertion (e.g., an insertion of an A nucleotide) following nucleotide residue 721 in a WT pennycress FAD2 coding sequence (e.g., SEQ ID NO:35 or SEQ ID NO:36) can result in a frameshift of the codons in the coding sequence and a modified polypeptide. For example, a modified pennycress FAD2 coding sequence having an insertion of an A nucleotide following nucleotide residue 721 in a WT pennycress FAD2 coding sequence (e.g., SEQ ID NO:35 or SEQ ID NO:36) can encode a FAD2 polypeptide having a substituted C-terminal end. A representative polypeptide sequence of a pennycress FAD2 polypeptide having a substituted C-terminal end is as follows, with the substituted sequence highlighted (SEQ ID NO:37):

MSKFDKIYDDDNSGGSQNMGAGGRMTVPTSSKKSETDALKRVPCEKPPFT

LGELKKAIPQHCFNRSIPRSFSYLIWDIIIASCFYYVATTYFSLLPQPLS

YLAWPL<u>LLGLSRLCLNRSLGHSSRMRPPRLQRLPMA</u>

In some cases, a loss-of-function modification in a FAD2 coding sequence can be as described elsewhere. For example, a loss-of-function modification in a FAD2 coding sequence can be as described in Table 6.

In some cases, the oilseed (e.g., pennycress) plants described herein (e.g., having reduced levels of PUFAs and/or increased levels of oleic acid) can include one or more modifications in a ROD1 gene. A representative nucleotide sequence of a WT pennycress ROD1 gene is as follows (SEQ ID NO:9), with upper case letters representing the ROD1 coding sequence and the lower case letters representing introns:

ATGTCAACTAAAACCGTCGTCCCTCTCCGTCGCAGATCTAAGCCCCTTAA

CGGAAATCACACTAACGGCGTCGCCATTGACGGAAGCCTCGACGACGACC

ACAACCGTCGCATCGGATCAGTAAATAGCCAAATGGATAACATTGCTAAG

AAAACGGACGACGGCTACGCAAACGGCGGAGGAGGAGGAGGAGGAGGCGA

GGGAAAAGCAAGGCGTCGTTTATGACGTGGACGGCGCGTGACGTTGTGTA

CGTGGTACCATTGGATACCGTGTTTGTTCGCGGTCGGGGTTCTGTTCTTC

ACGGGCGTGGAGTACACGCTCCAGATGATTCCCGCGAGGTCTGAGCCGTT

CGATATTGGGTTTGTGGCCACGCGCTCTCTGAATCGCGTCTTGGCAAATT

CACCGGATCTTAACACCGTCTTAGCCGCTCTAAACACGgtaatttcgtac taattaatttagggtaaaaaatatagtatttaataatgactatcctcaat tcctttcatgcttcacctaatattttgtttttttcgttgtcattaaaat cgtaataatatattgagttagtcaaatgaaaaaaacaagtggcggtagtg attggaaacaaatctcagatcttttatctgtttaataaggtatttaatta tccagctggaattatgctgtcaagtgtcaacacagtagtagttagtggac aacatgcaatggaatttctcaatagaaaaaggtcttaattagtatagata ataaaaatgtagttaatgtaatctctttgctaagtagttatcataatcat cttttttaacaactgccattttgtctgtgtgtttgttttacaacgaagtag tagtagaatagatcgcttttttagcttttgaaagtttcgaacccaaggaaa agggacacatgggttatgagttggagacacgatcacatgcaaacagagag attggttaaattatcgacttttttgtagtacttttttaaaaaaaaactattt atataaaaaacatggtggatggtggggacagGTGTTCGTAGGGATGCAAA

CGACGTATATTGTATGGACATGGTTAATGGAAGGACGACCACGAGCCACC

ATCTCGGCTTGCTTCATGTTTACTTGTCGAGGCATTCTTGGTTACTCTAC

TCAGCTCCCTCTTCCTCAGgttccaatcaacactttttcttctatctcgtc ttttcttaattaaaataattaccaattaactaaatgctaatcagatatat catagttccaacgttttggacgtgtgatttccattggccactaccatata aaacaacagagtctctttattcattattcaatatatatttgagtattgat attattcatagggaggtttcatttgtactatcaataaaatttctacaact cttggattttttctgctacattttgtagttatttttttaattacttttaa aaacttgtgaataggagagactaatagtagtacgtaatatgattgtatca aatgctttaacatgtgggggtttgggttaactatcatcatttcatagatca ctattttgttttcgtttgttacctaactttttgttatctttgaaaaataa tgttccacgagttgattgactggacataaaaatcagattctctcactcat ttacgttctacggttctagccactcgtttttttcttttttctttctgtggt gtaacacgtagataatggattttctatgtgtgtcgtcttgctcaagaata ataaatgtggttaaaggttaaatatagctctggaaattaattatctcctc tttttttattaaccagGATTTTCTAGGATCAGGTGTCGATTTTCCGGTGG

GAAACGTCTCGTTCTTCCTCTTCTACTCGGGTCACGTCGCCGGTTCGATG

ATCGCATCTTTGGACATGAGGAGAATGCAGAGGATGAGACTAGCGATGCT

TTTTGACATCCTCAATGTATTACAATCGATCAGGCTGCTCGGGACGAGAG

GACACTACACGATTGATCTCGCTGTCGGAGTTGGCGCTGGGATTCTCTTT

GATTCATTCGCCGGCAAGTACGAAGAGATGATAAGCAAGAGACACAATTT

AGTCAATGGTTTTGGTTTGATTTCGAAAGACTCGCTAGTCAATTAA

Another representative nucleotide sequence of a WT pennycress ROD1 coding sequence is as follows (SEQ ID NO:38):

ATGTCAACTAAAACCGTCGTCCCTCTCCGTCGCAGATCTAA

GCCCCTTAACGGAAATCACACTAACGGCGTCGCCATTGACG

GAAGCCTCGACGACGACCACAACCGTCGCATCGGATCAGTA

-continued

```
AATAGCCAAATGGATAACATTGCTAAGAAAACGGACGACGG

CTACGCAAACGGCGGAGGAGGAGGAGGAGGAGGGAAAAGCA

AGGCGTCGTTTATGACGTGGACGGCGCGTGACGTTGTGTAC

GTGGCGAGGTACCATTGGATACCGTGTTTGTTCGCGGTCGG

GGTTCTGTTCTTCACGGGCGTGGAGTACACGCTCCAGATGA

TTCCCGCGAGGTCTGAGCCGTTCGATATTGGGTTTGTGGCC

ACGCGCTCTCTGAATCGCGTCTTGGCAAATTCACCGGATCT

TAACACCGTCTTAGCCGCTCTAAACACGGTGTTCGTAGGGA

TGCAAACGACGTATATTGTATGGACATGGTTAATGGAAGGA

CGACCACGAGCCACCATCTCGGCTTGCTTCATGTTTACTTG

TCGAGGCATTCTTGGTTACTCTACTCAGCTCCCTCTTCCTC

AGGATTTTCTAGGATCAGGTGTCGATTTTCCGGTGGGAAAC

GTCTCGTTCTTCCTCTTCTACTCGGGTCACGTCGCCGGTTC

GATGATCGCATCTTTGGACATGAGGAGAATGCAGAGGATGA

GACTAGCGATGCTTTTTGACATCCTCAATGTATTACAATCG

ATCAGGCTGCTCGGGACGAGAGGACACTACACGATTGATCT

CGCTGTCGGAGTTGGCGCTGGGATTCTCTTTGATTCATTCG

CCGGCAAGTACGAAGAGATGATAAGCAAGAGACACAATTTA

GTCAATGGTTTTGGTTTGATTTCGAAAGACTCGCTAGTCAA

TTAA
```

In some cases, a WT pennycress ROD1 gene can have a sequence that deviates from the sequence set forth above (SEQ ID NO:9 or SEQ ID NO:38), sometimes referred to as a variant sequence, provided the variant sequence encodes a WT pennycress ROD1 polypeptide. A representative polypeptide sequence of a WT pennycress ROD1 polypeptide is as follows (SEQ ID NO:10):

```
MSTKTVVPLRRRSKPLNGNHTNGVAIDGSLDDDHNRRIGSV

NSQMDNIAKKTDDGYANGGGGGGGGKSKASFMTWTARDVVY

VARYHWIPCLFAVGVLFFTGVEYTLQMIPARSEPFDIGFVA

TRSLNRVLANSPDLNTVLAALNTDFLGSGVDFPVGNVSFFL

FYSGHVAGSMIASLDMRRMQRMRLAMLFDILNVLQSIRLLG

TRGHYTIDLAVGVGAGILFDSFAGKYEEMISKRHNLVNGFG

LISKDSLVN
```

In some cases, a WT pennycress ROD1 polypeptide can have a sequence that deviates from the polypeptide sequence set forth above (SEQ ID NO:10), sometimes referred to as a variant sequence, provided the polypeptide maintains its WT function. For example, a ROD1 polypeptide can have at least 80 (e.g., at least 85, at least 90, at least 95, at least 98, or at least 99) percent sequence identity to SEQ ID NO:10. A ROD1 polypeptide can have one or more (e.g., 2, 3, 4, 5, 6, 7, 8, 9, or 10) amino acid modifications (e.g., substitutions) relative to SEQ ID NO: 10.

In some cases, oilseed (e.g., pennycress) plants described herein (e.g., having reduced levels of PUFAs and/or increased levels of oleic acid) can include a loss-of-function modification in an ROD1 gene (e.g., in an ROD1 coding sequence). As used herein, a loss-of-function modification in an ROD1 gene can be any modification that is effective to reduce ROD1 polypeptide expression or ROD1 polypeptide function. In some cases, reduced ROD1 polypeptide expression or reduced ROD1 polypeptide function can be eliminated ROD1 polypeptide expression or eliminated ROD1 polypeptide function. Examples of genetic modifications include, without limitation, deletions, insertions, substitutions, frameshifts, duplications, and rearrangements.

In some cases, oilseed (e.g., pennycress) plants described herein (e.g., having reduced levels of PUFAs and/or increased levels of oleic acid) can include a substitution (e.g., a single base-pair substitution) relative to the WT pennycress ROD1 coding sequence (e.g., SEQ ID NO:9 or SEQ ID NO:38). The single base-pair substitution can be a substitution of any appropriate nucleotide. For example, a modified ROD1 coding sequence can include a G to A substitution at nucleotide residue 1918 in a WT pennycress ROD1 coding sequence (e.g., SEQ ID NO:9). A representative nucleotide sequence of a modified pennycress ROD1 coding sequence having a loss-of-function G to A substitution at nucleotide residue 1918 (e.g., nucleotide residue 1918 as corresponding to the numbering of a genomic ROD1 coding sequence such as the sequence set forth in SEQ ID NO:9) is as follows (SEQ ID NO:11):

```
ATGTCAACTAAAACCGTCGTCCCTCTCCGTCGCAGATCTAAGCCCCTTAA

CGGAAATCACACTAACGGCGTCGCCATTGACGGAAGCCTCGACGACGACC

ACAACCGTCGCATCGGATCAGTAAATAGCCAAATGGATAACATTGCTAAG

AAAACGGACGACGGCTACGCAAACGGCGGAGGAGGAGGAGGAGGAGGGAA

AAGCAAGGCGTCGTTTATGACGTGGACGGCGCGTGACGTTGTGTACGTGG

CGAGGTACCATTGGATACCGTGTTTGTTCGCGGTCGGGGTTCTGTTCTTC

ACGGGCGTGGAGTACACGCTCCAGATGATTCCCGCGAGGTCTGAGCCGTT

CGATATTGGGTTTGTGGCCACGCGCTCTCTGAATCGCGTCTTGGCAAATT

CACCGGATCTTAACACCGTCTTAGCCGCTCTAAACACGGTAATTTCGTAC

TAATTAATTTAGGGTAAAAAATATAGTATTTAATAATGACTATCCTCAAT

TCCTTTCATGCTTCACCTAATATTTTGTTTTTTTTCGTTGTCATTAAAAT

CGTAATAATATATTGAGTTAGTCAAATGAAAAAAACAAGTGGCGGTAGTG

ATTGGAAACAAATCTCAGATCTTTTATCTGTTTAATAAGGTATTTAATTA

TCCAGCTGGAATTATGCTGTCAAGTGTCAACACAGTAGTAGTAACATGCA

ATGGAATTTCTCAATAGAAAAAGGTCTTAATTAGTATAGATAATTAGTGG

ACAAAAATGTAGTTAATGTAATCTCTTTGCTAAGTAGTTATCATAATCAT

CTTTTTAACAACTGCCATTTTGTCTGTGTGTTTGTTTTACAACGAAGTAG

TAGTAGAATAGATCGCTTTTTAGCTTTTGAAAGTTTCGAACCCAAGGAAA

AGGGACACATGGGTTATGAGTTGGAGACACGATCACATGCAAACAGAGAG

ATTGGTTAAATTATCGACTTTTTGTAGTACTTTTTAAAAAAAAACTATTT

ATATAAAAAACATGGTGGATGGTGGGGACAGGTGTTCGTAGGGATGCAAA

CGACGTATATTGTATGGACATGGTTAATGGAAGGACGACCACGAGCCACC

ATCTCGGCTTGCTTCATGTTTACTTGTCGAGGCATTCTTGGTTACTCTAC

TCAGCTCCCTCTTCCTCAGGTTCCAATCAACACTTTTCTTCTATCTCTTT
```

```
TCTTAATTAAAATAATTACCAATTAACTAAATGCTAATCAGTCGATATAT

CATAGTTCCAACGTTTTGGACGTGTGATTTCCATTGGCCACTACCATATA

AAACAACAGAGTCTCTTTATTCATTATTCAATATATATTTGAGTATTGAT

ATTATTCATAGGGAGGTTTCATTTGTACTATCAATAAAATTTCTACAACT

CTTGGATTTTTTCTGCTACATTTTGTAGTTATTTTTTAATTACTTTTAA

AAACTTGTGAATAGGAGAGACTAATAGTAGTACGTAATATGATTGTATCA

AATGCTTTAACATGTGGGGTTTGGGTTAACTATCATCATTTCATAGATCA

CTATTTTGTTTTCGTTTGTTACCTAACTTTTTGTTATCTTTGAAAAATAA

TGTTCCACGAGTTGATTGACTGGACATAAAAATCAGATTCTCTCACTCAT

TTACGTTCTACGGTTCTAGCCACTCGTTTTTTCTTTTTCTTTCTGTGGT

GTAACACGTAGATAATGGATTTTCTATGTGTGTCGTCTTGCTCAAGAATA

ATAAATGTGGTTAAAGGTTAAATATAGCTCTGGAAATTAATTATCTCCTC

TTTTTTTATTAACCAGGATTTTCTAGGATCAGGTGTCGATTTTCCGGTGG

GAAACGTCTCGTTCTTCCTCTTCTACTCGGGTCACGTCGCCGGTTCGATG

ATCGCATCTTTGGACATȺGGAGAATGCAGAGGATGAGACTAGCGATGCT

TTTTGACATCCTCAATGTATTACAATCGATCAGGCTGCTCGGGACGAGAG

GACACTACACGATTGATCTCGCTGTCGGAGTTGGCGCTGGGATTCTCTTT

GATTCATTCGCCGGCAAGTACGAAGAGATGATAAGCAAGAGACACAATTT

AGTCAATGGTTTTGGTTTGATTTCGAAAGACTCGCTAGTCAATTAA
```

Another representative nucleotide sequence of a modified pennycress ROD1 coding sequence having a loss-of-function G to A substitution at nucleotide residue 1918 (e.g., nucleotide residue 1918 as corresponding to the numbering of a genomic ROD1 coding sequence such as the sequence set forth in SEQ ID NO:9) is as follows (SEQ ID NO:39):

```
ATGTCAACTAAAACCGTCGTCCCTCTCCGTCGCAGATCTA

AGCCCCTTAACGGAAATCACACTAACGGCGTCGCCATTGA

CGGAAGCCTCGACGACGACCACAACCGTCGCATCGGATCA

GTAAATAGCCAAATGGATAACATTGCTAAGAAAACGGACG

ACGGCTACGCAAACGGCGGAGGAGGAGGAGGAGGGGAA

AAGCAAGGCGTCGTTTATGACGTGGACGGCGCGTGACGTT

GTGTACGTGGCGAGGTACCATTGGATACCGTGTTTGTTCG

CGGTCGGGGTTCTGTTCTTCACGGGCGTGGAGTACACGCT

CCAGATGATTCCCGCGAGGTCTGAGCCGTTCGATATTGGG

TTTGTGGCCACGCGCTCTCTGAATCGCGTCTTGGCAAATT

CACCGGATCTTAACACCGTCTTAGCCGCTCTAAACACGGT

GTTCGTAGGGATGCAAACGACGTATATTGTATGGACATGG

TTAATGGAAGGACGACCACGAGCCACCATCTCGGCTTGCT

TCATGTTTACTTGTCGAGGCATTCTTGGTTACTCTACTCA

GCTCCCTCTTCCTCAGGATTTTCTAGGATCAGGTGTCGAT

TTTCCGGTGGGAAACGTCTCGTTCTTCCTCTTCTACTCGG

GTCACGTCGCCGGTTCGATGATCGCATCTTTGGACATȺ
```

```
AGGAGAATGCAGAGGATGAGACTAGCGATGCTTTTTGACA

TCCTCAATGTATTACAATCGATCAGGCTGCTCGGGACGAG

AGGACACTACACGATTGATCTCGCTGTCGGAGTTGGCGCT

GGGATTCTCTTTGATTCATTCGCCGGCAAGTACGAAGAGA

TGATAAGCAAGAGACACAATTTAGTCAATGGTTTTGGTTT

GATTTCGAAAGACTCGCTAGTCAATTAA
```

A modified pennycress ROD1 coding sequence having a G to A substitution at nucleotide residue 1918 in a WT pennycress ROD1 coding sequence (e.g., SEQ ID NO:11 or SEQ ID NO: 39) can result in a ROD1 polypeptide having an amino acid substitution. For example, a modified pennycress ROD1 coding sequence having a G to A substitution at nucleotide residue 1918 in a WT pennycress ROD1 coding sequence (e.g., SEQ ID NO:11 or SEQ ID NO: 39) can encode a ROD1 polypeptide having a M to I amino acid substitution at amino acid residue 180. A representative polypeptide sequence of pennycress ROD1 polypeptide having a M to I amino acid substitution at amino acid residue 180 (e.g., amino acid residue 180 as corresponding to the numbering of a WT ROD1 polypeptide such as the sequence set forth in SEQ ID NO:10) is as follows (SEQ ID NO:12):

```
MSTKTVVPLRRRSKPLNGNHTNGVAIDGSLDDDHNRRIGSV

NSQMDNIAKKTDDGYANGGGGGGGGKSKASFMTWTARDVVY

VARYHWIPCLFAVGVLFFTGVEYTLQMIPARSEPFDIGFVA

TRSLNRVLANSPDLNTVLAALNTDFLGSGVDFPVGNVSFFL

FYSGHVAGSMIASLDȺRRMQRMRLAMLFDILNVLQSIRL

LGTRGHYTIDLAVGVGAGILFDSFAGKYEEMISKRHNLVNG

FGLISKDSLVN
```

For example, a modified ROD1 coding sequence can include a G to A substitution at nucleotide residue 1983 in a WT pennycress ROD1 coding sequence (e.g., SEQ ID NO:9). A representative nucleotide sequence of a modified pennycress ROD1 coding sequence having a loss-of-function G to A substitution at nucleotide residue 1983 (e.g., nucleotide residue 1983 as corresponding to the numbering of a genomic ROD1 coding sequence such as the sequence set forth in SEQ ID NO:9) is as follows (SEQ ID NO:13):

```
ATGTCAACTAAAACCGTCGTCCCTCTCCGTCGCAGATCTAAGCCCCTTAA

CGGAAATCACACTAACGGCGTCGCCATTGACGGAAGCCTCGACGACGACC

ACAACCGTCGCATCGGATCAGTAAATAGCCAAATGGATAACATTGCTAAG

AAAACGGACGACGGCTACGCAAACGGCGGAGGAGGAGGAGGAGGAGGGGG

AAAAGCAAGGCGTCGTTTATGACGTGGACGGCGCGTGACGTTGTGTACGT

CGAGGTACCATTGGATACCGTGTTTGTTCGCGGTCGGGGTTCTGTTCTTC

ACGGGCGTGGAGTACACGCTCCAGATGATTCCCGCGAGGTCTGAGCCGTT

CGATATTGGGTTTGTGGCCACGCGCTCTCTGAATCGCGTCTTGGCAAATT

CACCGGATCTTAACACCGTCTTAGCCGCTCTAAACACGGTAATTTCGTAC

TAATTAATTTAGGGTAAAAAATATAGTATTTAATAATGACTATCCTCAAT
```

-continued

```
TCCTTTCATGCTTCACCTAATATTTTGTTTTTTTCGTTGTCATTAAAAT
CGTAATAATATATTGAGTTAGTCAAATGAAAAAAACAAGTGGCGGTAGTG
ATTGGAAACAAATCTCAGATCTTTTATCTGTTTAATAAGGTATTTAATTA
TCCAGCTGGAATTATGCTGTCAAGTGTCAACACAGTAGTAGTAACATGCA
ATGGAATTTCTCAATAGAAAAAGGTCTTAATTAGTATAGATAATTAGTGG
ACAAAAATGTAGTTAATGTAATCTCTTTGCTAAGTAGTTATCATAATCAT
CTTTTTAACAACTGCCATTTTGTCTGTGTGTTTGTTTTACAACGAAGTAG
TAGTAGAATAGATCGCTTTTTAGCTTTTGAAAGTTTCGAACCCAAGGAAA
AGGGACACATGGGTTATGAGTTGGAGACACGATCACATGCAAACAGAGAG
ATTGGTTAAATTATCGACTTTTTGTAGTACTTTTTAAAAAAAACTATTT
ATATAAAAACATGGTGGATGGTGGGACAGGTGTTCGTAGGGATGCAAA
CGACGTATATTGTATGGACATGGTTAATGGAAGGACGACCACGAGCCACC
ATCTCGGCTTGCTTCATGTTTACTTGTCGAGGCATTCTTGGTTACTCTAC
TCAGCTCCCTCTTCCTCAGGTTCCAATCAACACTTTTCTTCTATCTCTTT
TCTTAATTAAAATAATTACCAATTAACTAAATGCTAATCAGTCGATATAT
CATAGTTCCAACGTTTTGGACGTGTGATTTCCATTGGCCACTACCATATA
AAACAACAGAGTCTCTTTATTCATTATTCAATATATATTTGAGTATTGAT
ATTATTCATAGGGAGGTTTCATTTGTACTATCAATAAAATTTCTACAACT
CTTGGATTTTTTCTGCTACATTTTGTAGTTATTTTTTAATTACTTTTAA
AAACTTGTGAATAGGAGAGACTAATAGTAGTACGTAATATGATTGTATCA
AATGCTTTAACATGTGGGGTTTGGGTTAACTATCATCATTTCATAGATCA
CTATTTTGTTTTCGTTTGTTACCTAACTTTTTGTTATCTTTGAAAAATAA
TGTTCCACGAGTTGATTGACTGGACATAAAAATCAGATTCTCTCACTCAT
TTACGTTCTACGGTTCTAGCCACTCGTTTTTTTCTTTTTCTTTCTCTTGC
GTGGTGTAACACGTAGATAATGGATTTTCTATGTGTGTCGTTCAAGAATA
ATAAATGTGGTTAAAGGTTAAATATAGCTCTGGAAATTAATTATCTCCTC
TTTTTTTATTAACCAGGATTTTCTAGGATCAGGTGTCGATTTTCCGGTGG
GAAACGTCTCGTTCTTCCTCTTCTACTCGGGTCACGTCGCCGGTTCGATG
ATCGCATCTTTGGACATGAGGAGAATGCAGAGGATGAGACTAGCGATGCT
TTTTGACATCCTCAATGTATTACAATCGATCAXGCTGCTCGGGACGAGAG
GACACTACACGATTGATCTCGCTGTCGGAGTTGGCGCTGGGATTCTCTTT
GATTCATTCGCCGGCAAGTACGAAGAGATGATAAGCAAGAGACACAATTT
AGTCAATGGTTTTGGTTTGATTTCGAAAGACTCGCTAGTCAATTAA
```

Another representative nucleotide sequence of a modified pennycress ROD1 coding sequence having a loss-of-function G to A substitution at nucleotide residue 1983 (e.g., nucleotide residue 1983 as corresponding to the numbering of a genomic ROD1 coding sequence such as the sequence set forth in SEQ ID NO:9) is as follows (SEQ ID NO:40):

```
ATGTCAACTAAAACCGTCGTCCCTCTCCGTCGCAGATCTAA
GCCCCTTAACGGAAATCACACTAACGGCGTCGCCATTGACG
GAAGCCTCGACGACGACCACAACCGTCGCATCGGATCAGTA
AATAGCCAAATGGATAACATTGCTAAGAAAACGGACGACGG
CTACGCAAACGGCGGAGGAGGAGGAGGAGGGAAAAGCA
AGGCGTCGTTTATGACGTGGACGGCGCGTGACGTTGTGTAC
GTGGCGAGGTACCATTGGATACCGTGTTTGTTCGCGGTCGG
GGTTCTGTTCTTCACGGGCGTGGAGTACACGCTCCAGATGA
TTCCCGCGAGGTCTGAGCCGTTCGATATTGGGTTTGTGGCC
ACGCGCTCTCTGAATCGCGTCTTGGCAAATTCACCGGATCT
TAACACCGTCTTAGCCGCTCTAAACACGGTGTTCGTAGGGA
TGCAAACGACGTATATTGTATGGACATGGTTAATGGAAGGA
CGACCACGAGCCACCATCTCGGCTTGCTTCATGTTTACTTG
TCGAGGCATTCTTGGTTACTCTACTCAGCTCCCTCTTCCTC
AGGATTTTCTAGGATCAGGTGTCGATTTTCCGGTGGGAAAC
GTCTCGTTCTTCCTCTTCTACTCGGGTCACGTCGCCGGTTC
GATGATCGCATCTTTGGACATGAGGAGAATGCAGAGGATGA
GACTAGCGATGCTTTTTGACATCCTCAATGTATTACAATCG
ATCAXGCTGCTCGGGACGAGAGGACACTACACGATTGATCT
CGCTGTCGGAGTTGGCGCTGGGATTCTCTTTGATTCATTCG
CCGGCAAGTACGAAGAGATGATAAGCAAGAGACACAATTTA
GTCAATGGTTTTGGTTTGATTTCGAAAGACTCGCTAGTCAA
TTAA
```

A modified pennycress ROD1 coding sequence having a G to A substitution at nucleotide residue 1983 in a WT pennycress ROD1 coding sequence (e.g., SEQ ID NO:13 or SEQ ID NO: 40) can result in a ROD1 polypeptide having an amino acid substitution. For example, a modified pennycress ROD1 coding sequence having a G to A substitution at residue 1983 in a WT pennycress ROD1 coding sequence (e.g., SEQ ID NO:13 or SEQ ID NO:40) can encode a ROD1 polypeptide having a R to K amino acid substitution at amino acid residue 202. A representative polypeptide sequence of a pennycress ROD1 polypeptide having a R to K amino acid substitution at amino acid residue 202 (e.g., amino acid residue 202 as corresponding to the numbering of a WT ROD1 polypeptide such as the sequence set forth in SEQ ID NO:10) is as follows (SEQ ID NO:14):

```
MSTKTVVPLRRRSKPLNGNHTNGVAIDGSLDDDHNRRIGSV
NSQMDNIAKKTDDGYANGGGGGGGKSKASFMTWTARDVVY
VARYHWIPCLFAVGVLFFTGVEYTLQMIPARSEPFDIGFVA
TRSLNRVLANSPDLNTVLAALNTDFLGSGVDFPVGNVSFFL
FYSGHVAGSMIASLDMRRMQRMRLAMLFDILNVLQSIXLLG
TRGHYTIDLAVGVGAGILFDSFAGKYEEMISKRHNLVNGFG
LISKDSLVN
```

In some cases, oilseed (e.g., pennycress) plants described herein (e.g., having reduced levels of PUFAs and/or increased levels of oleic acid) can include a deletion relative to the WT pennycress ROD1 coding sequence (e.g., SEQ ID NO:9 or SEQ ID NO:38). A deletion can include any number of nucleotides. For example, a deletion can include the entire length of the gene and/or regulatory sequences. For example, a deletion can include from about 1 nucleotide to about 50 nucleotides (e.g., about 18 nucleotides such as a 18 bp deletion). In some cases, a modified ROD1 coding sequence can include a 18 bp deletion in a WT pennycress ROD1 coding sequence (e.g., SEQ ID NO:9). A deletion can include any appropriate nucleotides within a ROD1 coding sequence. In some cases, a modified ROD1 coding sequence having a 18 bp deletion in a WT pennycress ROD1 coding sequence (e.g., SEQ ID NO:1), can have a 18 bp deletion of nucleotide residues 167-184 in a WT pennycress ROD1 coding sequence (e.g., SEQ ID NO:9). A representative nucleotide sequence of a modified pennycress ROD1 coding sequence having a 18 bp deletion of nucleotide residues 167-184 (e.g., nucleotide residues 167-184 as corresponding to the numbering of a genomic ROD1 coding sequence such as the sequence set forth in SEQ ID NO:9) is as follows, with the deleted nucleotide residues (SEQ ID NO:41):

ATGTCAACTAAAACCGTCGTCCCTCTCCGTCGCAGATCTAAGCCCCTTAA

CGGAAATCACACTAACGGCGTCGCCATTGACGGAAGCCTCGACGACGACC

ACAACCGTCGCATCGGATCAGTAAATAGCCAAATGGATAACATTGCTAAG

AAAACGGACGACGGCT[ *[acgcaaacggcggaggag]* ]GAGGAGGAGGA

GGGAAAAGCAAGGCGTCGTTTATGACGTGGACGGCGCGTGACGTTGTGTA

CGTGGCGAGGTACCATTGGATACCGTGTTTGTTCGCGGTCGGGGTTCTGT

TCTTCACGGGCGTGGAGTACACGCTCCAGATGATTCCCGCGAGGTCTGAG

CCGTTCGATATTGGGTTTGTGGCCACGCGCTCTCTGAATCGCGTTAAACA

CTTGGCAAATTCACCGGATCTTAACACCGTCTTAGCCGCTCCGgtaattt cgtactaattaatttagggtaaaaaatatagtatttaataatgactatcc tcaattcctttcatgcttcacctaatattttgttttttttcgttgtcatt aaaatcgtaataatatattgagttagtcaaatgaaaaaaacaagtggcgg tagtgattggaaacaaatctcagatcttttatctgtttaataaggtattt aattatccagctggaattatgctgtcaagtgtcaacacagtagtagtaac atgcaatggaatttctcaatagaaaaaggtcttaattagtatagataatt agtggacaaaaatgtagttaatgtaatctctttgctaagtagttatcata atcatcttttttaacaactgccatttttgtctgtgtgtttgttttacaacga agtagtagtagaatagatcgcttttttagcttttgaaagtttcgaacccaa ggaaaagggacacatgggttatgagttggagacacgatcacatgcaaaca gagagattggttaaattatcgacttttttgtagtacttttttaaaaaaaaac tatttatataaaaaacatggtggatggtggggacagGTGTTCGTAGGGAT

GCAAACGACGTATATTGTATGGACATGGTTAATGGAAGGACGACCACGAG

CCACCATCTCGGCTTGCTTCATGTTTACTTGTCGAGGCATTCTTGGTTAC

TCTACTCAGCTCCCTCTTCCTCAGgttccaatcaacacttttcttctatc tcttttcttaattaaaataattaccaattaactaaatgctaatcagtcga tatatcatagttccaacgttttggacgtgtgatttccattggccactacc atataaaacaacagagtctctttattcattattcaatatatatttgagta ttgatattattcataggagggtttcatttgtactatcaataaaatttcta caactcttggattttttctgctacattttgtagttattttttttaattact tttaaaaacttgtgaataggagagactaatagtagtacgtaatatgattg tatcaaatgctttaacatgtggggtttgggttaactatcatcatttcata gatcactattttgttttcgtttgttacctaacttttttgttatctttgaaa aataatgttccacgagttgattgactggacataaaaatcagattctctca ctcatttacgttctacggttctagccactcgttttttttcttttttctttct gtggtgtaacacgtagataatggatttttctatgtgtgtcgtcttgctcaa gaataataaatgtggttaaaggttaaatatagctctggaaattaattatc tcctctttttttattaaccagGATTTTCTAGGATCAGGTGTCGATTTTCC

GGTGGGAAACGTCTCGTTCTTCCTCTTCTACTCGGGTCACGTCGCCGGTT

CGATGATCGCATCTTTGGACATGAGGAGAATGCAGAGGATGAGACTAGCG

ATGCTTTTTGACATCCTCAATGTATTACAATCGATCAGGCTGCTCGGGAC

GAGAGGACACTACACGATTGATCTCGCTGTCGGAGTTGGCGCTGGGATTC

TCTTTGATTCATTCGCCGGCAAGTACGAAGAGATGATAAGCAAGAGACAC

AATTTAGTCAATGGTTTTGGTTTGATTTCGAAAGACTCGCTAGTCAATTA

A

Another representative nucleotide sequence of a modified pennycress ROD1 coding sequence having a 18 bp deletion of nucleotide residues 167-184 (e.g., nucleotide residues 167-184 as corresponding to the numbering of a genomic ROD1 coding sequence such as the sequence set forth in SEQ ID NO:9) is as follows, with the deleted nucleotide residues (SEQ ID NO: 42):

ATGTCAACTAAAACCGTCGTCCCTCTCCGTCGCAGATCTAAG

CCCCTTAACGGAAATCACACTAACGGCGTCGCCATTGACGGA

AGCCTCGACGACGACCACAACCGTCGCATCGGATCAGTAAAT

AGCCAAATGGATAACATTGCTAAGAAAACGGACGACGGCT

[ *[acgcaaacggcggaggag]* ]GAGGAGGAGGAGGGAAAAG

CAAGGCGTCGTTTATGACGTGGACGGCGCGTGACGTTGTGTA

CGTGGCGAGGTACCATTGGATACCGTGTTTGTTCGCGGTCGG

GGTTCTGTTCTTCACGGGCGTGGAGTACACGCTCCAGATGAT

TCCCGCGAGGTCTGAGCCGTTCGATATTGGGTTTGTGGCCAC

GCGCTCTCTGAATCGCGTCTTGGCAAATTCACCGGATCTTAA

CACCGTCTTAGCCGCTCTAAACACGGTGTTCGTAGGGATGCA

AACGACGTATATTGTATGGACATGGTTAATGGAAGGACGACC

ACGAGCCACCATCTCGGCTTGCTTCATGTTTACTTGTCGAGG

CATTCTTGGTTACTCTACTCAGCTCCCTCTTCCTCAGGATTT

TCTAGGATCAGGTGTCGATTTTCCGGTGGGAAACGTCTCGTT

CTTCCTCTTCTACTCGGGTCACGTCGCCGGTTCGATGATCGC

ATCTTTGGACATGAGGAGAATGCAGAGGATGAGACTAGCGAT

GCTTTTTGACATCCTCAATGTATTACAATCGATCAGGCTGCT

CGGGACGAGAGGACACTACACGATTGATCTCGCTGTCGGAGT

TGGCGCTGGGATTCTCTTTGATTCATTCGCCGGCAAGTACGA

AGAGATGATAAGCAAGAGACACAATTTAGTCAATGGTTTTGG

TTTGATTTCGAAAGACTCGCTAGTCAATTAA

A modified pennycress ROD1 coding sequence having a 18 bp deletion of nucleotide residues 167-184 in a WT pennycress ROD1 coding sequence (e.g., SEQ ID NO:41 or SEQ ID NO: 42) can result in a premature STOP codon and disruption of the gene. For example, a modified pennycress ROD1 coding sequence having a 18 bp deletion of nucleotide residues 167-184 in a WT pennycress ROD1 coding sequence (e.g., SEQ ID NO:41 or SEQ ID NO: 42) can encode a truncated ROD1 polypeptide. A representative polypeptide sequence of a truncated pennycress ROD1 polypeptide is as follows (SEQ ID NO:43):

MSTKTVVPLRRRSKPLNGNHTNGVAIDG

SLDDDHNRRIGSVNSQMDNIAKKTDDG

In some cases, oilseed (e.g., pennycress) plants described herein (e.g., having reduced levels of PUFAs and/or increased levels of oleic acid) can include an insertion relative to the WT pennycress ROD1 coding sequence (e.g., SEQ ID NO:9 or SEQ ID NO:38). An insertion can include any number of nucleotides. For example, a deletion can include the entire length of the gene and/or regulatory sequences. For example, an insertion can include from about 1 nucleotide to about 50 nucleotides (e.g., about 1 nucleotide such as a single base-pair insertion). In some cases, a modified ROD1 coding sequence can include a single base-pair insertion in a WT pennycress ROD1 coding sequence (e.g., SEQ ID NO:9 or SEQ ID NO: 38). An insertion can be an insertion of any appropriate nucleotide(s) (e.g., A, T, G, C, and any combinations thereof). In some cases, a single base-pair insertion can be an insertion of an A nucleotide. In some cases, a single base-pair insertion can be an insertion of a T nucleotide. An insertion can be in any location within a ROD1 coding sequence. In some cases, a modified ROD1 coding sequence having a single base-pair insertion in a WT pennycress ROD1 coding sequence, can have a single base-pair insertion following nucleotide residue 173 in a WT pennycress ROD1 coding sequence. For example, a modified ROD1 coding sequence can include a single bp of an A nucleotide following nucleotide residue 173 in a WT pennycress ROD1 coding sequence. A representative nucleotide sequence of a modified pennycress ROD1 coding sequence having a single bp of an A nucleotide following nucleotide residue 173 (e.g., nucleotide residue 173 as corresponding to the numbering of a genomic ROD1 coding sequence such as the sequence set forth in SEQ ID NO:9) is as follows, with the inserted nucleotide residue highlighted (SEQ ID NO:44):

ATGTCAACTAAAACCGTCGTCCCTCTCCGTCGCAGATCTAAGCCCCTTAA

CGGAAATCACACTAACGGCGTCGCCATTGACGGAAGCCTCGACGACGACC

ACAACCGTCGCATCGGATCAGTAAATAGCCAAATGGATAACATTGCTAAG

AAAACGGACGACGGCTACGCAAACGGCGGAGGAGGAGGAGGAGGGA

AAAGCAAGGCGTCGTTTATGACGTGGACGGCGCGTGACGTTGTGTACGTG

GCGAGGTACCATTGGATACCGTGTTTGTTCGCGGTCGGGGTTCTGTTCTT

CACGGGCGTGGAGTACACGCTCCAGATGATTCCCGCGAGGTCTGAGCCGT

TCGATATTGGGTTTGTGGCCACGCGCTCTCTGAATCGCGTCTTGGCAAAT

TCACCGGATCTTAACACCGTCTTAGCCGCTCTAAACACGgtaatttcgta ctaattaatttagggtaaaaaatatagtatttaataatgactatcctcaa ttcctttcatgcttcacctaatattttgttttttttcgttgtcattaaaa tcgtaataatatattgagttagtcaaatgaaaaaaacaagtggcggtctt tagtgattggaaacaaatctcagattatctgtttaataaggtaacagtag ttttaattatccagctggaattatgctgtcaagtgtcaacagtaacatgc aatggaatttctcaatagaaaaaggtcttaattagtatagataattagtg gacaaaaatgtagttaatgtaatctctttgctaagtagttatcataatca tcttttaacaactgccattttgtctgtgtgtttgttttacaacgaagta gtagtagaatagatcgcttttttagcttttgaaagtttcgaacccaaggaa aagggacacatgggttatgagttggagacacgatcacatgcaaacagaga gattggttaaattatcgacttttttgtagtacttttaaaaaaaaactatt tatataaaaaacatggtggatggtggggacagGTGTTCGTAGGGATGCAA

ACGACGTATATTGTATGGACATGGTTAATGGAAGGACGACCACGAGCCAC

CATCTCGGCTTGCTTCATGTTTACTTGTCGAGGCATTCTTGGTTACTCTA

CTCAGCTCCCTCTTCCTCAGgttccaatcaacacttttcttctatctctt ttcttaattaaaataattaccaattaactaaatgctaatcagtcgatata tcatagttccaacgttttggacgtgtgatttccattggccactaccatat aaaacaacagagtctctttattcattattcaatatatatttgagtattga tattattcatagggaggtttcatttgtactatcaataaaatttctacaac tcttggattttttctgctacattttgtagttattttttttaattacttttta aaaacttgtgaataggagagactaatagtagtacgtaatatgattgtatc aaatgctttaacatgtggggtttgggttaactatcatcattcatagatc actattttgttttcgtttgttacctaacttttttgttatctttgaaaaata atgttccacgagttgattgactggacataaaaatcagattctctcactca tttacgttctacggttctagccactcgttttttttcttttttctttctgtgg tgtaacacgtagataatggattttctatgtgtgtcgtcttgctcaagact ataatgtgtggttaaaggttaaatatagctctggaaattaattatctc cttttttttattaaccagGATTTTCTAGGATCAGGTGTCGATTTTCCGGTG

GGAAACGTCTCGTTCTTCCTCTTCTACTCGGGTCACGTCGCCGGTTCGAT

GATCGCATCTTTGGACATGAGGAGAATGCAGAGGATGAGACTAGCGATGC

TTTTTGACATCCTCAATGTATTACAATCGATCAGGCTGCTCGGGACGAGA

GGACACTACACGATTGATCTCGCTGTCGGAGTTGGCGCTGGGATTCTCTT

TGATTCATTCGCCGGCAAGTACGAAGAGATGATAAGCAAGAGACACAATT

TAGTCAATGGTTTTGGTTTGATTTCGAAAGACTCGCTAGTCAATTAA

Another representative nucleotide sequence of a modified pennycress ROD1 coding sequence having a single bp of an A nucleotide following nucleotide residue 173 (e.g., nucleotide residue 173 as corresponding to the numbering of a genomic ROD1 coding sequence such as the sequence set forth in SEQ ID NO:9) is as follows, with the inserted nucleotide residue highlighted (SEQ ID NO:45):

```
ATGTCAACTAAAACCGTCGTCCCTCTCCGTC
GCAGATCTAAGCCCCTTAACGGAAATCACAC
TAACGGCGTCGCCATTGACGGAAGCCTCGAC
GACGACCACAACCGTCGCATCGGATCAGTAA
ATAGCCAAATGGATAACATTGCTAAGAAAAC
GGACGACGGCTACGCAAAACGGCGGAGGAGG
AGGAGGAGGAGGGAAAAGCAAGGCGTCGTTT
ATGACGTGGACGGCGCGTGACGTTGTGTACG
TGGCGAGGTACCATTGGATACCGTGTTTGTT
CGCGGTCGGGGTTCTGTTCTTCACGGGCGTG
GAGTACACGCTCCAGATGATTCCCGCGAGGT
CTGAGCCGTTCGATATTGGGTTTGTGGCCAC
GCGCTCTCTGAATCGCGTCTTGGCAAATTCA
CCGGATCTTAACACCGTCTTAGCCGCTCTAA
ACACGGTGTTCGTAGGGATGCAAACGACGTA
TATTGTATGGACATGGTTAATGGAAGGACGA
CCACGAGCCACCATCTCGGCTTGCTTCATGT
TTACTTGTCGAGGCATTCTTGGTTACTCTAC
TCAGCTCCCTCTTCCTCAGGATTTTCTAGGA
TCAGGTGTCGATTTTCCGGTGGGAAACGTCT
CGTTCTTCCTCTTCTACTCGGGTCACGTCGC
CGGTTCGATGATCGCATCTTTGGACATGAGG
AGAATGCAGAGGATGAGACTAGCGATGCTTT
TTGACATCCTCAATGTATTACAATCGATCAG
GCTGCTCGGGACGAGAGGACACTACACGATT
GATCTCGCTGTCGGAGTTGGCGCTGGGATTC
TCTTTGATTCATTCGCCGGCAAGTACGAAGA
GATGATAAGCAAGAGACACAATTTAGTCAAT
GGTTTTGGTTTGATTTCGAAAGACTCGCTAG
TCAATTAA
```

A modified pennycress ROD1 coding sequence having a single bp insertion (e.g., an insertion of an A nucleotide) following nucleotide residue 173 in a WT pennycress ROD1 coding sequence (e.g., SEQ ID NO:44 or SEQ ID NO:45) can result in a frameshift of the codons in the coding sequence and a modified polypeptide. For example, a modified pennycress ROD1 coding sequence having an insertion of an A nucleotide following nucleotide residue 173 in a WT pennycress ROD1 coding sequence (e.g., SEQ ID NO:44 or SEQ ID NO:45) can encode a ROD1 polypeptide having a substituted C-terminal end. A representative polypeptide sequence of a pennycress ROD1 polypeptide having a substituted C-terminal end is as follows, with the substituted sequence highlighted (SEQ ID NO:46):

```
MSTKTVVPLRRRSKPLNGNHTNGVAIDGSLDDDHNRRIGSVNSQMDNIAK
KTDDGYAKRRRRRRRREKQGVVYDVDGA
```

For example, a modified ROD1 coding sequence can include a single bp of an T nucleotide following nucleotide residue 173 in a WT pennycress ROD1 coding sequence. A representative nucleotide sequence of a modified pennycress ROD1 coding sequence having a single bp of an T nucleotide following nucleotide residue 173 (e.g., nucleotide residue 173 as corresponding to the numbering of a genomic ROD1 coding sequence such as the sequence set forth in SEQ ID NO:9) is as follows, with the inserted nucleotide residue highlighted (SEQ ID NO:47):

```
ATGTCAACTAAAACCGTCGTCCCTCTCCGTCGCAGATCTAAGCCCCTTAA
CGGAAATCACACTAACGGCGTCGCCATTGACGGAAGCCTCGACGACGACC
ACAACCGTCGCATCGGATCAGTAAATAGCCAAATGGATAACATTGCTAAG
AAAACGGACGACGGCTACGCAAATCGGCGGAGGAGGAGGAGGAGGAGGGA
AAAGCAAGGCGTCGTTTATGACGTGGACGGCGCGTGACGTTGTGTACGTGG
CGAGGTACCATTGGATACCGTGTTTGTTCGCGGTCGGGGTTCTGTTCTTCA
CGGGCGTGGAGTACACGCTCCAGATGATTCCCGCGAGGTCTGAGCCGTTCG
ATATTGGGTTTGTGGCCACGCGCTCTCTGAATCGCGTCTTGGCAAATTCAC
CGGATCTTAACACCGTCTTAGCCGCTCTAAACACGgtaatttcgtactaat
taatttagggtaaaaaatatagtatttaataatgactatcctcaattcctt
tcatgcttcacctaatattttgttttttcgttgtcattaaaatcgtaat
aatatattgagttagtcaaatgaaaaaaacaagtggcggtagtgattggaa
acaaatctcagatcttttatctgtttaataaggtatttaattatccagctg
gaattatgctgtcaagtgtcaacacagtagtagtaacatgcaatggaattt
ctcaatagaaaaaggtcttaattagtatagataattagtggacaaaaatgt
agttaatgtaatctctttgctaagtagttatcataatcatctttttaacaa
ctgccattttgtctgtgtgtttgttttacaacgaagtagtagtagaataga
tcgcttttagcttttgaaagtttcgaacccaaggaaaagggacacatggg
ttatgagttggagacacgatcacatgcaaacagagagattggttaaattat
cgacttttgtagtactttttaaaaaaaaactatttatataaaaaacatgg
tggatggtggggacagGTGTTCGTAGGGATGCAAACGACGTATATTGTATG
GACATGGTTAATGGAAGGACGACCACGAGCCACCATCTCGGCTTGCTTCAT
GTTTACTTGTCGAGGCATTCTTGGTTACTCTACTCAGCTCCCTCTTCCTCA
Ggttccaatcaacacttttcttctatctcttttcttaattaaaataattac
caattaactaaatgctaatcagtcgatatatcatagttccaacgttttgga
cgtgtgatttccattggccactaccatataaaacaacagagtctctttatt
cattattcaatatatatttgagtattgatattattcatagggaggtttcat
ttgtactatcaataaaatttctacaactcttggatttttttctgctacattt
tgtagttattttttttaattacttttaaaaacttgtgaataggagagactaa
tagtagtacgtaatatgattgtatcaaatgctttaacatgtggggtttggg
```

```
ttaactatcatcatttcatagatcactattttgttttcgtttgttacctaa cttttgttatctttgaaaaataatgttccacgagttgattgacttcgttt tggacataaaaatcagattctctcactcatttacgttctacggttctagcc actttctttttctttctgtggtgtaacacgtagataatggattttctatgt gtgtcgtcttgctcaagaataataaatgtggttaaaggttaaatatagctc tggaaattaattatctcctcttttttttattaaccagGATTTTCTAGGATCA

GGTGTCGATTTTCCGGTGGGAAACGTCTCGTTCTTCCTCTTCTACTCGGGT

CACGTCGCCGGTTCGATGATCGCATCTTTGGACATGAGGAGAATGCAGAGG

ATGAGACTAGCGATGCTTTTTGACATCCTCAATGTATTACAATCGATCAGG

CTGCTCGGGACGAGAGGACACTACACGATTGATCTCGCTGTCGGAGTTGGC

GCTGGGATTCTCTTTGATTCATTCGCCGGCAAGTACGAAGAGATGATAAGC

AAGAGACACAATTTAGTCAATGGTTTTGGTTTGATTTCGAAAGACTCGCTA

GTCAATTAA
```

Another representative nucleotide sequence of a modified pennycress ROD1 coding sequence having a single bp of an T nucleotide following nucleotide residue 173 (e.g., nucleotide residue 173 as corresponding to the numbering of a genomic ROD1 coding sequence such as the sequence set forth in SEQ ID NO:9) is as follows, with the inserted nucleotide residue highlighted (SEQ ID NO:48):

```
ATGTCAACTAAAACCGTCGTCCCTCTCCGTCGCAGATCTAAGCCCCTTAA

CGGAAATCACACTAACGGCGTCGCCATTGACGGAAGCCTCGACGACGACC

ACAACCGTCGCATCGGATCAGTAAATAGCCAAATGGATAACATTGCTAAG

AAAACGGACGACGGCTACGCAAATCGGCGGAGGAGGAGGAGGAGGAGGGA

AAAGCAAGGCGTCGTTTATGACGTGGACGGCGCGTGACGTTGTGTACGTG

GCGAGGTACCATTGGATACCGTGTTTGTTCGCGGTCGGGGTTCTGTTCTT

CACGGGCGTGGAGTACACGCTCCAGATGATTCCCGCGAGGTCTGAGCCGT

TCGATATTGGGTTTGTGGCCACGCGCTCTCTGAATCGCGTCTTGGCAAAT

TCACCGGATCTTAACACCGTCTTAGCCGCTCTAAACACGGTGTTCGTAGG

GATGCAAACGACGTATATTGTATGGACATGGTTAATGGAAGGACGACCAC

GAGCCACCATCTCGGCTTGCTTCATGTTTACTTGTCGAGGCATTCTTGGT

TACTCTACTCAGCTCCCTCTTCCTCAGGATTTTCTAGGATCAGGTGTCGA

TTTTCCGGTGGGAAACGTCTCGTTCTTCCTCTTCTACTCGGGTCACGTCG

CCGGTTCGATGATCGCATCTTTGGACATGAGGAGAATGCAGAGGATGAGA

CTAGCGATGCTTTTTGACATCCTCAATGTATTACAATCGATCAGGCTGCT

CGGGACGAGAGGACACTACACGATTGATCTCGCTGTCGGAGTTGGCGCTG

GGATTCTCTTTGATTCATTCGCCGGCAAGTACGAAGAGATGATAAGCAAG

AGACACAATTTAGTCAATGGTTTTGGTTTGATTTCGAAAGACTCGCTAGT

CAATTAA
```

A modified pennycress ROD1 coding sequence having a single bp insertion (e.g., an insertion of a T nucleotide) following nucleotide residue 173 in a WT pennycress ROD1 coding sequence (e.g., SEQ ID NO:47 or SEQ ID NO:48) can result in a frameshift of the codons in the coding sequence and a modified polypeptide. For example, a modified pennycress ROD1 coding sequence having an insertion of a T nucleotide following nucleotide residue 173 in a WT pennycress ROD1 coding sequence (e.g., SEQ ID NO:47 or SEQ ID NO:48) can encode a ROD1 polypeptide having a substituted C-terminal end. A representative polypeptide sequence of a pennycress ROD1 polypeptide having a substituted C-terminal end is as follows, with the substituted sequence highlighted (SEQ ID NO:49):

```
MSTKTVVPLRRRSKPLNGNHTNGVAIDGSLDDDHNRRIGSVNSQMDNIAK

KTDDGYANRRRRRRRREKQGVVYDVDGA
```

In some cases, a loss-of-function modification in a ROD1 coding sequence can be as described elsewhere. For example, a loss-of-function modification in a ROD1 coding sequence can be as described in Table 6.

In some cases, the oilseed (e.g. pennycress) plants described herein (e.g., having reduced levels of PUFAs and/or increased levels of oleic acid) also can have reduced or eliminated levels of erucic acid. For example, pennycress plants having reduced levels of PUFAs and/or increased levels of oleic acid also can have one or more modifications in a gene that encodes a polypeptide involved in fatty acid biosynthesis. Examples of polypeptides involved in fatty acid biosynthesis include, without limitation, fatty acid elongase 1 (FAE1) and polypeptides involved in the regulation (e.g., expression, activity, and/or degradation) of fatty acid elongases. For example, a pennycress plant having reduced levels of PUFAs and/or increased levels of oleic acid also can have one or more modifications in FAE1. A representative nucleotide sequence of a WT pennycress FAE1 coding sequence is as follows (SEQ ID NO:15):

```
ATGACGTCCGTTAACGTTAAGCTCCTTTACCATTACGTCATCACCAACTT

TTTCAACCTTTGCTTCTTCCCGTTAGCGGCGATCGTTGCCGGAAAAGCCT

CTCGGCTTACCACAAACGATCTTCACCACTTCTACTATTCCTATCTCCAA

CACAACCTAATAACCATATCTCTACTCTTTGCCTTCACCGTTTTCGGTTT

GGCTCTCTACATCGTAACCCGGCCCAAACCGGTTTACCTCGTTGACCATT

CCTGCTACCTTCCACCATCGCATCTTAGAAGCAGTATCTCTAAGGTCATG

GATATCTTCTATCAAGTAAGATTAGCCGATCCTTTACGGAACGCGGCAAG

CGATGATTCGTCCTGGCTTGATTTCTTGAGGAAGATTCAGGAGCGGTCTG

GTCTAGGCGATGAAACCCACGGCCCCGAGGGACTGCTTCAGGTCCCTCCA

CGGAAGACTTTTGCCGCGGCGCGTGAAGAAACAGAGCAAGTGATCATCGG

TGCGCTCGAAAAACTATTCGAGAACACCAAAGTTAACCCTAAAGAGATTG

GTATACTTGTGGTGAACTCAAGCATGTTTAATCCGACTCCTTCGCTCTCG

GCGATGGTTGTTAATACTTTCAAGCTCCGAAGCAACATCAGAAGCTTTAA

TCTTGGAGGAATGGGTTGTAGTGCCGGCGTTATAGCCATTGATCTGGCTA

AGGACTTGTTGCATGTCCATAAAAACACTTATGCTCTTGTGGTGAGCACA

GAGAACATCACTTACAACATTTATGCTGGTGATAACAGATCCATGATGGT

TTCGAATTGCTTGTTCCGTGTTGGTGGGGCCGCGATTTTGCTCTCCAACA

AGCCGAGGGACCGGAGACGGTCCAAGTACCAGCTACTTCACACGGTTCGG
```

```
ACGCATACCGGAGCTGACGACAAGTCTTTCCGATGTGTGCAACAAGAAGA

CGACGAGAGCGGTAAAACCGGGGTGTGTTTGTCCAAGGACATAACCGGTG

TTGCCGGGAGAACTGTTCAGAAAAACATAACAACATTGGGTCCGTTGGTT

CTTCCTTTTAGCGAGAAATTTCTTTTTTTCGTTACCTTCATCGCCAAGAA

ACTCTTTAAAGACAAGATCAAACATTACTACGTCCCGGATTTCAAGCTTG

CTATCGACCATTTTTGTATTCATGCCGGAGGCAGAGCCGTGATCGATGTG

CTACAGAAGAACTTAGGTCTATTGCCGATCGATGTGGAGGCATCTAGGTC

AACGTTACATAGATTTGGGAACACTTCGTCTAGCTCAATTTGGTATGAAT

TGGCGTACATAGAGGCAAAAGGAAGGATGAAGAGAGGGAACAAAGTTTGG

CAGATTGCTTTAGGGTCAGGGTTTAAGTGTAATAGTGCGGTTTGGGTGGC

TCTACGCAATGTCAAGGCTTCGACAAATAGTCCTTGGGAACATTGCATTG

ATAGATATCCAGATGCAATTGATTCTGATTCGGGTAAGTCAGAGACTCGT

GTCCAAAACGGTCGGTCCTAA
```

In some cases, a WT pennycress FAE1 gene can have a sequence that deviates from the sequence set forth above (SEQ ID NO:15), sometimes referred to as a variant sequence, provided the variant sequence encodes a WT pennycress FAE1 polypeptide. A representative polypeptide sequence of a WT pennycress FAE1 polypeptide is as follows (SEQ ID NO:16):

```
MTSVNVKLLYHYVITNFFNLCFFPLAAIVAGKASRLTTNDLHHFYYSYLQ

HNLITISLLFAFTVFGLALYIVTRPKPVYLVDHSCYLPPSHLRSSISKVM

DIFYQVRLADPLRNAASDDSSWLDFLRKIQERSGLGDETHGPEGLLQVPP

RKTFAAAREETEQVIIGALEKLFENTKVNPKEIGILVVNSSMFNPTPSLS

AMVVNTFKLRSNIRSFNLGGMGCSAGVIAIDLAKDLLHVHKNTYALVVST

ENITYNIYAGDNRSMMVSNCLFRVGGAAILLSNKPRDRRRSKYQLLHTVR

THTGADDKSFRCVQQEDDESGKTGVCLSKDITGVAGRTVQKNITTLGPLV

LPFSEKFLFFVTFIAKKLFKDKIKHYYVPDFKLAIDHFCIHAGGRAVIDV

LQKNLGLLPIDVEASRSTLHRFGNTSSSSIWYELAYIEAKGRMKRGNKVW

QIALGSGFKCNSAVWVALRNVKASTNSPWEHCIDRYPDAIDSDSGKSETR

VQNGRS
```

In some cases, a WT pennycress FAE1 polypeptide can have a sequence that deviates from the polypeptide sequence set forth above (SEQ ID NO:16), sometimes referred to as a variant sequence, provided the polypeptide maintains its WT function. For example, a FAE1 polypeptide can have at least 80 (e.g., at least 85, at least 90, at least 95, at least 98, or at least 99) percent sequence identity to SEQ ID NO:16. A FAE1 polypeptide can have one or more (e.g., 2, 3, 4, 5, 6, 7, 8, 9, or 10) amino acid modifications (e.g., substitutions) relative to SEQ ID NO: 16.

In some cases, the oilseed (e.g. pennycress) plants described herein (e.g., having reduced levels of PUFAs and/or increased levels of oleic acid) also having reduced levels of erucic acid can include a loss-of-function modification in an FAE1 gene (e.g., in an FAE1 coding sequence). As used herein, a loss-of-function modification in an FAE1 gene can be any modification that is effective to reduce FAE1 polypeptide expression or FAE1 polypeptide function.

In some cases, reduced FAE1 polypeptide expression or reduced FAE1 polypeptide function can be eliminated FAE1 polypeptide expression or eliminated FAE1 polypeptide function. Examples of genetic modifications include, without limitation, deletions, insertions, substitutions, frameshifts, duplications, and rearrangements.

In some cases, oilseed plants having reduced levels of PUFAs and/or increased levels of oleic acid and also having reduced levels of erucic acid described herein can include a substitution (e.g., a single base-pair insertion) relative to the WT pennycress FAE1 coding sequence (e.g., SEQ ID NO:15). The single base-pair substitution can be a substitution of any appropriate nucleotide. For example, a modified FAE1 coding sequence can include an C to T substitution at nucleotide residue 1018 in a WT pennycress FAE1 coding sequence (e.g., SEQ ID NO:15). A representative nucleotide sequence of a modified pennycress FAE1 coding sequence having a loss-of-function C to T substitution at nucleotide 1018 (e.g., nucleotide residue 1983 as corresponding to the numbering of a genomic FAE1 coding sequence such as the sequence set forth in SEQ ID NO: 15) is as follows (SEQ ID NO:17):

```
ATGACGTCCGTTAACGTTAAGCTCCTTTACCATTACGTCATCACCAACTT

TTTCAACCTTTGCTTCTTCCCGTTAGCGGCGATCGTTGCCGGAAAAGCCT

CTCGGCTTACCACAAACGATCTTCACCACTTCTACTATTCCTATCTCCAA

CACAACCTAATAACCATATCTCTACTCTTTGCCTTCACCGTTTTCGGTTT

GGCTCTCTACATCGTAACCCGGCCCAAACCGGTTTACCTCGTTGACCATT

CCTGCTACCTTCCACCATCGCATCTTAGAAGCAGTATCTCTAAGGTCATG

GATATCTTCTATCAAGTAAGATTAGCCGATCCTTTACGGAACGCGGCAAG

CGATGATTCGTCCTGGCTTGATTTCTTGAGGAAGATTCAGGAGCGGTCTG

GTCTAGGCGATGAAACCCACGGCCCCGAGGGACTGCTTCAGGTCCCTCCA

CGGAAGACTTTTGCCGCGGCGCGTGAAGAAACAGAGCAAGTGATCATCGG

TGCGCTCGAAAAACTATTCGAGAACACCAAAGTTAACCCTAAAGAGATTG

GTATACTTGTGGTGAACTCAAGCATGTTTAATCCGACTCCTTCGCTCTCG

GCGATGGTTGTTAATACTTTCAAGCTCCGAAGCAACATCAGAAGCTTTAA

TCTTGGAGGAATGGGTTGTAGTGCCGGCGTTATAGCCATTGATCTGGCTA

AGGACTTGTTGCATGTCCATAAAAACACTTATGCTCTTGTGGTGAGCACA

GAGAACATCACTTACAACATTTATGCTGGTGATAACAGATCCATGATGGT

TTCGAATTGCTTGTTCCGTGTTGGTGGGGCCGCGATTTTGCTCTCCAACA

AGCCGAGGGACCGGAGACGGTCCAAGTACCAGCTACTTCACACGGTTCGG

ACGCATACCGGAGCTGACGACAAGTCTTTCCGATGTGTGCAACAAGAAGA

CGACGAGAGCGGTAAAACCGGGGTGTGTTTGTCCAAGGACATAACCGGTG

TTGCCGGGAGAACTGTTXAGAAAAACATAACAACATTGGGTCCGTTGGTT

CTTCCTTTTAGCGAGAAATTTCTTTTTTTCGTTACCTTCATCGCCAAGAA

ACTCTTTAAAGACAAGATCAAACATTACTACGTCCCGGATTTCAAGCTTG

CTATCGACCATTTTTGTATTCATGCCGGAGGCAGAGCCGTGATCGATGTG

CTACAGAAGAACTTAGGTCTATTGCCGATCGATGTGGAGGCATCTAGGTC

AACGTTACATAGATTTGGGAACACTTCGTCTAGCTCAATTTGGTATGAAT
```

```
TGGCGTACATAGAGGCAAAAGGAAGGATGAAGAGAGGGAACAAAGTTTGG

CAGATTGCTTTAGGGTCAGGGTTTAAGTGTAATAGTGCGGTTTGGGTGGC

TCTACGCAATGTCAAGGCTTCGACAAATAGTCCTTGGGAACATTGCATTG

ATAGATATCCAGATGCAATTGATTCTGATTCGGGTAAGTCAGAGACTCGT

GTCCAAAACGGTCGGTCCTAA
```

A modified pennycress FAE1 coding sequence having a C to T substitution at nucleotide residue 1018 in a WT pennycress FAE1 coding sequence (e.g., SEQ ID NO:17) can result in a premature STOP codon and disruption of the gene. For example, a modified pennycress FAE1 coding sequence having a C to T substitution at residue 1018 in a WT pennycress FAE1 coding sequence (e.g., SEQ ID NO:17) can encode a truncated FAE1 polypeptide. A representative polypeptide sequence of a truncated pennycress FAE1 polypeptide is as follows (SEQ ID NO:18):

```
MTSVNVKLLYHYVITNFFNLCFFPLAAIVAGKASRLTTNDLHHFYYSYLQ

HNLITISLLFAFTVFGLALYIVTRPKPVYLVDHSCYLPPSHLRSSISKVM

DIFYQVRLADP-LRNAASDDSSWLDFLRKIQERSGLGDETHGPEGLLQVP

PRKTFAAAREETEQVIIGALEKLFENTKVNPKEIGILVVNSSMFNPTPSL

SAMVVNTFKLRSNIRSFNLGGMGCSAGVIAIDLAKDLLHVHKNTYALVVS

TENITYNIYAGDNRSMMVSNCLFRVGGAAILLSNKPRDRRRSKYQLLHTV

RTHTGADDKSFRCVQQEDDESGKTGVCLSKDITGVAGRTV
```

For example, a modified FAE1 coding sequence can include an G to A substitution at nucleotide residue 1349 in a WT pennycress FAE1 coding sequence (e.g., SEQ ID NO:15). A representative nucleotide sequence of a modified pennycress FAE1 coding sequence having a loss-of-function G to A substitution at nucleotide residue 1349 (e.g., nucleotide residue 1349 as corresponding to the numbering of a genomic FAE1 coding sequence such as the sequence set forth in SEQ ID NO:15) is as follows (SEQ ID NO:50):

```
ATGACGTCCGTTAACGTTAAGCTCCTTTACCATTACGTCATCACCAACTT

TTTCAACCTTTGCTTCTTCCCGTTAGCGGCGATCGTTGCCGGAAAAGCCT

CTCGGCTTACCACAAACGATCTTCACCACTTCTACTATTCCTATCTCCAA

CACAACCTAATAACCATATCTCTACTCTTTGCCTTCACCGTTTTCGGTTT

GGCTCTCTACATCGTAACCCGGCCCAAACCGGTTTACCTCGTTGACCATT

CCTGCTACCTTCCACCATCGCATCTTAGAAGCAGTATCTCTAAGGTCATG

GATATCTTCTATCAAGTAAGATTAGCCGATCCTTTACGGAACGCGGCAAG

CGATGATTCGTCCTGGCTTGATTTCTTGAGGAAGATTCAGGAGCGGTCTG

GTCTAGGCGATGAAACCCACGGCCCCGAGGGACTGCTTCAGGTCCCTCCA

CGGAAGACTTTTGCCGCGGCGCGTGAAGAAACAGAGCAAGTGATCATCGG

TGCGCTCGAAAAACTATTCGAGAACACCAAAGTTAACCCTAAAGAGATTG

GTATACTTGTGGTGAACTCAAGCATGTTTAATCCGACTCCTTCGCTCTCG

GCGATGGTTGTTAATACTTTCAAGCTCCGAAGCAACATCAGAAGCTTTAA

TCTTGGAGGAATGGGTTGTAGTGCCGGCGTTATAGCCATTGATCTGGCTA
```

```
AGGACTTGTTGCATGTCCATAAAAACACTTATGCTCTTGTGGTGAGCACA

GAGAACATCACTTACAACATTTATGCTGGTGATAACAGATCCATGATGGT

TTCGAATTGCTTGTTCCGTGTTGGTGGGGCCGCGATTTTGCTCTCCAACA

AGCCGAGGGACCGGAGACGGTCCAAGTACCAGCTACTTCACACGGTTCGG

ACGCATACCGGAGCTGACGACAAGTCTTTCCGATGTGTGCAACAAGAAGA

CGACGAGAGCGGTAAAACCGGGGTGTGTTTGTCCAAGGACATAACCGGTG

TTGCCGGGAGAACTGTTTAGAAAAACATAACAACATTGGGTCCGTTGGTT

CTTCCTTTTAGCGAGAAATTTCTTTTTTTCGTTACCTTCATCGCCAAGAA

ACTCTTTAAAGACAAGATCAAACATTACTACGTCCCGGATTTCAAGCTTG

CTATCGACCATTTTTGTATTCATGCCGGAGGCAGAGCCGTGATCGATGTG

CTACAGAAGAACTTAGGTCTATTGCCGATCGATGTGGAGGCATCTAGGTC

AACGTTACATAGATTTGGGAACACTTCGTCTAGCTCAATTTGGTATGAAT

TGGCGTACATAGAGGCAAAAGGAAGGATGAAGAGAGGGAACAAAGTTTAG

CAGATTGCTTTAGGGTCAGGGTTTAAGTGTAATAGTGCGGTTTGGGTGGC

TCTACGCAATGTCAAGGCTTCGACAAATAGTCCTTGGGAACATTGCATTG

ATAGATATCCAGATGCAATTGATTCTGATTCGGGTAAGTCAGAGACTCGT

GTCCAAAACGGTCGGTCCTAA
```

A modified pennycress FAE1 coding sequence having a G to A substitution at nucleotide residue 1349 in a WT pennycress FAE1 coding sequence (e.g., SEQ ID NO:50) can result in a premature STOP codon and disruption of the gene. For example, a modified pennycress FAE1 coding sequence having a G to A substitution at residue 1349 in a WT pennycress FAE1 coding sequence (e.g., SEQ ID NO:50) can encode a truncated FAE1 polypeptide. A representative polypeptide sequence of a truncated pennycress FAE1 polypeptide is as follows (SEQ ID NO:51):

```
MTSVNVKLLYHYVITNFFNLCFFPLAAIVAGKASRLTTNDLHHFYYSYLQ

HNLITISLLFAFTVFGLALYIVTRPKPVYLVDHSCYLPPSHLRSSISKVM

DIFYQVRLADPLRNAASDDSSWLDFLRKIQERSGLGDETHGPEGLLQVPP

RKTFAAAREETEQVIIGALEKLFENTKVNPKEIGILVVNSSMFNPTPSLS

AMVVNTFKLRSNIRSFNLGGMGCSAGVIAIDLAKDLLHVHKNTYALVVST

ENITYNIYAGDNRSMMVSNCLFRVGGAAILLSNKPRDRRRSKYQLLHTVR

THTGADDKSFRCVQQEDDESGKTGVCLSKDITGVAGRTVQKNITTLGPLV

LPFSEKFLFFVTFIAKKLFKDKIKHYYVPDFKLAIDHFCIHAGGRAVIDV

LQKNLGLLPIDVEASRSTLHRFGNTSSSSIWYELAYIEAKGRMKRGNKV
```

In some cases, oilseed (e.g., pennycress) plants described herein (e.g., having reduced levels of PUFAs and/or increased levels of oleic acid) can include a deletion relative to the WT pennycress FAE1 coding sequence (e.g., SEQ ID NO:15). A deletion can include any number of nucleotides. For example, a deletion can include the entire length of the gene and/or regulatory sequences. For example, a deletion can include from about 1 nucleotide to about 50 nucleotides (e.g., about 4 nucleotides such as a 4 bp deletion). In some cases, a modified FAE1 coding sequence can include a 2 bp deletion in a WT pennycress FAE1 coding sequence. A deletion can include any appropriate nucleotides within a FAE1 coding sequence. In some cases, a modified FAE1 coding sequence having a 4 bp deletion in a WT pennycress FAE1 coding sequence, can have a 4 bp deletion of nucleotide residues 213-216 in a WT pennycress FAE1 coding sequence. A representative nucleotide sequence of a modified pennycress FAE1 coding sequence having a 4 bp deletion of nucleotide residues 213-216 (e.g., nucleotide residues 213-216 as corresponding to the numbering of a genomic FAE1 coding sequence such as the sequence set forth in SEQ ID NO:15) is as follows, with the deleted nucleotide residues (SEQ ID NO:52):

ATGACGTCCGTTAACGTTAAGCTCCTTTACCATTACGTCATCACCAACTT

TTTCAACCTTTGCTTCTTCCCGTTAGCGGCGATCGTTGCCGGAAAAGCCT

CTCGGCTTACCACAAACGATCTTCACCACTTCTACTATTCCTATCTCCAA

CACAACCTAATAACCATATCTCTACTCTTTGCCTTCACCGTTTTCGGTTT

-continued
GGCTCTCTACAT[cgta]ACCCGGCCCAAACCGGTTTACCTCGTTGAC

CATTCCTGCTACCTTCCACCATCGCATCTTAGAAGCAGTATCTCTAAGGT

CATGGATATCTTCTATCAAGTAAGATTAGCCGATCCTTTACGGAACGCGG

CAAGCGATGATTCGTCCTGGCTTGATTTCTTGAGGAAGATTCAGGAGCGG

TCTGGTCTAGGCGATGAAACCCACGGCCCCGAGGGACTGCTTCAGGTCCC

TCCACGGAAGACTTTTGCCGCGGCGCGTGAAGAAACAGAGCAAGTGATCA

TCGGTGCGCTCGAAAAACTATTCGAGAACACCAAAGTTAACCCTAAAGAG

ATTGGTATACTTGTGGTGAACTCAAGCATGTTTAATCCGACTCCTTCGCT

CTCGGCGATGGTTGTTAATACTTTCAAGCTCCGAAGCAACATCAGAAGCT

TTAATCTTGGAGGAATGGGTTGTAGTGCCGGCGTTATAGCCATTGATCTG

GCTAAGGACTTGTTGCATGTCCATAAAAACACTTATGCTCTTGTGGTGAG

CACAGAGAACATCACTTACAACATTTATGCTGGTGATAACAGATCCATGA

TGGTTTCGAATTGCTTGTTCCGTGTTGGTGGGGCGCGATTTTGCTCTCC

AACAAGCCGAGGGACCGGAGACGGTCCAAGTACCAGCTACTTCACACGGT

TCGGACGCATACCGGAGCTGACGACAAGTCTTTCCGATGTGTGCAACAAG

AAGACGACGAGAGCGGTAAAACCGGGGTGTGTTTGTCCAAGGACATAACC

GGTGTTGCCGGGAGAACTGTTTAGAAAAACATAACAACATTGGGTCCGTT

GGTTCTTCCTTTTAGCGAGAAATTTCTTTTTTTCGTTACCTTCATCGCCA

AGAAACTCTTTAAAGACAAGATCAAACATTACTACGTCCCGGATTTCAAG

CTTGCTATCGACCATTTTGTATTCATGCCGGAGGCAGAGCCGTGATCGA

TGTGCTACAGAAGAACTTAGGTCTATTGCCGATCGATGTGGAGGCATCTA

GGTCAACGTTACATAGATTTGGGAACACTTCGTCTAGCTCAATTTGGTAT

GAATTGGCGTACATAGAGGCAAAAGGAAGGATGAAGAGAGGGAACAAAGT

-continued
TTGGCAGATTGCTTTAGGGTCAGGGTTTAAGTGTAATAGTGCGGTTTGGG

TGGCTCTACGCAATGTCAAGGCTTCGACAAATAGTCCTTGGGAACATTGC

ATTGATAGATATCCAGATGCAATTGATTCTGATTCGGGTAAGTCAGAGAC

TCGTGTCCAAAACGGTCGGTCCTAA

A modified pennycress FAE1 coding sequence having a 4 bp deletion of nucleotide residues 213-216 in a WT pennycress FAE1 coding sequence (e.g., SEQ ID NO:52) can result in a frameshift of the codons in the coding sequence and a modified polypeptide. For example, a modified pennycress FAE1 coding sequence having a 4 bp deletion of nucleotide residues 213-216 in a WT pennycress FAE1 coding sequence (e.g., SEQ ID NO:52) can encode a FAE1 polypeptide having a substituted C-terminal end. A representative polypeptide sequence of a pennycress FAE1 polypeptide having a substituted C-terminal end is as follows, with the substituted sequence highlighted (SEQ ID NO:53):

MTSVNVKLLYHYVITNFFNLCFFPLAAIVAGKASRLTTNDLHHFYYSYLQHNLITISLLFAF

TVFGLALYIPGPNRFTSLTIPATFHHRILEAVSLRSWISSIK

In some cases, a loss-of-function modification in an FAE1 coding sequence can be as described elsewhere (see, e.g., International Application No.: PCT/US2018/015536, filed Jan. 26, 2018). For example, a loss-of-function modification in an FAE1 coding sequence can be as described in Table 6.

Any appropriate method can be used to introduce one or more modifications into one or more polypeptides involved in fatty acid biosynthesis (e.g., FAD2 and/or ROD1) to produce oilseed (e.g. pennycress) plants described herein (e.g., having reduced levels of PUFAs and/or increased levels of oleic acid). Examples of methods for modifying a coding sequence include, without limitation, genome editing (e.g., genome editing with engineered nucleases (GEEN)) and introduction of a transgene (e.g., gene transfer). For example, genome editing can be used to produce oilseed plants described herein. Genome editing can insert, replace, or remove DNA from a genome using one or more site-specific nucleases (SSN) and, in some cases, a repair template (RT). Nucleases can be targeted to a specific position in the genome, where their action can introduce a particular modification to the endogenous sequences. For example, a SSN can introduce a targeted double-strand break (DSB) in the genome, such that cellular DSB repair mechanisms incorporate a RT into the genome in a configuration that produces heritable genome edits (e.g., a loss-of-function modification in a coding sequence) in the cell, in a plant regenerated from the cell, and in any progeny of the regenerated plant. Nucleases useful for genome editing include, without limitation, CRISPR-associated (Cas) nucleases, zinc finger nucleases (ZFNs), transcription activator-like effector (TALE) nucleases, and homing endonucleases (HE; also referred to as meganucleases).

In some cases, a CRISPR/Cas system can be used to introduce one or more loss-of-function modifications described herein into the coding sequence of a gene involved in fatty acid biosynthesis (e.g., a FAD2 coding sequence, a ROD1 coding sequence, and/or a FAE1 coding sequence). For example, a CRISPR/Cas vector can include at least one guide sequence (e.g., a protospacer sequence) specific to a coding sequence of a gene involved in fatty acid biosynthesis upstream of a protospacer adjacent motif (PAM). A Cas enzyme will bind to and cleave within a target sequence (e.g., a nucleic acid sequence specific to a coding sequence of a gene involved in fatty acid biosynthesis) only if the target site is followed by a PAM sequence. For example, the canonical PAM includes the sequence 5'-NGG-3', where N is any nucleotide followed by two guanine (G) nucleotides. In some cases, a PAM sequence can be a 5'-TTGGGT-3' sequence. In some cases, a PAM can be a 5'-CGG-3' sequence. A guide sequence useful for introducing one or more loss-of-function modifications described herein into a FAD2 coding sequence can include a nucleic acid sequence specific to FAD2. A representative nucleotide sequence of a guide sequence that can be used to direct a Cas nuclease to the FAD2 gene is as follows: TACTTGGCTTG-GCCTCTCTA; SEQ ID NO:60.

In some cases, a guide sequence useful for introducing one or more loss-of-function modifications described herein into a ROD1 coding sequence can include a nucleic acid sequence specific to ROD1. A representative nucleotide sequence of a guide sequence that can be used to direct a Cas nuclease to the ROD1 gene is as follows:

SEQ ID NO: 61
GACGACGGCTACGCAAACGG; .

The Cas component of a CRISP/Cas system described herein can be any appropriate Cas nuclease. Examples of Cas nucleases include, without limitation, Cas1, Cas2, Cas3, Cas9, Cas10, and Cpf1. In some cases, the Cas component of a CRISPR/Cas system designed to introduce one or more loss-of-function modifications described herein into an FAD2 coding sequence can be a Cas9 nuclease. In some cases, the Cas component of a CRISPR/Cas system designed to introduce one or more loss-of-function modifications described herein into a ROD1 coding sequence can be a Cas9 nuclease. For example, the Cas9 nuclease of a CRISPR/Cas9 system described herein can be a *Staphylococcus aureus* Cas9 (SaCas9). One example of a SaCas9 is described in, for example, Steinert et al., 2015, *Plant J.*, 84:1295-305. For example, the Cas9 nuclease of a CRISPR/Cas9 system described herein can be a *Streptococcus pyogenes* Cas9 (spCas9). One example of a spCas9 is described in, for example, Fauser et al., 2014 *The Plant Journal* 79:348-359.

The genome editing reagents described herein can be introduced into an oilseed plant by any appropriate method. In some cases, nucleic acids encoding the genome editing reagents can be introduced into a plant cell using *Agrobacterium* or *Ensifer* mediated transformation, particle bombardment, liposome delivery, nanoparticle delivery, electroporation, polyethylene glycol (PEG) transformation, or any other method suitable for introducing a nucleic acid into a plant cell. In some cases, the SSN or other expressed gene editing reagents can be delivered as RNAs or as proteins to a plant cell and the RT, if one is used, can be delivered as DNA.

The oilseed plants described herein (e.g., having reduced levels of PUFAs and/or increased levels of oleic acid) can be identified by, for example, an NIR analyzer (e.g., as described in the Examples).

The invention will be further described in the following examples, which do not limit the scope of the invention described in the claims.

EXAMPLES

Example 1: Creation of Mutant Pennycress Having Reduced Polyunsaturated Fatty Acids and Increased Oleic Acid The plant oil pathways have been well studied in plants leading to a good understanding of most of the steps needed to produce triglycerides in the seeds for the storage of energy (see, e.g., Baud et al., 2010 *Prog Lipid Res*. 49:235-49). This study used a mutagenesis approach to create changes in *Thlaspi arvense* (pennycress) genes required for seed oil biosynthesis, and to identify modifications resulting in improvements in the oil produced in the pennycress seeds.

Materials and Methods

Mutagenesis of Pennycress

Figure 1B:
FIG. 1 shows images of M1-generation pennycress plants. A) Spring plants produced stems and flowers from which the M2 seed generation was harvested. B) A representative M1 plant with yellow sectors indicating successful mutagenesis.
Figure 1A:
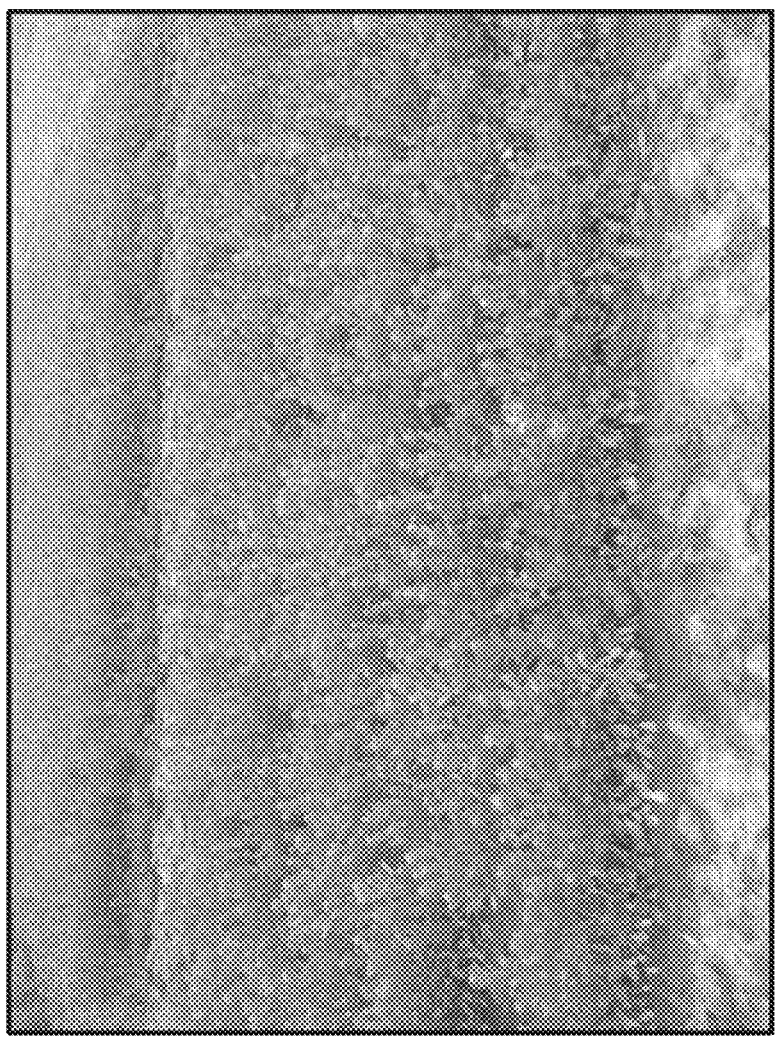

Seeds of wild type pennycress seeds were treated with 0.2% ethyl methane sulfonate (EMS) for 18 hours. After extensive washing the seeds were planted into outdoor fields during the late summer or early fall to produce an M1 generation of mutagenized plants. In the spring the plants produced stems and flowers on which the M2 seed generation was harvested (FIG. 1A). Within the M1 plants, some plants were observed to have whole yellow sectors (FIG. 1B). These are sectors are an indication that the mutagenesis was successful.

M2 seeds were collected from the M1 plants harvested in the late spring and stored in coin envelopes. During the late summer and fall, the M2 seeds were sowed into rows in outdoor fields. M3 generation seeds were collected from individual mature M2 plants.

Near Infrared (NIR) Analysis

Individual lots of M3 were subjected to NIR analysis using a DA 7250 NIR analyzer obtained from Perten Instruments (A PerkinElmer Company). During the scan the M3 seeds were illuminated with a source emitting electron magnetic irradiation at wavelengths between 900 nm and 1800 nm. The intensity of the reflectance at wavelengths in the interval was captured and graphed. Calibration data from Perten was used to estimate the chemical composition of the seeds. Oleic acid, linoleic acid, linolenic acid, and erucic acid contents were among the various chemicals whose values were estimated.

NIR scans from individual M2 plants can be used to predict the fatty acid composition of M3 seeds.

Identification of Modifications

NIR data were scanned for lines containing reductions in the polyunsaturated fatty acids linoleic and linolenic, and DNA sequence analyses were used to identify mutations contained in these lines.

Results

Representative fatty acid values are shown in the table below.

TABLE 1

Representative fatty acid values (mol %) as estimated by NIR analysis

| Sample ID | Oleic acid | linoleic acid | Linolenic acid | Eicosenoic acid | Erucic acid |
|---|---|---|---|---|---|
| T0745 | 14.79955235 | 20.51507036 | 2.53159467 | 8.573022617 | 31.67953013 |
| T0744 | 14.93120636 | 27.17738413 | 4.664446377 | −4.543202684 | 31.16348549 |
| T0743 | 15.61387165 | 25.84299463 | 4.514246747 | 3.058789361 | 30.04795916 |
| T0742 | 15.76455467 | 23.64706067 | 4.342384262 | 6.779652812 | 24.33612948 |
| T0741 | 15.90532904 | 28.21620556 | 5.350052936 | −0.818181873 | 25.90248326 |
| T0740 | 16.00133485 | 21.93260585 | 4.171607449 | 2.482171504 | 46.1588523 |
| T0739 | 16.06306692 | 21.97438235 | 4.237128469 | 8.277606298 | 27.92484176 |
| T0738 | 16.5366078 | 23.83781686 | 4.614421725 | 3.095980927 | 25.01061724 |
| T0737 | 16.70245261 | 23.68691826 | 4.623859944 | 3.576003649 | 27.98868851 |
| T0736 | 16.8503985 | 24.08822445 | 4.735771502 | 3.042741402 | 26.78524793 |
| T0735 | 16.87190624 | 22.36053836 | 4.398099705 | −0.2069512 | 59.83350747 |
| T0734 | 17.14276391 | 25.59749004 | 5.045853447 | 3.872586506 | 37.83489645 |
| T0733 | 17.19986386 | 24.33689862 | 4.812422885 | −0.782421576 | 38.35454529 |
| T0732 | 17.24961067 | 27.21970684 | 5.474862832 | 2.469515228 | 35.76026281 |
| T0731 | 17.44499999 | 23.02451821 | 4.706171389 | 4.359985844 | 31.87046772 |
| T0730 | 17.49471226 | 23.79467595 | 4.92819546 | 4.144043154 | 19.50746395 |
| T0729 | 17.58550412 | 22.98954776 | 4.778151342 | 4.505788866 | 30.40805684 |
| T0728 | 17.69566811 | 25.69240115 | 5.392805144 | 4.27951338 | 35.93746888 |

Reductions in PUFAs in FAD2 Mutants

Some plants with reduced PUFA contained an altered FATTY ACID DEHYDROGENASE 2 (FAD2) gene. FAD2 functions to add an extra double bond to oleic acid (18:1) to make the doubly polyunsaturated linoleic (18:2). Linoleic acid then serves as a substrate for FATTY ACID DEHYDROGENASE 3 (FAD3), which adds another double bond to make the triple unsaturated linolenic (18:3). Seeds from these lines were subjected to NIR analysis and the NIR results were confirmed using gas chromatography-mass spectrometry (GC-MS).

Figure 2:
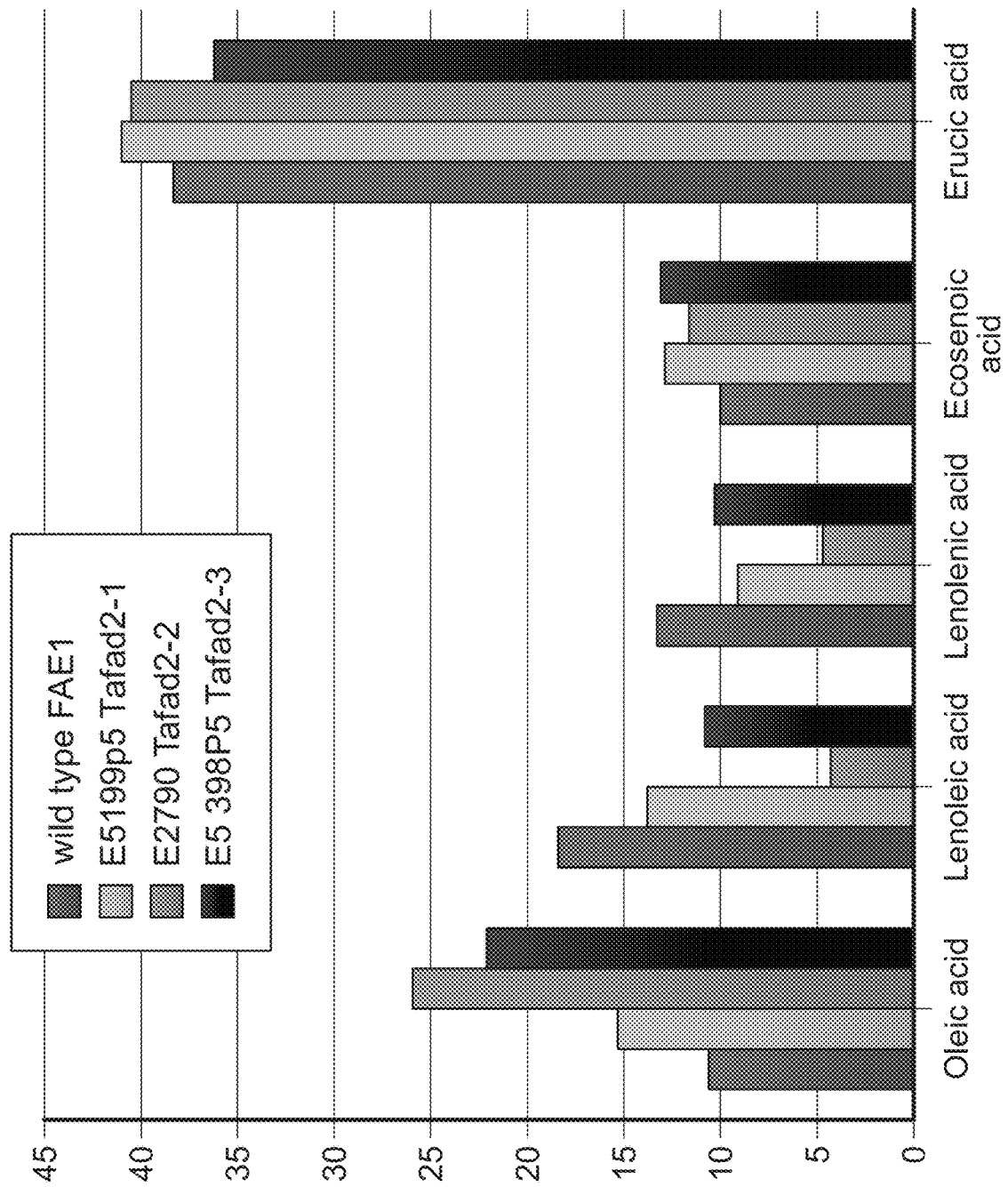
FIG. 2 contains a graph showing reductions in PUFAs in pennycress FAD2 mutants.

The plants with reduced FAD2 activity, Tafad2-1, Tafad2-2, and Tafad2-3, all produced oils with reduced levels of PUFAs (FIG. 2). The mole % levels of the major PUFAs, linoleic acid and linolenic acid, were greatly reduced. This was especially apparent for the Tafad2-2 line with linoleic reduced from 17.9 mol % to 3.4 mol % and linolenic reduced from 12.2 mol % to 4.1 mol % compared to wildtype, respectively. In addition, the levels of oleic acid dramatically increased in all three mutants compared to wild type. The level in Tafad2-2 showed the largest increase by increasing 2.5 fold over wild type.

These altered FAD2 lines were characterized to assess the DNA change responsible for the altered fatty acid biosynthesis.

Characterization of FAD2 Mutants

DNA sequence analyses showed that three such lines having reduced PUFAs contained mutations in the pennycress FAD2 gene (FIG. 3). Seeds from these lines were characterized to identify the FAD2 modifications responsible for the reduced PUFAs.

Tafad2-1, -2, and -3 all contained DNA base changes in the coding regions of the FAD2 gene. In Tafad2-1 this resulted in a change of an aspartic amino acid being replaced by an arginine (SEQ ID NO:4). The normal aspartic acid is conserved in both *Arabidopsis thaliana* and in *Glycine max* (soybean) (FIG. 3). In Tafad2-2, the change resulted in a switch from glycine to aspartic acid (SEQ ID NO:6). The glycine is highly conserved at this position in both monocots (*Oryza sativa* (rice)) and dicots (soybean) (FIG. 3). The dramatic change this highly conserved in amino acid was likely responsible of the more extreme change in PUFA levels seen for Tafad2-2 (FIG. 2). In Tafad2-3, the change resulted in a switch of histidine to tyrosine (SEQ ID NO:8). Again the histidine amino acid is very highly conserved (FIG. 3).

Reductions in PUFAs in ROD1 Mutants

Some plants with reduced PUFA contained alterations in the REDUCED OLEATE DESATURATION 1 (ROD1) gene. Seeds from these lines were subjected to NIR analysis and the NIR results were confirmed using GC-MS.

Figure 4:
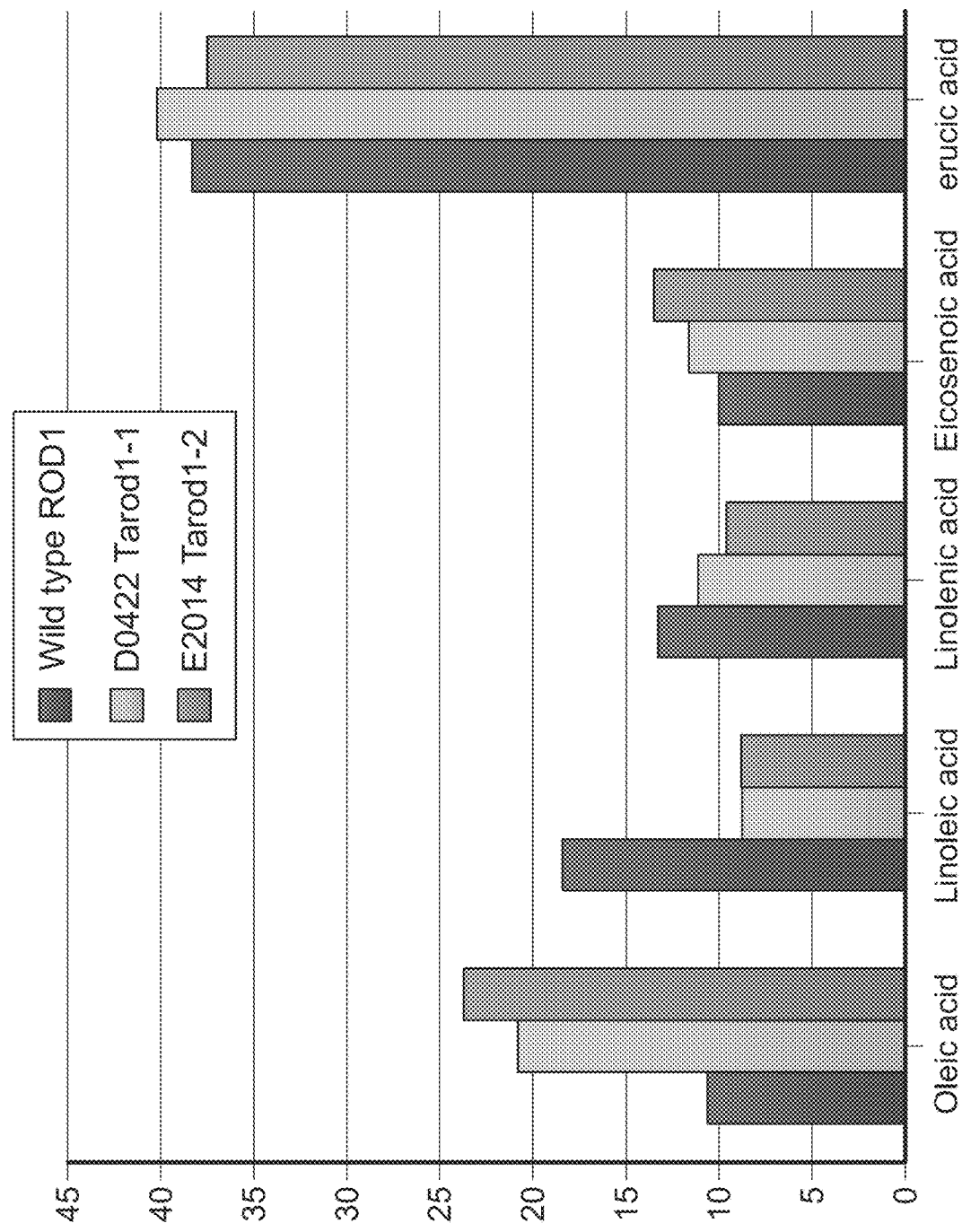
FIG. 4 contains a graph showing reductions in PUFAs in pennycress ROD1 mutants.

The plants with reduced ROD1 activity, D0422 Tarod1-1 and E2014 Tarod1-2, produced oils with reduced levels of PUFAs (FIG. 4). The mole % levels of linolenic acid were greatly reduced. Both lines showed similar reductions from 18.4 mol % in wild type down to 8.8 mol % in the mutant lines. In addition, both mutants showed over a two fold increase in oleic acid over wild type.

These altered ROD1 lines were characterized to assess the DNA change responsible for the altered fatty acid biosynthesis.

Characterization of ROD1 Mutants

DNA sequence analyses showed that three such lines having reduced PUFAs contained mutations in the pennycress ROD1 gene (FIG. 5). Seeds from these lines were characterized to identify the ROD1 modifications responsible for the reduced PUFAs.

D0422 Tarod1-1 and E2014 Tarod1-2 each contained DNA base changes in the coding regions of the ROD1 gene. Tarod1-1 contains a switch from methionine to isoleucine (SEQ ID NO:12) while Tarod1-2 contains a switch from arginine to lysine (SEQ ID NO:14). Both of methionine and arginine are highly conserved in both monocots and dicots (FIG. 5).

Conclusion

The oils produced by both Tafad2 and Tarod1 lines contain reduced levels of PUFAs, while still producing erucic acid. In some applications for making bioproducts, erucic acid is desirable. These oils have enhanced stability that allow them to be subjected to harsher biosynthetic protocols that require erucic acid.

Example 2: Creation of Double Mutant Pennycress Having Reduced Polyunsaturated Fatty Acids and Increased Oleic Acid To improve and widen the utility of the Tarod1 and Tafad2 oils described in Example 1, these lines have been crossed with the Tafae1-1 line.

Materials and Methods

Tarod1-1 was crossed with Tafae1-1 to create a double Tafae1-1 Tarod1-1 line and Tafad2-2 was crossed with Tafae1-1 to create a double Tafae1-1 Tafad2-2 line.

The resulting F1 plants were allowed to self-fertilize. F2 seeds were scored for the homozygosity for either both Tafad2-2 and Tafae1-1 or for both Tarod1-1 and Tafae1-1 using PCR based DNA markers for the mutations in the respective genes to assess the genotypes of the seeds. Oil was extracted from seeds and subjected to NIR analysis and the NIR results were confirmed using GC-MS. Both of the double lines show a dramatic improvement in oil quality.

Results

Double FAE-FAD2 Lines

Figure 6:
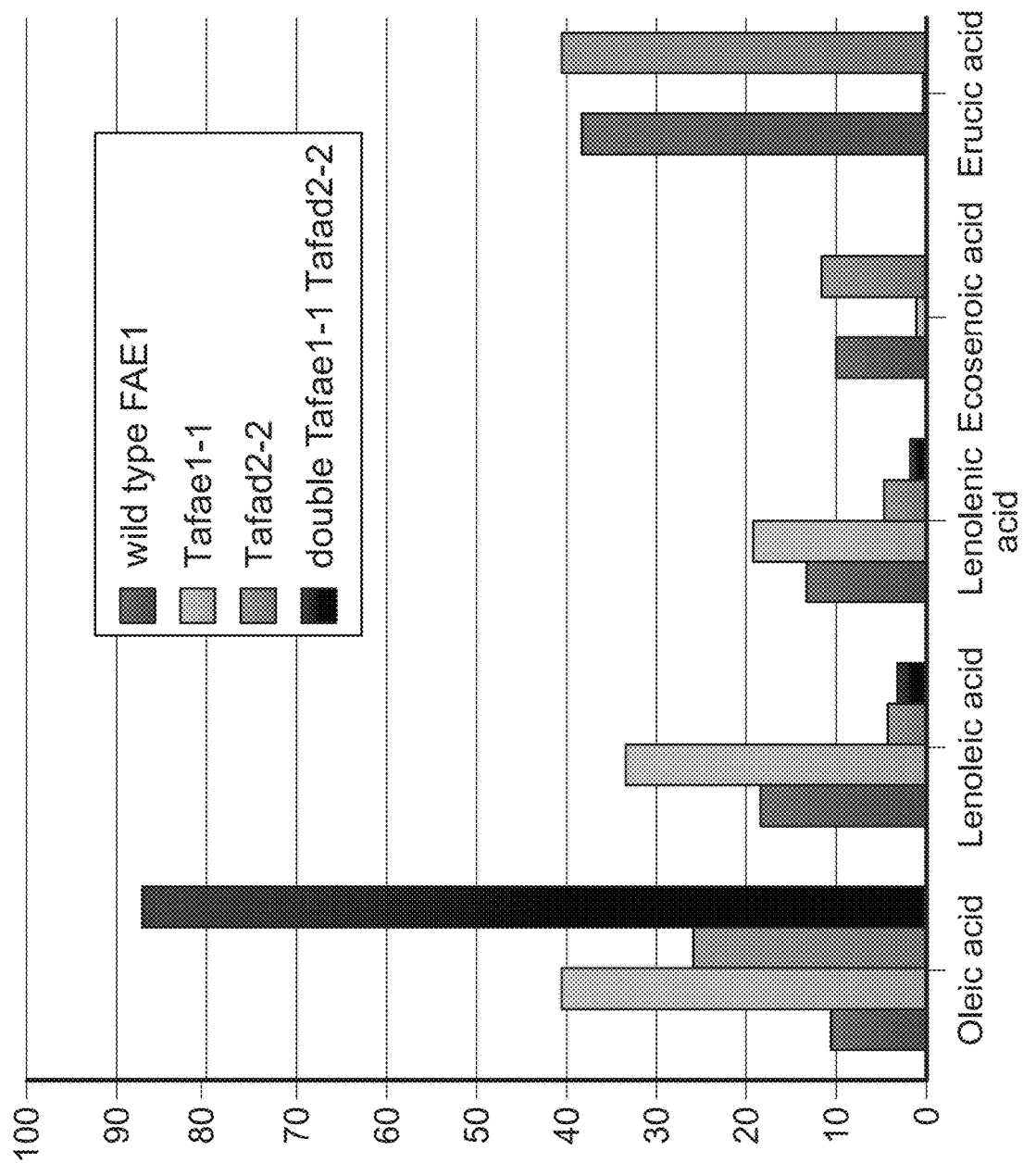
FIG. 6 contains a graph showing that Tafae1 and Tafad2 double mutants produced oil having an extreme increase in oleic acid while maintaining very low levels of linoleic acid and linolenic acid along with zero erucic acid.

The plants with reduced FAE1 activity and reduced FAD2 activity, the double Tafae1-1 Tafad2-2 line, produced an extremely high level of oleic and very low levels of PUFA (FIG. 6). The double mutant seed contained over 80 mol % of oleic acid while maintaining very low levels of the PUF As lenoleic and linolenic along with zero erucic acid.

Figure 7:
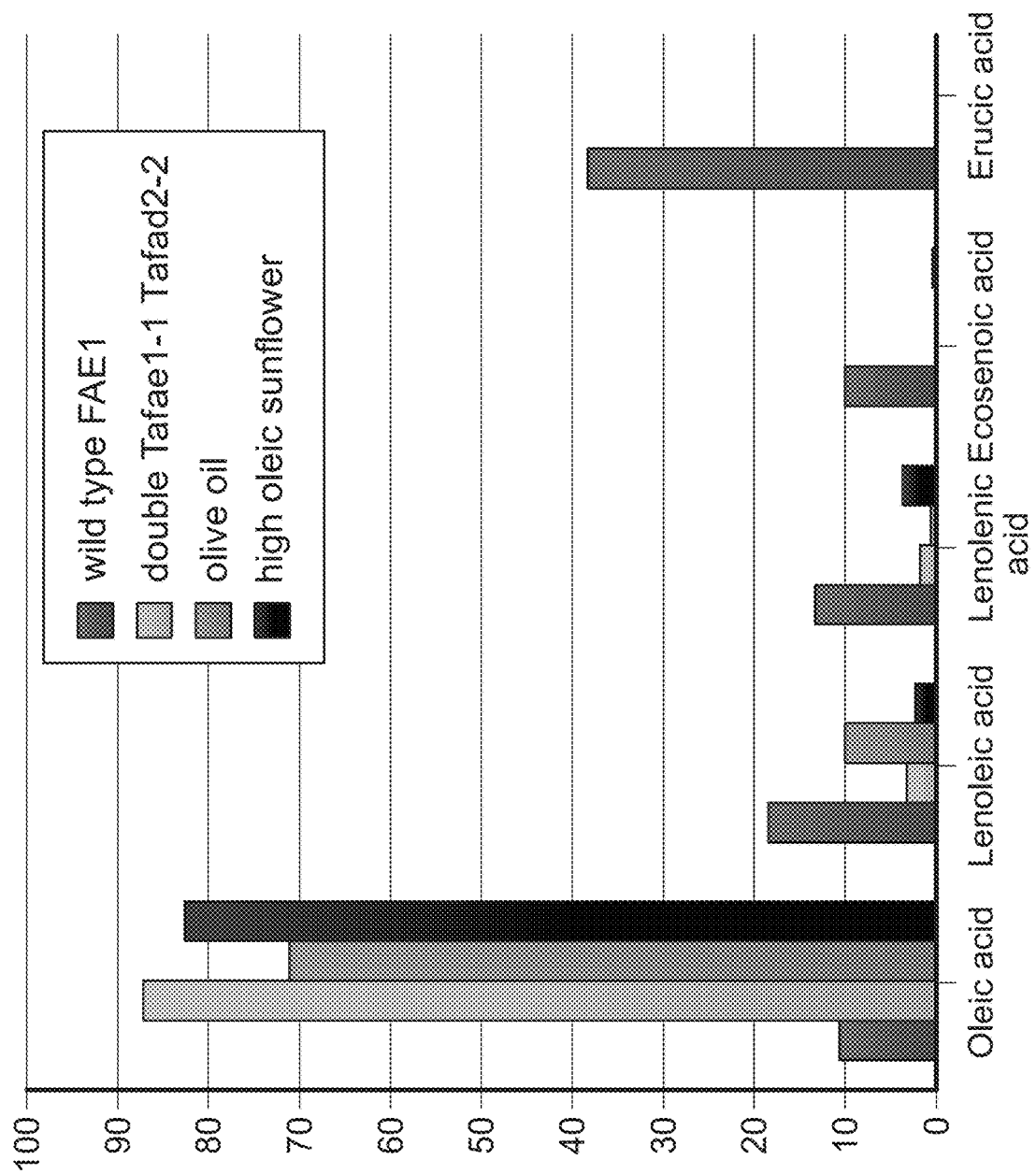
FIG. 7 contains a graph showing that Tafae1 and Tafad2 double mutants produced oil having a similar fatty acid composition to olive oil and high oleic sunflower.

The fatty acid profile of the double Tafae1-1 Tafad2-2 line was compared the fatty acid profiles of olive oil and sunflower oil (FIG. 7). The oil from the double Tafae1-1 Tafad2-2 line had a similar profile as olive oil and high oleic sunflower oil.

Double FAE-ROD1 Lines

Figure 8:
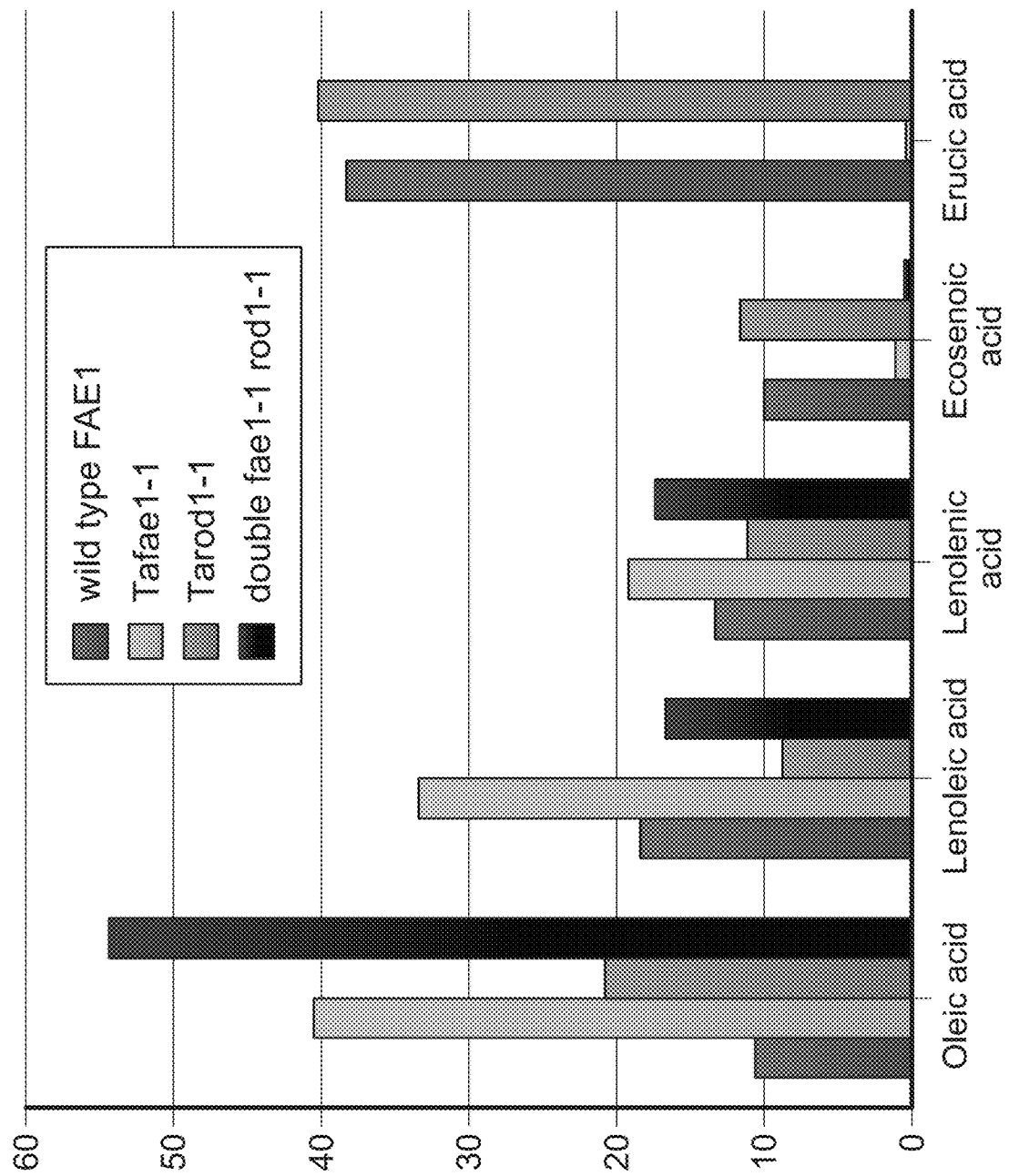
FIG. 8 contains a graph showing that Tafae1 and Tarod1 double mutants produced oil having an increase in oleic acid while maintaining lower levels of linoleic acid and linolenic acid along with near zero erucic acid.

The plants with reduced FAE1 activity and reduced ROD1 activity, the double Tafae1-1 Tarod1-1 line, produced a high level of oleic and very low levels of PUFA (FIG. 8). The double mutant seed contained ~55 mol % of oleic acid while maintaining lower levels of the PUF As lenoleic and linolenic along with near zero erucic acid.

Figure 9:
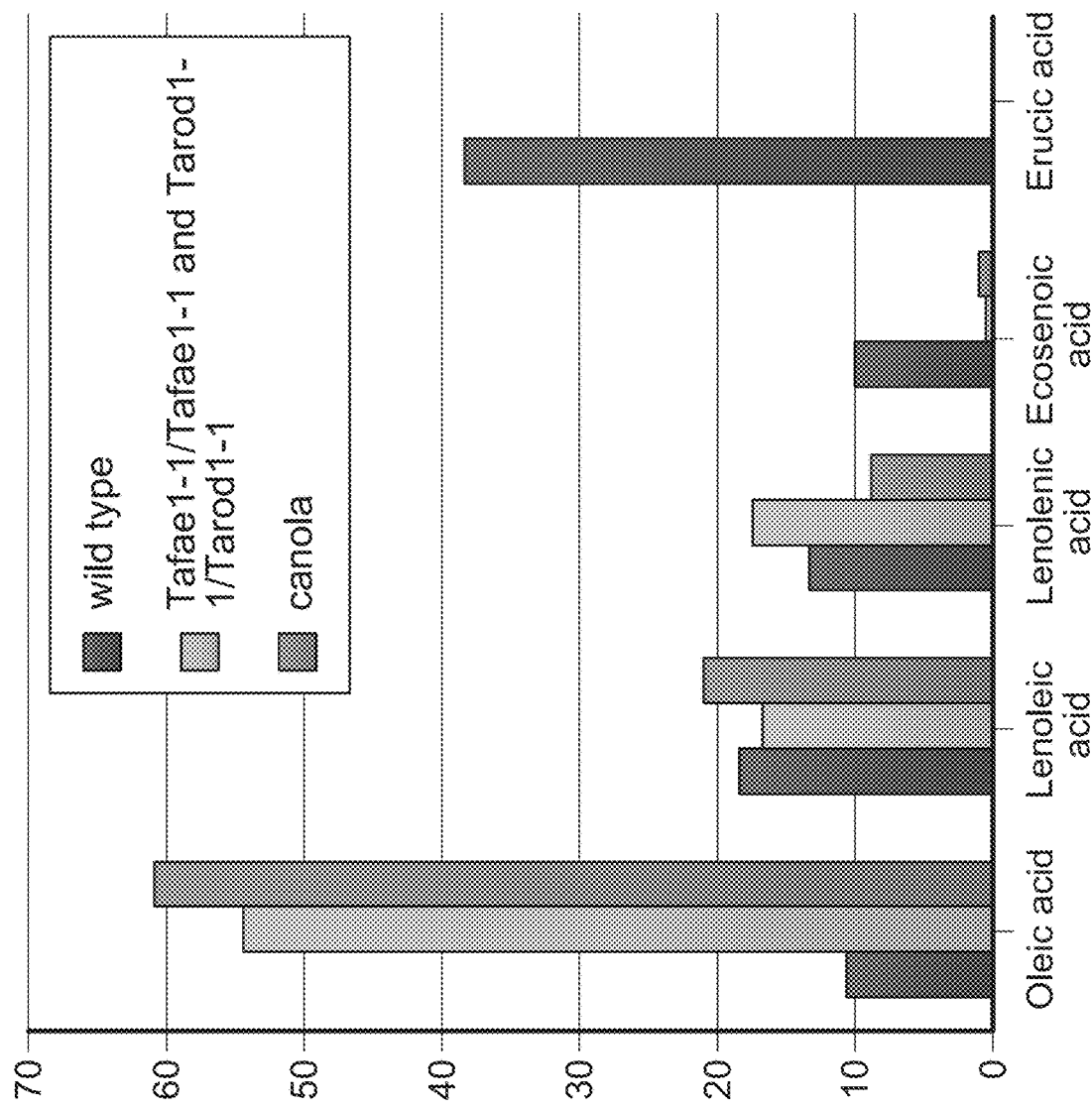
FIG. 9 contains a graph showing that Tafae1 and Tarod1 double mutants produced oil having a similar fatty acid composition to canola oil.
Figure 10:
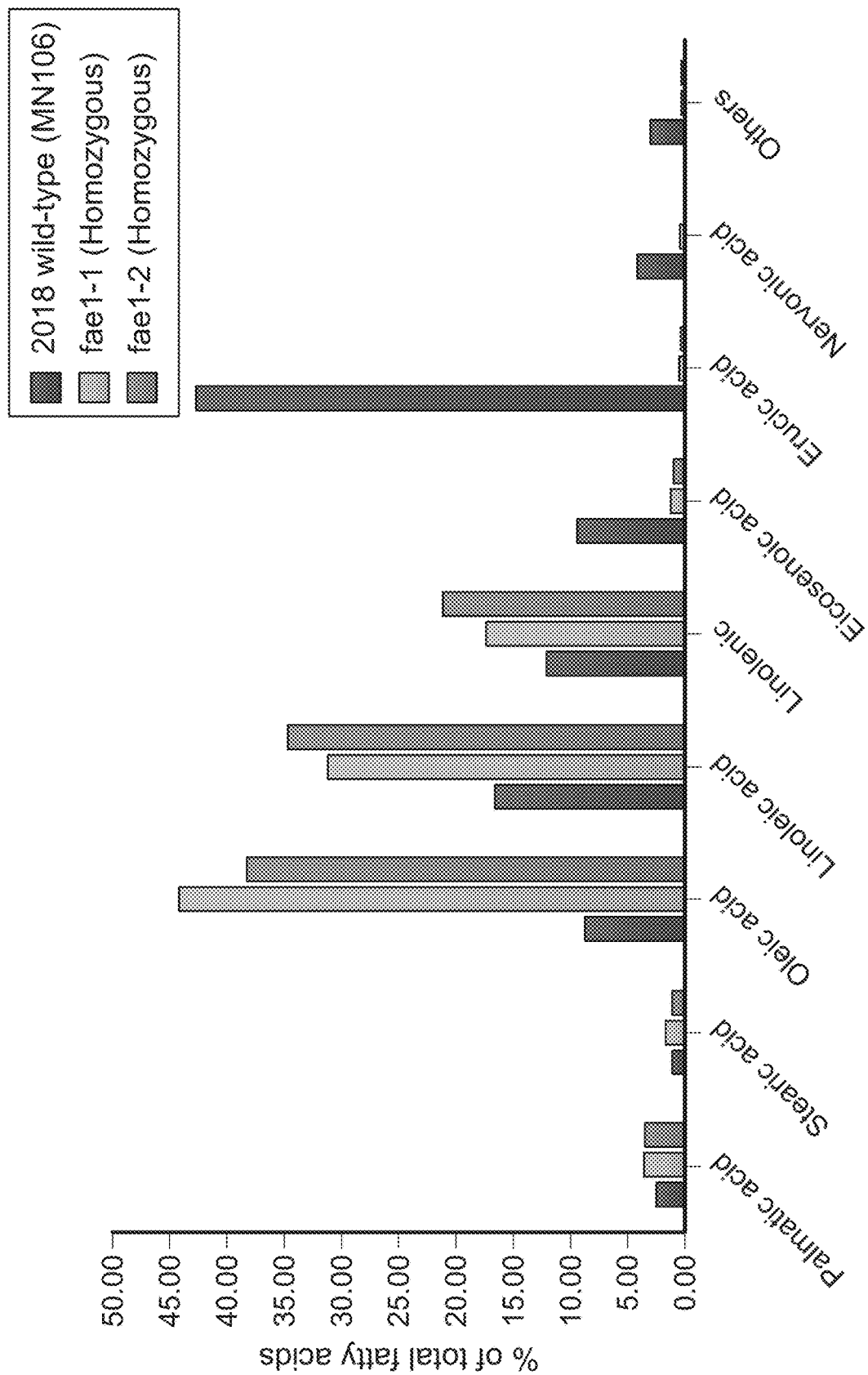
FIG. 10 contains a graph showing gas chromatograph analysis of wild type and two zero erucic acid containing fae1 mutants. Lines predicted to have low erucic by NIR analysis were subjected to gas chromatography for confirmation. Very low levels of erucic acid were present in the seeds from Tafae1-1 and Tafae1-2. Oleic acid increased approximately 4 fold in both mutants, whereas linoleic acid was increased by 1.8 fold and linolenic acid was increased by 1.5 fold.

The fatty acid profile of the double Tafae1-1 Tarod1-1 line was compared the fatty acid profile of canola (FIG. 7). The oil from the double Tafae1-1 Tarod1-1 line had a similar profile as canola oil (FIG. 9).

Conclusion

These newly created new pennycress varieties produced oils that rival those of the major crop species canola and olive oil. These new oils have wide applications both in the production of food products and in the production of non-food bioproducts.

Example 3: Creation of Mutant Pennycress Having Reduced Polyunsaturated Fatty Acids and Increased Oleic Acid Two types of plants with reduced PUFA were identified using both EMS mutagenesis and CRISPR-Cas9 gene editing approaches facilitated by bioinformatics-enabled sequence analyses.

Materials and Methods

Mutagenesis 42 grams of seeds derived from pennycress accession MN106 were collected as described elsewhere (see, e.g., Dorn et al., 2013 The Plant Journal, 75:1028-38), and were treated with 180 ml 0.2% ethyl methanesulfonate (EMS) in a chemical flow hood. The solution and seeds were kept mixed on a rotating platform for 14 hours at room temperature. The seeds were thereafter extensively rinsed with distilled water to remove all traces of the EMS. The seeds were then dried for 24 hours on filter paper in a chemical flow hood. These seeds were considered to be the progenitors of the M1 generation of plants.

Growing of the M1 Generation

The mutagenized seeds were sowed into two small field plots. These plots were allowed to grow over winter. The following spring abundant albino sectors were noted on the flowering plants (FIG. 1). Such sectoring is the hallmark of a successful mutagenesis.

Collection and Growing of M2 Seeds

Seeds were collected from mature M1 plants. M2 seeds from batches of 10 M1 plants were pooled together. In all, 500 pools representing 5000 mutagenized M1 plants were collected. In August, each pool was sowed in a field into an individual row. Robust growth was noted in October. During the following June, M3 seeds were collected from approximately 8000 mature M2 individual plants and stored individual packets.

NIR Spectral Analysis to Identify Lines with Reduced Erucic Acid

M3 seeds from each packet were scanned using a Perten DA7250 NIR spectroscopy analyzer to assess the quality of oil seeds as described elsewhere (Chopra et al., 2019 *Industrial Crops and Products* 128:55-61; Sidhu et al., 2014 *Applied Engineering in Agriculture*, 30:69-76; Golebiowski et al, 2005 *Journal of near Infrared Spectroscopy*, 13:255-264; Riu et al., 2006 *Spectroscopy and Spectral Analysis*, 26:2190-2192; and Xin et al., 2014 *Journal of Agricultural and Food Chemistry*, 62:7977-7988). These analyses captured information related to the approximate levels of, for example, the main fatty acids found in pennycress (eicosenoic, steric, palmitic, oleic, linoleic, linolenic, and erucic acids).

M3 seeds from candidate lines were sowed into small plots in a field during the second week of March. These M4 plants matured in July and M4 seeds were collected from five individual M3 plants in each plot. During the next fall, these seeds were scanned with the same NIR instrument as before, and a family of individuals segregating for an increase in oleic acid were identified. The NIR results were confirmed using gas chromatography-mass spectrometry (GC-MS).

Allele-Specific Markers for Co-Segregation Analysis and Progeny Selection

For each plant sample, pre-amplification was performed in a reaction volume of 10 µl consisting of 0.5 µM of each of the locus and common primers, 1× of Q5 High-Fidelity (2×) Master Mix and 1 µl of DNA extracted using the Sigma ready extract. Thermal cycling consisted of an initial activation step 94° C. for 3 minutes, followed by 20 cycles of 94° C. for 15 seconds, 60° C. for 30 seconds and 72° C. for 30 seconds. PCR amplicons were then diluted 1:20 for use in allele specific genotyping. Allele-specific genotyping was performed on PCR mixes consisting of a final volume of 10 µl containing 1× KASP Reaction Mix, 0.10 µl allele specific primer mix, and 1 µl of diluted PCR product. Thermal cycling was performed on a LightCycler 480 (Roche, Branford, CT) using the following parameters: 15 minutes at 94° C.; 10 touchdown cycles of 20 seconds at 94° C., 60 seconds at 65-57° C. (dropping 0.8° C. per cycle); and 26 cycles of 20 seconds at 94° C., 60 seconds at 57° C. A final read at 37° C. for 5 seconds was taken using the in-built plate reader.

Using this approach we could identify double mutants that were homozygous to fae1-1/rod1-1 or fae1-1/fad2-2.

Methylation of Fatty Acids and Gas Chromatography on Single Seeds

One seed is crushed with 500 µl of hexane containing C17:0 internal standard and methylation was performed by adding 0.5 ml of methanolic-sodium hydroxide and incubating at 95° C. for 10 minutes, followed by addition of 0.5 ml of boron trifluoride methanol and incubating for another 10 minutes at 95° C. Methylated oil was separated by addition of 1 ml each of saturated sodium chloride and hexane without internal standard. Anhydrous sodium thiosulphate was added to the extracted methylated oil to remove any remaining water molecules. Samples were then transferred to GC vials for analysis of fatty-acid methyl esters (FAMES). External standards were prepared using RM-3 and RM-5 from Sigma to estimate and identify the peaks detected in our samples. Briefly, FID detection was performed using a Hewlet Packard 5890 Gas Chromatograph with a 7673A auto-sampler. FAMES were separated using a Supelco Omegawax® 250 FUSED SILICA Capillary Column 30 m×0.25 mm×0.25 µm film thickness.

Creation of High Oleic Acid Pennycress by Direct Targeting of FAD2 and ROD1 with CRISPR-Cas9

Construction of the *Thlaspi arvense* (Pennycress) FAD2 Gene-Specific CRISPR-Cas9 Vector The constructs and cloning procedures used for generation of the *Thlaspi arvense* (pennycress) FAD2-specific CRISPR-Cas9 construct were as described elsewhere (see, e.g., Steinert et al., 2015, *Plant J.*, 84:1295-305; and Fauser et al., 2014 *The Plant Journal* 79:348-359). The plant selectable marker (formerly NPT) was replaced with a hygromycin resistance (Hygromycin phosphotransferase (HPT)) gene in the pDe-SaCas9 binary vector to create a pDe-SaCas9_Hyg vector.

The following oligos were annealed to create a 20-mer protospacer specific to the pennycress FAD2 sequence:

```
PennyFAD2_CRISPR_FWD:
                                      (SEQ ID NO: 62)
5' ATTGTACTTGGCTTGGCCTCTCTA 3'
and PennyFAD2_CRISPR_REV:
                                      (SEQ ID NO: 63)
5' AAACTAGAGAGGCCAAGCCAAGTA 3'.
```

Construction of the *Thlaspi arvense* (Pennycress) ROD1 Gene-Specific CRISPR-Cas9 Vector The constructs and cloning procedures used for generation of the *Thlaspi arvense* (pennycress) ROD1-specific CRISPR-Cas9 construct were as described elsewhere (see, e.g., Fauser et al., 2014 *The Plant Journal* 79:348-359). The plant selectable marker in the pDe-Cas9 binary vector (formerly basta) was swapped for hygromycin resistance (the Hygromycin phosphotransferase (hpt) gene) to create a pDe-Cas9_Hyg vector.

The following oligos were annealed to create a 20-mer protospacer specific to the pennycress ROD1 sequence:

```
PennyROD1_CRISPR_FWD:
                                      (SEQ ID NO: 64)
5' ATTGGACGACGGCTACGCAAACGG 3'
and PennyROD1_CRISPR_REV:
                                      (SEQ ID NO: 65)
5' AAACCCGTTTGCGTAGCCGTCGTC 3'.
```

Vector Transformation into *Agrobacterium tumefaciens* Strain GV3101

The pDe-SaCas9_Hyg vector containing the pennycress FAD2 sequence-specific protospacer and the pDe-Cas9_Hyg vector containing the pennycress ROD1 sequence-specific protospacer were transformed into *Agrobacterium tumefaciens* strain GV3101 using the freeze/thaw method as described elsewhere (see, e.g., indiana.edu/~pikweb/Protocols % 20 page.html). The transformation product was plated on 1% agar Luria broth (LB) plates with gentamicin (50 µg/ml), rifampicin (50 µg/ml), and spectinomycin (75 µg/ml). Single colonies were selected after two days of growth at 28° C.

Plant Transformation (Pennycress Floral Dip)

On Day 1, *Agrobacterium* were inoculated with 5 mL of LB+5 µL appropriate antibiotics (e.g., rifampicin (50 µg/ml), spectinomycin (75 µg/ml), and/or gentamicin (50 µg/ml)), and the inoculated *Agrobacterium* were allowed to grow with shaking overnight at 28° C. On Day 2, in the early morning, the *Agrobacterium* culture from Day 1, was inoculated with 25 mL of Luria Broth+25 µL appropriate antibiotics (e.g., rifampicin (50 µg/ml), spectinomycin (75 µg/ml), and/or gentamicin (50 µg/ml)), and the inoculated *Agrobacterium* were allowed to grow with shaking overnight at 28° C. On Day 2, in the late afternoon, the *Agrobacterium* culture from earlier on Day 2, 25 mL of the culture was inoculated with 250 mL of Luria Broth+250 µL appropriate antibiotic(s) (e.g., rifampicin (50 µg/ml), spectinomycin (75 µg/ml), and/or gentamicin (50 µg/ml)), and the inoculated *Agrobacterium* were allowed to grow with shaking overnight at 28° C. On Day 3, when the culture had grown to an $OD_{600}$ of ~1 (or when it looked thick and silky), the *Agrobacterium* culture was decanted into large centrifuge tubes (all evenly weighted with analytical balance), and spun at 3,500 RPM at room temperature for 10 minutes to pellet cells. The supernatant was decanted. The pelleted cells were resuspended in a solution of 5% sucrose 0.02% Silwet L-77. The resuspended *Agrobacterium* cells were poured into clean beakers and placed in a vacuum chamber. Newly flowering inflorescences of pennycress were fully submerged into the beakers, and subjected to a pressure of 14.7 PSI for 10 minutes. After racemes of pennycress plants (Spring32 variety) were dipped, they were covered loosely with Saran wrap to maintain humidity and kept in the dark overnight before being uncovered and placed back in the environmental growth chamber.

Screening Transgenic Plants and Growth Conditions

Pennycress seeds were surface sterilized by first rinsing in 70% ethanol then a 10-minute incubation in a 30% bleach, 0.05% SDS solution before being rinsed two times with sterile water and plated on selective plates (0.8% agar/one half-strength Murashige and Skoog salts with hygromycin B selection at 40 U ml$^{-1}$). Plates were wrapped in parafilm and kept in an environmental growth chamber at 21° C., 16:8 day/night for 8 days until hygromycin selection was apparent.

Surviving hygromycin-resistant seedlings were transplanted into autoclaved Reddiearth soil mix and grown in an environmental growth chamber set to 16 hour days/8 hour nights at 21° C. and 50% humidity. When the plants had formed multiple rosette leaves, about 100 mg portions of leaves were harvested and placed in 2 ml screw cap tubes then flash-frozen in liquid nitrogen and stored at −80° C. until processed using the following CTAB method to extract genomic DNA for PCR amplification and sequencing to identify mutations.

Cetyl Trimethylammonium Bromide (CTAB) Genomic DNA Extraction

An extraction buffer was prepared as follows:

| Extraction Buffer (500 ml) | |
| --- | --- |
| 0.35 M sorbitol | 32 g |
| 0.1 M Tris base | 6 g |
| 5 mM EDTA-Na2 | 0.84 g (or EDTA-Na4 1.0 g) |

Sterile water was added to bring the total volume to 500 ml. The buffer was adjusted to pH 7.5 with high concentration HCl.

A lysis buffer was prepared as follows:

| Lysis Buffer (500 ml) | |
| --- | --- |
| 0.2 M Tris-base | 12.1 g |
| 0.05 M EDTA-Na2 | 8.4 g (or EDTA-Na4 10 g) |
| 2 M NaCl | 58.5 g |
| 2% CTAB | 10 g |
| 1% PVP | 5 g |

Sterile water was added to bring the total volume to 500 ml.

Equal parts of extraction buffers and lysis buffer were mixed and 10 units per 500 µL of RNAseA (Thermo #EN0531) was added to make a working solution.

Leaf plant tissue placed in 2 ml screw cap tubes that had been flash-frozen in liquid nitrogen then stored at −80° C. was ground in a Qiagen TissueLyser ball mill using a tube holder that had been precooled to −80° C. After grinding and before thawing, 500 µL of the working solution was added to the ground tissue. The mixture was vortexed and then incubated in a 65° C. water bath for 20 minutes. 500 µL of 24:1 chloroform-isoamyl mixture was added, and the tubes were inverted 6 times. The tubes were spun at 12,000 RPM at 4° C. for 10 minutes. 400 µL of the supernatant was moved to a new tube. 1 mL of cold 95% ETOH was added to the supernatant, and the tubes were inverted 6 times. The tubes were spun at 12,000 RPM for 15 minutes, and the supernatant was discarded. 400 µL of −20° C. 70% ETOH was added to the pellet. The tubes were spun at 12,000 RPM for 2 minutes, and the supernatant was discarded. The DNA pellet was air dried. Once dry, the pellet was resuspended in 200 µL sterile water. DNA concentrations were analyzed using a Nanodrop and normalized to 200 ng/µl.

PCR Amplification and Gel Purification of FAD2 Gene

PCR primers used to amplify 1,459 bp of the FAD2 gene from the DNA preps of individual plants are as follows:

```
pennyFAD2_OuterF1
                                 (SEQ ID NO: 66)
5' AATTACCACCCGTTCTTGTGC 3', pennyFAD2_OuterR1
                                 (SEQ ID NO: 67)
5' TCTACGATCCCAACAAAACAGC 3'.
```

PCR was performed using a Phusion (NEB #M0530) polymerase, and the following cycling parameters: 1 cycle of 1 minute at 98° C.; 32 repeated cycles of 98° C. for 10 seconds, 55° C. for 15 seconds, and 72° C. for 2 minutes; followed by 1 cycle of 5 minutes at 72° C.

PCR products were run on a 1% agarose gel. Bands of the expected 1,459 bp size were cut out and DNA was purified using the GeneJET Gel Extraction kit (#K0692).

PCR Amplification and Gel Purification of ROD1 Gene

PCR primers used to amplify 2,418 bp of the ROD1 gene from the DNA preps of individual plants are as follows:

```
pennyROD1_OuterF1
                                 (SEQ ID NO: 68)
5' TTCTTCCTTCGAAATCTCCGC 3', pennyROD1_OuterR1
                                 (SEQ ID NO: 69)
5' AAGACCATAAGAAGTACACGCC 3'.
```

PCR was performed using a Phusion (NEB #M0530) polymerase, and the following cycling parameters: 1 cycle of 1 minute at 98° C.; 32 repeated cycles of 98° C. for 10 seconds, 55° C. for 15 seconds, and 72° C. for 2 minutes; followed by 1 cycle of 5 minutes at 72° C.

PCR products were run on a 1% agarose gel. Bands of the expected 2,418 bp size were cut out and DNA was purified using the GeneJET Gel Extraction kit (#K0692).

```
Sequencing and Sequence Analysis.
Gel purified FAD2 sequences were sequenced with
the primer pennyFAD2_OuterF1
(5' AATTACCACCCGTTCTTGTGC 3'(SEQ ID NO: 66)).

Gel purified ROD1 sequences were sequenced with
the primer pennyROD1_OuterF1
(5' TTCTTCCTTCGAAATCTCCGC 3'(SEQ ID NO: 68)).
Sequences were analyzed using Benchling software.
```

Lipid Analysis

Total oil was quantified by gas chromatographic (GC) analysis of fatty acid methyl esters extracted from pennycress seeds as described elsewhere (see, e.g., McGinn et al., 2018 *Plant Biotechnology Journal* doi.org/10.1111/pbi.13014; Kim et al., 2015 *Journal of Experimental Botany* 2015: erv225).

Total lipids were extracted for analysis of fatty acid composition using a modified version of a Bligh and Dyer method as described elsewhere (see, e.g., Bligh et al., 1959 *Canadian Journal of Biochemistry and Physiology* 37:911-917).

In some cases, the materials and methods can be as described elsewhere (see, e.g., Chopra et al., 2018 *The Plant Journal* 96:1093-1105; McGinn et al., 2018 *Plant Biotechnology Journal* doi.org/10.1111/pbi.13014; and Chopra et al., 2019 *Industrial Crops and Products* 128:55-61.

Results

FAD2 Mutants

Figure 12:
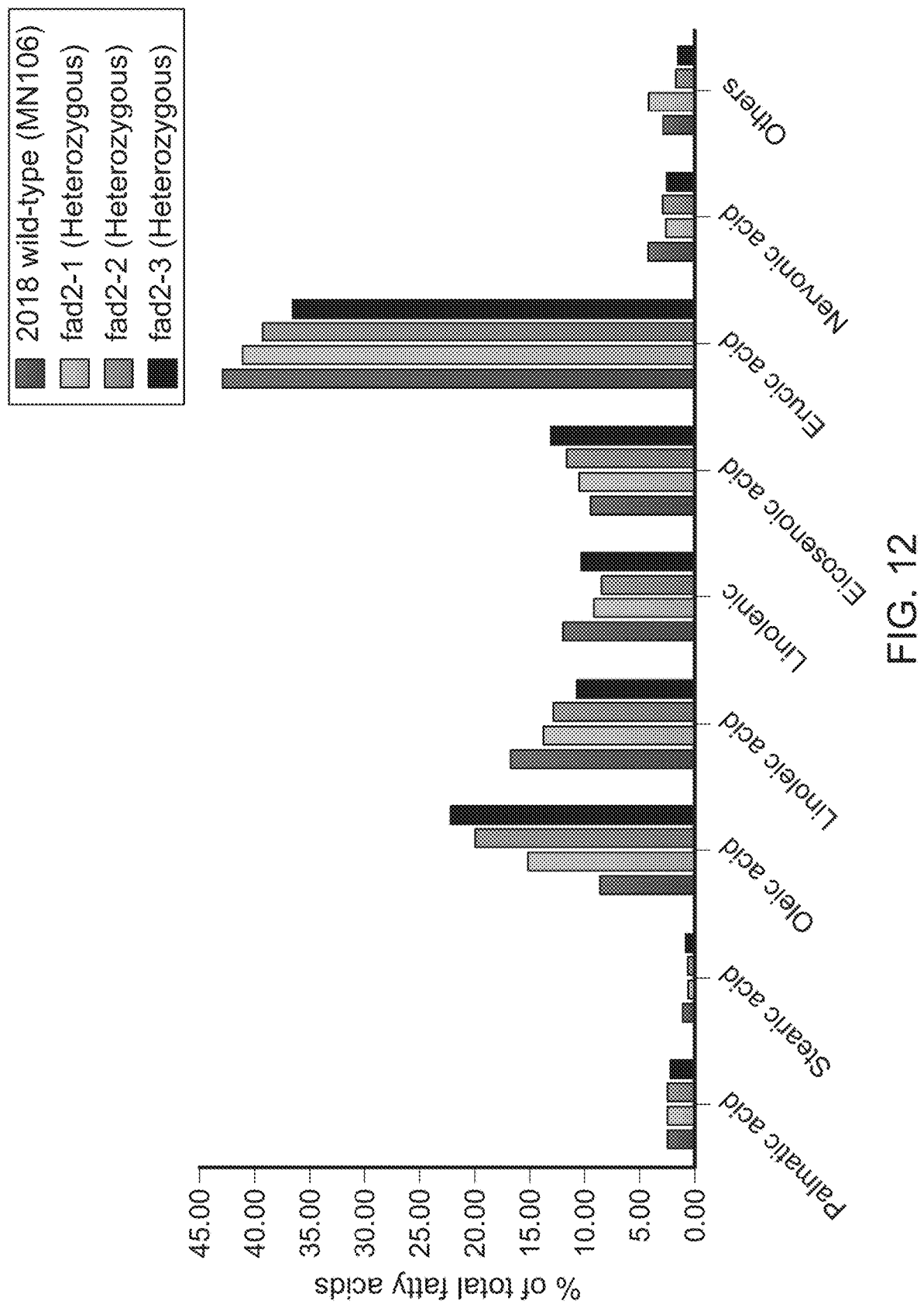
FIG. 12 contains a graph showing reductions in PUFAs in pennycress FAD2 mutants. NIR data were scanned for lines containing reductions in linoleic acid and linolenic acid. DNA sequence analyses showed that three such lines contained mutations in the pennycress FAD2 gene. Seeds from these lines annotated as E5 398P5 Tafad2-1, E2790 Tafad2-2, and E5 199P5 Tafad2-3 were subjected to GC analysis. The mol % levels of the major PUFAs linoleic and linolenic were greatly reduced. This was especially apparent for the Tafad2-2 line with linoleic reduced from 17.9 to 3.4 and linolenic reduced from 12.2 to 4.1 (mol %) compared to wild type, respectively. In addition, the levels of oleic acid dramatically increased in all three mutants compared to wild type. The level in Tafad2-2 showed the largest increase by increasing 2.5 fold over wild type.
Figure 18:
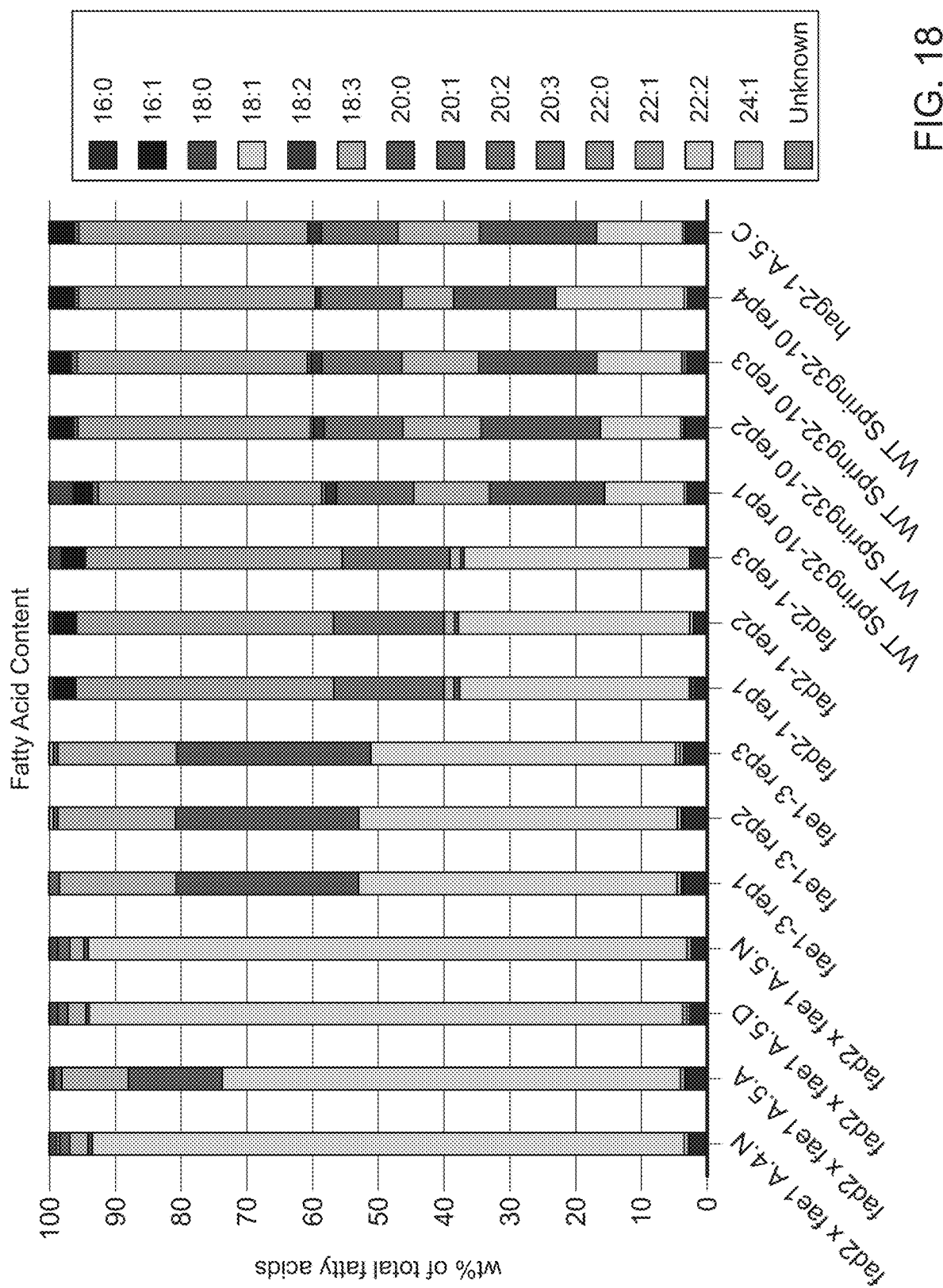
FIG. 18 contains a graph showing fatty acid content in seeds from pennycress single mutant lines and double mutant lines.

Some plants having reduced PUFAs contained an altered FAD2 gene. The FAD2 gene encodes the FAD2 polypeptide, which functions to add an extra double bond to oleic acid (18:1) to make the doubly polyunsaturated linoleic (18:2). Linoleic acid then serves as a substrate for FATTY ACID DEHYDROGENASE3 (FAD3), which adds another double bond to make the triple unsaturated linolenic (18:3). Representative fatty acid values (mol %) in plants having an altered FAD2 gene, as estimated by NIR analysis, are shown in Table 2 and Table 3. For results in Table 2, approximately 100 mg of seeds was used to determine the fatty-acid compositions, and analyses were repeated at least twice. For results in Table 3, a single seed was used to determine the fatty-acid compositions, and analyses were repeated at least four times. The plants with an altered FAD2 gene, and thus having reduced FAD2 polypeptide activity (e.g., fad2-1, fad2-2, fad2-3, fad2-4, fad2-5, and fad2-6) produced oils with reduced levels of PUFAs (FIGS. 12 and 18, and Tables 2, 3, 4, and 5). In particular, homozygous fad2 alleles generated from EMS or CRISPR-Cas9 produced oils with extremely low levels of both linoleic and linolenic acids (FIGS. 12 and 18, and Tables 3, 4, and 5). At the same time the levels of oleic acid increased. Homozygous fad2 alleles showed a 2.5 fold increase in oleic acid over the starting wild type material. These altered FAD2 lines have been extensively characterized to assess the DNA change responsible for the altered fatty acid biosynthesis. As can be seen in all fad2 alleles generated through EMS or CRISPR-Cas9 contain DNA and amino acid changes in the coding regions of the FAD2 gene (Table 6). In Tafad2-1 this results in a change of an aspartic amino acid being replaced by an arginine (FIG. 13 and Table 6). The normal aspartic acid is conserved in both *Arabidopsis thaliana* and in *Glycine max* (soybean) (FIG. 13). In Tafad2-2 the change results in a switch from glycine to aspartic acid (FIG. 13 and Table 6). The glycine is highly conserved at this position in both monocots (*Oryza sativa* (rice)) and dicots (soybean). The dramatic change in this highly conserved amino acid is likely responsible of the more extreme change in PUFA levels seen for Tafad2-2 (FIG. 12). In Tafad2-3, the change results in a switch of histidine to tyrosine (FIG. 13 and Table 6). Again the histidine amino acid is very highly conserved (FIG. 13). In Tafad2-4 and Tafad2-5 CRISPR-Cas9 generated alleles, premature stop codons were gained due to deletion of 2 bp and 29 bp, respectively (Table 6). In Tafad2-6 CRISPR-Cas9 generated alleles, a premature stop codon was gained due to insertion of 1 bp (Table 6). All the regions of CRISPR-Cas9 generated alleles were highly conserved.

ROD1 Mutants

Figure 14:
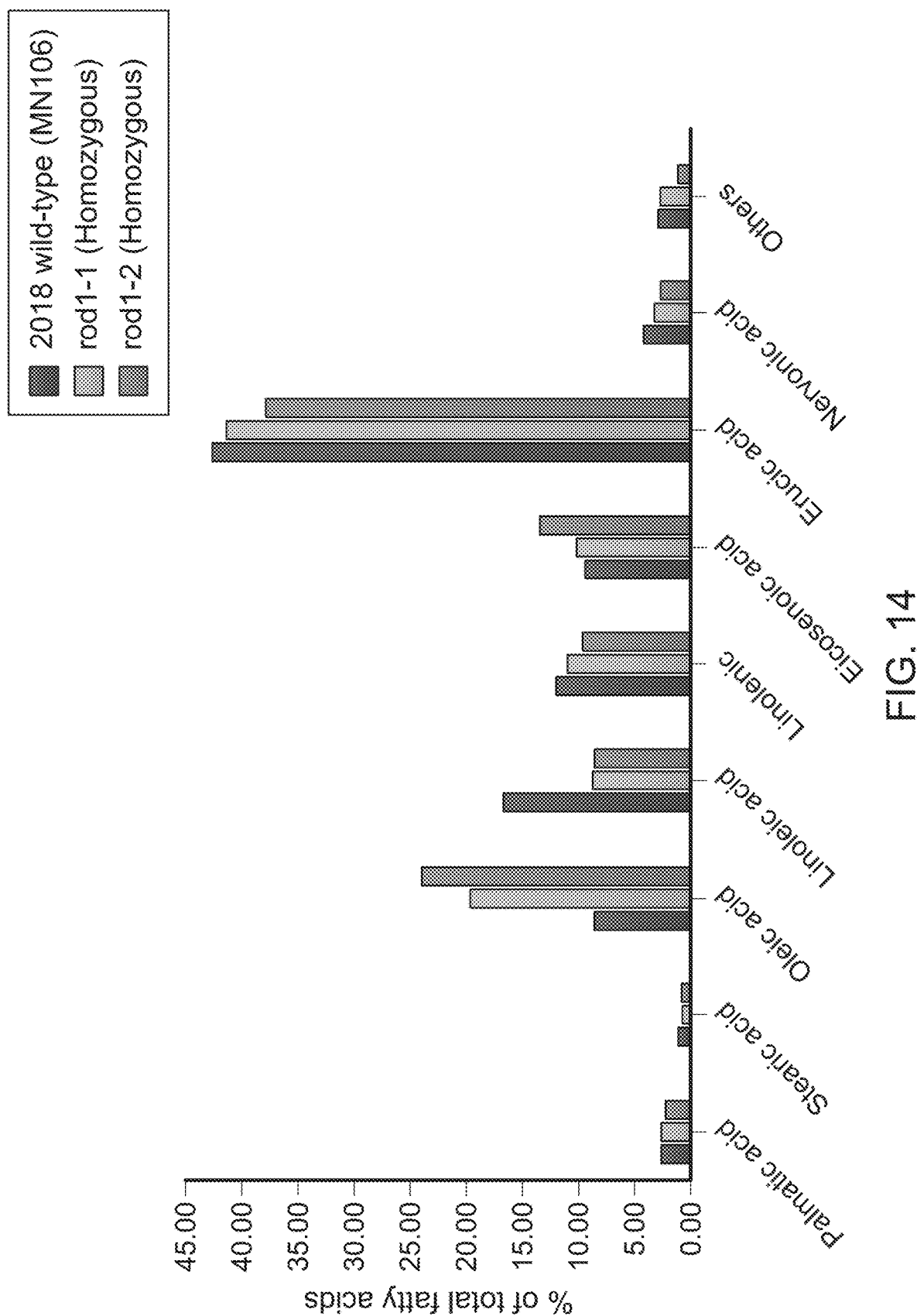
FIG. 14 contains a graph showing fatty acid content in pennycress lines having a reduction in linoleic acid due to mutations in the ROD1. NIR data were scanned for lines containing reductions in the polyunsaturated fatty acid linoleic. DNA sequence analysis showed that two such lines contained mutations in the pennycress ROD1 gene. Seeds from these lines annotated as D0422 Tarod1-1 and E2014 Tarod1-2 were subjected to GC analysis. As shown above the mol % levels of the major PUFA linoleic acid was greatly reduced. The two mutants showed similar reductions 18.4 in wild type down to 8.8 in the mutants. In addition, both mutants showed over a two fold increases in oleic acid over wild type.
Figure 16:
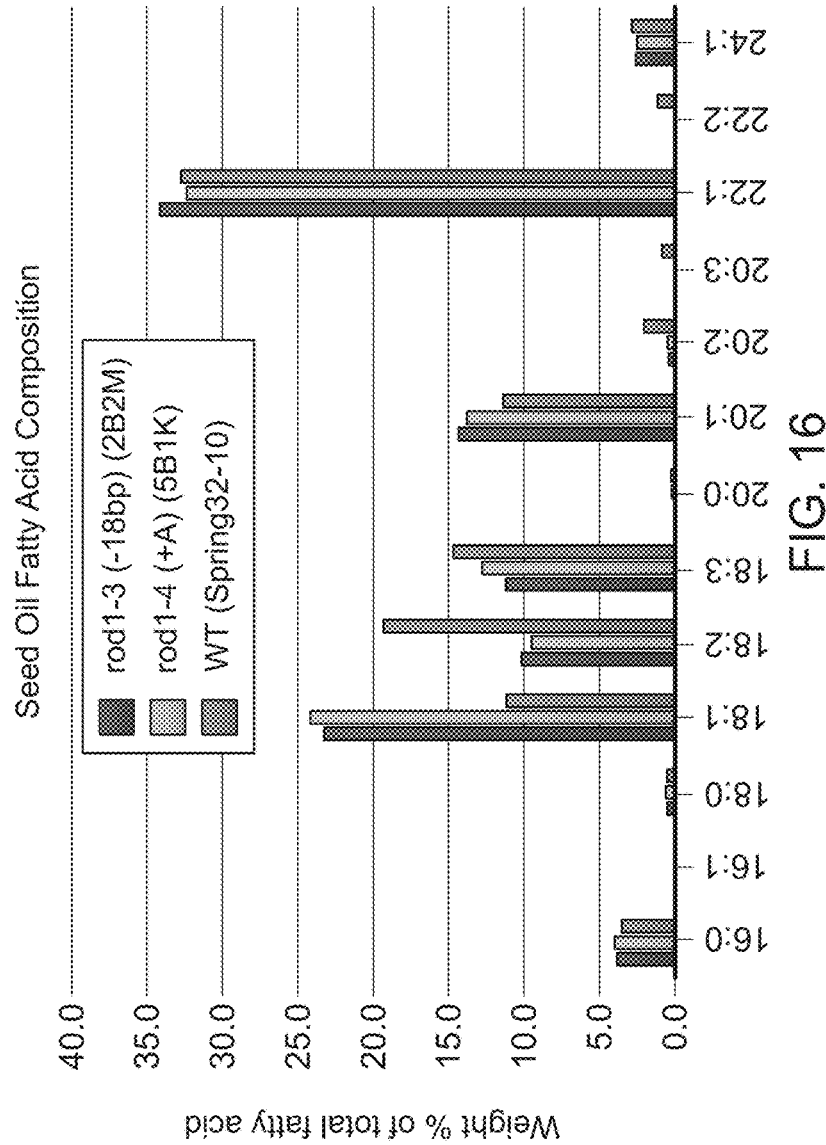
FIG. 16 contains a graph showing fatty acid content in pennycress lines having a reduction in linoleic acid due to mutations induced through CRISPR-Cas9 in the ROD1.

Some plants with reduced PUFAs contained alterations in the ROD1 gene. Both EMS generated Tarod1-1 and Tarod-2 contained altered ROD1 genes (FIG. 14). These two lines show similar reductions in the PUFA linoleic acid (18:2) (FIG. 14). Tarod1-1 contains a switch from methionine to isoleucine (FIG. 15 and Table 6) while Tarod1-2 contains a switch from arginine to lysine (FIG. 15 and Table 6). Both of methionine and arginine are highly conserved in both monocots and dicots (FIG. 15). In CRISPR-Cas9 generated rod1 alleles (rod1-3, rod1-4 and rod1-5), reductions in the PUFAs was observed (FIG. 16 and Table 5). Specifically, rod1-3 had an 18 bp deletion in the highly conserved regions resulting in a premature stop codon (Table 6). In rod1-4 and rod1-5 insertion of 1 bp in each led to frameshifts resulting in premature stop codons (Table 6). All of the CRISPR-Cas9 generated alleles were induced in highly conserved regions (FIG. 15).

The oils produced by both Tafad2 and Tarod1 lines contain reduced levels of PUFAs, while still producing erucic acid. In some applications for making bioproducts erucic acid is desirable. Thus, these Tafad2 and Tarod1 lines do have value over wild type oil. These oils have enhanced stability that allows them to be subjected to harsher biosynthetic protocols that require erucic acid. Specifically, Tafad2 alleles show increase in erucic acid compared to their respective wild-type plants (Table 3 and Table 4). This can be beneficial for high erucic markets.

Double FAE-ROD1 Lines and FAE-FAD2 Lines

Figure 17:
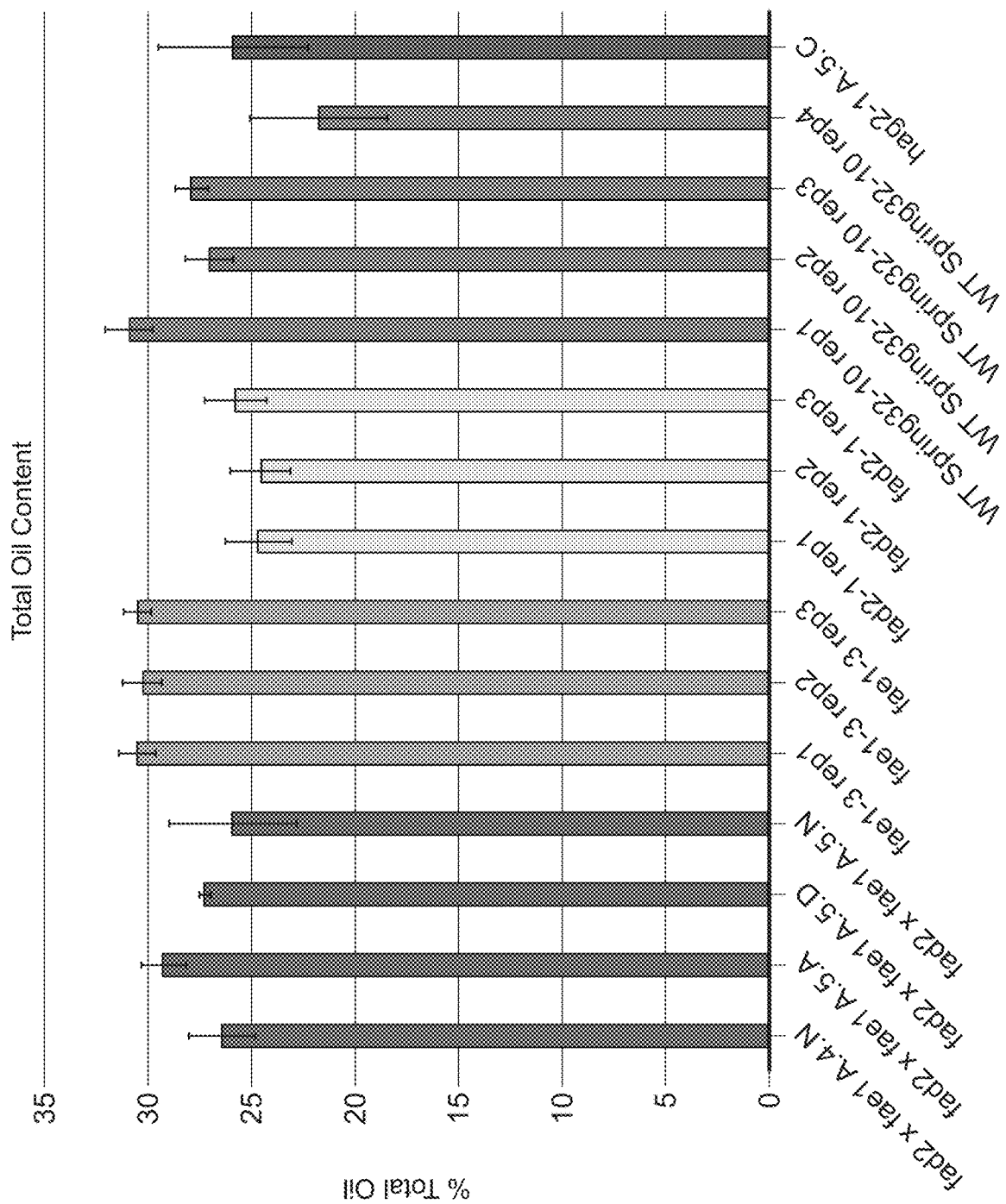
FIG. 17 contains a graph showing total oil content in seeds from pennycress single mutant lines and double mutant lines.
Figure 19:
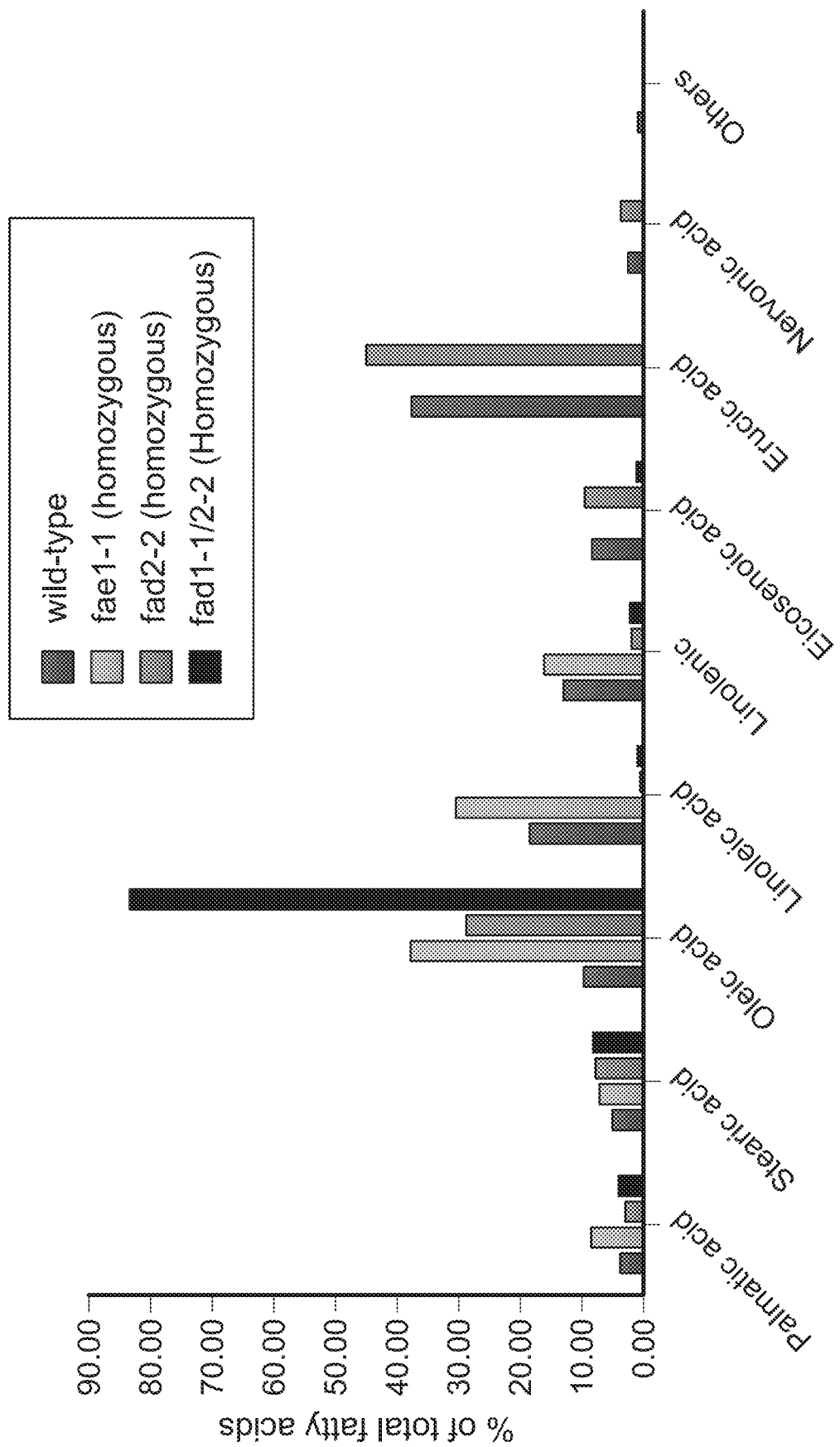
FIG. 19 contains a graph showing that combining Tafae1 and Tafad2 mutations results in extreme increase in oleic acid. The Tafad2-2 and Tafae1-1 mutants were crossed. The resulting F1 plants were allowed to self fertilize. F2 seeds were scored for the homozygosity for both Tafad2-2 and Tafae1-1 using PCR based DNA markers that used the mutations in the respective genes as markers to assess the genotypes of the seeds. Oil was extracted from seeds that homozygous for both Tafad2-2 and Tafae1-1 and subjected to GC analysis. The double mutant seed contained over 80 mol % of oleic acid while maintaining very low levels of the PUFAs linoleic and linolenic along with zero erucic acid.

To improve and widen the utility of the Tarod1 and Tafad2 oils, these lines have been crossed with the Tafae1-1 line and Tafae1-3 mutant lines. In particular, Tarod1-1 was crossed with Tafae1-1 to create a double Tafae1-1 Tarod1-1 line, Tafad2-2 was crossed with Tafae1-1 to create a double Tafae1-1 Tafad2-2 line, and Tafad2-4 was crossed with Tafae1-3 to create a double Tafad2-4 Tafae1-3 line. All of the double lines produced seeds having typical total oil content (FIG. 17), and show a dramatic improvement in oil quality by increasing oleic acid content of seed oil (FIG. 18). The double Tafae1-1 Tafad2-2 and Tafae1-3 Tafad2-4 lines produced an extremely high level of oleic with very low levels of PUFA while maintaining the zero erucic acid trait (FIGS. 6, 7, and 19, and Tables 3 and 4). This oil has similar features as olive oil and high oleic sunflower oil (FIG. 20). The double Tafae1-1 Tarod1-1 line shows a vast increase in oleic acid while still exhibiting the greatly reduced erucic trait (FIGS. 8, 9, and 21, and Tables 2 and 3). This oil has a very similar fatty acid profile as canola oil (FIG. 22).

TABLE 2

Seed oil fatty acid composition from a bulk seed sample from fae1-1, rod1-1, and fad2-2 single mutant as well as fae1-1 × fad2-2 double mutant, fae1-1 × rod1-1 double mutant EMS generated lines compared to wild type.

| Line | C-16:0 | C-18:0 | C-18:1 | C-18:2 | C-18:3 | C-20:1 | C-22:1 | C-24:1 | Others |
|---|---|---|---|---|---|---|---|---|---|
| 2017 wild-type (MN106) | 2.35 | 0.57 | 12.66 | 18.73 | 11.35 | 10.57 | 37.93 | 2.96 | 2.88 |
| 2017 wild-type (MN106) | 2.41 | 0.57 | 11.46 | 18.55 | 12.05 | 10.08 | 38.92 | 2.99 | 2.95 |
| 2017 wild-type (MN106) | 2.28 | 0.55 | 11.67 | 18.83 | 12.20 | 10.46 | 38.01 | 2.90 | 3.11 |
| 2018 wild-type (MN106) | 2.45 | 1.02 | 8.53 | 16.38 | 11.78 | 9.40 | 43.25 | 4.27 | 2.93 |
| 2018 wild-type (MN106) | 2.48 | 1.01 | 8.65 | 16.64 | 11.97 | 9.44 | 42.72 | 4.17 | 2.91 |
| fae1-1 (Homozygous) | 3.54 | 1.52 | 44.11 | 31.19 | 17.28 | 1.21 | 0.48 | 0.44 | 0.22 |
| fae1-2 (Homozygous) | 3.48 | 1.02 | 38.26 | 34.62 | 21.06 | 0.94 | 0.28 | 0.00 | 0.33 |
| rod1-1 (Homozygous) | 2.53 | 0.66 | 19.76 | 8.57 | 11.05 | 10.30 | 41.35 | 3.21 | 2.58 |
| rod1-2 (Homozygous) | 2.21 | 0.62 | 24.07 | 8.47 | 9.66 | 13.41 | 37.70 | 2.64 | 1.22 |
| fad2-1 (Heterozygous) | 2.61 | 0.57 | 15.33 | 13.79 | 9.13 | 10.66 | 41.00 | 2.63 | 4.28 |
| fad2-2 (Heterozygous) | 2.56 | 0.63 | 19.88 | 12.84 | 8.56 | 11.59 | 39.31 | 2.89 | 1.74 |
| fad2-3 (Heterozygous) | 2.15 | 0.93 | 22.11 | 10.78 | 10.35 | 13.05 | 36.24 | 2.58 | 1.80 |
| fae1-1 × rod1-1 | 3.81 | 1.85 | 61.33 | 13.63 | 18.60 | 0.78 | 0.00 | 0.00 | 0.00 |
| fae1-1 × rod1-1 | 3.85 | 1.86 | 61.79 | 13.75 | 18.75 | 0.00 | 0.00 | 0.00 | 0.00 |

WT = Wild Type (MN106 background). In parentheses are descriptions of the mutations. Values are in weight percent.

TABLE 3

Seed oil fatty acid composition of single seeds from fae1-1, rod1-1, and fad2-2 single mutant as well as fae1-1 × fad2-2 double mutant, fae1-1 × rod1-1 double mutant EMS generated lines compared to wild type.

| Genotype | Palmatic | Stearic | Oleic | Linoleic | Linolenic | Eicosenoic | Erucic | Nervonic | Others |
|---|---|---|---|---|---|---|---|---|---|
| wild-type | 3.78 | 4.94 | 9.69 | 18.46 | 12.98 | 8.58 | 37.70 | 2.87 | 0.99 |
| fae1-1 (homozygous) | 8.49 | 7.20 | 37.40 | 30.48 | 16.27 | 0.15 | 0.00 | 0.00 | 0.00 |
| fad2-2 (homozygous) | 3.09 | 7.92 | 28.59 | 0.00 | 2.14 | 9.72 | 44.79 | 3.75 | 0.00 |
| rod1-1 (Homozygous) | 3.60 | 5.74 | 16.81 | 8.58 | 10.69 | 9.64 | 41.05 | 3.89 | 0.00 |
| fae1-1/fad2-2 (Homozygous) | 4.03 | 8.20 | 83.02 | 1.01 | 2.40 | 1.34 | 0.00 | 0.00 | 0.00 |
| fae1-1/rod1-1 (Homozygous) | 4.42 | 5.86 | 60.27 | 15.70 | 12.71 | 1.04 | 0.00 | 0.00 | 0.00 |

WT = Wild Type (MN106 background). In parentheses are descriptions of the mutations. Values are in weight percent.

TABLE 4

Seed oil fatty acid composition from fae1 and fad2 single mutant as well as fae1 × fad2 double mutant CRISPR-Cas9-generated lines compared to wild type.

| Line | Seed oil fatty acids amounts (values in weight percents) | | | | | | | | | | | | | | | |
|---|---|---|---|---|---|---|---|---|---|---|---|---|---|---|---|---|
|  | 16:0 | 16:1 | 18:0 | 18:1 | 18:2 | 18:3 | 20:0 | 20:1 | 20:2 | 20:3 | 22:0 | 22:1 | 22:2 | 24:1 | Unknown | Total |
| WT (Spring32-10) rep1 | 2.9 | 0.3 | 0.4 | 11.7 | 17.7 | 11.6 | 0.1 | 11.6 | 1.8 | 0.4 | 0.0 | 34.1 | 0.7 | 3.2 | 3.5 | 100.0 |
| WT (Spring32-10) rep2 | 3.1 | 0.3 | 0.4 | 12.0 | 18.4 | 11.8 | 0.0 | 11.9 | 1.8 | 0.4 | 0.0 | 35.4 | 0.7 | 3.3 | 0.3 | 100.0 |
| WT (Spring32-10) rep3 | 3.0 | 0.3 | 0.4 | 12.6 | 18.3 | 11.5 | 0.0 | 12.3 | 1.8 | 0.4 | 0.0 | 35.1 | 0.6 | 3.3 | 0.3 | 100.1 |
| WT (Spring32-10) rep4 | 2.8 | 0.2 | 0.5 | 19.5 | 15.5 | 8.0 | 0.0 | 12.1 | 0.9 | 0.0 | 0.0 | 36.1 | 0.4 | 4.0 | 0.0 | 100.0 |
| fad2-4 × fae1-3 (A4N) | 2.4 | 0.3 | 0.6 | 90.1 | 0.5 | 2.8 | 0.0 | 1.6 | 0.0 | 0.0 | 0.0 | 0.0 | 0.0 | 0.3 | 1.1 | 100.0 |
| fad2-4 × fae1-3 (A5D) | 2.6 | 0.3 | 0.6 | 90.5 | 0.6 | 2.6 | 0.0 | 1.5 | 0.0 | 0.0 | 0.0 | 0.0 | 0.0 | 0.1 | 1.2 | 100.0 |
| fad2-4 × fae1-3 (A5N) | 2.4 | 0.1 | 0.6 | 91.2 | 0.5 | 2.3 | 0.0 | 1.5 | 0.0 | 0.0 | 0.0 | 0.0 | 0.0 | 0.1 | 1.3 | 100.0 |
| fae1-3 (-4bp) (745D1) | 3.5 | 0.2 | 0.7 | 48.4 | 28.0 | 17.7 | 0.0 | 0.9 | 0.0 | 0.0 | 0.0 | 0.0 | 0.0 | 0.3 | 0.2 | 100.0 |
| fae1-3 (-4bp) (745D2) | 3.5 | 0.3 | 0.8 | 48.6 | 27.8 | 17.8 | 0.0 | 1.0 | 0.0 | 0.0 | 0.0 | 0.0 | 0.0 | 0.3 | 0.0 | 100.0 |
| fae1-3 (-4bp) (745D3) | 3.6 | 0.3 | 0.8 | 46.5 | 29.7 | 17.9 | 0.0 | 0.9 | 0.0 | 0.0 | 0.0 | 0.0 | 0.0 | 0.3 | 0.0 | 100.0 |
| fad2-4 (-2bp) (1791D1) | 2.1 | 0.1 | 0.4 | 35.1 | 0.6 | 1.8 | 0.0 | 16.5 | 0.0 | 0.0 | 0.0 | 39.4 | 0.0 | 3.4 | 0.6 | 100.0 |
| fad2-4 (-2bp) (1791D2) | 2.1 | 0.0 | 0.4 | 35.2 | 0.5 | 1.8 | 0.0 | 16.7 | 0.0 | 0.0 | 0.0 | 39.3 | 0.0 | 3.4 | 0.6 | 100.0 |
| fad2-4 (-2bp) (1791D3) | 2.0 | 0.2 | 0.4 | 34.4 | 0.3 | 1.6 | 0.0 | 16.7 | 0.0 | 0.0 | 0.0 | 39.1 | 0.0 | 3.5 | 1.8 | 100.0 |

WT = Wild Type (Spring32-10 background). In parentheses are descriptions of the mutations and alternative line names. Values are in weight percent.

TABLE 5

Seed oil fatty acid composition from rod1 and fad2 mutant lines (independent CRISPR-Cas9-generated) versus wild type.

| Line | Seed oil fatty acid amounts (values in weight percents) | | | | | | | | | | | | | | Unknown | Total |
|---|---|---|---|---|---|---|---|---|---|---|---|---|---|---|---|---|
|  | 16:0 | 16:1 | 18:0 | 18:1 | 18:2 | 18:3 | 20:0 | 20:1 | 20:2 | 20:3 | 22:0 | 22:1 | 22:2 | 24:1 | known | Total |
| WT (Spring32-10) rep1a | 3.1 | 0.4 | 0.5 | 11.4 | 18.6 | 13.4 | 0.0 | 11.6 | 2.0 | 0.5 | 0.0 | 34.4 | 0.7 | 3.2 | 0.1 | 100 |
| WT (Spring32-10) rep2a | 3.1 | 0.4 | 0.5 | 11.5 | 18.9 | 13.4 | 0.0 | 11.6 | 2.0 | 0.5 | 0.0 | 34.1 | 0.7 | 3.2 | 0.0 | 100 |
| WT (Spring32-10) rep3a | 3.1 | 0.4 | 0.5 | 11.2 | 18.9 | 13.5 | 0.0 | 11.5 | 2.1 | 0.5 | 0.0 | 34.3 | 0.8 | 3.3 | 0.0 | 100 |
| rod1-3 (-18bp) (2B2k) | 3.2 | 0.4 | 0.5 | 22.3 | 8.3 | 11.4 | 0.0 | 14.1 | 0.4 | 0.3 | 0.0 | 36.2 | 0.0 | 2.9 | 0.0 | 100 |
| rod1-4 (+A) (5B3E) | 3.4 | 0.4 | 0.5 | 22.5 | 8.3 | 11.2 | 0.0 | 14.5 | 0.4 | 0.0 | 0.0 | 35.9 | 0.0 | 2.9 | 0.0 | 100 |
| WT (Spring32-10) rep1b | 3.1 | 0.3 | 0.5 | 9.8 | 18.5 | 15.1 | 0.0 | 10.7 | 2.1 | 0.6 | 0.0 | 35.3 | 0.9 | 3.2 | 0.0 | 100 |
| WT (Spring32-10) rep2b | 3.0 | 0.4 | 0.5 | 8.9 | 18.3 | 15.8 | 0.0 | 10.2 | 2.2 | 0.6 | 0.0 | 35.6 | 1.0 | 3.1 | 0.2 | 100 |
| WT (Spring32-10) rep3b | 3.2 | 0.3 | 0.5 | 9.6 | 19.2 | 15.2 | 0.0 | 10.7 | 2.1 | 0.6 | 0.0 | 34.7 | 0.9 | 3.1 | 0.1 | 100 |

TABLE 5-continued

Seed oil fatty acid composition from rod1 and fad2 mutant lines (independent CRISPR-Cas9-generated) versus wild type.

| Line | Seed oil fatty acid amounts (values in weight percents) | | | | | | | | | | | | | | Un-known | Total |
|---|---|---|---|---|---|---|---|---|---|---|---|---|---|---|---|---|
| | 16:0 | 16:1 | 18:0 | 18:1 | 18:2 | 18:3 | 20:0 | 20:1 | 20:2 | 20:3 | 22:0 | 22:1 | 22:2 | 24:1 | | |
| fad2-5 (-29bp) (1791A6E) | 2.5 | 0.1 | 0.4 | 34.0 | 0.5 | 2.7 | 0.0 | 14.2 | 0.0 | 0.0 | 0.0 | 41.4 | 0.0 | 3.6 | 0.6 | 100 |
| fad2-6 (+A) (1791A6P) | 2.4 | 0.1 | 0.4 | 35.0 | 0.5 | 2.5 | 0.0 | 14.9 | 0.0 | 0.0 | 0.0 | 39.8 | 0.0 | 3.8 | 0.5 | 100 |

WT = Wild Type (Spring32-10 background). In parentheses are descriptions of the mutations and alternative line names. Values are in weight percent.

TABLE 6

Summary of mutations in the genes involved in modification fatty-acid compositions of pennycress seed and oil.

| Name | Type | Function/Nature of the mutation | nucleotide residues of relevant SEQ ID NOs | Other Names Used |
|---|---|---|---|---|
| Ta-fae1-1 | Coding region | AGAACTGTT[C/T]AGAAAAACATA | 1009-1029 of SEQ ID NO: 15 compared to 1009-1029 of SEQ ID NO: 17 | V296, E3814, fae1-1 |
| Ta-fae1-1 | Protein | Truncated protein, Q->Stop change | | |
| Ta-fae1-2 | Coding region | ACAAAGTTT[G/A]GCAGATTGCTT | 1340-1360 of SEQ ID NO: 15 compared to 1340-1360 of SEQ ID NO: 50 | K1822, fae1-2 |
| Ta-fae1-2 | Protein | Truncated protein, W->Stop change | | |
| Ta-fae1-3 | Coding region | TCTACAT[CGTA/-]ACCCGGCC | 206-244 of SEQ ID NO: 15 compared to 206-220 of SEQ ID NO: 52 | 745D1, 745D2, 745D3 |
| Ta-fae1-3 | Protein | Frame shift caused by 4 bp deletion | | |
| Ta-fad2-1 | Coding region | TCTGAAACC[G/A]ATGCCTTAA | 504-522 of SEQ ID NO: 1 and 100-118 of SEQ ID NO: 25 compared to 504-522 of SEQ ID NO: 3 and 100-118 SEQ ID NO: 26, respectively | E5-199P5 |
| Ta-fad2-1 | Protein | Presumed LOF due to D -> N change | | |
| Ta-fad2-2 | Coding region | ACAGTCG[G/A]TCTGATCT | 819-834 of SEQ ID NO: 1 and 415-430 of SEQ ID NO: 25 compared to 819-834 of SEQ ID NO: 5 and 415-430 SEQ ID NO: 27, respectively | E2970, E5-133P2 |
| Ta-fad2-2 | Protein | Presumed LOF due to G -> D change | | |
| Ta-fad2-3 | Coding region | CGTTGCCT[C/T]ACTACGAT | 1291-1307 of SEQ ID NO: 1 and 887-903 of SEQ ID NO: 25 compared to 1291-1307 of SEQ ID NO: 7 and 887-903 of SEQ ID NO: 28, respectively | E5-398P5 |
| Ta-fad2-3 | Protein | Presumed LOF due to H -> Y change | | |
| Ta-fad2-4 | Coding region | TTGGCTTGGC[CT/-]CTCTATTGGGTCT | 708-732 of SEQ ID NO: 1 and 304-328 of SEQ ID NO: 25 compared to 708-730 of SEQ ID NO: 29 and 304-326 of SEQ ID NO: 30, respectively | 1791A6D |
| Ta-fad2-4 | Protein | Frame shift caused by 2 bp deletion | | |
| Ta-fad2-5 | Coding region | TACTTGGCT[TGGCCTCTCTATTGGGTCTGTCAAGGCTG:]TGTCTTACC | 705-752 of SEQ ID NO: 1 and 301-348 of SEQ ID NO: 25 compared to 705-723 of SEQ ID NO: 32 and 301-319 of SEQ ID NO: 33, respectively | 1791A6E |
| Ta-fad2-5 | Protein | Frame shift caused by 29 bp deletion | | |
| Ta-fad2-6 | Coding region | CTTGGCCTCT[-/A]CTATTGGGTCTG | 712-733 of SEQ ID NO: 1 and 308-329 of SEQ ID NO: 25 compared to 712-734 of SEQ ID NO: 35 and 308-330 of SEQ ID NO: 36, respectively | 1791A6P |
| Ta-fad2-6 | Protein | Frame shift caused by insertion | | |
| Ta-rod1-1 | Coding region | TGGACAT[G/A]AGGAGAATGCA | 1911-1929 of SEQ ID NO: 9 and 671-689 of SEQ ID NO: 38 compared to 1911-1929 of SEQ ID NO: 11 and 671-689 of SEQ ID NO: 39, respectively | d0422 |
| Ta-rod1-1 | Protein | Presumed LOF due to M -> I change | | |

TABLE 6-continued

Summary of mutations in the genes involved in
modification fatty-acid compositions of pennycress seed and oil.

| Name | Type | Function/Nature of the mutation | nucleotide residues of relevant SEQ ID NOs | Other Names Used |
|---|---|---|---|---|
| Ta-rod1-2 | Coding region | ATCGATCA[G/A]GCTGCTCGGGA | 1975-1994 of SEQ ID NO: 9 and 735-754 of SEQ ID NO: 38 compared to 1975-1994 of SEQ ID NO: 13 and 735-754 of SEQ ID NO: 40, respectively | E5-370P5, E5-370P6 |
| Ta-rod1-2 | Protein | Presumed LOF due to R -> K change | | |
| Ta-rod1-3 | Coding region | GACGGCT[ACGCAAACGGCGGAGGAG/-]GAGGAGGA | 160-192 of SEQ ID NO: 9 and 160-192 of SEQ ID NO: 38 compared to 160-174 of SEQ ID NO: 41 and 160-174 of SEQ ID NO: 42, respectively | 2B2K |
| Ta-rod1-3 | Protein | Frame shift caused by 18 bp deletion | | |
| Ta-rod1-4 | Coding region | CGGCTACGCAAA[-/A]CGGCGGAGGAGG | 162-185 of SEQ ID NO: 9 and 162-185 of SEQ ID NO: 38 compared to 162-186 of SEQ ID NO: 44 and 162-186 of SEQ ID NO: 45, respectively | 5B3E |
| Ta-rod1-4 | Protein | Frame shift caused by insertion | | |
| Ta-rod1-5 | Coding region | CTACGCAAA[-/T]CGGCGGAGGA | 165-183 of SEQ ID NO: 9 and 165-183 of SEQ ID NO: 38 compared to 184 of SEQ ID NO: 47 and 165-184 of SEQ ID NO: 48, respectively | 6C2B |
| Ta-rod1-5 | Protein | Frame shift caused by insertion | | |

Conclusion

In conclusion, this invention creates new utility for the undomesticated plant species, pennycress. We show that we have created new pennycress varieties whose oils rival those of the major crop species canola and olive oil. This goes without saying that the profiles of both of the oils are better than that produced by standard soybean lines, which exhibit lower levels of oleic and higher levels of PUFAs. These new oils have wide applications in either being used for the production of either food products or non-food bio products.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A pennycress plant having reduced levels of polyunsaturated fatty acids (PUFAs) and/or increased levels of oleic acid, said pennycress plant comprising:
    a genome comprising a modified reduced oleate desaturation 1 (ROD1) gene, wherein the modified ROD1 gene comprises a loss-of-function modification effective to knock-out expression levels of ROD1 polypeptides and/or ROD1 polypeptide activity;
    wherein an unmodified coding sequence of the ROD1 gene encodes a ROD1 polypeptide having the amino acid sequence shown in SEQ ID NO:10; and
    wherein the modification in the ROD1 gene is effective to reduce levels of PUFAs and/or increase levels of oleic acid in the plant compared to a corresponding pennycress plant lacking the modification in the ROD1 gene.

2. The pennycress plant of claim 1, wherein said modified ROD1 gene is set forth in SEQ ID NO:11 or SEQ ID NO:39.

3. The pennycress plant of claim 1, wherein said modified ROD1 gene is set forth in SEQ ID NO:41 or SEQ ID NO:42.

4. The pennycress plant of claim 1, wherein said modified ROD1 gene is set forth in SEQ ID NO:44 or SEQ ID NO:45.

5. The pennycress plant of claim 1, wherein said modified ROD1 gene is set forth in SEQ ID NO:47 or SEQ ID NO:48.

6. The pennycress plant of claim 1, wherein the genome of said pennycress plant further comprises a modified fatty acid elongase 1 (FAE1) gene, wherein an unmodified coding sequence of the FAE1 gene encodes a FAE1 polypeptide having the amino acid sequence shown in SEQ ID NO: 16, wherein the modified FAE1 gene comprises a loss-of-function modification effective to knock-out expression levels of FAE1 polypeptides and/or to knock-out FAE1 polypeptide activity compared to a corresponding pennycress plant lacking the modification in the FAE1 gene.

7. The pennycress plant of claim 1, wherein said PUFAs comprise one or more of linoleic acid (18:2) and linolenic acid (18:3).

8. The pennycress plant of claim 7, wherein said PUFA is linoleic acid, and wherein said reduced level of said linoleic acid comprises 1 mole % to 15 mole % linoleic acid.

9. The pennycress plant of claim 7, wherein said PUFA is linolenic acid, and wherein said reduced level of said linolenic acid comprises about 1 mole % to 11 mole % linolenic acid.

10. A seed produced by the pennycress plant of claim 1, wherein the seed comprises a genome comprising the modified reduced oleate desaturation 1 (ROD1) gene, wherein the modified ROD1 gene comprises a loss-of-function modification effective to knock-out expression levels of ROD1 polypeptides and/or ROD1 polypeptide activity;
    wherein an unmodified coding sequence of the ROD1 gene encodes a ROD1 polypeptide having the amino acid sequence shown in SEQ ID NO:10; and
    wherein the modification in the ROD1 gene is effective to reduce levels of PUFAs and/or increase levels of oleic acid in the plant compared to a corresponding pennycress plant lacking the modification in the ROD1 gene.

11. The pennycress plant of claim 1, wherein the modified ROD1 gene encodes the ROD1 polypeptide set forth in SEQ ID NO: 12.

12. The pennycress plant of claim 1, wherein the modified ROD1 gene encodes the ROD1 polypeptide set forth in SEQ ID NO:43.

13. The pennycress plant of claim 1, wherein the modified ROD1 gene encodes the ROD1 polypeptide set forth in SEQ ID NO:46.

14. The pennycress plant of claim 1, wherein the modified ROD1 gene encodes the ROD1 polypeptide set forth in SEQ ID NO:49.

\* \* \* \* \*

UNITED STATES PATENT AND TRADEMARK OFFICE
CERTIFICATE OF CORRECTION

| | |
|---|---|
| PATENT NO. | : 12,221,612 B2 |
| APPLICATION NO. | : 16/969434 |
| DATED | : February 11, 2025 |
| INVENTOR(S) | : Michael David Marks et al. |

It is certified that error appears in the above-identified patent and that said Letters Patent is hereby corrected as shown below:

On the Title Page

Column 2 (Item (56) Other Publications), Line 15, delete "elevation."" and insert -- elevation," -- therefor.

In the Claims

Column 174, Line 45 (Approx.), in Claim 9, delete "about" after "comprises".

Signed and Sealed this
First Day of April, 2025

Coke Morgan Stewart
*Acting Director of the United States Patent and Trademark Office*